(12) United States Patent
King et al.

(10) Patent No.: US 11,028,383 B2
(45) Date of Patent: *Jun. 8, 2021

(54) POLYPEPTIDE ASSEMBLIES AND METHODS FOR THE PRODUCTION THEREOF

(71) Applicants: UNIVERSITY OF WASHINGTON, Seattle, WA (US); UNIVERSITY OF UTAH, Salt Lake City, UT (US)

(72) Inventors: Neil King, Seattle, WA (US); Wesley Sundquist, Salt Lake City, UT (US); Joerg Votteler, Salt Lake City, UT (US); Yang Hsia, Seattle, WA (US); David Baker, Seattle, WA (US); Jacob Bale, Seattle, WA (US); Marc Lajoie, Seattle, WA (US); Gabriel Butterfield, Seattle, WA (US); Elizabeth Gray, Seattle, WA (US); Daniel Stetson, Seattle, WA (US)

(73) Assignees: University of Washington, Seattle, WA (US); University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/676,253

(22) Filed: Nov. 6, 2019

(65) Prior Publication Data
US 2020/0224186 A1 Jul. 16, 2020

Related U.S. Application Data

(63) Continuation of application No. 15/541,201, filed as application No. PCT/US2016/020090 on Feb. 29, 2016, now Pat. No. 10,501,733.

(60) Provisional application No. 62/126,331, filed on Feb. 27, 2015.

(51) Int. Cl.
| | | |
|---|---|---|
| C12N 9/88 | (2006.01) | |
| C07K 14/00 | (2006.01) | |
| C07K 14/435 | (2006.01) | |

(52) U.S. Cl.
CPC ............ C12N 9/88 (2013.01); C07K 14/00 (2013.01); C07K 14/435 (2013.01); C12Y 401/02014 (2013.01); *C07K 2319/03* (2013.01); *C07K 2319/06* (2013.01); *C07K 2319/735* (2013.01)

(58) Field of Classification Search
CPC .......................... C12N 9/88; C12Y 401/02014
See application file for complete search history.

(56) References Cited

U.S. PATENT DOCUMENTS

| 9,314,557 | B2 | 4/2016 | Ricci et al. | |
|---|---|---|---|---|
| 9,630,994 | B2* | 4/2017 | Baker | C07K 14/00 |
| 10,501,733 | B2* | 12/2019 | King | C07K 14/435 |
| 2009/0246142 | A1 | 10/2009 | Bhatia et al. | |
| 2011/0200560 | A1 | 8/2011 | Zhang | |
| 2012/0321653 | A1* | 12/2012 | Mamoun | A61P 43/00 424/186.1 |
| 2013/0251502 | A1 | 9/2013 | Ketcham et al. | |
| 2013/0274441 | A1 | 10/2013 | Baker et al. | |
| 2015/0356240 | A1 | 12/2015 | Baker et al. | |

FOREIGN PATENT DOCUMENTS

| WO | 2009/109428 | | 9/2009 |
|---|---|---|---|
| WO | 2014/0124301 | | 8/2014 |
| WO | 2014/152751 | | 9/2014 |
| WO | 2015188669 | A1 | 12/2015 |

OTHER PUBLICATIONS

BioAfrica 2019, MA-P17 Matrix Protein, on the web at bioafrica.net/proteomics/GAG-MAprot.html.*
Zhaxybayeva et al.2009; On the chimeric nature, thermophili origin, and phylogenetic placement of the Thermotogales. Proc. Natl, Acad. Sci. 106(14): 5865-5870, plus 16 pages of Supporting Information, plus sequence alignments.*
Albritton, et al., "Observers for Sensorless Control of Industrial Magnetic Bearings," IEEE, pp. 973-978, 1995.
Hoshi, et al., "Magnetically Suspended Centrifugal Blood Pump With a Radial Magnetic Driver," ASAIO Journal, 2005.
Hoshi, et al., "Third-generation Blood Pumps With Mechanical Noncontact Magnetic Bearings," Artificial Organs, vol. 30, No. 5, pp. 324-338, 2006.
Li, et al. "Design Principles for Multicuhannel Fringing Electric Field Sensors," Li, IEEE Sensors Journal, vol. 6, No. 2, 2006.
Qian, et al., "Study on stable equilibrium of levitated impeller in rotary pump with passive magnetic bearings," Journal of Medical Engineering & Technology, vol. 30, No. 2, pp. 78-82, 2006.
Schuhmann, et al., "Improving Operational Performance of Active Magnetic Bearings Using Kalman Filter and State Feedback Control," IEEE transactions on industrial electronics, vol. 59, No. 2, pp. 821—2019, 2012.

(Continued)

*Primary Examiner* — Karen Cochrane Carlson
(74) *Attorney, Agent, or Firm* — McDonnell Boehnen Hulbert & Berghoff LLP

(57) ABSTRACT

The application discloses multimeric assemblies including multiple oligomeric substructures, where each oligomeric substructure includes multiple proteins that self-interact around at least one axis of rotational symmetry, where each protein includes one or more polypeptide-polypeptide interface ("O interface"); and one or more polypeptide domain that is capable of effecting membrane scission and release of an enveloped multimeric assembly from a cell by recruiting the ESCRT machinery to the site of budding by binding to one or more proteins in the eukaryotic ESCRT complex ("L domain"); and where the multimeric assembly includes one or more subunits comprising one or more polypeptide domain that is capable of interacting with a lipid bilayer ("M domain"), as well as membrane-enveloped versions of the multimeric assemblies.

Figure 1:
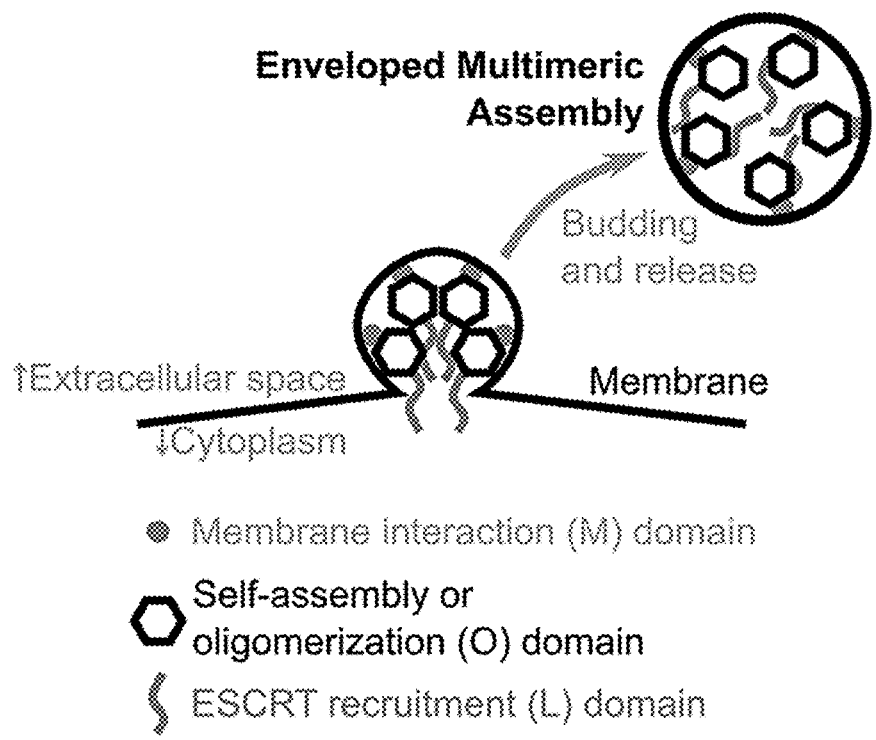

20 Claims, 13 Drawing Sheets
Specification includes a Sequence Listing.

(56) References Cited

OTHER PUBLICATIONS

Grenfell, et al., "Vaccine Self-Assembling Immune Matrix is a New Delivery Platform That Enhances Immune Responses to Recombinant HBsAg in Mice," Clin Vaccine Immunol. Mar. 2015;22(3):336-43. Epub Jan. 21, 2015.
Tagalakis, et al., "Multifunctional, self-assembling anionic peptide-lipid nanocomplexes for targeted siRNA delivery," Biomaterials. Sep. 2014;35(29):8406-15. Epub Jun. 28, 2014.
Zhang, et al., "Unfolding a molecular trefoil derived from a zwitterionic metallopeptide to form self-assembled nanostructures," Nat Commun. Feb. 19, 2015;6:6165.
Hurley, et al. "Membrane budding and scission by the ESCRT machinery: it's all in the neck," Nature Reviews Mol Cell Biol (2010) 11:556-566.
The International Search report (ISR) for PCT/US2016/020090, dated Jun. 10, 2016, pp. 1-4.
The Written Opinion of the International Searching Authority for PCT/US2016/020090, dated Jun. 10, 2016, pp. 1-5.

\* cited by examiner

SEQUENCE LISTING

<160> NUMBER OF SEQ ID NOS: 328

<210> SEQ ID NO 1
<211> LENGTH: 184
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (25)..(25)
<223> OTHER INFORMATION: Xaa is any amino acid
<220> FEATURE:
<221> NAME/KEY: MISC_FEATURE
<222> LOCATION: (28)..(28)
<223> OTHER INFORMATION: Xaa is any amino acid
<220> FEATURE:
<221> NAME/KEY: MISC_FEATURE
<222> LOCATION: (30)..(30)
<223> OTHER INFORMATION: Xaa is any amino acid
<220> FEATURE:
<221> NAME/KEY: MISC_FEATURE
<222> LOCATION: (35)..(35)
<223> OTHER INFORMATION: Xaa is any amino acid
<220> FEATURE:
<221> NAME/KEY: MISC_FEATURE
<222> LOCATION: (38)..(39)
<223> OTHER INFORMATION: Xaa is any amino acid
<220> FEATURE:
<221> NAME/KEY: MISC_FEATURE
<222> LOCATION: (41)..(41)
<223> OTHER INFORMATION: Xaa is any amino acid
<220> FEATURE:
<221> NAME/KEY: MISC_FEATURE
<222> LOCATION: (49)..(50)
<223> OTHER INFORMATION: Xaa is any amino acid
<220> FEATURE:
<221> NAME/KEY: MISC_FEATURE
<222> LOCATION: (55)..(55)
<223> OTHER INFORMATION: Xaa is any amino acid
<220> FEATURE:
<221> NAME/KEY: MISC_FEATURE
<222> LOCATION: (68)..(70)

```
<223> OTHER INFORMATION: Xaa is any amino acid
<220> FEATURE:
<221> NAME/KEY: MISC_FEATURE
<222> LOCATION: (72)..(72)
<223> OTHER INFORMATION: Xaa is any amino acid
<220> FEATURE:
<221> NAME/KEY: MISC_FEATURE
<222> LOCATION: (75)..(76)
<223> OTHER INFORMATION: Xaa is any amino acid
<220> FEATURE:
<221> NAME/KEY: MISC_FEATURE
<222> LOCATION: (78)..(79)
<223> OTHER INFORMATION: Xaa is any amino acid
<220> FEATURE:
<221> NAME/KEY: MISC_FEATURE
<222> LOCATION: (83)..(83)
<223> OTHER INFORMATION: Xaa is any amino acid
<220> FEATURE:
<221> NAME/KEY: MISC_FEATURE
<222> LOCATION: (86)..(88)
<223> OTHER INFORMATION: Xaa is any amino acid
<220> FEATURE:
<221> NAME/KEY: MISC_FEATURE
<222> LOCATION: (90)..(90)
<223> OTHER INFORMATION: Xaa is any amino acid
<220> FEATURE:
<221> NAME/KEY: MISC_FEATURE
<222> LOCATION: (92)..(95)
<223> OTHER INFORMATION: Xaa is any amino acid
<220> FEATURE:
<221> NAME/KEY: MISC_FEATURE
<222> LOCATION: (103)..(103)
<223> OTHER INFORMATION: Xaa is any amino acid
<220> FEATURE:
<221> NAME/KEY: MISC_FEATURE
<222> LOCATION: (114)..(114)
<223> OTHER INFORMATION: Xaa is any amino acid
<220> FEATURE:
<221> NAME/KEY: MISC_FEATURE
<222> LOCATION: (117)..(117)
<223> OTHER INFORMATION: Xaa is any amino acid
<220> FEATURE:
<221> NAME/KEY: MISC_FEATURE
<222> LOCATION: (120)..(120)
<223> OTHER INFORMATION: Xaa is any amino acid
<220> FEATURE:
<221> NAME/KEY: MISC_FEATURE
<222> LOCATION: (127)..(127)
<223> OTHER INFORMATION: Xaa is any amino acid
<220> FEATURE:
<221> NAME/KEY: MISC_FEATURE
<222> LOCATION: (130)..(130)
<223> OTHER INFORMATION: Xaa is any amino acid
<220> FEATURE:
<221> NAME/KEY: MISC_FEATURE
<222> LOCATION: (133)..(133)
<223> OTHER INFORMATION: Xaa is any amino acid
<220> FEATURE:
<221> NAME/KEY: MISC_FEATURE
<222> LOCATION: (143)..(143)
<223> OTHER INFORMATION: Xaa is any amino acid
<220> FEATURE:
<221> NAME/KEY: MISC_FEATURE
<222> LOCATION: (162)..(162)
<223> OTHER INFORMATION: Xaa is any amino acid
<220> FEATURE:
<221> NAME/KEY: MISC_FEATURE
<222> LOCATION: (171)..(172)
<223> OTHER INFORMATION: Xaa is any amino acid
<220> FEATURE:
<221> NAME/KEY: MISC_FEATURE
<222> LOCATION: (174)..(175)
<223> OTHER INFORMATION: Xaa is any amino acid
<220> FEATURE:
<221> NAME/KEY: MISC_FEATURE
<222> LOCATION: (178)..(179)
<223> OTHER INFORMATION: Xaa is any amino acid
<220> FEATURE:
<221> NAME/KEY: MISC_FEATURE
```

<222> LOCATION: (183)..(184)
<223> OTHER INFORMATION: Xaa is any amino acid

<400> SEQUENCE: 1

Met Xaa Xaa Ala Ile Gly Ile Leu Glu Leu Xaa Ser Ile Ala Ala Gly
1               5                   10                  15

Met Glu Leu Gly Asp Ala Met Leu Xaa Ser Ala Xaa Val Xaa Leu Leu
            20                  25                  30

Val Ser Xaa Thr Ile Xaa Xaa Gly Xaa Phe Leu Leu Met Leu Gly Gly
        35                  40                  45

Xaa Xaa Gly Ala Ile Gln Xaa Ala Ile Glu Thr Gly Thr Ser Gln Ala
    50                  55                  60

Gly Glu Leu Xaa Xaa Xaa Ser Xaa Val Leu Xaa Xaa Ile Xaa Xaa Ser
65                  70                  75                  80

Val Leu Xaa Ala Ile Xaa Xaa Xaa Asn Xaa Val Xaa Xaa Xaa Xaa Ala
                85                  90                  95

Val Gly Ile Val Glu Thr Xaa Ser Val Ala Ala Cys Ile Ser Ala Ala
            100                 105                 110

Asp Xaa Ala Val Xaa Gly Ser Xaa Val Thr Leu Val Arg Val Xaa Met
        115                 120                 125

Ala Xaa Gly Ile Xaa Gly Lys Cys Tyr Met Val Val Ala Gly Xaa Val
    130                 135                 140

Ser Asp Val Ala Leu Ala Val Thr Val Ala Ser Ser Ala Gly Ala
145                 150                 155                 160

Tyr Xaa Leu Leu Val Tyr Ala Ser Leu Ile Xaa Xaa Pro Xaa Xaa Ala
                165                 170                 175

Met Xaa Xaa Gln Met Val Xaa Xaa
            180

<210> SEQ ID NO 2
<211> LENGTH: 184
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 2

Met Ser Gln Ala Ile Gly Ile Leu Glu Leu Thr Ser Ile Ala Lys Gly
1               5                   10                  15

Met Glu Leu Gly Asp Ala Met Leu Lys Ser Ala Asn Val Asp Leu Leu
            20                  25                  30

Val Ser Lys Thr Ile Cys Pro Gly Lys Phe Leu Leu Met Leu Gly Gly
        35                  40                  45

Asp Ile Gly Ala Ile Gln Gln Ala Ile Glu Thr Gly Thr Ser Gln Ala
    50                  55                  60

Gly Glu Met Leu Val Asp Ser Leu Val Leu Ala Asn Ile His Pro Ser
65                  70                  75                  80

Val Leu Pro Ala Ile Ser Gly Leu Asn Ser Val Asp Lys Arg Gln Ala
                85                  90                  95

Val Gly Ile Val Glu Thr Trp Ser Val Ala Ala Cys Ile Ser Ala Ala
            100                 105                 110

Asp Arg Ala Val Lys Gly Ser Asn Val Thr Leu Val Arg Val His Met
        115                 120                 125

```
Ala Phe Gly Ile Gly Gly Lys Cys Tyr Met Val Val Ala Gly Asp Val
    130                 135                 140

Ser Asp Val Asn Asn Ala Val Thr Val Ala Ser Glu Ser Ala Gly Glu
145                 150                 155                 160

Lys Gly Leu Leu Val Tyr Arg Ser Val Ile Pro Arg Pro His Glu Ala
                165                 170                 175

Met Trp Arg Gln Met Val Glu Gly
            180
```

```
<210> SEQ ID NO 3
<211> LENGTH: 184
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 3
```

```
Met Ser Gln Ala Ile Gly Ile Leu Glu Leu Thr Ser Ile Ala Ala Gly
1               5                   10                  15

Met Glu Leu Gly Asp Ala Met Leu Lys Ser Ala Asn Val Asp Leu Leu
            20                  25                  30

Val Ser Lys Thr Ile Ser Pro Gly Lys Phe Leu Leu Met Leu Gly Gly
        35                  40                  45

Asp Ile Gly Ala Ile Gln Gln Ala Ile Glu Thr Gly Thr Ser Gln Ala
    50                  55                  60

Gly Glu Leu Leu Val Asp Ser Leu Val Leu Ala Asn Ile His Pro Ser
65                  70                  75                  80

Val Leu Pro Ala Ile Ser Gly Leu Asn Ser Val Asp Lys Arg Gln Ala
                85                  90                  95

Val Gly Ile Val Glu Thr Trp Ser Val Ala Ala Cys Ile Ser Ala Ala
            100                 105                 110

Asp Arg Ala Val Lys Gly Ser Asn Val Thr Leu Val Arg Val His Met
        115                 120                 125

Ala Phe Gly Ile Gly Gly Lys Cys Tyr Met Val Val Ala Gly Asp Val
    130                 135                 140

Ser Asp Val Ala Leu Ala Val Thr Val Ala Ser Ser Ser Ala Gly Ala
145                 150                 155                 160

Tyr Gly Leu Leu Val Tyr Ala Ser Leu Ile Pro Arg Pro His Glu Ala
                165                 170                 175

Met Trp Arg Gln Met Val Glu Gly
            180
```

```
<210> SEQ ID NO 4
<211> LENGTH: 199
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (2)..(10)
<223> OTHER INFORMATION: Xaa is any amino acid
<220> FEATURE:
<221> NAME/KEY: MISC_FEATURE
```

```
<222> LOCATION: (13)..(13)
<223> OTHER INFORMATION: Xaa is any amino acid
<220> FEATURE:
<221> NAME/KEY: MISC_FEATURE
<222> LOCATION: (16)..(16)
<223> OTHER INFORMATION: Xaa is any amino acid
<220> FEATURE:
<221> NAME/KEY: MISC_FEATURE
<222> LOCATION: (19)..(19)
<223> OTHER INFORMATION: Xaa is any amino acid
<220> FEATURE:
<221> NAME/KEY: MISC_FEATURE
<222> LOCATION: (21)..(21)
<223> OTHER INFORMATION: Xaa is any amino acid
<220> FEATURE:
<221> NAME/KEY: MISC_FEATURE
<222> LOCATION: (41)..(41)
<223> OTHER INFORMATION: Xaa is S or V
<220> FEATURE:
<221> NAME/KEY: MISC_FEATURE
<222> LOCATION: (42)..(42)
<223> OTHER INFORMATION: Xaa is any amino acid
<220> FEATURE:
<221> NAME/KEY: MISC_FEATURE
<222> LOCATION: (44)..(44)
<223> OTHER INFORMATION: Xaa is L or M
<220> FEATURE:
<221> NAME/KEY: MISC_FEATURE
<222> LOCATION: (45)..(45)
<223> OTHER INFORMATION: Xaa is K or M
<220> FEATURE:
<221> NAME/KEY: MISC_FEATURE
<222> LOCATION: (46)..(46)
<223> OTHER INFORMATION: Xaa is any amino acid
<220> FEATURE:
<221> NAME/KEY: MISC_FEATURE
<222> LOCATION: (58)..(59)
<223> OTHER INFORMATION: Xaa is any amino acid
<220> FEATURE:
<221> NAME/KEY: MISC_FEATURE
<222> LOCATION: (61)..(61)
<223> OTHER INFORMATION: Xaa is any amino acid
<220> FEATURE:
<221> NAME/KEY: MISC_FEATURE
<222> LOCATION: (75)..(75)
<223> OTHER INFORMATION: Xaa is any amino acid
<220> FEATURE:
<221> NAME/KEY: MISC_FEATURE
<222> LOCATION: (78)..(79)
<223> OTHER INFORMATION: Xaa is any amino acid
<220> FEATURE:
<221> NAME/KEY: MISC_FEATURE
<222> LOCATION: (92)..(92)
<223> OTHER INFORMATION: Xaa is any amino acid
<220> FEATURE:
<221> NAME/KEY: MISC_FEATURE
<222> LOCATION: (94)..(94)
<223> OTHER INFORMATION: Xaa is any amino acid
<220> FEATURE:
<221> NAME/KEY: MISC_FEATURE
<222> LOCATION: (97)..(97)
<223> OTHER INFORMATION: Xaa is any amino acid
<220> FEATURE:
<221> NAME/KEY: MISC_FEATURE
<222> LOCATION: (111)..(111)
<223> OTHER INFORMATION: Xaa is any amino acid
<220> FEATURE:
<221> NAME/KEY: MISC_FEATURE
<222> LOCATION: (114)..(114)
<223> OTHER INFORMATION: Xaa is any amino acid
<220> FEATURE:
<221> NAME/KEY: MISC_FEATURE
<222> LOCATION: (116)..(118)
<223> OTHER INFORMATION: Xaa is any amino acid
<220> FEATURE:
<221> NAME/KEY: MISC_FEATURE
<222> LOCATION: (121)..(121)
<223> OTHER INFORMATION: Xaa is any amino acid
<220> FEATURE:
```

```
<221> NAME/KEY: MISC_FEATURE
<222> LOCATION: (123)..(123)
<223> OTHER INFORMATION: Xaa is any amino acid
<220> FEATURE:
<221> NAME/KEY: MISC_FEATURE
<222> LOCATION: (125)..(125)
<223> OTHER INFORMATION: Xaa is any amino acid
<220> FEATURE:
<221> NAME/KEY: MISC_FEATURE
<222> LOCATION: (130)..(130)
<223> OTHER INFORMATION: Xaa is any amino acid
<220> FEATURE:
<221> NAME/KEY: MISC_FEATURE
<222> LOCATION: (148)..(148)
<223> OTHER INFORMATION: Xaa is any amino acid
<220> FEATURE:
<221> NAME/KEY: MISC_FEATURE
<222> LOCATION: (151)..(151)
<223> OTHER INFORMATION: Xaa is any amino acid
<220> FEATURE:
<221> NAME/KEY: MISC_FEATURE
<222> LOCATION: (163)..(164)
<223> OTHER INFORMATION: Xaa is any amino acid
<220> FEATURE:
<221> NAME/KEY: MISC_FEATURE
<222> LOCATION: (166)..(168)
<223> OTHER INFORMATION: Xaa is any amino acid
<220> FEATURE:
<221> NAME/KEY: MISC_FEATURE
<222> LOCATION: (172)..(172)
<223> OTHER INFORMATION: Xaa is any amino acid
<220> FEATURE:
<221> NAME/KEY: MISC_FEATURE
<222> LOCATION: (175)..(175)
<223> OTHER INFORMATION: Xaa is any amino acid
<220> FEATURE:
<221> NAME/KEY: MISC_FEATURE
<222> LOCATION: (177)..(181)
<223> OTHER INFORMATION: Xaa is any amino acid
<220> FEATURE:
<221> NAME/KEY: MISC_FEATURE
<222> LOCATION: (183)..(183)
<223> OTHER INFORMATION: Xaa is any amino acid
<220> FEATURE:
<221> NAME/KEY: MISC_FEATURE
<222> LOCATION: (185)..(186)
<223> OTHER INFORMATION: Xaa is any amino acid

<400> SEQUENCE: 4

Met Xaa Xaa Xaa Xaa Xaa Xaa Xaa Xaa Lys Trp Xaa Asp Ala Xaa
1               5                   10                  15

Phe Asp Xaa Thr Xaa Ile Asn Glu Arg Leu Arg Ala Lys Val Ile Cys
            20                  25                  30

Phe Ala Leu Asn His Thr Asn Pro Xaa Xaa Thr Xaa Xaa Xaa Lys Val
        35                  40                  45

Leu Ile Asp Ala Leu Phe Gln Thr Thr Xaa Xaa Asn Xaa Ser Ile Ser
    50                  55                  60

Ile Pro Phe Asp Thr Asp Tyr Gly Trp Asn Xaa Lys Leu Xaa Xaa Asn
65                  70                  75                  80

Val Tyr Val Asn Thr Asn Cys Tyr Phe Met Asp Xaa Gly Xaa Ile Thr
                85                  90                  95

Xaa Gly Asp Asn Val Phe Ile Gly Pro Asn Cys Gly Phe Tyr Xaa Ala
            100                 105                 110

Thr Xaa Pro Xaa Xaa Xaa His His Xaa Asn Xaa Gly Xaa Glu Lys Ala
        115                 120                 125

Gly Xaa Ile His Ile Gly Ser Asn Thr Trp Phe Gly His Val Ala
    130                 135                 140

Val Leu Pro Xaa Val Thr Xaa Gly Glu Gly Ser Val Ile Gly Ala Gly
145                 150                 155                 160
```

```
Ser Val Xaa Xaa Lys Xaa Xaa Pro His Ser Xaa Ala Val Xaa Asn
            165                 170                 175

Xaa Xaa Xaa Xaa Xaa Arg Xaa Ile Xaa Xaa Asp Leu Pro Ser Glu Thr
            180                 185                 190

Leu Asn Asp Glu Thr Ile Lys
        195

<210> SEQ ID NO 5
<211> LENGTH: 199
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 5

Met Thr Glu Lys Glu Lys Met Leu Ala Glu Lys Trp Tyr Asp Ala Asn
1               5                   10                  15

Phe Asp Gln Tyr Leu Ile Asn Glu Arg Ala Arg Ala Lys Asp Ile Cys
            20                  25                  30

Phe Glu Leu Asn His Thr Arg Pro Ser Ala Thr Asn Lys Arg Lys Glu
        35                  40                  45

Leu Ile Asp Gln Leu Phe Gln Thr Thr Thr Asp Asn Val Ser Ile Ser
    50                  55                  60
Ile Pro Phe Asp Thr Asp Tyr Gly Trp Asn Val Lys Leu Gly Lys Asn
65                  70                  75                  80

Val Tyr Val Asn Thr Asn Cys Tyr Phe Met Asp Gly Gly Gln Ile Thr
                85                  90                  95

Ile Gly Asp Asn Val Phe Ile Gly Pro Asn Cys Gly Phe Tyr Thr Ala
            100                 105                 110

Thr His Pro Leu Asn Phe His His Arg Asn Glu Gly Phe Glu Lys Ala
        115                 120                 125

Gly Pro Ile His Ile Gly Ser Asn Thr Trp Phe Gly Gly His Val Ala
    130                 135                 140

Val Leu Pro Gly Val Thr Ile Gly Glu Gly Ser Val Ile Gly Ala Gly
145                 150                 155                 160

Ser Val Val Thr Lys Asp Ile Pro Pro His Ser Leu Ala Val Gly Asn
                165                 170                 175

Pro Cys Lys Val Val Arg Lys Ile Asp Asn Leu Pro Ser Glu Thr
            180                 185                 190

Leu Asn Asp Glu Thr Ile Lys
        195

<210> SEQ ID NO 6
<211> LENGTH: 184
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 6

Met Ser Gln Ala Ile Gly Ile Leu Glu Leu Thr Ser Ile Ala Lys Gly
1               5                   10                  15
```

Met Glu Leu Gly Asp Ala Met Leu Lys Ser Ala Asn Val Asp Leu Leu
                20                  25                  30

Val Ser Lys Thr Ile Cys Pro Gly Lys Phe Leu Met Leu Gly
        35                  40                  45

Asp Ile Gly Ala Ile Gln Gln Ala Ile Glu Thr Gly Thr Ser Gln Ala
    50                  55                  60

Gly Glu Met Leu Val Asp Ser Leu Val Leu Ala Asn Ile His Pro Ser
65                  70                  75                  80

Val Leu Pro Ala Ile Ser Gly Leu Asn Ser Val Asp Lys Arg Gln Ala
                85                  90                  95

Val Gly Ile Val Glu Thr Trp Ser Val Ala Ala Cys Ile Ser Ala Ala
            100                 105                 110

Asp Arg Ala Val Lys Gly Ser Asn Val Thr Leu Val Arg Val His Met
            115                 120                 125

Ala Phe Gly Ile Gly Gly Lys Cys Tyr Met Val Val Ala Gly Asp Val
        130                 135                 140

Ser Asp Val Asn Asn Ala Val Thr Val Ala Ser Glu Ser Ala Gly Glu
145                 150                 155                 160

Lys Gly Leu Leu Val Tyr Arg Ser Val Ile Pro Arg Pro His Glu Ala
                165                 170                 175

Met Trp Arg Gln Met Val Glu Gly
            180

<210> SEQ ID NO 7
<211> LENGTH: 199
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 7

Met Thr Glu Lys Glu Lys Met Leu Ala Glu Lys Trp Tyr Asp Ala Asn
1               5                   10                  15

Phe Asp Gln Thr Leu Ile Asn Glu Arg Leu Arg Ala Lys Val Ile Cys
                20                  25                  30

Phe Ala Leu Asn His Thr Asn Pro Ser Ala Thr Leu Lys Arg Lys Val
            35                  40                  45

Leu Ile Asp Ala Leu Phe Gln Thr Thr Asp Asn Val Ser Ile Ser
    50                  55                  60

Ile Pro Phe Asp Thr Asp Tyr Gly Trp Asn Val Lys Leu Gly Lys Asn
65                  70                  75                  80

Val Tyr Val Asn Thr Asn Cys Tyr Phe Met Asp Gly Gln Ile Thr
                85                  90                  95

Ile Gly Asp Asn Val Phe Ile Gly Pro Asn Cys Gly Phe Tyr Thr Ala
            100                 105                 110

Thr His Pro Leu Asn Phe His His Arg Asn Glu Gly Phe Glu Lys Ala
            115                 120                 125

Gly Pro Ile His Ile Gly Ser Asn Thr Trp Phe Gly Gly His Val Ala
        130                 135                 140

Val Leu Pro Gly Val Thr Ile Gly Glu Gly Ser Val Ile Gly Ala Gly
145                 150                 155                 160

Ser Val Val Thr Lys Asp Ile Pro Pro His Ser Leu Ala Val Gly Asn

```
                          165                 170                 175
Pro Cys Lys Val Val Arg Lys Ile Asp Asn Asp Leu Pro Ser Glu Thr
            180                 185                 190

Leu Asn Asp Glu Thr Ile Lys
        195

<210> SEQ ID NO 8
<211> LENGTH: 199
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 8

Met Thr Glu Lys Glu Lys Met Leu Ala Glu Lys Trp Tyr Asp Ala Asn
1               5                   10                  15

Phe Asp Gln Thr Leu Ile Asn Glu Arg Leu Arg Ala Lys Val Ile Cys
            20                  25                  30

Phe Ala Leu Asn His Thr Asn Pro Val Ala Thr Met Met Arg Lys Val
        35                  40                  45

Leu Ile Asp Ala Leu Phe Gln Thr Thr Thr Asp Asn Val Ser Ile Ser
    50                  55                  60

Ile Pro Phe Asp Thr Asp Tyr Gly Trp Asn Val Lys Leu Gly Lys Asn
65                  70                  75                  80

Val Tyr Val Asn Thr Asn Cys Tyr Phe Met Asp Gly Gly Gln Ile Thr
                85                  90                  95

Ile Gly Asp Asn Val Phe Ile Gly Pro Asn Cys Gly Phe Tyr Thr Ala
            100                 105                 110

Thr His Pro Leu Asn Phe His His Arg Asn Glu Gly Phe Glu Lys Ala
        115                 120                 125

Gly Pro Ile His Ile Gly Ser Asn Thr Trp Phe Gly Gly His Val Ala
    130                 135                 140

Val Leu Pro Gly Val Thr Ile Gly Glu Gly Ser Val Ile Gly Ala Gly
145                 150                 155                 160

Ser Val Val Thr Lys Asp Ile Pro Pro His Ser Leu Ala Val Gly Asn
                165                 170                 175

Pro Cys Lys Val Val Arg Lys Ile Asp Asn Asp Leu Pro Ser Glu Thr
            180                 185                 190

Leu Asn Asp Glu Thr Ile Lys
        195

<210> SEQ ID NO 9
<211> LENGTH: 199
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (41)..(41)
<223> OTHER INFORMATION: Xaa is S or V
<220> FEATURE:
<221> NAME/KEY: MISC_FEATURE
<222> LOCATION: (44)..(44)
```

```
<223> OTHER INFORMATION: Xaa is L or M
<220> FEATURE:
<221> NAME/KEY: MISC_FEATURE
<222> LOCATION: (45)..(45)
<223> OTHER INFORMATION: Xaa is K or M

<400> SEQUENCE: 9

Met Thr Glu Lys Glu Lys Met Leu Ala Glu Lys Trp Tyr Asp Ala Asn
1               5                   10                  15

Phe Asp Gln Thr Leu Ile Asn Glu Arg Leu Arg Ala Lys Val Ile Cys
                20                  25                  30

Phe Ala Leu Asn His Thr Asn Pro Xaa Ala Thr Xaa Xaa Arg Lys Val
            35                  40                  45

Leu Ile Asp Ala Leu Phe Gln Thr Thr Thr Asp Asn Val Ser Ile Ser
        50                  55                  60

Ile Pro Phe Asp Thr Asp Tyr Gly Trp Asn Val Lys Leu Gly Lys Asn
65                  70                  75                  80

Val Tyr Val Asn Thr Asn Cys Tyr Phe Met Asp Gly Gly Gln Ile Thr
                85                  90                  95

Ile Gly Asp Asn Val Phe Ile Gly Pro Asn Cys Gly Phe Tyr Thr Ala
                100                 105                 110

Thr His Pro Leu Asn Phe His His Arg Asn Glu Gly Phe Glu Lys Ala
            115                 120                 125

Gly Pro Ile His Ile Gly Ser Asn Thr Trp Phe Gly His Val Ala
130                 135                 140

Val Leu Pro Gly Val Thr Ile Gly Glu Gly Ser Val Ile Gly Ala Gly
145                 150                 155                 160

Ser Val Val Thr Lys Asp Ile Pro Pro His Ser Leu Ala Val Gly Asn
                165                 170                 175

Pro Cys Lys Val Val Arg Lys Ile Asp Asn Asp Leu Pro Ser Glu Thr
            180                 185                 190

Leu Asn Asp Glu Thr Ile Lys
            195

<210> SEQ ID NO 10
<211> LENGTH: 159
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 10

Met Gly Glu Val Pro Ile Gly Asp Pro Lys Glu Leu Asn Gly Met Glu
1               5                   10                  15

Ile Ala Ala Val Tyr Leu Gln Pro Ile Glu Met Glu Pro Arg Gly Ile
                20                  25                  30

Asp Leu Ala Ala Ser Leu Ala Asp Ile His Leu Glu Ala Asp Ile His
            35                  40                  45

Ala Leu Lys Asn Asn Pro Asn Gly Phe Pro Glu Gly Phe Trp Met Pro
        50                  55                  60

Tyr Leu Thr Ile Ala Tyr Ala Leu Ala Asn Ala Asp Thr Gly Ala Ile
65                  70                  75                  80

Lys Thr Gly Thr Leu Met Pro Val Ala Asp Asp Gly Pro His Tyr
                85                  90                  95
```

```
Gly Ala Asn Ile Ala Met Glu Lys Asp Lys Lys Gly Phe Gly Val
            100                 105                 110

Gly Thr Tyr Ala Leu Thr Phe Leu Ile Ser Asn Pro Glu Lys Gln Gly
        115                 120                 125

Phe Gly Arg His Val Asp Glu Glu Thr Gly Val Gly Lys Trp Phe Glu
    130                 135                 140

Pro Phe Val Val Thr Tyr Phe Phe Lys Tyr Thr Gly Thr Pro Lys
145                 150                 155

<210> SEQ ID NO 11
<211> LENGTH: 184
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 11

Met Ser Gln Ala Ile Gly Ile Leu Glu Leu Thr Ser Ile Ala Lys Gly
1               5                   10                  15

Met Glu Leu Gly Asp Ala Met Leu Lys Ser Ala Asn Val Asp Leu Leu
            20                  25                  30

Val Ser Lys Thr Ile Ser Pro Gly Lys Phe Leu Leu Met Leu Gly Gly
        35                  40                  45

Asp Ile Gly Ala Ile Gln Gln Ala Ile Glu Thr Gly Thr Ser Gln Ala
    50                  55                  60

Gly Glu Met Leu Val Asp Ser Leu Val Leu Ala Asn Ile His Pro Ser
65                  70                  75                  80

Val Leu Pro Ala Ile Ser Gly Leu Asn Ser Val Asp Lys Arg Gln Ala
                85                  90                  95

Val Gly Ile Val Glu Thr Trp Ser Val Ala Ala Cys Ile Ser Ala Ala
            100                 105                 110

Asp Leu Ala Val Lys Gly Ser Asn Val Thr Leu Val Arg Val His Met
        115                 120                 125

Ala Phe Gly Ile Gly Gly Lys Cys Tyr Met Val Val Ala Gly Asp Val
    130                 135                 140

Leu Asp Val Ala Ala Val Ala Thr Ala Ser Leu Ala Ala Gly Ala
145                 150                 155                 160

Lys Gly Leu Leu Val Tyr Ala Ser Ile Ile Pro Arg Pro His Glu Ala
                165                 170                 175

Met Trp Arg Gln Met Val Glu Gly
            180

<210> SEQ ID NO 12
<211> LENGTH: 103
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 12

Met Glu Glu Val Val Leu Ile Thr Val Pro Ser Ala Leu Val Ala Val
1               5                   10                  15
```

```
Lys Ile Ala His Ala Leu Val Glu Glu Arg Leu Ala Ala Cys Val Asn
             20                  25                  30

Ile Val Pro Gly Leu Thr Ser Ile Tyr Arg Trp Gln Gly Ser Val Val
         35                  40                  45

Ser Asp His Glu Leu Leu Leu Val Lys Thr Thr Thr His Ala Phe
 50                  55                  60

Pro Lys Leu Lys Glu Arg Val Lys Ala Leu His Pro Tyr Thr Val Pro
 65                  70                  75                  80

Glu Ile Val Ala Leu Pro Ile Ala Glu Gly Asn Arg Glu Tyr Leu Asp
                 85                  90                  95

Trp Leu Arg Glu Asn Thr Gly
            100
```

<210> SEQ ID NO 13
<211> LENGTH: 122
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 13

```
Met Val Arg Gly Ile Arg Gly Ala Ile Thr Val Glu Glu Asp Thr Pro
 1               5                  10                  15

Ala Ala Ile Leu Ala Ala Thr Ile Glu Leu Leu Leu Lys Met Leu Glu
             20                  25                  30

Ala Asn Gly Ile Gln Ser Tyr Glu Glu Leu Ala Ala Val Ile Phe Thr
         35                  40                  45

Val Thr Glu Asp Leu Thr Ser Ala Phe Pro Ala Glu Ala Ala Arg Leu
 50                  55                  60

Ile Gly Met His Arg Val Pro Leu Leu Ser Ala Arg Glu Val Pro Val
 65                  70                  75                  80

Pro Gly Ser Leu Pro Arg Val Ile Arg Val Leu Ala Leu Trp Asn Thr
                 85                  90                  95

Asp Thr Pro Gln Asp Arg Val Arg His Val Tyr Leu Asn Glu Ala Val
            100                 105                 110

Arg Leu Arg Pro Asp Leu Glu Ser Ala Gln
            115                 120
```

<210> SEQ ID NO 14
<211> LENGTH: 177
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 14

```
Met Ser Lys Ala Lys Ile Gly Ile Val Thr Val Ser Asp Arg Ala Ser
 1               5                  10                  15

Ala Gly Ile Thr Ala Asp Ile Ser Gly Lys Ala Ile Ile Leu Ala Leu
             20                  25                  30

Asn Leu Tyr Leu Thr Ser Glu Trp Glu Pro Ile Tyr Gln Val Ile Pro
         35                  40                  45
```

-continued

```
Asp Glu Gln Asp Val Ile Glu Thr Thr Leu Ile Lys Met Ala Asp Glu
 50                  55                  60

Gln Asp Cys Cys Leu Ile Val Thr Thr Gly Gly Thr Gly Pro Ala Lys
 65                  70                  75                  80

Arg Asp Val Thr Pro Glu Ala Thr Glu Ala Val Cys Asp Arg Met Met
                 85                  90                  95

Pro Gly Phe Gly Glu Leu Met Arg Ala Glu Ser Leu Lys Glu Val Pro
             100                 105                 110

Thr Ala Ile Leu Ser Arg Gln Thr Ala Gly Leu Arg Gly Asp Ser Leu
         115                 120                 125

Ile Val Asn Leu Pro Gly Asp Pro Ala Ser Ile Ser Asp Cys Leu Leu
130                 135                 140

Ala Val Phe Pro Ala Ile Pro Tyr Cys Ile Asp Leu Met Glu Gly Pro
145                 150                 155                 160

Tyr Leu Glu Cys Asn Glu Ala Met Ile Lys Pro Phe Arg Pro Lys Ala
                165                 170                 175

Lys

<210> SEQ ID NO 15
<211> LENGTH: 122
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 15

Met Val Arg Gly Ile Arg Gly Ala Ile Thr Val Asn Ser Asp Thr Pro
  1               5                  10                  15

Thr Ser Ile Ile Ile Ala Thr Ile Leu Leu Glu Lys Met Leu Glu
                 20                  25                  30

Ala Asn Gly Ile Gln Ser Tyr Glu Glu Leu Ala Ala Val Ile Phe Thr
             35                  40                  45

Val Thr Glu Asp Leu Thr Ser Ala Phe Pro Ala Glu Ala Ala Arg Gln
 50                  55                  60

Ile Gly Met His Arg Val Pro Leu Leu Ser Ala Arg Glu Val Pro Val
 65                  70                  75                  80

Pro Gly Ser Leu Pro Arg Val Ile Arg Val Leu Ala Leu Trp Asn Thr
                 85                  90                  95

Asp Thr Pro Gln Asp Arg Val Arg His Val Tyr Leu Ser Glu Ala Val
            100                 105                 110

Arg Leu Arg Pro Asp Leu Glu Ser Ala Gln
        115                 120

<210> SEQ ID NO 16
<211> LENGTH: 172
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 16

Met Arg Ile Thr Thr Lys Val Gly Asp Lys Gly Ser Thr Arg Leu Phe
```

```
            1               5                  10                 15
Gly Gly Glu Glu Val Trp Lys Asp Ser Pro Ile Ile Glu Ala Asn Gly
                20                  25                 30

Thr Leu Asp Glu Leu Thr Ser Phe Ile Gly Glu Ala Lys His Tyr Val
                35                  40                 45

Asp Glu Glu Met Lys Gly Ile Leu Glu Ile Gln Asn Asp Ile Tyr
 50                  55                  60

Lys Ile Met Gly Glu Ile Gly Ser Lys Gly Lys Ile Glu Gly Ile Ser
 65                  70                  75                 80

Glu Glu Arg Ile Ala Trp Leu Leu Lys Leu Ile Leu Arg Tyr Met Glu
                85                  90                 95

Met Val Asn Leu Lys Ser Phe Val Leu Pro Gly Gly Thr Leu Glu Ser
                100                 105                110

Ala Lys Leu Asp Val Cys Arg Thr Ile Ala Arg Arg Ala Leu Arg Lys
                115                 120                125

Val Leu Thr Val Thr Arg Glu Phe Gly Ile Gly Ala Glu Ala Ala
                130                 135                140

Tyr Leu Leu Ala Leu Ser Asp Leu Leu Phe Leu Leu Ala Arg Val Ile
145                 150                 155                160

Glu Ile Glu Lys Asn Lys Leu Lys Glu Val Arg Ser
                165                 170
```

<210> SEQ ID NO 17
<211> LENGTH: 123
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 17

```
Met Pro His Leu Val Ile Glu Ala Thr Ala Asn Leu Arg Leu Glu Thr
 1               5                  10                 15

Ser Pro Gly Glu Leu Leu Glu Gln Ala Asn Lys Ala Leu Phe Ala Ser
                20                  25                 30

Gly Gln Phe Gly Glu Ala Asp Ile Lys Ser Arg Phe Val Thr Leu Glu
                35                  40                 45

Ala Tyr Arg Gln Gly Thr Ala Ala Val Glu Arg Ala Tyr Leu His Ala
 50                  55                  60

Cys Leu Ser Ile Leu Asp Gly Arg Asp Ile Ala Thr Arg Thr Leu Leu
 65                  70                  75                 80

Gly Ala Ser Leu Cys Ala Val Leu Ala Glu Ala Val Ala Gly Gly Gly
                85                  90                 95

Glu Glu Gly Val Gln Val Ser Val Glu Val Arg Glu Met Glu Arg Leu
                100                 105                110

Ser Tyr Ala Lys Arg Val Val Ala Arg Gln Arg
                115                 120
```

<210> SEQ ID NO 18
<211> LENGTH: 158
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE

```
<222> LOCATION: (1)..(1)
<223> OTHER INFORMATION: optionally absent

<400> SEQUENCE: 18

Met Glu Ser Val Asn Thr Ser Phe Leu Ser Pro Ser Leu Val Thr Ile
1               5                   10                  15

Arg Asp Phe Asp Asn Gly Gln Phe Ala Val Leu Arg Ile Gly Arg Thr
            20                  25                  30

Gly Phe Pro Ala Asp Lys Gly Asp Ile Asp Leu Cys Leu Asp Lys Met
        35                  40                  45

Ile Gly Val Arg Ala Ala Gln Ile Phe Leu Gly Asp Asp Thr Glu Asp
50                  55                  60

Gly Phe Lys Gly Pro His Ile Arg Ile Arg Cys Val Asp Ile Asp Asp
65                  70                  75                  80

Lys His Thr Tyr Asn Ala Met Val Tyr Val Asp Leu Ile Val Gly Thr
                85                  90                  95

Gly Ala Ser Glu Val Glu Arg Glu Thr Ala Glu Glu Ala Lys Leu
            100                 105                 110

Ala Leu Arg Val Ala Leu Gln Val Asp Ile Ala Asp Glu His Ser Cys
            115                 120                 125

Val Thr Gln Phe Glu Met Lys Leu Arg Glu Glu Leu Leu Ser Ser Asp
    130                 135                 140

Ser Phe His Pro Asp Lys Asp Glu Tyr Tyr Lys Asp Phe Leu
145                 150                 155

<210> SEQ ID NO 19
<211> LENGTH: 113
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 19

Met Pro Val Ile Gln Thr Phe Val Ser Thr Pro Leu Asp His His Lys
1               5                   10                  15

Arg Leu Leu Leu Ala Ile Ile Tyr Arg Ile Val Thr Arg Val Val Leu
            20                  25                  30

Gly Lys Pro Glu Asp Leu Val Met Met Thr Phe His Asp Ser Thr Pro
        35                  40                  45

Met His Phe Phe Gly Ser Thr Asp Pro Val Ala Cys Val Arg Val Glu
50                  55                  60

Ala Leu Gly Gly Tyr Gly Pro Ser Glu Pro Glu Lys Val Thr Ser Ile
65                  70                  75                  80

Val Thr Ala Ala Ile Thr Ala Val Cys Gly Ile Val Ala Asp Arg Ile
                85                  90                  95

Phe Val Leu Tyr Phe Ser Pro Leu His Cys Gly Trp Asn Gly Thr Asn
            100                 105                 110

Phe

<210> SEQ ID NO 20
<211> LENGTH: 205
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (1)..(1)
<223> OTHER INFORMATION: optionally absent

<400> SEQUENCE: 20

Met Lys Met Glu Glu Leu Phe Lys Lys His Lys Ile Val Ala Val Leu
1               5                   10                  15

Arg Ala Asn Ser Val Glu Glu Ala Lys Lys Lys Ala Leu Ala Val Phe
            20                  25                  30

Leu Gly Gly Val His Leu Ile Glu Ile Thr Phe Thr Val Pro Asp Ala
        35                  40                  45

Asp Thr Val Ile Lys Glu Leu Ser Phe Leu Lys Glu Met Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Thr Ile Leu
        115                 120                 125

Lys Leu Phe Pro Gly Glu Val Val Gly Pro Gln Phe Val Lys Ala Met
130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Pro Val Glu Val Ala Glu Lys
            180                 185                 190

Ala Lys Ala Phe Val Glu Lys Ile Arg Gly Cys Thr Glu
        195                 200                 205

<210> SEQ ID NO 21
<211> LENGTH: 205
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 21

Met Lys Met Glu Glu Leu Phe Lys Lys His Lys Ile Val Ala Val Leu
1               5                   10                  15

Arg Ala Asn Ser Val Glu Glu Ala Lys Glu Lys Ala Leu Ala Val Phe
            20                  25                  30

Glu Gly Gly Val His Leu Ile Glu Ile Thr Phe Thr Val Pro Asp Ala
        35                  40                  45

Asp Thr Val Ile Lys Glu Leu Ser Phe Leu Lys Glu Lys Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
```

```
                100                 105                 110
Thr Pro Thr Glu Leu Val Lys Ala Met Lys Leu Gly His Thr Ile Leu
        115                 120                 125

Lys Leu Phe Pro Gly Glu Val Val Gly Pro Gln Phe Val Lys Ala Met
130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Pro Asp Glu Val Arg Glu Lys
            180                 185                 190

Ala Lys Ala Phe Val Glu Lys Ile Arg Gly Cys Thr Glu
            195                 200                 205

<210> SEQ ID NO 22
<211> LENGTH: 4
<212> TYPE: PRT
<213> ORGANISM: Artificial Sequence
<220> FEATURE:
<223> OTHER INFORMATION: Synthetic

<400> SEQUENCE: 22

Glx Glx Glx Glx
1

<210> SEQ ID NO 23
<211> LENGTH: 4
<212> TYPE: PRT
<213> ORGANISM: Artificial Sequence
<220> FEATURE:
<223> OTHER INFORMATION: Synthetic

<400> SEQUENCE: 23

Glx Glx Glx Glx
1

<210> SEQ ID NO 24
<211> LENGTH: 4
<212> TYPE: PRT
<213> ORGANISM: Artificial Sequence
<220> FEATURE:
<223> OTHER INFORMATION: Synthetic

<400> SEQUENCE: 24

Glx Glx Glx Glx
1

<210> SEQ ID NO 25
<211> LENGTH: 4
<212> TYPE: PRT
<213> ORGANISM: Artificial Sequence
<220> FEATURE:
<223> OTHER INFORMATION: Synthetic

<400> SEQUENCE: 25

Glx Glx Glx Glx
1

<210> SEQ ID NO 26
<211> LENGTH: 4
<212> TYPE: PRT
<213> ORGANISM: Artificial Sequence
<220> FEATURE:
<223> OTHER INFORMATION: Synthetic
```

<400> SEQUENCE: 26

Glx Glx Glx Glx
1

<210> SEQ ID NO 27
<211> LENGTH: 4
<212> TYPE: PRT
<213> ORGANISM: Artificial Sequence
<220> FEATURE:
<223> OTHER INFORMATION: Synthetic

<400> SEQUENCE: 27

Glx Glx Glx Glx
1

<210> SEQ ID NO 28
<211> LENGTH: 4
<212> TYPE: PRT
<213> ORGANISM: Artificial Sequence
<220> FEATURE:
<223> OTHER INFORMATION: Synthetic

<400> SEQUENCE: 28

Glx Glx Glx Glx
1

<210> SEQ ID NO 29
<211> LENGTH: 4
<212> TYPE: PRT
<213> ORGANISM: Artificial Sequence
<220> FEATURE:
<223> OTHER INFORMATION: Synthetic

<400> SEQUENCE: 29

Glx Glx Glx Glx
1

<210> SEQ ID NO 30
<211> LENGTH: 4
<212> TYPE: PRT
<213> ORGANISM: Artificial Sequence
<220> FEATURE:
<223> OTHER INFORMATION: Synthetic

<400> SEQUENCE: 30

Glx Glx Glx Glx
1

<210> SEQ ID NO 31
<211> LENGTH: 4
<212> TYPE: PRT
<213> ORGANISM: Artificial Sequence
<220> FEATURE:
<223> OTHER INFORMATION: Synthetic

<400> SEQUENCE: 31

Glx Glx Glx Glx
1

<210> SEQ ID NO 32
<211> LENGTH: 4
<212> TYPE: PRT
<213> ORGANISM: Artificial Sequence
<220> FEATURE:
<223> OTHER INFORMATION: Synthetic

```
<400> SEQUENCE: 32

Glx Glx Glx Glx
1

<210> SEQ ID NO 33
<211> LENGTH: 4
<212> TYPE: PRT
<213> ORGANISM: Artificial Sequence
<220> FEATURE:
<223> OTHER INFORMATION: Synthetic

<400> SEQUENCE: 33

Glx Glx Glx Glx
1

<210> SEQ ID NO 34
<211> LENGTH: 4
<212> TYPE: PRT
<213> ORGANISM: Artificial Sequence
<220> FEATURE:
<223> OTHER INFORMATION: Synthetic

<400> SEQUENCE: 34

Glx Glx Glx Glx
1

<210> SEQ ID NO 35
<211> LENGTH: 4
<212> TYPE: PRT
<213> ORGANISM: Artificial Sequence
<220> FEATURE:
<223> OTHER INFORMATION: Synthetic

<400> SEQUENCE: 35

Glx Glx Glx Glx
1

<210> SEQ ID NO 36
<211> LENGTH: 4
<212> TYPE: PRT
<213> ORGANISM: Artificial Sequence
<220> FEATURE:
<223> OTHER INFORMATION: Synthetic

<400> SEQUENCE: 36

Glx Glx Glx Glx
1

<210> SEQ ID NO 37
<211> LENGTH: 4
<212> TYPE: PRT
<213> ORGANISM: Artificial Sequence
<220> FEATURE:
<223> OTHER INFORMATION: Synthetic

<400> SEQUENCE: 37

Glx Glx Glx Glx
1

<210> SEQ ID NO 38
<211> LENGTH: 4
<212> TYPE: PRT
<213> ORGANISM: Artificial Sequence
<220> FEATURE:
<223> OTHER INFORMATION: Synthetic

<400> SEQUENCE: 38
```

Glx Glx Glx Glx
1

<210> SEQ ID NO 39
<211> LENGTH: 4
<212> TYPE: PRT
<213> ORGANISM: Artificial Sequence
<220> FEATURE:
<223> OTHER INFORMATION: Synthetic

<400> SEQUENCE: 39

Glx Glx Glx Glx
1

<210> SEQ ID NO 40
<211> LENGTH: 4
<212> TYPE: PRT
<213> ORGANISM: Artificial Sequence
<220> FEATURE:
<223> OTHER INFORMATION: Synthetic

<400> SEQUENCE: 40

Glx Glx Glx Glx
1

<210> SEQ ID NO 41
<211> LENGTH: 4
<212> TYPE: PRT
<213> ORGANISM: Artificial Sequence
<220> FEATURE:
<223> OTHER INFORMATION: Synthetic

<400> SEQUENCE: 41

Glx Glx Glx Glx
1

<210> SEQ ID NO 42
<211> LENGTH: 4
<212> TYPE: PRT
<213> ORGANISM: Artificial Sequence
<220> FEATURE:
<223> OTHER INFORMATION: Synthetic

<400> SEQUENCE: 42

Glx Glx Glx Glx
1

<210> SEQ ID NO 43
<211> LENGTH: 4
<212> TYPE: PRT
<213> ORGANISM: Artificial Sequence
<220> FEATURE:
<223> OTHER INFORMATION: Synthetic

<400> SEQUENCE: 43

Glx Glx Glx Glx
1

<210> SEQ ID NO 44
<211> LENGTH: 4
<212> TYPE: PRT
<213> ORGANISM: Artificial Sequence
<220> FEATURE:
<223> OTHER INFORMATION: Synthetic

<400> SEQUENCE: 44

Glx Glx Glx Glx
1

<210> SEQ ID NO 45
<211> LENGTH: 4
<212> TYPE: PRT
<213> ORGANISM: Artificial Sequence
<220> FEATURE:
<223> OTHER INFORMATION: Synthetic

<400> SEQUENCE: 45

Glx Glx Glx Glx
1

<210> SEQ ID NO 46
<211> LENGTH: 4
<212> TYPE: PRT
<213> ORGANISM: Artificial Sequence
<220> FEATURE:
<223> OTHER INFORMATION: Synthetic

<400> SEQUENCE: 46

Glx Glx Glx Glx
1

<210> SEQ ID NO 47
<211> LENGTH: 4
<212> TYPE: PRT
<213> ORGANISM: Artificial Sequence
<220> FEATURE:
<223> OTHER INFORMATION: Synthetic

<400> SEQUENCE: 47

Glx Glx Glx Glx
1

<210> SEQ ID NO 48
<211> LENGTH: 4
<212> TYPE: PRT
<213> ORGANISM: Artificial Sequence
<220> FEATURE:
<223> OTHER INFORMATION: Synthetic

<400> SEQUENCE: 48

Glx Glx Glx Glx
1

<210> SEQ ID NO 49
<211> LENGTH: 4
<212> TYPE: PRT
<213> ORGANISM: Artificial Sequence
<220> FEATURE:
<223> OTHER INFORMATION: Synthetic

<400> SEQUENCE: 49

Glx Glx Glx Glx
1

<210> SEQ ID NO 50
<211> LENGTH: 4
<212> TYPE: PRT
<213> ORGANISM: Artificial Sequence
<220> FEATURE:
<223> OTHER INFORMATION: Synthetic

<400> SEQUENCE: 50

Glx Glx Glx Glx

```
<210> SEQ ID NO 51
<211> LENGTH: 4
<212> TYPE: PRT
<213> ORGANISM: Artificial Sequence
<220> FEATURE:
<223> OTHER INFORMATION: Synthetic

<400> SEQUENCE: 51

Glx Glx Glx Glx
1

<210> SEQ ID NO 52
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 52

Met Gly Cys Val Gln Cys Lys Asp Lys Glu Ala Thr Lys Leu Thr Glu
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 53

Met Gly Cys Ile Lys Ser Lys Arg Lys Asp Asn Leu Asn Asp Asp Glu
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 54

Met Gly Cys Val Cys Ser Ser Asn Pro Glu Asp Asp Trp Met Glu Asn
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 55
```

```
Met Gly Cys Met Lys Ser Lys Phe Leu Gln Val Gly Gly Asn Thr Gly
1               5                   10                  15
```

<210> SEQ ID NO 56
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 56

```
Met Gly Cys Val Phe Cys Lys Lys Leu Glu Pro Val Ala Thr Ala Lys
1               5                   10                  15
```

<210> SEQ ID NO 57
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 57

```
Met Gly Cys Val His Cys Lys Glu Lys Ile Ser Gly Lys Gly Gln Gly
1               5                   10                  15
```

<210> SEQ ID NO 58
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 58

```
Met Gly Leu Leu Ser Ser Lys Arg Gln Val Ser Glu Lys Gly Lys Gly
1               5                   10                  15
```

<210> SEQ ID NO 59
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 59

```
Met Gly Gln Gln Pro Gly Lys Val Leu Gly Asp Gln Arg Arg Pro Ser
1               5                   10                  15
```

<210> SEQ ID NO 60
<211> LENGTH: 16
<212> TYPE: PRT
<213> ORGANISM: Artificial Sequence
<220> FEATURE:
<223> OTHER INFORMATION: Synthetic

```
<220> FEATURE:
<221> NAME/KEY: MISC_FEATURE
<222> LOCATION: (1)..(1)
<223> OTHER INFORMATION: optionally absent

<400> SEQUENCE: 60

Met Gly Gln Gln Val Gly Arg Val Gly Glu Ala Pro Gly Leu Gln Gln
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 61

Met Gly Asn Ala Ala Ala Ala Lys Lys Gly Ser Glu Gln Glu Ser Val
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 62

Met Gly Asn Ala Ala Thr Ala Lys Lys Gly Ser Glu Val Glu Ser Val
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 63

Met Gly Ala Gln Leu Ser Leu Val Val Gln Ala Ser Pro Ser Ile Ala
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 64

Met Gly His Ala Leu Cys Val Cys Ser Arg Gly Thr Val Ile Ile Asp
1               5                   10                  15
```

-continued

```
<210> SEQ ID NO 65
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 65

Met Gly Gln Leu Cys Cys Phe Pro Phe Ser Arg Asp Glu Gly Lys Ile
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 66

Met Gly Asn Glu Ala Ser Tyr Pro Leu Glu Met Cys Ser His Phe Asp
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 67

Met Gly Asn Ser Gly Ser Lys Gln His Thr Lys His Asn Ser Lys Lys
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 68

Met Gly Cys Thr Leu Ser Ala Glu Asp Lys Ala Ala Val Glu Arg Ser
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
```

```
<400> SEQUENCE: 69

Met Gly Cys Thr Leu Ser Ala Glu Glu Arg Ala Ala Leu Glu Arg Ser
1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 70

Met Gly Ala Gly Ala Ser Ala Glu Glu Lys His Ser Arg Glu Leu Glu
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 71

Met Gly Cys Arg Gln Ser Ser Glu Glu Lys Glu Ala Ala Arg Arg Ser
1               5                   10                  15

<210> SEQ ID NO 72
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 72

Met Gly Leu Ser Phe Thr Lys Leu Phe Ser Arg Leu Phe Ala Lys Lys
1               5                   10                  15

<210> SEQ ID NO 73
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 73

Met Gly Asn Ile Phe Gly Asn Leu Leu Lys Ser Leu Ile Gly Lys Lys
1               5                   10                  15

<210> SEQ ID NO 74
<211> LENGTH: 16
<212> TYPE: PRT
<213> ORGANISM: Artificial Sequence
<220> FEATURE:
```

```
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 74

Met Gly Leu Thr Val Ser Ala Leu Phe Ser Arg Ile Phe Gly Lys Lys
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 75

Met Gly Lys Val Leu Ser Lys Ile Phe Gly Asn Lys Glu Met Arg Ile
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 76

Met Gly Asn Ser Lys Ser Gly Ala Leu Ser Lys Glu Ile Leu Glu Glu
1               5                   10                  15

<210> SEQ ID NO 77
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 77

Met Gly Lys Gln Asn Ser Lys Leu Arg Pro Glu Val Met Gln Asp Leu
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 78

Met Gly Lys Arg Ala Ser Lys Leu Lys Pro Glu Glu Val Glu Glu Leu
1               5                   10                  15
```

```
<210> SEQ ID NO 79
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 79

Met Gly Lys Gln Asn Ser Lys Leu Arg Pro Glu Val Leu Gln Asp Leu
1               5                   10                  15

<210> SEQ ID NO 80
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 80

Met Gly Ser Arg Ala Ser Thr Leu Leu Arg Asp Glu Glu Leu Glu Glu
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 81

Met Gly Ser Lys Leu Ser Lys Lys Lys Gly Tyr Asn Val Asn Asp
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 82

Met Gly Lys Gln Asn Ser Lys Leu Arg Pro Glu Met Leu Gln Asp Leu
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
```

<400> SEQUENCE: 83

Met Gly Asn Val Met Glu Gly Lys Ser Val Glu Glu Leu Ser Ser Thr
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 84

Met Gly Gln Gln Phe Ser Trp Glu Glu Ala Glu Glu Asn Gly Ala Val
1               5                   10                  15

<210> SEQ ID NO 85
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 85

Met Gly Asn Thr Lys Ser Gly Ala Leu Ser Lys Glu Ile Leu Glu Glu
1               5                   10                  15

<210> SEQ ID NO 86
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 86

Met Gly Lys Gln Asn Ser Lys Leu Arg Pro Glu Val Leu Gln Asp Leu
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 87

Met Gly Ala Gln Phe Ser Lys Thr Ala Ala Lys Gly Glu Ala Thr Ala
1               5                   10                  15

<210> SEQ ID NO 88
<211> LENGTH: 16
<212> TYPE: PRT
<213> ORGANISM: Artificial Sequence

```
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 88

Met Gly Ser Gln Ser Ser Lys Ala Pro Arg Gly Asp Val Thr Ala Glu
1               5                   10                  15

<210> SEQ ID NO 89
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 89

Met Gly Asn Arg His Ala Lys Ala Ser Ser Pro Gln Gly Phe Asp Val
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 90

Met Gly Gln Asp Gln Thr Lys Gln Gln Ile Glu Lys Gly Leu Gln Leu
1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 91

Met Gly Gln Ala Leu Ser Ile Lys Ser Cys Asp Phe His Ala Ala Glu
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 92

Met Gly Asn Arg Ala Phe Lys Ala His Asn Gly His Tyr Leu Ser Ala
1               5                   10                  15
```

```
<210> SEQ ID NO 93
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 93

Met Gly Ala Arg Ala Ser Val Leu Ser Gly Gly Glu Leu Asp Arg Trp
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 94

Met Gly Gln Thr Val Thr Thr Pro Leu Ser Leu Thr Leu Asp His Trp
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 95

Met Gly Gln Ala Val Thr Thr Pro Leu Ser Leu Thr Leu Asp His Trp
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 96

Met Gly Asn Ser Pro Ser Tyr Asn Pro Pro Ala Gly Ile Ser Pro Ser
1               5                   10                  15

<210> SEQ ID NO 97
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
```

<223> OTHER INFORMATION: optionally absent

<400> SEQUENCE: 97

Met Gly Gln Thr Leu Thr Thr Pro Leu Ser Leu Thr Leu Thr His Phe
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 98

Met Gly Gln Thr Ile Thr Thr Pro Leu Ser Leu Thr Leu Asp His Trp
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 99

Met Gly Gln Thr Val Thr Thr Pro Leu Ser Leu Thr Leu Glu His Trp
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 100

Met Gly Gln Glu Leu Ser Gln His Glu Arg Tyr Val Glu Gln Leu Lys
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 101

Met Gly Val Ser Gly Ser Lys Gly Gln Lys Leu Phe Val Ser Val Leu
1               5                   10                  15

<210> SEQ ID NO 102
<211> LENGTH: 16
<212> TYPE: PRT

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 102

Met Gly Gly Lys Trp Ser Lys Ser Ser Val Val Gly Trp Pro Thr Val
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 103

Met Gly Gln His Pro Ala Lys Ser Met Asp Val Arg Arg Ile Glu Gly
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 104

Met Gly Ala Gln Val Ser Arg Gln Asn Val Gly Thr His Ser Thr Gln
1               5                   10                  15

<210> SEQ ID NO 105
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 105

Met Gly Leu Ala Phe Ser Gly Ala Arg Pro Cys Cys Cys Arg His Asn
1               5                   10                  15

<210> SEQ ID NO 106
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 106

Met Gly Asn Arg Gly Ser Ser Thr Ser Ser Arg Pro Pro Leu Ser Ser
```

<210> SEQ ID NO 107
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 107

Met Gly Ser Tyr Phe Val Pro Pro Ala Asn Tyr Phe Phe Lys Asp Ile
1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 108

Met Gly Ala Gln Leu Ser Thr Leu Ser Arg Val Val Leu Ser Pro Val
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 109

Met Gly Asn Leu Lys Ser Val Gly Gln Glu Pro Gly Pro Pro Cys Gly
1               5                   10                  15

<210> SEQ ID NO 110
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 110

Met Gly Ser Lys Arg Ser Val Pro Ser Arg His Arg Ser Leu Thr Thr
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE -continued

```
<222> LOCATION: (1)..(1)
<223> OTHER INFORMATION: optionally absent

<400> SEQUENCE: 111

Met Gly Asn Gly Glu Ser Gln Leu Ser Ser Val Pro Ala Gln Lys Leu
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 112

Met Gly Ala His Leu Val Arg Arg Tyr Leu Gly Asp Ala Ser Val Glu
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 113

Met Gly Gly Lys Leu Ser Lys Lys Lys Gly Tyr Asn Val Asn Asp
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 114

Met Gly Ser Cys Cys Ser Cys Pro Asp Lys Asp Thr Val Pro Asp Asn
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 115

Met Gly Ser Ser Glu Val Ser Ile Ile Pro Gly Leu Gln Lys Glu Glu
1               5                   10                  15

<210> SEQ ID NO 116
<211> LENGTH: 16
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 116

Met Leu Cys Cys Met Arg Arg Thr Lys Gln Val Glu Lys Asn Asp Glu
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 117

Met Gly Cys Leu Gly Asn Ser Lys Thr Glu Asp Gln Arg Asn Glu
1               5                   10                  15

<210> SEQ ID NO 118
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 118

Met Thr Leu Glu Ser Ile Met Ala Cys Cys Leu Ser Glu Glu Ala Lys
1               5                   10                  15

Glu Ala

<210> SEQ ID NO 119
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 119

Met Ser Gly Val Val Arg Thr Leu Ser Arg Cys Leu Leu Pro Ala Glu
1               5                   10                  15

Ala Gly

<210> SEQ ID NO 120
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
```

```
<223> OTHER INFORMATION: optionally absent

<400> SEQUENCE: 120

Met Ala Asp Phe Leu Pro Ser Arg Ser Val Cys Phe Pro Gly Cys Val
1               5                   10                  15

Leu Thr Asn

<210> SEQ ID NO 121
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 121

Met Ala Arg Ser Leu Arg Trp Arg Cys Cys Pro Trp Cys Leu Thr Glu
1               5                   10                  15

Asp Glu Lys Ala Ala
            20

<210> SEQ ID NO 122
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 122

Met Leu Cys Cys Met Arg Arg Thr Lys Gln Val Glu Lys Asn Asp Asp
1               5                   10                  15

Asp Gln Lys Ile Glu Gln Asp Gly Ile
            20                  25

<210> SEQ ID NO 123
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 123

Met Gln Cys Cys Gly Leu Val His Arg Arg Val Arg Val
1               5                   10

<210> SEQ ID NO 124
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 124
```

```
Met Asp Cys Leu Cys Ile Val Thr Thr Lys Lys Tyr Arg Tyr Gln Asp
1               5                   10                  15

Glu Asp Thr Pro
            20

<210> SEQ ID NO 125
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 125

Met Cys Lys Gly Leu Ala Gly Leu Pro Ala Ser Cys Leu Arg Ser Ala
1               5                   10                  15

Lys Asp Met Lys
            20

<210> SEQ ID NO 126
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 126

Met Gly Cys Ile Lys Ser Lys Glu Asp Lys Gly Pro Ala Met Lys Tyr
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 127

Met Gly Cys Val Gln Cys Lys Asp Lys Glu Ala Thr Lys Leu Thr Glu
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 128

Met Gly Cys Ile Lys Ser Lys Arg Lys Asp Asn Leu Asn Asp Asp Glu
1               5                   10                  15
```

```
<210> SEQ ID NO 129
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 129

Met Gly Cys Val Cys Ser Ser Asn Pro Glu Asp Asp Trp Met Glu Asn
1               5                   10                  15

<210> SEQ ID NO 130
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 130

Met Gly Cys Met Lys Ser Lys Phe Leu Gln Val Gly Gly Asn Thr Gly
1               5                   10                  15

<210> SEQ ID NO 131
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 131

Met Gly Cys Val Phe Cys Lys Lys Leu Glu Pro Val Ala Thr Ala Lys
1               5                   10                  15

<210> SEQ ID NO 132
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 132

Met Gly Cys Val His Cys Lys Glu Lys Ile Ser Gly Lys Gly Gln Gly
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
```

```
<400> SEQUENCE: 133

Met Gly Cys Thr Leu Ser Ala Glu Asp Lys Ala Ala Val Glu Arg Ser
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 134

Met Gly Cys Thr Leu Ser Ala Glu Glu Arg Ala Ala Leu Glu Arg Ser
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 135

Met Gly Cys Arg Gln Ser Ser Glu Glu Lys Glu Ala Ala Arg Arg Ser
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 136

Met Gly Gln Leu Cys Cys Phe Pro Phe Ser Arg Asp Glu Gly Lys
1               5                   10                  15

<210> SEQ ID NO 137
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 137

Met Gly Asn Leu Lys Ser Val Gly Gln Glu Pro Gly Pro Pro Cys Gly
1               5                   10                  15

Leu Gly Leu Gly Leu Gly Leu Gly Leu Cys Gly Lys
            20                  25

<210> SEQ ID NO 138
<211> LENGTH: 13
```

```
<212> TYPE: PRT
<213> ORGANISM: Artificial Sequence
<220> FEATURE:
<223> OTHER INFORMATION: Synthetic

<400> SEQUENCE: 138

Ser Gly Pro Gly Cys Met Ser Cys Lys Cys Val Leu Ser
1               5                   10

<210> SEQ ID NO 139
<211> LENGTH: 13
<212> TYPE: PRT
<213> ORGANISM: Artificial Sequence
<220> FEATURE:
<223> OTHER INFORMATION: Synthetic

<400> SEQUENCE: 139

Gly Thr Gln Gly Cys Met Gly Leu Pro Cys Val Val Met
1               5                   10

<210> SEQ ID NO 140
<211> LENGTH: 13
<212> TYPE: PRT
<213> ORGANISM: Artificial Sequence
<220> FEATURE:
<223> OTHER INFORMATION: Synthetic

<400> SEQUENCE: 140

Thr Pro Gly Cys Val Lys Ile Lys Lys Cys Val Ile Met
1               5                   10

<210> SEQ ID NO 141
<211> LENGTH: 13
<212> TYPE: PRT
<213> ORGANISM: Artificial Sequence
<220> FEATURE:
<223> OTHER INFORMATION: Synthetic

<400> SEQUENCE: 141

Asp Met Lys Lys His Arg Cys Lys Cys Cys Ser Ile Met
1               5                   10

<210> SEQ ID NO 142
<211> LENGTH: 17
<212> TYPE: PRT
<213> ORGANISM: Artificial Sequence
<220> FEATURE:
<223> OTHER INFORMATION: Synthetic

<400> SEQUENCE: 142

Ser Lys Asp Gly Lys Lys Lys Lys Ser Lys Thr Lys Cys Val Ile
1               5                   10                  15

Met

<210> SEQ ID NO 143
<211> LENGTH: 14
<212> TYPE: PRT
<213> ORGANISM: Artificial Sequence
<220> FEATURE:
<223> OTHER INFORMATION: Synthetic

<400> SEQUENCE: 143

Lys Lys Lys Lys Lys Lys Ser Lys Thr Lys Cys Val Ile Met
1               5                   10

<210> SEQ ID NO 144
```

```
<211> LENGTH: 8
<212> TYPE: PRT
<213> ORGANISM: Artificial Sequence
<220> FEATURE:
<223> OTHER INFORMATION: Synthetic

<400> SEQUENCE: 144

Ser Lys Thr Lys Cys Val Ile Met
1               5

<210> SEQ ID NO 145
<211> LENGTH: 130
<212> TYPE: PRT
<213> ORGANISM: Artificial Sequence
<220> FEATURE:
<223> OTHER INFORMATION: Synthetic

<400> SEQUENCE: 145

His Gly Leu Gln Asp Asp Pro Asp Leu Gln Ala Leu Leu Lys Gly Ser
1               5                   10                  15

Gln Leu Leu Lys Val Lys Ser Ser Trp Arg Arg Glu Arg Phe Tyr
            20                  25                  30

Lys Leu Gln Glu Asp Cys Lys Thr Ile Trp Gln Glu Ser Arg Lys Val
        35                  40                  45

Met Arg Ser Pro Glu Ser Gln Leu Phe Ser Ile Glu Asp Ile Gln Glu
    50                  55                  60

Val Arg Met Gly His Arg Thr Glu Gly Leu Glu Lys Phe Ala Arg Asp
65                  70                  75                  80

Ile Pro Glu Asp Arg Cys Phe Ser Ile Val Phe Lys Asp Gln Arg Asn
                85                  90                  95

Thr Leu Asp Leu Ile Ala Pro Ser Pro Ala Asp Ala Gln His Trp Val
            100                 105                 110

Gln Gly Leu Arg Lys Ile Ile His Ser Gly Ser Met Asp Gln Arg
        115                 120                 125

Gln Lys
    130

<210> SEQ ID NO 146
<211> LENGTH: 140
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 146

Met Asp Ser Gly Arg Asp Phe Leu Thr Leu His Gly Leu Gln Asp Asp
1               5                   10                  15

Pro Asp Leu Gln Ala Leu Leu Lys Gly Ser Gln Leu Leu Lys Val Lys
            20                  25                  30

Ser Ser Ser Trp Arg Arg Glu Arg Phe Tyr Lys Leu Gln Glu Asp Cys
        35                  40                  45

Lys Thr Ile Trp Gln Glu Ser Arg Lys Val Met Arg Ser Pro Glu Ser
    50                  55                  60

Gln Leu Phe Ser Ile Glu Asp Ile Gln Glu Val Arg Met Gly His Arg
65                  70                  75                  80

Thr Glu Gly Leu Glu Lys Phe Ala Arg Asp Ile Pro Glu Asp Arg Cys
                85                  90                  95
```

```
Phe Ser Ile Val Phe Lys Asp Gln Arg Asn Thr Leu Asp Leu Ile Ala
            100                 105                 110

Pro Ser Pro Ala Asp Ala Gln His Trp Val Gln Gly Leu Arg Lys Ile
        115                 120                 125

Ile His His Ser Gly Ser Met Asp Gln Arg Gln Lys
    130                 135                 140

<210> SEQ ID NO 147
<211> LENGTH: 140
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 147

Met Asp Ser Gly Arg Asp Phe Leu Thr Leu His Gly Leu Gln Asp Asp
1               5                   10                  15

Pro Asp Leu Gln Ala Leu Leu Lys Gly Ser Gln Leu Leu Lys Val Lys
            20                  25                  30

Ser Ser Ser Trp Arg Arg Glu Arg Phe Tyr Lys Leu Gln Glu Asp Cys
        35                  40                  45

Lys Thr Ile Trp Gln Glu Ser Arg Lys Val Met Arg Ser Pro Glu Ser
    50                  55                  60

Gln Leu Phe Ser Ile Glu Asp Ile Gln Glu Val Arg Met Gly His Arg
65                  70                  75                  80

Thr Glu Gly Leu Glu Lys Phe Ala Arg Asp Ile Pro Glu Asp Arg Cys
                85                  90                  95

Phe Ser Ile Val Phe Lys Asp Gln Arg Asn Thr Leu Asp Leu Ile Ala
            100                 105                 110

Pro Ser Pro Ala Asp Val Gln His Trp Val Gln Gly Leu Arg Lys Ile
        115                 120                 125

Ile Asp Arg Ser Gly Ser Met Asp Gln Arg Gln Lys
    130                 135                 140

<210> SEQ ID NO 148
<211> LENGTH: 140
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 148

Met Asp Ser Gly Arg Asp Phe Leu Thr Leu His Gly Leu Gln Asp Asp
1               5                   10                  15

Glu Asp Leu Gln Ala Leu Leu Lys Gly Ser Gln Leu Leu Lys Val Lys
            20                  25                  30

Ser Ser Ser Trp Arg Arg Glu Arg Phe Tyr Lys Leu Gln Glu Asp Cys
        35                  40                  45

Lys Thr Ile Trp Gln Glu Ser Arg Lys Val Met Arg Thr Pro Glu Ser
    50                  55                  60

Gln Leu Phe Ser Ile Glu Asp Ile Gln Glu Val Arg Met Gly His Arg
65                  70                  75                  80
```

```
Thr Glu Gly Leu Glu Lys Phe Ala Arg Asp Val Pro Glu Asp Arg Cys
                85                  90                  95

Phe Ser Ile Val Phe Lys Asp Gln Arg Asn Thr Leu Asp Leu Ile Ala
            100                 105                 110

Pro Ser Pro Ala Asp Ala Gln His Trp Val Leu Gly Leu His Lys Ile
        115                 120                 125

Ile His His Ser Gly Ser Met Asp Gln Arg Gln Lys
    130                 135                 140

<210> SEQ ID NO 149
<211> LENGTH: 130
<212> TYPE: PRT
<213> ORGANISM: Artificial Sequence
<220> FEATURE:
<223> OTHER INFORMATION: Synthetic

<400> SEQUENCE: 149

His Gly Leu Gln Asp Asp Glu Asp Leu Gln Ala Leu Leu Lys Gly Ser
1               5                   10                  15

Gln Leu Leu Lys Val Lys Ser Ser Trp Arg Arg Glu Arg Phe Tyr
            20                  25                  30

Lys Leu Gln Glu Asp Cys Lys Thr Ile Trp Gln Glu Ser Arg Lys Val
        35                  40                  45

Met Arg Thr Pro Glu Ser Gln Leu Phe Ser Ile Glu Asp Ile Gln Glu
    50                  55                  60

Val Arg Met Gly His Arg Thr Glu Gly Leu Glu Lys Phe Ala Arg Asp
65                  70                  75                  80

Val Pro Glu Asp Arg Cys Phe Ser Ile Val Phe Lys Asp Gln Arg Asn
                85                  90                  95

Thr Leu Asp Leu Ile Ala Pro Ser Pro Ala Asp Ala Gln His Trp Val
            100                 105                 110

Leu Gly Leu His Lys Ile Ile His His Ser Gly Ser Met Asp Gln Arg
        115                 120                 125

Gln Lys
    130

<210> SEQ ID NO 150
<211> LENGTH: 178
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 150

Met Ser Gly Gly Lys Tyr Val Asp Ser Glu Gly His Leu Tyr Thr Val
1               5                   10                  15

Pro Ile Arg Glu Gln Gly Asn Ile Tyr Lys Pro Asn Asn Lys Ala Met
            20                  25                  30

Ala Glu Glu Met Asn Glu Lys Gln Val Tyr Asp Ala His Thr Lys Glu
        35                  40                  45

Ile Asp Leu Val Asn Arg Asp Pro Lys His Leu Asn Asp Asp Val Val
    50                  55                  60

Lys Ile Asp Phe Glu Asp Val Ile Ala Glu Pro Glu Gly Thr His Ser
65                  70                  75                  80
```

Phe Asp Gly Ile Trp Lys Ala Ser Phe Thr Thr Phe Thr Val Thr Lys
                85                  90                  95

Tyr Trp Phe Tyr Arg Leu Leu Ser Ala Leu Phe Gly Ile Pro Met Ala
            100                 105                 110

Leu Ile Trp Gly Ile Tyr Phe Ala Ile Leu Ser Phe Leu His Ile Trp
        115                 120                 125

Ala Val Val Pro Cys Ile Lys Ser Phe Leu Ile Glu Ile Gln Cys Ile
    130                 135                 140

Ser Arg Val Tyr Ser Ile Tyr Val His Thr Phe Cys Asp Pro Leu Phe
145                 150                 155                 160

Glu Ala Ile Gly Lys Ile Phe Ser Asn Ile Arg Ile Asn Thr Gln Lys
                165                 170                 175

Glu Ile

<210> SEQ ID NO 151
<211> LENGTH: 178
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 151

Met Ser Gly Gly Lys Tyr Val Asp Ser Glu Gly His Leu Tyr Thr Val
1               5                   10                  15

Pro Ile Arg Glu Gln Gly Asn Ile Tyr Lys Pro Asn Asn Lys Ala Met
            20                  25                  30

Ala Asp Glu Leu Ser Gly Lys Gln Val Tyr Asp Ala His Thr Lys Glu
        35                  40                  45

Ile Asp Leu Val Asn Arg Asp Pro Lys His Leu Asn Asp Asp Val Val
    50                  55                  60

Lys Ile Asp Phe Glu Asp Val Ile Ala Glu Pro Glu Gly Thr His Ser
65                  70                  75                  80

Phe Asp Gly Ile Trp Lys Ala Ser Phe Thr Thr Phe Thr Val Thr Lys
                85                  90                  95

Tyr Trp Phe Tyr Arg Leu Leu Ser Ala Leu Phe Gly Ile Pro Met Ala
            100                 105                 110

Leu Ile Trp Gly Ile Tyr Phe Ala Ile Leu Ser Phe Leu His Ile Trp
        115                 120                 125

Ala Val Val Pro Cys Ile Lys Ser Phe Leu Ile Glu Ile Gln Cys Ile
    130                 135                 140

Ser Arg Val Tyr Ser Ile Tyr Val His Thr Val Cys Asp Pro Leu Phe
145                 150                 155                 160

Glu Ala Val Gly Lys Ile Phe Ser Asn Val Arg Ile Asn Leu Gln Lys
                165                 170                 175

Glu Ile

<210> SEQ ID NO 152
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)

```
<223> OTHER INFORMATION: Xaa is T or S

<400> SEQUENCE: 152

Pro Xaa Ala Pro
1

<210> SEQ ID NO 153
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is a hydrophobic residue
<220> FEATURE:
<221> NAME/KEY: MISC_FEATURE
<222> LOCATION: (3)..(4)
<223> OTHER INFORMATION: X is any amino acid or absent
<220> FEATURE:
<221> NAME/KEY: MISC_FEATURE
<222> LOCATION: (5)..(5)
<223> OTHER INFORMATION: or a hydrophobic residue
<220> FEATURE:
<221> NAME/KEY: MISC_FEATURE
<222> LOCATION: (6)..(8)
<223> OTHER INFORMATION: X is any amino acid or absent
<220> FEATURE:
<221> NAME/KEY: MISC_FEATURE
<222> LOCATION: (9)..(9)
<223> OTHER INFORMATION: Xaa is L or I

<400> SEQUENCE: 153

Xaa Tyr Xaa Xaa Pro Xaa Xaa Xaa Xaa
1               5

<210> SEQ ID NO 154
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is any amino acid

<400> SEQUENCE: 154

Pro Pro Xaa Tyr
1

<210> SEQ ID NO 155
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is T or S
<220> FEATURE:
<221> NAME/KEY: MISC_FEATURE
<222> LOCATION: (6)..(6)
<223> OTHER INFORMATION: Xaa is any amino acid

<400> SEQUENCE: 155

Pro Xaa Ala Pro Pro Xaa Tyr
1               5
```

```
<210> SEQ ID NO 156
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is T or S
<220> FEATURE:
<221> NAME/KEY: MISC_FEATURE
<222> LOCATION: (7)..(7)
<223> OTHER INFORMATION: Xaa is any amino acid

<400> SEQUENCE: 156

Pro Xaa Ala Pro Tyr Pro Xaa Leu
1               5

<210> SEQ ID NO 157
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is T or S

<400> SEQUENCE: 157

Pro Pro Xaa Tyr Pro Xaa Ala Pro
1               5

<210> SEQ ID NO 158
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is any amino acid

<400> SEQUENCE: 158

Pro Pro Xaa Tyr Tyr Pro Xaa Leu
1               5

<210> SEQ ID NO 159
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is any amino acid

<400> SEQUENCE: 159
```

```
Tyr Pro Xaa Leu Pro Pro Xaa Tyr
1               5

<210> SEQ ID NO 160
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is any amino acid

<400> SEQUENCE: 160

Tyr Pro Xaa Leu Pro Pro Xaa Tyr
1               5

<210> SEQ ID NO 161
<211> LENGTH: 7
<212> TYPE: PRT
<213> ORGANISM: Artificial Sequence
<220> FEATURE:
<223> OTHER INFORMATION: Synthetic

<400> SEQUENCE: 161

Pro Thr Ala Pro Pro Glu Glu
1               5

<210> SEQ ID NO 162
<211> LENGTH: 6
<212> TYPE: PRT
<213> ORGANISM: Artificial Sequence
<220> FEATURE:
<223> OTHER INFORMATION: Synthetic

<400> SEQUENCE: 162

Tyr Pro Leu Thr Ser Leu
1               5

<210> SEQ ID NO 163
<211> LENGTH: 7
<212> TYPE: PRT
<213> ORGANISM: Artificial Sequence
<220> FEATURE:
<223> OTHER INFORMATION: Synthetic

<400> SEQUENCE: 163

Pro Thr Ala Pro Pro Glu Tyr
1               5

<210> SEQ ID NO 164
<211> LENGTH: 4
<212> TYPE: PRT
<213> ORGANISM: Artificial Sequence
<220> FEATURE:
<223> OTHER INFORMATION: Synthetic

<400> SEQUENCE: 164

Tyr Pro Asp Leu
1

<210> SEQ ID NO 165
```

```
<211> LENGTH: 4
<212> TYPE: PRT
<213> ORGANISM: Artificial Sequence
<220> FEATURE:
<223> OTHER INFORMATION: Synthetic

<400> SEQUENCE: 165

Phe Pro Ile Val
1

<210> SEQ ID NO 166
<211> LENGTH: 7
<212> TYPE: PRT
<213> ORGANISM: Artificial Sequence
<220> FEATURE:
<223> OTHER INFORMATION: Synthetic

<400> SEQUENCE: 166

Pro Thr Ala Pro Pro Glu Tyr
1               5

<210> SEQ ID NO 167
<211> LENGTH: 4
<212> TYPE: PRT
<213> ORGANISM: Artificial Sequence
<220> FEATURE:
<223> OTHER INFORMATION: Synthetic

<400> SEQUENCE: 167

Pro Thr Ala Pro
1

<210> SEQ ID NO 168
<211> LENGTH: 4
<212> TYPE: PRT
<213> ORGANISM: Artificial Sequence
<220> FEATURE:
<223> OTHER INFORMATION: Synthetic

<400> SEQUENCE: 168

Pro Pro Glu Tyr
1

<210> SEQ ID NO 169
<211> LENGTH: 6
<212> TYPE: PRT
<213> ORGANISM: Artificial Sequence
<220> FEATURE:
<223> OTHER INFORMATION: Synthetic

<400> SEQUENCE: 169

Tyr Pro Leu Thr Ser Leu
1               5

<210> SEQ ID NO 170
<211> LENGTH: 18
<212> TYPE: PRT
<213> ORGANISM: Artificial Sequence
<220> FEATURE:
<223> OTHER INFORMATION: Synthetic

<400> SEQUENCE: 170

Ala Ala Gly Ala Tyr Asp Pro Ala Arg Lys Leu Leu Glu Gln Tyr Ala
1               5                   10                  15

Lys Lys
```

```
<210> SEQ ID NO 171
<211> LENGTH: 80
<212> TYPE: PRT
<213> ORGANISM: Artificial Sequence
<220> FEATURE:
<223> OTHER INFORMATION: Synthetic

<400> SEQUENCE: 171

Pro Asn Cys Phe Asn Ser Ser Ile Asn Ile His Glu Met Glu Ile
1               5                   10                  15

Gln Leu Lys Asp Ala Leu Glu Lys Asn Gln Gln Trp Leu Val Tyr Asp
            20                  25                  30

Gln Gln Arg Glu Val Tyr Val Lys Gly Leu Leu Ala Lys Ile Phe Glu
        35                  40                  45

Leu Glu Lys Lys Thr Glu Thr Ala Ala His Ser Leu Pro Gln Gln Thr
    50                  55                  60

Lys Lys Pro Glu Ser Glu Gly Tyr Leu Gln Glu Lys Gln Lys Cys
65                  70                  75                  80

<210> SEQ ID NO 172
<211> LENGTH: 52
<212> TYPE: PRT
<213> ORGANISM: Artificial Sequence
<220> FEATURE:
<223> OTHER INFORMATION: Synthetic

<400> SEQUENCE: 172

Leu Gln Ser Arg Pro Glu Pro Thr Ala Pro Glu Glu Ser Phe Arg
1               5                   10                  15

Ser Gly Val Glu Thr Thr Thr Pro Pro Gln Lys Gln Glu Pro Ile Asp
            20                  25                  30

Lys Glu Leu Tyr Pro Leu Thr Ser Leu Arg Ser Leu Phe Gly Asn Asp
        35                  40                  45

Pro Ser Ser Gln
    50

<210> SEQ ID NO 173
<211> LENGTH: 20
<212> TYPE: PRT
<213> ORGANISM: Artificial Sequence
<220> FEATURE:
<223> OTHER INFORMATION: Synthetic

<400> SEQUENCE: 173

Arg Arg Val Ile Leu Pro Thr Ala Pro Pro Glu Tyr Met Glu Ala Ile
1               5                   10                  15

Tyr Pro Val Arg
            20

<210> SEQ ID NO 174
<211> LENGTH: 51
<212> TYPE: PRT
<213> ORGANISM: Artificial Sequence
<220> FEATURE:
<223> OTHER INFORMATION: Synthetic

<400> SEQUENCE: 174

Pro Ile Gln Gln Lys Ser Gln His Asn Lys Ser Val Val Gln Glu Thr
1               5                   10                  15

Pro Gln Thr Gln Asn Leu Tyr Pro Asp Leu Ser Glu Ile Lys Lys Glu
            20                  25                  30

Tyr Asn Val Lys Glu Lys Asp Gln Val Glu Asp Leu Asn Leu Asp Ser
```

```
                    35                  40                  45

Leu Trp Glu
    50

<210> SEQ ID NO 175
<211> LENGTH: 20
<212> TYPE: PRT
<213> ORGANISM: Artificial Sequence
<220> FEATURE:
<223> OTHER INFORMATION: Synthetic

<400> SEQUENCE: 175

Asn Pro Arg Gln Ser Ile Lys Ala Phe Pro Ile Val Ile Asn Ser Asp
1               5                   10                  15

Gly Gly Glu Lys
            20

<210> SEQ ID NO 176
<211> LENGTH: 10
<212> TYPE: PRT
<213> ORGANISM: Artificial Sequence
<220> FEATURE:
<223> OTHER INFORMATION: Synthetic

<400> SEQUENCE: 176

Pro Thr Ala Pro Pro Glu Tyr Gly Gly Ser
1               5                   10

<210> SEQ ID NO 177
<211> LENGTH: 7
<212> TYPE: PRT
<213> ORGANISM: Artificial Sequence
<220> FEATURE:
<223> OTHER INFORMATION: Synthetic

<400> SEQUENCE: 177

Pro Thr Ala Pro Gly Gly Ser
1               5

<210> SEQ ID NO 178
<211> LENGTH: 7
<212> TYPE: PRT
<213> ORGANISM: Artificial Sequence
<220> FEATURE:
<223> OTHER INFORMATION: Synthetic

<400> SEQUENCE: 178

Pro Pro Glu Tyr Gly Gly Ser
1               5

<210> SEQ ID NO 179
<211> LENGTH: 9
<212> TYPE: PRT
<213> ORGANISM: Artificial Sequence
<220> FEATURE:
<223> OTHER INFORMATION: Synthetic

<400> SEQUENCE: 179

Tyr Pro Leu Thr Ser Leu Gly Gly Ser
1               5

<210> SEQ ID NO 180
<211> LENGTH: 7
<212> TYPE: PRT
<213> ORGANISM: Artificial Sequence
<220> FEATURE:
```

<223> OTHER INFORMATION: Synthetic

<400> SEQUENCE: 180

Tyr Pro Asp Leu Gly Gly Ser
1               5

<210> SEQ ID NO 181
<211> LENGTH: 7
<212> TYPE: PRT
<213> ORGANISM: Artificial Sequence
<220> FEATURE:
<223> OTHER INFORMATION: Synthetic

<400> SEQUENCE: 181

Phe Pro Ile Val Gly Gly Ser
1               5

<210> SEQ ID NO 182
<211> LENGTH: 52
<212> TYPE: PRT
<213> ORGANISM: Artificial Sequence
<220> FEATURE:
<223> OTHER INFORMATION: Synthetic

<400> SEQUENCE: 182

Leu Gln Ser Arg Pro Glu Ala Ala Ala Pro Glu Glu Ser Phe Arg
1               5                   10                  15

Ser Gly Val Glu Thr Thr Thr Pro Pro Gln Lys Gln Glu Pro Ile Asp
            20                  25                  30

Lys Glu Leu Tyr Pro Leu Thr Ser Leu Arg Ser Leu Phe Gly Asn Asp
        35                  40                  45

Pro Ser Ser Gln
    50

<210> SEQ ID NO 183
<211> LENGTH: 4
<212> TYPE: PRT
<213> ORGANISM: Artificial Sequence
<220> FEATURE:
<223> OTHER INFORMATION: Synthetic

<400> SEQUENCE: 183

Pro Thr Ala Pro
1

<210> SEQ ID NO 184
<211> LENGTH: 52
<212> TYPE: PRT
<213> ORGANISM: Artificial Sequence
<220> FEATURE:
<223> OTHER INFORMATION: Synthetic

<400> SEQUENCE: 184

Leu Gln Ser Arg Pro Glu Pro Thr Ala Pro Glu Glu Ser Phe Arg
1               5                   10                  15

Ser Gly Val Glu Thr Thr Thr Pro Pro Gln Lys Gln Glu Pro Ile Asp
            20                  25                  30

Lys Glu Leu Ala Ala Leu Thr Ser Leu Arg Ser Leu Phe Gly Asn Asp
        35                  40                  45

Pro Ser Ser Gln
    50

<210> SEQ ID NO 185

```
<211> LENGTH: 19
<212> TYPE: PRT
<213> ORGANISM: Artificial Sequence
<220> FEATURE:
<223> OTHER INFORMATION: Synthetic

<400> SEQUENCE: 185

Ser Arg Glu Lys Pro Tyr Lys Glu Val Thr Glu Asp Leu Leu His Leu
1               5                   10                  15

Asn Ser Leu

<210> SEQ ID NO 186
<211> LENGTH: 51
<212> TYPE: PRT
<213> ORGANISM: Artificial Sequence
<220> FEATURE:
<223> OTHER INFORMATION: Synthetic

<400> SEQUENCE: 186

Gln Ser Arg Pro Glu Pro Thr Ala Pro Pro Glu Glu Ser Phe Arg Ser
1               5                   10                  15

Gly Val Glu Thr Thr Thr Pro Pro Gln Lys Gln Glu Pro Ile Asp Lys
                20                  25                  30

Glu Leu Tyr Pro Leu Thr Ser Leu Arg Ser Leu Phe Gly Asn Asp Pro
            35                  40                  45

Ser Ser Gln
        50

<210> SEQ ID NO 187
<211> LENGTH: 17
<212> TYPE: PRT
<213> ORGANISM: Artificial Sequence
<220> FEATURE:
<223> OTHER INFORMATION: Synthetic

<400> SEQUENCE: 187

Asp Pro Gln Ile Pro Pro Pro Pro Tyr Val Glu Pro Thr Ala Pro Gln
1               5                   10                  15

Val

<210> SEQ ID NO 188
<211> LENGTH: 11
<212> TYPE: PRT
<213> ORGANISM: Artificial Sequence
<220> FEATURE:
<223> OTHER INFORMATION: Synthetic

<400> SEQUENCE: 188

Leu Leu Thr Glu Asp Pro Pro Pro Tyr Arg Asp
1               5                   10

<210> SEQ ID NO 189
<211> LENGTH: 11
<212> TYPE: PRT
<213> ORGANISM: Artificial Sequence
<220> FEATURE:
<223> OTHER INFORMATION: Synthetic

<400> SEQUENCE: 189

Thr Ala Ser Ala Pro Pro Pro Tyr Val Gly
1               5                   10

<210> SEQ ID NO 190
<211> LENGTH: 15
```

```
<212> TYPE: PRT
<213> ORGANISM: Artificial Sequence
<220> FEATURE:
<223> OTHER INFORMATION: Synthetic

<400> SEQUENCE: 190

Thr Pro Gln Thr Gln Asn Leu Tyr Pro Asp Leu Ser Glu Ile Lys
1               5                   10                  15

<210> SEQ ID NO 191
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 191

Met Arg Arg Val Ile Leu Pro Thr Ala Pro Pro Glu Tyr Met Glu Ala
1               5                   10                  15

Ile

<210> SEQ ID NO 192
<211> LENGTH: 16
<212> TYPE: PRT
<213> ORGANISM: Artificial Sequence
<220> FEATURE:
<223> OTHER INFORMATION: Synthetic

<400> SEQUENCE: 192

Asn Thr Tyr Met Gln Tyr Leu Asn Pro Pro Tyr Ala Asp His Ser
1               5                   10                  15

<210> SEQ ID NO 193
<211> LENGTH: 21
<212> TYPE: PRT
<213> ORGANISM: Artificial Sequence
<220> FEATURE:
<223> OTHER INFORMATION: Synthetic

<400> SEQUENCE: 193

Leu Gly Ile Ala Pro Pro Pro Tyr Glu Glu Asp Thr Ser Met Glu Tyr
1               5                   10                  15

Ala Pro Ser Ala Pro
            20

<210> SEQ ID NO 194
<211> LENGTH: 16
<212> TYPE: PRT
<213> ORGANISM: Artificial Sequence
<220> FEATURE:
<223> OTHER INFORMATION: Synthetic

<400> SEQUENCE: 194

Asp Asp Leu Trp Leu Pro Pro Pro Glu Tyr Val Pro Leu Lys Glu Leu
1               5                   10                  15

<210> SEQ ID NO 195
<211> LENGTH: 20
<212> TYPE: PRT
<213> ORGANISM: Artificial Sequence
<220> FEATURE:
<223> OTHER INFORMATION: Synthetic
```

-continued

```
<400> SEQUENCE: 195

Ala Ala Pro Thr Ala Pro Pro Thr Gly Ala Ala Asp Ser Ile Pro Pro
1               5                   10                  15

Pro Tyr Ser Pro
            20

<210> SEQ ID NO 196
<211> LENGTH: 11
<212> TYPE: PRT
<213> ORGANISM: Artificial Sequence
<220> FEATURE:
<223> OTHER INFORMATION: Synthetic

<400> SEQUENCE: 196

Thr Ala Pro Ser Ser Pro Pro Tyr Glu Glu
1               5                   10

<210> SEQ ID NO 197
<211> LENGTH: 14
<212> TYPE: PRT
<213> ORGANISM: Artificial Sequence
<220> FEATURE:
<223> OTHER INFORMATION: Synthetic

<400> SEQUENCE: 197

Gln Ser Ile Lys Ala Phe Pro Ile Val Ile Asn Ser Asp Gly
1               5                   10

<210> SEQ ID NO 198
<211> LENGTH: 22
<212> TYPE: PRT
<213> ORGANISM: Artificial Sequence
<220> FEATURE:
<223> OTHER INFORMATION: Synthetic

<400> SEQUENCE: 198

Asp Arg Arg Arg Arg Gly Ser Arg Pro Ser Gly Ala Glu Arg Arg
1               5                   10                  15

Arg Arg Ala Ala Ala Ala
            20

<210> SEQ ID NO 199
<211> LENGTH: 97
<212> TYPE: PRT
<213> ORGANISM: Artificial Sequence
<220> FEATURE:
<223> OTHER INFORMATION: Synthetic

<400> SEQUENCE: 199

Ala Val Pro Glu Thr Arg Pro Asn His Thr Ile Tyr Ile Asn Asn Leu
1               5                   10                  15

Asn Glu Lys Ile Lys Lys Asp Glu Leu Lys Lys Ser Leu His Ala Ile
                20                  25                  30

Phe Ser Arg Phe Gly Gln Ile Leu Asp Ile Leu Val Ser Arg Ser Leu
            35                  40                  45

Lys Met Arg Gly Gln Ala Phe Val Ile Phe Lys Glu Val Ser Ser Ala
        50                  55                  60

Thr Asn Ala Leu Arg Ser Met Gln Gly Phe Pro Phe Tyr Asp Lys Pro
65                  70                  75                  80

Met Arg Ile Gln Tyr Ala Lys Thr Asp Ser Asp Ile Ile Ala Lys Met
                85                  90                  95

Lys
```

<210> SEQ ID NO 200
<211> LENGTH: 55
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 200

Met Gln Lys Gly Asn Phe Arg Asn Gln Arg Lys Thr Val Lys Cys Phe
1               5                   10                  15

Asn Cys Gly Lys Glu Gly His Ile Ala Lys Asn Cys Arg Ala Pro Arg
            20                  25                  30

Lys Lys Gly Cys Trp Lys Cys Gly Lys Glu Gly His Gln Met Lys Asp
        35                  40                  45

Cys Thr Glu Arg Gln Ala Asn
    50                  55

<210> SEQ ID NO 201
<211> LENGTH: 14
<212> TYPE: PRT
<213> ORGANISM: Artificial Sequence
<220> FEATURE:
<223> OTHER INFORMATION: Synthetic

<400> SEQUENCE: 201

Arg Pro Arg Gly Thr Arg Gly Lys Gly Arg Arg Ile Arg Arg
1               5                   10

<210> SEQ ID NO 202
<211> LENGTH: 96
<212> TYPE: PRT
<213> ORGANISM: Artificial Sequence
<220> FEATURE:
<223> OTHER INFORMATION: Synthetic

<400> SEQUENCE: 202

Glu Gln Ala Pro Glu Asp Gln Gly Pro Gln Arg Glu Pro His Asn Glu
1               5                   10                  15

Trp Thr Leu Glu Leu Leu Glu Glu Leu Lys Arg Glu Ala Val Arg His
            20                  25                  30

Phe Pro Arg Pro Trp Leu His Gly Leu Gly Gln His Ile Tyr Glu Thr
        35                  40                  45

Tyr Gly Asp Thr Trp Ala Gly Val Glu Ala Ile Ile Arg Ile Leu Gln
    50                  55                  60

Gln Leu Leu Phe Ile His Phe Arg Ile Gly Cys Gln His Ser Arg Ile
65                  70                  75                  80

Gly Ile Ile Gln Gln Arg Arg Ala Arg Arg Asn Gly Ala Ser Arg Ser
                85                  90                  95

<210> SEQ ID NO 203
<211> LENGTH: 384
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 203

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
50                  55                  60

Pro Met Met Ser Thr Phe Lys Val Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp Gly Ser
        275                 280                 285

Glu Gln Ala Pro Glu Asp Gln Gly Pro Gln Arg Glu Pro His Asn Glu
290                 295                 300

Trp Thr Leu Glu Leu Leu Glu Glu Leu Lys Arg Glu Ala Val Arg His
305                 310                 315                 320

Phe Pro Arg Pro Trp Leu His Gly Leu Gly Gln His Ile Tyr Glu Thr
                325                 330                 335

Tyr Gly Asp Thr Trp Ala Gly Val Glu Ala Ile Ile Arg Ile Leu Gln
            340                 345                 350

Gln Leu Leu Phe Ile His Phe Arg Ile Gly Cys Gln His Ser Arg Ile
        355                 360                 365

Gly Ile Ile Gln Gln Arg Arg Ala Arg Arg Asn Gly Ala Ser Arg Ser
370                 375                 380
```

<210> SEQ ID NO 204
<211> LENGTH: 32
<212> TYPE: RNA

<213> ORGANISM: Artificial Sequence
<220> FEATURE:
<223> OTHER INFORMATION: Synthetic

<400> SEQUENCE: 204
ggucugggcg cacuucggug acgguacagg cc                          32

<210> SEQ ID NO 205
<211> LENGTH: 21
<212> TYPE: RNA
<213> ORGANISM: Artificial Sequence
<220> FEATURE:
<223> OTHER INFORMATION: Synthetic

<400> SEQUENCE: 205
aauccauugc acuccggauu u                                      21

<210> SEQ ID NO 206
<211> LENGTH: 44
<212> TYPE: RNA
<213> ORGANISM: Artificial Sequence
<220> FEATURE:
<223> OTHER INFORMATION: Synthetic

<400> SEQUENCE: 206
ggcgacuggu gaguacgcca aaaauuuuga cuagcggagg cuag              44

<210> SEQ ID NO 207
<211> LENGTH: 28
<212> TYPE: RNA
<213> ORGANISM: Artificial Sequence
<220> FEATURE:
<223> OTHER INFORMATION: Synthetic

<400> SEQUENCE: 207
ggcucgugua gcucauuagc uccgagcc                               28

<210> SEQ ID NO 208
<211> LENGTH: 972
<212> TYPE: RNA
<213> ORGANISM: Artificial Sequence
<220> FEATURE:
<223> OTHER INFORMATION: Synthetic

<400> SEQUENCE: 208
ggucugggcg cacuucggug acgguacagg ccuaggauua cugcucggug acuuauaauc    60
auccuccccg ccaccaugga cuacaaagac gacgaugaca aagguucuga cccagaaacg   120
cuggugaaag uaaaagaugc ugaagaucag uugggugcac gaguggguua caucgaacug   180
gaucucaaca gcgguaagau ccuugagagu uuucgcgccg aagaacguuu uccaaugaug   240
agcacuuuua aaguucugcu auguggcgcg guauuauccc guauugacgc cgggcaagag   300
caacucgguc gccgcauaca cuauucucag aaugacuugg uugaguacuc accagucaca   360
gaaaagcauc uuacggaugg caugacagua agagaauuau gcagugcugc cauaaccaug   420
agugauaaca cugcggccaa cuuacuucug acaacgaucg gaggaccgaa ggagcuaacc   480
gcuuuuuugc acaacauggg ggaucaugua acucgccuug aucguuggga accggagcug   540
aaugaagcca uaccaaacga cgagcgugac accacgaugc cuguagcaau ggcaacaacg   600
uugcgcaaac uauuaacugg cgaacuacuu acucuagcuu cccggcaaca auuaauagac   660
uggauggagg cggauaaagu ugcaggacca cuucugcgcu cggcccuucc ggcuggcugg   720
uuuauugcug auaaaucugg agccggugag cgugggcucu gcgguaucau ugcagcacug   780

```
gggccagaug guaagcccuc ccguaucgua guuaucuaca cgacgggag ucaggcaacu    840 auggaugaac gaaauagaca gaucgcugag auaggugccu cacugauuaa gcauugguaa    900
cgagcacaca uccuauuugg gccuagcaac caacaguaug ggucugggcg cacuucggug    960
acgguacagg cc                                                       972
```

```
<210> SEQ ID NO 209
<211> LENGTH: 950
<212> TYPE: RNA
<213> ORGANISM: Artificial Sequence
<220> FEATURE:
<223> OTHER INFORMATION: Synthetic

<400> SEQUENCE: 209
aauccauugc acuccggauu uuaggauuac ugcucgguga cuuauaauca uccuccccgc     60
caccauggac uacaaagacg acgaugacaa agguucugac ccagaaacgc uggugaaagu    120
aaaagaugcu gaagaucagu ugggugcacg aguggguuac aucgaacugg aucucaacag    180
cgguaagauc cuugagaguu uucgccccga agaacguuuu ccaaugauga gcacuuuuaa    240
aguucugcua uguggcgcgg uauuaucccg uauugacgcc gggcaagagc aaccucgucg    300
ccgcauacac uauucucaga augacuuggu ugaguacuca ccagucacag aaaagcaucu    360
uacggauggc augacaguaa gagaauuaug cagugcugcc auaaccauga gugauaacac    420
ugcggccaac uuacuucuga caacgaucgg aggaccgaag gagcuaaccg cuuuuuugca    480
caacaugggg gaucauguaa cucgccuuga ucguugggaa ccggagcuga augaagccau    540
accaaacgac gagcgugaca ccacgaugcc uguagcaaug gcaacaacgu ugcgcaaacu    600
auuaacuggc gaacuacuua cucuagcuuc ccggcaacaa uuaauagacu ggauggaggc    660
ggauaaaguu gcaggaccac uucugcgcuc ggcccuuccg gcuggcuggu uuauugcuga    720
uaaaucugga gccggugagc guggucucg cguaucauu gcagcacugg gccagauggg    780
uaagcccucc cguaucguag uuaucuacac gacggggagu caggcaacua uggaugaacg    840
aaauagacag aucgcugaga uaggugccuc acugauuaag cauugguaac gagcacacau    900
ccuauuuggg ccuagcaacc aacaguauga auccauugca cuccggauuu                950
```

```
<210> SEQ ID NO 210
<211> LENGTH: 996
<212> TYPE: RNA
<213> ORGANISM: Artificial Sequence
<220> FEATURE:
<223> OTHER INFORMATION: Synthetic

<400> SEQUENCE: 210
ggcgacuggu gaguacgcca aaauuuuga cuagcggagg cuaguaggau uacugcucgg      60
ugacuuauaa ucauccuccc cgccaccaug gacuacaaag acgacgauga caaagguucu    120
gacccagaaa cgcuggugaa aguaaaagau gcugaagauc aguugggugc acagaggggu    180
uacaucgaac uggaucucaa cagcgguaag auccuugaga guuucgcccc gaagaacgu    240 uuuccaauga ugagcacuuu uaaaguucug cuaugugggcg cgguauuauc ccguauugac    300
gccgggcaag agcaacucgg ucgccgcaua cacuauucuc agaaugacuu gguugaguac    360
ucaccaguca cagaaaagca ucuuacggau ggcaugacag uaagagaauu augcagugcu    420
gccauaacca ugagugauaa cacugcggcc aacuuacuuc ugacaacgau cggaggaccg    480
aaggagcuaa ccgcuuuuuu gcacaacaug ggggaucaug uaacucgccu ugaucguugg    540
```

| | |
|---|---|
| gaaccggagc ugaaugaagc cauaccaaac gacgagcgug acaccacgau gccuguagca | 600 |
| auggcaacaa cguugcgcaa acuauuaacu ggcgaacuac uuacucuagc uucccggcaa | 660 |
| caauuaauag acuggaugga ggcggauaaa guugcaggac cacuucugcg cucggcccuu | 720 |
| ccggcuggcu gguuuauugc ugauaaaucu ggagccggug agcguggguc ucgcgguauc | 780 |
| auugcagcac uggggccaga ugguaagccc ucccguaucg uaguuaucua cacgacgggg | 840 |
| agucaggcaa cuauggauga acgaaauaga cagaucgcug agauaggugc ucacugauu | 900 |
| aagcauuggu aacgagcaca cauccuauuu gggccuagca accaacagua ugggcgacug | 960 |
| gugaguacgc caaaaauuuu gacuagcgga ggcuag | 996 |

```
<210> SEQ ID NO 211
<211> LENGTH: 964
<212> TYPE: RNA
<213> ORGANISM: Artificial Sequence
<220> FEATURE:
<223> OTHER INFORMATION: Synthetic

<400> SEQUENCE: 211
```

| | |
|---|---|
| ggcucgugua gcucauuagc uccgagccua ggauuacugc ucggugacuu auaaucaucc | 60 |
| uccccgccac cauggacuac aaagacgacg augacaaagg uucugaccca gaaacgcugg | 120 |
| ugaaaguaaa agaugcugaa gaucaguugg gugcacgagu gguuacauc gaacuggauc | 180 |
| ucaacagcgg uaagauccuu gagaguuuuc gccccgaaga acguuuucca augaugagca | 240 |
| cuuuuaaagu ucugcuaugu ggcgcgguau uaucccguau ugacgccggg caagagcaac | 300 |
| ucggucgccg cauacacuau ucucagaaug acuggguuga guacuacca gucacagaaa | 360 |
| agcaucuuac ggauggcaug acaguaagag aauuaugcag ugcugccaua accaugagug | 420 |
| auaacacugc ggccaacuua cuucugacaa cgaucgaggg accgaaggag cuaaccgcuu | 480 |
| uuuugcacaa caugggggau cauguaacuc gccuugaucg uugggaaccg gagcugaaug | 540 |
| aagccauacc aaacgacgag cgugacacca cgaugccugu agcaauggca caacguugc | 600 |
| gcaaacuauu aacuggcgaa cuacuuacuc uagcuucccg gcaacaauua auagacugga | 660 |
| uggaggcgga uaaaguugca ggaccacuuc ugcgcucggc ccuuccggcu ggcugguuua | 720 |
| uugcugauaa aucuggagcc ggugagcgug gguucgcgg uaucauugca gcacgggc | 780 |
| cagauggua gccccucccgu aucuaguua ucuacgac ggggagucag gcaacuaugg | 840 |
| augaacgaaa uagacagauc gcugagauag gugccucacu gauuaagcau gguaacgag | 900 |
| cacacauccu auugggccu agcaaccaac aguaugggcu cguguagcuc auuagcuccg | 960 |
| agcc | 964 |

```
<210> SEQ ID NO 212
<211> LENGTH: 978
<212> TYPE: RNA
<213> ORGANISM: Artificial Sequence
<220> FEATURE:
<223> OTHER INFORMATION: Synthetic

<400> SEQUENCE: 212
```

| | |
|---|---|
| ggucugggcg cacuucggug acgguacagg ccuaggauua cugcucggug acuuauaauc | 60 |
| auccucccg ccaccaugga acagaaacug auuagcgaag aagaucuggg uucugaccca | 120 |
| gaaacgcugg ugaaaguaaa agaugcugaa gaucaguugg gugcacgagu gguuacauc | 180 |
| gaacuggauc ucaacagcgg uaagauccuu gagaguuuuc gccccgaaga acguuuucca | 240 |
| augaugagca cuuuuaaagu ucugcuaugu ggcgcgguau uaucccguau ugacgccggg | 300 |

```
caagagcaac ucggucgccg cauacacuau ucucagaaug acuugguuga guacucacca      360
gucacagaaa agcaucuuac ggauggcaug acaguaagag aauuaugcag ugcugccaua      420
accaugagug auaacacugc ggccaacuua cuucugacaa cgaucggagg accgaaggag      480
cuaaccgcuu uuuugcacaa caugggggau cauguaacuc gccuugaucg uugggaaccg      540
gagcugaaug aagccauacc aaacgacgag cgugacacca cgaugccugu agcaauggca      600
acaacguugc gcaaacuauu aacggcgaau cacuuacuc uagcuucccg gcaacaauua      660
auagacugga uggaggcgga uaaaguugca ggaccacuuc ugcgcucggc ccuuccggcu      720
ggcugguuua uugcugauaa aucuggagcc ggugagcgug ggucucgcgg uaucauugca      780
gcacuggggc cagaugguaa gcccucccgu aucuaguua cuacacgac ggggagucag      840 gcaacuaugg augaacgaaa uagacagauc gcugagauag ugccucacu gauuaagcau      900 ugguaacgag cacacauccu auuugggccu agcaaccaac aguaugggu ugggcgcacu      960 ucggugacgg uacaggcc                                                    978

<210> SEQ ID NO 213
<211> LENGTH: 956
<212> TYPE: RNA
<213> ORGANISM: Artificial Sequence
<220> FEATURE:
<223> OTHER INFORMATION: Synthetic

<400> SEQUENCE: 213
aauccauugc acuccggauu uuaggauuac ugcucgguga cuuauaauca uccuccccgc       60
caccauggaa cagaaacuga uuagcgaaga agaucuggu ucugaccag aaacgcuggu       120 gaaaguaaaa gaugcugaag aucaguuggg ugcacgagug gguuacaucg aacuggaucu      180
caacagcggu aagauccuug agaguuuucg ccccgaagaa cguuuccaa ugaugagcac      240 uuuuaaaguu cugcuaugug gcgcgguauu aucccguauu gacgccgggc aagagcaacu      300
cggucgccgc auacacuauu ucucagaauga cuugguugag uacucaccag ucacagaaaa      360
gcaucuuacg gauggcauga caguaagaga auuaugcagu gcugccauaa ccaugaguga      420
uaacacugcg gccaacuuac uucugacaac gaucggagga ccgaaggagc uaaccgcuuu      480
uuugcacaac auggggauc auguaacucg ccuugaucgu ugggaaccgg agcugaauga      540
agccauacca aacgacgagc gugacaccac gaugccugua gcaauggcaa caacguugcg      600
caaacuauua acggcgaac uacuuacucu agcuucccgg caacaauuaa uagacuggau      660
ggaggcggau aaaguugcag gaccacucu gcgcucggcc cuuccggcug gcgguuuau      720 ugcugauaaa ucuggagccg gugagcgugg gucucgcggu aucauugcag cacuggggcc      780
agaugguaag cccucccgua ucuaguuau cuacacgacg gggagucagg caacuaugga      840
ugaacgaaau agacagaucg cugagauagg ugccucacug auuaagcauu gguaacgagc      900
acacauccua uuugggccua gcaaccaaca guaugaaucc auugcacucc ggauuu         956

<210> SEQ ID NO 214
<211> LENGTH: 1002
<212> TYPE: RNA
<213> ORGANISM: Artificial Sequence
<220> FEATURE:
<223> OTHER INFORMATION: Synthetic

<400> SEQUENCE: 214
ggcgacuggu gaguacgcca aaaauuuuga cuagcggagg cuaguaggau uacugcucgg       60
```

|  |  |  |  |  |  |
|---|---|---|---|---|---|
| ugacuuauaa | ucauccuccc | cgccaccaug | aacagaaac | ugauuagcga | agaagaucug | 120 |
| gguucugacc | cagaaacgcu | ggugaaagua | aaagaugcug | aagaucaguu | gggugcacga | 180 |
| gugGguuaca | ucgaacugga | ucucaacagc | gguaagaucc | uugagaguuu | ucgccccgaa | 240 |
| gaacguuuuc | caaugaugag | cacuuuuaaa | guucugcuau | guggcgcggu | auuaucccgu | 300 |
| auugacgccg | ggcaagagca | acucggucgc | cgcauacacu | auucucagaa | ugacuugguu | 360 |
| gaguacucac | caguccacaga | aaagcaucuu | acggauggca | ugacaguaag | agaauuaugc | 420 |
| agugcugcca | uaaccaugag | ugauaacacu | gcggccaacu | acuucugac | aacgaucgga | 480 |
| ggaccgaagg | agcuaaccgc | uuuuuugcac | aacauggggg | aucauguaac | ucgccuugau | 540 |
| cguugggaac | cggagcugaa | ugaagccaua | ccaaacgacg | agcgugacac | cacgaugccu | 600 |
| guagcaaugg | caacaacguu | gcgcaaacua | uuaacuggcg | aacuacuuac | ucuagcuucc | 660 |
| cggcaacaau | uaauagacug | gauggaggcg | gauaaaguug | caggaccacu | ucugcgcucg | 720 |
| gcccuuccgg | cuggcugguu | uauugcugau | aaaucuggag | ccggugagcg | ugggucucgc | 780 |
| gguaucauug | cagcacuggg | gccagauggu | aagcccuccc | guaucguagu | uaucuacacg | 840 |
| acggggaguc | aggcaacuau | ggaugaacga | aauagacaga | ucgcugagau | aggugccuca | 900 |
| cugauuaagc | auugguaacg | agcacacauc | cuauuuggcu | cuagcaacca | acaguauggg | 960 |
| cgacugguga | uacgccaaaa | aauuuugacu | agcggaggcu | ag |  | 1002 |

<210> SEQ ID NO 215
<211> LENGTH: 970
<212> TYPE: RNA
<213> ORGANISM: Artificial Sequence
<220> FEATURE:
<223> OTHER INFORMATION: Synthetic

<400> SEQUENCE: 215

|  |  |  |  |  |  |
|---|---|---|---|---|---|
| ggcucgugua | gcucauuagc | uccgagccua | ggauuacugc | ucggugacuu | auaaucaucc | 60 |
| uccccgccac | cauggaacag | aaacugauua | gcgaagaaga | ucugguucu | gacccagaaa | 120 |
| cgcuggugaa | aguaaaagau | gcugaagauc | aguugggugc | acgaguGggu | uacaucgaac | 180 |
| uggaucucaa | cagcgguaag | auccuugaga | guuucgcccc | gaagaacgu | uuccaauga | 240 |
| ugagcacuuu | uaaaguucug | cuaugugGcg | cgguauuauc | ccguauugac | gccgggcaag | 300 |
| agcaacucgg | ucgccgcaua | cacuauucuc | agaaugacuu | gguugaguac | ucaccaguca | 360 |
| cagaaaagca | ucuuacggau | ggcaugacag | uaagagaauu | augcagugcu | gccauaacca | 420 |
| ugagugauaa | cacugcggcc | aacuuacuuc | ugacaacgau | cggaggaccg | aaggagcuaa | 480 |
| ccgcuuuuuu | gcacaacaug | ggggaucaug | uaacucgccu | ugaucguugg | gaaccggagc | 540 |
| ugaaugaagc | cauaccaaac | gacgagcgug | acaccacgau | gccuguagca | augGcaacaa | 600 |
| cguugcgcaa | acuauuaacu | ggcgaacuac | uuacucuagc | uucccggcaa | caauuaauag | 660 |
| acuggaugga | ggcggauaaa | guugcaggac | cacuucugcg | cucggcccuu | ccggcuggcu | 720 |
| gguuuauugc | ugauaaaucu | ggagccggug | agcguggguc | ucgcguauc | auugcagcac | 780 |
| uggggccaga | ugguaagccc | ucccguaucg | uaguuaucua | cacgacgggg | agucaggcaa | 840 |
| cuauggauga | acgaaauaga | cagaucgcug | agauaggugc | cucacugauu | aagcauuggu | 900 |
| aacgagcaca | cauccuauuu | gggccuagca | accaacagua | ugggcucgug | uagcucauua | 960 |
| gcuccgagcc |  |  |  |  |  | 970 |

<210> SEQ ID NO 216
<211> LENGTH: 897

<212> TYPE: RNA
<213> ORGANISM: Artificial Sequence
<220> FEATURE:
<223> OTHER INFORMATION: Synthetic

<400> SEQUENCE: 216

```
ggucugggcg cacuucggug acgguacagg ccuaggauua cugcucggug acuuauaauc      60
auccuccccg ccaccaugga acagaaacug auuagcgaag aagaucuggu gagcaagggc     120
gaggagcugu ucaccggggu ggugcccauc cuggucgagc uggacggcga cguaaacggc     180
cacaaguuca gcguguccgg cgagggcgag ggcgaugcca ccuacggcaa gcugacccug     240
aaguucaucu gcaccaccgg caagcugccc gugcccuggc ccacccucgu gaccacccug     300
accuacggcg ugcagugcuu cagccgcuac cccgaccaca ugaagcagca cgacuucuuc     360
aagucccgcca ugcccgaagg cuacguccag gagcgcacca ucuucuucaa ggacgacggc     420
aacuacaaga cccgcgccga ggugaaguuc gagggcgaca cccuggugaa ccgcaucgag     480
cugaagggca ucgacuucaa ggaggacggc aacauccugg gcacaagcu ggaguacaac      540
ucaacagcc acaacgucua uaucauggcc gacaagcaga gaacggcau caaggugaac       600
uucaagaucc gccacaacau cgaggacggc agcgugcagc ucgccgacca cuaccagcag     660
aacaccccca ucggcgacgg ccccgugcug cugcccgaca ccacuaccu gagcacccag      720
uccgcccuga gcaaagaccc caacgagaag cgcgaucaca uggccugcu ggaguucgug      780
accgccgccg ggaucacucu cggcauggac gagcuguaca aguaacgagc acacauccua     840
uuugggccua gcaaccaaca guaugggucu gggcgcacuu cggugacggu acaggcc         897
```

<210> SEQ ID NO 217
<211> LENGTH: 875
<212> TYPE: RNA
<213> ORGANISM: Artificial Sequence
<220> FEATURE:
<223> OTHER INFORMATION: Synthetic

<400> SEQUENCE: 217

```
aauccauugc acuccggauu uuaggauuac ugcucgguga cuuauaauca uccuccccgc      60
caccauggaa cagaaacuga uuagcgaaga agaucuggu agcaagggcg aggagcuguu      120
caccggggug gugcccaucc uggucgagcu ggacggcgac guaaacggcc acaaguucag     180
cguguccggc gagggcgagg gcgaugccac cuacggcaag cugacccuga aguucaucug     240
caccaccggc aagcugcccg ugcccuggcc cacccucgug accacccuga ccuacggcgu     300
gcagugcuuc agccgcuacc ccgaccacau gaagcagcac gacuucuuca aguccgccau     360
gcccgaaggc uacguccagg agcgcaccau cuucuucaag gacgacggca acuacaagac     420
ccgcgccgag gugaaguucg agggcgacac ccuggugaac cgcaucgagc ugaagggcau     480
cgacuucaag gaggacggca acauccuggg cacaagcug gaguacaacu acaacagcca     540
caacgucuau aucauggccg acaagcagaa gaacggcauc aaggugaacu ucaagauccg     600
ccacaacauc gaggacggca gcgugcagcu cgccgaccac uaccagcaga acacccccau     660
cggcgacggc cccgugcugc ugcccgacaa ccacuaccug agcacccagu ccgcccugag     720
caaagacccc aacgagaagc gcgaucacau ggucccugcg gaguucguga ccgccgccgg     780
gaucacucuc ggcauggacg agcuguacaa guaagcucca cauccuauu ugggccuag      840
caaccaacag uaugaaucca uugcacuccg gauuu                                 875
```

<210> SEQ ID NO 218

<211> LENGTH: 921
<212> TYPE: RNA
<213> ORGANISM: Artificial Sequence
<220> FEATURE:
<223> OTHER INFORMATION: Synthetic

<400> SEQUENCE: 218

```
ggcgacuggu gaguacgcca aaaauuuuga cuagcggagg cuaguaggau uacugcucgg      60
ugacuuauaa ucauccuccc cgccaccaug aacagaaac ugauuagcga agaagaucug      120
gugagcaagg gcgaggagcu guucaccggg guggugccca uccuggucga gcuggacggc     180
gacguaaacg gccacaaguu cagcgugucc ggcgagggcg agggcgaugc caccuacggc     240
aagcugaccc ugaaguucau cugcaccacc ggcaagcugc ccgugcccug gcccacccuc     300
gugaccaccc ugaccuacgg cgugcagugc uucagccgcu accccgacca caugaagcag     360
cacgacuucu ucaaguccgc caugcccgaa ggcuacgucc aggagcgcac caucuucuuc     420
aaggacgacg gcaacuacaa gacccgcgcc gaggugaagu ucgagggcga cacccuggug     480
aaccgcaucg agcugaaggg caucgacuuc aaggaggacg gcaacauccu ggggcacaag     540
cuggaguaca acuacaacag ccacaacguc uauaucaugg ccgacaagca gaagaacggc     600
aucaagguga cuucaagau ccgccacaac ucgaggacg cagcgugca gcucgccgac        660
cacuaccagc agaacacccc caucggcgac ggccccgugc ugcugcccga caaccacuac     720
cugagcaccc aguccgcccu gagcaaagac cccaacgaga gcgcgauca cauggccug      780
cuggaguucg ugaccgccgc cgggaucacu cucggcaugg acgagcugua caaguaacag    840
ccacacaucc uauuugggcc uagcaaccaa caguaugggc gacuggugag uacgccaaaa    900
auuuugacua gcggaggcua g                                              921
```

<210> SEQ ID NO 219
<211> LENGTH: 889
<212> TYPE: RNA
<213> ORGANISM: Artificial Sequence
<220> FEATURE:
<223> OTHER INFORMATION: Synthetic

<400> SEQUENCE: 219

```
ggcucgugua gcucauuagc uccgagccua ggauuacugc ucggugacuu auaaucaucc     60
uccccgccac cauggaacag aaacugauua gcgaagaaga ucuggugagc aagggcgagg    120
agcuguucac cggggguggug cccauccugg ucgagcugga cggcgacgua aacggccaca   180
aguucagcgu guccggcgag ggcgagggcg augccaccua cggcaagcug acccugaagu   240
ucaucugcac caccggcaag cugcccgugc ccuggcccac ccucgugacc acccugaccu    300
acggcgugca gugcuucagc cgcuaccccg accaugaa gcagcacgac uucuucaagu      360
ccgccaugcc cgaaggcuac guccaggagc gcaccaucuu cuucaaggac gacggcaacu    420
acaagacccg cgccgaggug aaguucgagg gcgacacccu ggugaaccgc aucgagcuga   480
agggcaucga cuucaaggag gacggcaaca uccuggggca aagcuggag uacaacuaca    540
acagccacaa cgucuauauc auggccgaca gcagaagaa cggcaucaag gugaacuuca    600
agauccgcca caacaucgag gacggcagcg ugcagcucgc cgaccacuac cagcagaaca    660
cccccaucgg cgacggcccc gugcugcugc ccgacaacca cuaccugagc acccaguccg    720
cccugagcaa agacccccaac gagaagcgcg aucacauggu ccugcuggag uucgugaccg    780
ccgcggggau cacucucggc auggacgagc uguacaagua agcgcacac auccuauuug     840
ggccuagcaa ccaacaguau gggcucgugu agcucauuag cuccgagcc                889
```

```
<210> SEQ ID NO 220
<211> LENGTH: 274
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (2)..(9)
<223> OTHER INFORMATION: Myc tag optionally absent

<400> SEQUENCE: 220

Met Asp Tyr Lys Asp Asp Asp Lys Gly Ser Asp Pro Glu Thr Leu
1               5                   10                  15

Val Lys Val Lys Asp Ala Glu Asp Gln Leu Gly Ala Arg Val Gly Tyr
            20                  25                  30

Ile Glu Leu Asp Leu Asn Ser Gly Lys Ile Leu Glu Ser Phe Arg Pro
        35                  40                  45

Glu Glu Arg Phe Pro Met Met Ser Thr Phe Lys Val Leu Leu Cys Gly
    50                  55                  60

Ala Val Leu Ser Arg Ile Asp Ala Gly Gln Glu Gln Leu Gly Arg Arg
65              70                  75                  80

Ile His Tyr Ser Gln Asn Asp Leu Val Glu Tyr Ser Pro Val Thr Glu
                85                  90                  95

Lys His Leu Thr Asp Gly Met Thr Val Arg Glu Leu Cys Ser Ala Ala
            100                 105                 110

Ile Thr Met Ser Asp Asn Thr Ala Ala Asn Leu Leu Leu Thr Thr Ile
        115                 120                 125

Gly Gly Pro Lys Glu Leu Thr Ala Phe Leu His Asn Met Gly Asp His
    130                 135                 140

Val Thr Arg Leu Asp Arg Trp Glu Pro Glu Leu Asn Glu Ala Ile Pro
145                 150                 155                 160

Asn Asp Glu Arg Asp Thr Thr Met Pro Val Ala Met Ala Thr Thr Leu
                165                 170                 175

Arg Lys Leu Leu Thr Gly Glu Leu Leu Thr Leu Ala Ser Arg Gln Gln
            180                 185                 190

Leu Ile Asp Trp Met Glu Ala Asp Lys Val Ala Gly Pro Leu Leu Arg
        195                 200                 205

Ser Ala Leu Pro Ala Gly Trp Phe Ile Ala Asp Lys Ser Gly Ala Gly
    210                 215                 220

Glu Arg Gly Ser Arg Gly Ile Ile Ala Ala Leu Gly Pro Asp Gly Lys
225                 230                 235                 240

Pro Ser Arg Ile Val Val Ile Tyr Thr Thr Gly Ser Gln Ala Thr Met
                245                 250                 255

Asp Glu Arg Asn Arg Gln Ile Ala Glu Ile Gly Ala Ser Leu Ile Lys
            260                 265                 270

His Trp

<210> SEQ ID NO 221
<211> LENGTH: 276
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (3)..(11)
<223> OTHER INFORMATION: Myc tag optionally absent

<400> SEQUENCE: 221
```

| Met | Glu | Gln | Lys | Leu | Ile | Ser | Glu | Glu | Asp | Leu | Gly | Ser | Asp | Pro | Glu |
|---|---|---|---|---|---|---|---|---|---|---|---|---|---|---|---|
| 1 | | | | 5 | | | | | 10 | | | | | 15 | |
| Thr | Leu | Val | Lys | Val | Lys | Asp | Ala | Glu | Asp | Gln | Leu | Gly | Ala | Arg | Val |
| | | | 20 | | | | | 25 | | | | | 30 | | |
| Gly | Tyr | Ile | Glu | Leu | Asp | Leu | Asn | Ser | Gly | Lys | Ile | Leu | Glu | Ser | Phe |
| | | 35 | | | | | 40 | | | | | 45 | | | |
| Arg | Pro | Glu | Glu | Arg | Phe | Pro | Met | Met | Ser | Thr | Phe | Lys | Val | Leu | Leu |
| | 50 | | | | | 55 | | | | | 60 | | | | |
| Cys | Gly | Ala | Val | Leu | Ser | Arg | Ile | Asp | Ala | Gly | Gln | Glu | Gln | Leu | Gly |
| 65 | | | | | 70 | | | | | 75 | | | | | 80 |
| Arg | Arg | Ile | His | Tyr | Ser | Gln | Asn | Asp | Leu | Val | Glu | Tyr | Ser | Pro | Val |
| | | | | 85 | | | | | 90 | | | | | 95 | |
| Thr | Glu | Lys | His | Leu | Thr | Asp | Gly | Met | Thr | Val | Arg | Glu | Leu | Cys | Ser |
| | | | 100 | | | | | 105 | | | | | 110 | | |
| Ala | Ala | Ile | Thr | Met | Ser | Asp | Asn | Thr | Ala | Ala | Asn | Leu | Leu | Leu | Thr |
| | | 115 | | | | | 120 | | | | | 125 | | | |
| Thr | Ile | Gly | Gly | Pro | Lys | Glu | Leu | Thr | Ala | Phe | Leu | His | Asn | Met | Gly |
| | 130 | | | | | 135 | | | | | 140 | | | | |
| Asp | His | Val | Thr | Arg | Leu | Asp | Arg | Trp | Glu | Pro | Glu | Leu | Asn | Glu | Ala |
| 145 | | | | | 150 | | | | | 155 | | | | | 160 |
| Ile | Pro | Asn | Asp | Glu | Arg | Asp | Thr | Thr | Met | Pro | Val | Ala | Met | Ala | Thr |
| | | | | 165 | | | | | 170 | | | | | 175 | |
| Thr | Leu | Arg | Lys | Leu | Leu | Thr | Gly | Glu | Leu | Leu | Thr | Leu | Ala | Ser | Arg |
| | | | 180 | | | | | 185 | | | | | 190 | | |
| Gln | Gln | Leu | Ile | Asp | Trp | Met | Glu | Ala | Asp | Lys | Val | Ala | Gly | Pro | Leu |
| | | 195 | | | | | 200 | | | | | 205 | | | |
| Leu | Arg | Ser | Ala | Leu | Pro | Ala | Gly | Trp | Phe | Ile | Ala | Asp | Lys | Ser | Gly |
| | 210 | | | | | 215 | | | | | 220 | | | | |
| Ala | Gly | Glu | Arg | Gly | Ser | Arg | Gly | Ile | Ile | Ala | Ala | Leu | Gly | Pro | Asp |
| 225 | | | | | 230 | | | | | 235 | | | | | 240 |
| Gly | Lys | Pro | Ser | Arg | Ile | Val | Val | Ile | Tyr | Thr | Thr | Gly | Ser | Gln | Ala |
| | | | | 245 | | | | | 250 | | | | | 255 | |
| Thr | Met | Asp | Glu | Arg | Asn | Arg | Gln | Ile | Ala | Glu | Ile | Gly | Ala | Ser | Leu |
| | | | 260 | | | | | 265 | | | | | 270 | | |
| Ile | Lys | His | Trp | | | | | | | | | | | | |
| | | | 275 | | | | | | | | | | | | |

```
<210> SEQ ID NO 222
<211> LENGTH: 249
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (3)..(11)
```

<223> OTHER INFORMATION: Myc tag optionally absent

<400> SEQUENCE: 222

Met Glu Gln Lys Leu Ile Ser Glu Glu Asp Leu Val Ser Lys Gly Glu
1               5                   10                  15

Glu Leu Phe Thr Gly Val Val Pro Ile Leu Val Glu Leu Asp Gly Asp
            20                  25                  30

Val Asn Gly His Lys Phe Ser Val Ser Gly Glu Gly Glu Gly Asp Ala
        35                  40                  45

Thr Tyr Gly Lys Leu Thr Leu Lys Phe Ile Cys Thr Thr Gly Lys Leu
    50                  55                  60

Pro Val Pro Trp Pro Thr Leu Val Thr Thr Leu Thr Tyr Gly Val Gln
65                  70                  75                  80

Cys Phe Ser Arg Tyr Pro Asp His Met Lys Gln His Asp Phe Phe Lys
                85                  90                  95

Ser Ala Met Pro Glu Gly Tyr Val Gln Glu Arg Thr Ile Phe Phe Lys
            100                 105                 110

Asp Asp Gly Asn Tyr Lys Thr Arg Ala Glu Val Lys Phe Glu Gly Asp
        115                 120                 125

Thr Leu Val Asn Arg Ile Glu Leu Lys Gly Ile Asp Phe Lys Glu Asp
    130                 135                 140

Gly Asn Ile Leu Gly His Lys Leu Glu Tyr Asn Tyr Asn Ser His Asn
145                 150                 155                 160

Val Tyr Ile Met Ala Asp Lys Gln Lys Asn Gly Ile Lys Val Asn Phe
                165                 170                 175

Lys Ile Arg His Asn Ile Glu Asp Gly Ser Val Gln Leu Ala Asp His
            180                 185                 190

Tyr Gln Gln Asn Thr Pro Ile Gly Asp Gly Pro Val Leu Leu Pro Asp
        195                 200                 205

Asn His Tyr Leu Ser Thr Gln Ser Ala Leu Ser Lys Asp Pro Asn Glu
    210                 215                 220

Lys Arg Asp His Met Val Leu Leu Glu Phe Val Thr Ala Ala Gly Ile
225                 230                 235                 240

Thr Leu Gly Met Asp Glu Leu Tyr Lys
                245

<210> SEQ ID NO 223
<211> LENGTH: 4
<212> TYPE: PRT
<213> ORGANISM: Artificial Sequence
<220> FEATURE:
<223> OTHER INFORMATION: Synthetic

<400> SEQUENCE: 223

Gly Ser Gly Ser
1

<210> SEQ ID NO 224
<211> LENGTH: 10
<212> TYPE: PRT
<213> ORGANISM: Artificial Sequence
<220> FEATURE:
<223> OTHER INFORMATION: Synthetic

<400> SEQUENCE: 224

Gly Ser Asp Gly Ser Gly Arg Ser Gly Ser
1               5                   10

<210> SEQ ID NO 225
<211> LENGTH: 12
<212> TYPE: PRT
<213> ORGANISM: Artificial Sequence
<220> FEATURE:
<223> OTHER INFORMATION: Synthetic

<400> SEQUENCE: 225

```
Gly Ser Lys Ser Gly Ser Gly Ser Asp Ser Gly Ser
1               5                   10
```

<210> SEQ ID NO 226
<211> LENGTH: 22
<212> TYPE: PRT
<213> ORGANISM: Artificial Sequence
<220> FEATURE:
<223> OTHER INFORMATION: Synthetic

<400> SEQUENCE: 226

```
Gly Ser Gly Ser Gly Asp Gly Gly Arg Gly Ser Arg Gly Gly Asp Gly
1               5                   10                  15
Ser Gly Gly Ser Ser Gly
            20
```

<210> SEQ ID NO 227
<211> LENGTH: 282
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (222)..(231)
<223> OTHER INFORMATION: Myc tag-optionally absent

<400> SEQUENCE: 227

```
Met Gly Ala Arg Ala Ser Gly Ser Lys Ser Gly Ser Gly Ser Asp Ser
1               5                   10                  15

Gly Ser Lys Met Glu Glu Leu Phe Lys Lys His Lys Ile Val Ala Val
            20                  25                  30

Leu Arg Ala Asn Ser Val Glu Glu Ala Lys Lys Lys Ala Leu Ala Val
        35                  40                  45

Phe Leu Gly Gly Val His Leu Ile Glu Ile Thr Phe Thr Val Pro Asp
    50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
        115                 120                 125

Met Thr Pro Thr Glu Leu Val Lys Ala Met Lys Leu Gly His Thr Ile
    130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175
```

```
Asn Leu Asp Asn Val Cys Glu Trp Phe Lys Ala Gly Val Leu Ala Val
            180                 185                 190

Gly Val Gly Ser Ala Leu Val Lys Gly Thr Pro Val Glu Val Ala Glu
        195                 200                 205

Lys Ala Lys Ala Phe Val Glu Lys Ile Arg Gly Cys Thr Glu Gln Lys
    210                 215                 220

Leu Ile Ser Glu Glu Asp Leu Gln Ser Arg Pro Glu Pro Thr Ala Pro
225                 230                 235                 240

Pro Glu Glu Ser Phe Arg Ser Gly Val Glu Thr Thr Thr Pro Pro Gln
                245                 250                 255

Lys Gln Glu Pro Ile Asp Lys Glu Leu Tyr Pro Leu Thr Ser Leu Arg
            260                 265                 270

Ser Leu Phe Gly Asn Asp Pro Ser Ser Gln
        275                 280
```

<210> SEQ ID NO 228
<211> LENGTH: 380
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(22)
<223> OTHER INFORMATION: optionally absent
<220> FEATURE:
<221> NAME/KEY: MISC_FEATURE
<222> LOCATION: (370)..(378)
<223> OTHER INFORMATION: FLAG tag- optionally absent

<400> SEQUENCE: 228

```
Met Val Arg Arg Val Ile Leu Pro Thr Ala Pro Pro Glu Tyr Met Glu
1               5                   10                  15

Ala Ile Tyr Pro Val Arg Gly Ser Gly Ser Lys Met Glu Glu Leu Phe
            20                  25                  30

Lys Lys His Lys Ile Val Ala Val Leu Arg Ala Asn Ser Val Glu Glu
        35                  40                  45

Ala Lys Lys Lys Ala Leu Ala Val Phe Leu Gly Gly Val His Leu Ile
    50                  55                  60

Glu Ile Thr Phe Thr Val Pro Asp Ala Asp Thr Val Ile Lys Glu Leu
65                  70                  75                  80

Ser Phe Leu Lys Glu Met Gly Ala Ile Ile Gly Ala Gly Thr Val Thr
                85                  90                  95

Ser Val Glu Gln Cys Arg Lys Ala Val Glu Ser Gly Ala Glu Phe Ile
            100                 105                 110

Val Ser Pro His Leu Asp Glu Glu Ile Ser Gln Phe Cys Lys Glu Lys
        115                 120                 125

Gly Val Phe Tyr Met Pro Gly Val Met Thr Pro Thr Glu Leu Val Lys
    130                 135                 140

Ala Met Lys Leu Gly His Thr Ile Leu Lys Leu Phe Pro Gly Glu Val
145                 150                 155                 160

Val Gly Pro Gln Phe Val Lys Ala Met Lys Gly Pro Phe Pro Asn Val
                165                 170                 175

Lys Phe Val Pro Thr Gly Gly Val Asn Leu Asp Asn Val Cys Glu Trp
            180                 185                 190

Phe Lys Ala Gly Val Leu Ala Val Gly Val Gly Ser Ala Leu Val Lys
        195                 200                 205

Gly Thr Pro Val Glu Val Ala Glu Lys Ala Lys Ala Phe Val Glu Lys
```

```
                    210                 215                 220
Ile Arg Gly Cys Thr Glu Gly Ser Asp Gly Ser Gly Arg Ser Gly Ser
225                 230                 235                 240

His Gly Leu Gln Asp Asp Pro Asp Leu Gln Ala Leu Leu Lys Gly Ser
                245                 250                 255

Gln Leu Leu Lys Val Lys Ser Ser Ser Trp Arg Arg Glu Arg Phe Tyr
            260                 265                 270

Lys Leu Gln Glu Asp Cys Lys Thr Ile Trp Gln Glu Ser Arg Lys Val
        275                 280                 285

Met Arg Ser Pro Glu Ser Gln Leu Phe Ser Ile Glu Asp Ile Gln Glu
    290                 295                 300

Val Arg Met Gly His Arg Thr Glu Gly Leu Glu Lys Phe Ala Arg Asp
305                 310                 315                 320

Ile Pro Glu Asp Arg Cys Phe Ser Ile Val Phe Lys Asp Gln Arg Asn
                325                 330                 335

Thr Leu Asp Leu Ile Ala Pro Ser Pro Ala Asp Ala Gln His Trp Val
            340                 345                 350

Gln Gly Leu Arg Lys Ile Ile His His Ser Gly Ser Met Asp Gln Arg
        355                 360                 365

Gln Lys Asp Tyr Lys Asp Asp Asp Lys Gly Ser
    370                 375                 380

<210> SEQ ID NO 229
<211> LENGTH: 282
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 229

Met Gly Ala Arg Ala Ser Gly Ser Lys Ser Gly Ser Gly Ser Asp Ser
1               5                   10                  15

Gly Ser Lys Met Glu Glu Leu Phe Lys Lys His Lys Ile Val Ala Val
            20                  25                  30

Leu Arg Ala Asn Ser Val Glu Glu Ala Lys Lys Lys Ala Leu Ala Val
        35                  40                  45

Phe Leu Gly Gly Val His Leu Ile Glu Ile Thr Phe Thr Val Pro Asp
    50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
        115                 120                 125

Met Thr Pro Thr Glu Leu Val Lys Ala Met Lys Leu Gly His Thr Ile
    130                 135                 140

Leu Lys Leu Phe Pro Gly Glu Val Val Gly Pro Gln Phe Val Lys Ala
145                 150                 155                 160
```

```
Met Lys Gly Pro Phe Pro Asn Val Lys Phe Val Pro Thr Gly Gly Val
            165                 170                 175

Asn Leu Lys Asn Val Cys Lys Trp Phe Lys Ala Gly Val Leu Ala Val
            180                 185                 190

Gly Val Gly Lys Ala Leu Val Lys Gly Thr Pro Val Glu Val Ala Lys
            195                 200                 205

Lys Ala Lys Ala Phe Val Lys Lys Ile Arg Gly Cys Thr Glu Gln Lys
210                 215                 220

Leu Ile Ser Glu Glu Asp Leu Gln Ser Arg Pro Glu Pro Thr Ala Pro
225                 230                 235                 240

Pro Glu Glu Ser Phe Arg Ser Gly Val Glu Thr Thr Thr Pro Pro Gln
            245                 250                 255

Lys Gln Glu Pro Ile Asp Lys Glu Leu Tyr Pro Leu Thr Ser Leu Arg
            260                 265                 270

Ser Leu Phe Gly Asn Asp Pro Ser Ser Gln
            275                 280

<210> SEQ ID NO 230
<211> LENGTH: 282
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 230

Met Gly Ala Arg Ala Ser Gly Ser Lys Ser Gly Ser Gly Ser Asp Ser
1               5                   10                  15

Gly Ser Lys Ile Glu Glu Leu Phe Lys Lys His Lys Ile Val Ala Val
            20                  25                  30

Leu Arg Ala Asn Ser Val Glu Glu Ala Lys Lys Lys Ala Leu Ala Val
            35                  40                  45

Phe Leu Gly Gly Val His Leu Ile Glu Ile Thr Phe Thr Val Pro Asp
        50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
        115                 120                 125

Met Thr Pro Thr Glu Leu Val Lys Ala Met Lys Leu Gly His Thr Ile
    130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175

Asn Leu Asp Asn Val Cys Glu Trp Phe Lys Ala Gly Val Leu Ala Val
            180                 185                 190
```

```
Gly Val Gly Ser Ala Leu Val Lys Gly Thr Pro Val Glu Val Ala Glu
            195                 200                 205

Lys Ala Lys Ala Phe Val Glu Lys Ile Arg Gly Cys Thr Glu Gln Lys
        210                 215                 220

Leu Ile Ser Glu Glu Asp Leu Gln Ser Arg Pro Glu Pro Thr Ala Pro
225                 230                 235                 240

Pro Glu Glu Ser Phe Arg Ser Gly Val Glu Thr Thr Thr Pro Pro Gln
                245                 250                 255

Lys Gln Glu Pro Ile Asp Lys Glu Leu Tyr Pro Leu Thr Ser Leu Arg
                260                 265                 270

Ser Leu Phe Gly Asn Asp Pro Ser Ser Gln
                275                 280

<210> SEQ ID NO 231
<211> LENGTH: 282
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 231

Met Gly Ala Gln Phe Ser Gly Ser Lys Ser Gly Ser Gly Ser Asp Ser
1               5                   10                  15

Gly Ser Lys Ile Glu Glu Leu Phe Lys Lys His Lys Ile Val Ala Val
            20                  25                  30

Leu Arg Ala Asn Ser Val Glu Glu Ala Lys Lys Lys Ala Leu Ala Val
        35                  40                  45

Phe Leu Gly Gly Val His Leu Ile Glu Ile Thr Phe Thr Val Pro Asp
    50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
        115                 120                 125

Met Thr Pro Thr Glu Leu Val Lys Ala Met Lys Leu Gly His Thr Ile
    130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175

Asn Leu Asp Asn Val Cys Glu Trp Phe Lys Ala Gly Val Leu Ala Val
            180                 185                 190

Gly Val Gly Ser Ala Leu Val Lys Gly Thr Pro Val Glu Val Ala Glu
        195                 200                 205

Lys Ala Lys Ala Phe Val Glu Lys Ile Arg Gly Cys Thr Glu Gln Lys
    210                 215                 220

Leu Ile Ser Glu Glu Asp Leu Gln Ser Arg Pro Glu Pro Thr Ala Pro
```

```
            225                 230                 235                 240

Pro Glu Glu Ser Phe Arg Ser Gly Val Glu Thr Thr Thr Pro Pro Gln
                245                 250                 255

Lys Gln Glu Pro Ile Asp Lys Glu Leu Tyr Pro Leu Thr Ser Leu Arg
                260                 265                 270

Ser Leu Phe Gly Asn Asp Pro Ser Ser Gln
                275                 280

<210> SEQ ID NO 232
<211> LENGTH: 289
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (230)..(238)
<223> OTHER INFORMATION: Myc tag-optionally absent

<400> SEQUENCE: 232

Met Gly Cys Ile Lys Ser Lys Arg Lys Asp Asn Leu Asn Gly Ser Lys
1               5                   10                  15

Ser Gly Ser Gly Ser Asp Ser Gly Ser Lys Ile Glu Glu Leu Phe Lys
                20                  25                  30

Lys His Lys Ile Val Ala Val Leu Arg Ala Asn Ser Val Glu Glu Ala
                35                  40                  45

Lys Lys Lys Ala Leu Ala Val Phe Leu Gly Gly Val His Leu Ile Glu
                50                  55                  60

Ile Thr Phe Thr Val Pro Asp Ala Asp Thr Val Ile Lys Glu Leu Ser
65                  70                  75                  80

Phe Leu Lys Glu Met Gly Ala Ile Ile Gly Ala Gly Thr Val Thr Ser
                85                  90                  95

Val Glu Gln Cys Arg Lys Ala Val Glu Ser Gly Ala Glu Phe Ile Val
                100                 105                 110

Ser Pro His Leu Asp Glu Glu Ile Ser Gln Phe Cys Lys Glu Lys Gly
                115                 120                 125

Val Phe Tyr Met Pro Gly Val Met Thr Pro Thr Glu Leu Val Lys Ala
                130                 135                 140

Met Lys Leu Gly His Thr Ile Leu Lys Leu Phe Pro Gly Glu Val Val
145                 150                 155                 160

Gly Pro Gln Phe Val Lys Ala Met Lys Gly Pro Phe Pro Asn Val Lys
                165                 170                 175

Phe Val Pro Thr Gly Gly Val Asn Leu Asp Asn Val Cys Glu Trp Phe
                180                 185                 190

Lys Ala Gly Val Leu Ala Val Gly Val Gly Ser Ala Leu Val Lys Gly
                195                 200                 205

Thr Pro Val Glu Val Ala Glu Lys Ala Lys Ala Phe Val Glu Lys Ile
                210                 215                 220

Arg Gly Cys Thr Glu Gln Lys Leu Ile Ser Glu Glu Asp Leu Gln Ser
225                 230                 235                 240

Arg Pro Glu Pro Thr Ala Pro Pro Glu Glu Ser Phe Arg Ser Gly Val
                245                 250                 255

Glu Thr Thr Thr Pro Pro Gln Lys Gln Glu Pro Ile Asp Lys Glu Leu
                260                 265                 270
```

Tyr Pro Leu Thr Ser Leu Arg Ser Leu Phe Gly Asn Asp Pro Ser Ser
        275                 280                 285

Gln

<210> SEQ ID NO 233
<211> LENGTH: 289
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (230)..(238)
<223> OTHER INFORMATION: Myc tag-optionally absent

<400> SEQUENCE: 233

Met Gly Cys Thr Leu Ser Ala Glu Glu Arg Ala Ala Leu Gly Ser Lys
1               5                   10                  15

Ser Gly Ser Gly Ser Asp Ser Gly Ser Lys Ile Glu Glu Leu Phe Lys
            20                  25                  30

Lys His Lys Ile Val Ala Val Leu Arg Ala Asn Ser Val Glu Glu Ala
        35                  40                  45

Lys Lys Lys Ala Leu Ala Val Phe Leu Gly Gly Val His Leu Ile Glu
    50                  55                  60

Ile Thr Phe Thr Val Pro Asp Ala Asp Thr Val Ile Lys Glu Leu Ser
65                  70                  75                  80

Phe Leu Lys Glu Met Gly Ala Ile Ile Gly Ala Gly Thr Val Thr Ser
                85                  90                  95

Val Glu Gln Cys Arg Lys Ala Val Glu Ser Gly Ala Glu Phe Ile Val
            100                 105                 110

Ser Pro His Leu Asp Glu Glu Ile Ser Gln Phe Cys Lys Glu Lys Gly
        115                 120                 125

Val Phe Tyr Met Pro Gly Val Met Thr Pro Thr Glu Leu Val Lys Ala
    130                 135                 140

Met Lys Leu Gly His Thr Ile Leu Lys Leu Phe Pro Gly Glu Val Val
145                 150                 155                 160

Gly Pro Gln Phe Val Lys Ala Met Lys Gly Pro Phe Pro Asn Val Lys
                165                 170                 175

Phe Val Pro Thr Gly Gly Val Asn Leu Asp Asn Val Cys Glu Trp Phe
            180                 185                 190

Lys Ala Gly Val Leu Ala Val Gly Val Gly Ser Ala Leu Val Lys Gly
        195                 200                 205

Thr Pro Val Glu Val Ala Glu Lys Ala Lys Ala Phe Val Glu Lys Ile
    210                 215                 220

Arg Gly Cys Thr Glu Gln Lys Leu Ile Ser Glu Glu Asp Leu Gln Ser
225                 230                 235                 240

Arg Pro Glu Pro Thr Ala Pro Pro Glu Glu Ser Phe Arg Ser Gly Val
                245                 250                 255

Glu Thr Thr Thr Pro Pro Gln Lys Gln Glu Pro Ile Asp Lys Glu Leu
            260                 265                 270

Tyr Pro Leu Thr Ser Leu Arg Ser Leu Phe Gly Asn Asp Pro Ser Ser
        275                 280                 285

Gln

<210> SEQ ID NO 234
<211> LENGTH: 289
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (230)..(238)
<223> OTHER INFORMATION: Myc tag-optionally absent

<400> SEQUENCE: 234

```
Met Leu Cys Cys Met Arg Arg Thr Lys Gln Val Glu Lys Gly Ser Lys
1               5                   10                  15

Ser Gly Ser Gly Ser Asp Ser Gly Ser Lys Ile Glu Glu Leu Phe Lys
            20                  25                  30

Lys His Lys Ile Val Ala Val Leu Arg Ala Asn Ser Val Glu Glu Ala
        35                  40                  45

Lys Lys Lys Ala Leu Ala Val Phe Leu Gly Gly Val His Leu Ile Glu
    50                  55                  60

Ile Thr Phe Thr Val Pro Asp Ala Asp Thr Val Ile Lys Glu Leu Ser
65                  70                  75                  80

Phe Leu Lys Glu Met Gly Ala Ile Ile Gly Ala Gly Thr Val Thr Ser
                85                  90                  95

Val Glu Gln Cys Arg Lys Ala Val Glu Ser Gly Ala Glu Phe Ile Val
            100                 105                 110

Ser Pro His Leu Asp Glu Glu Ile Ser Gln Phe Cys Lys Glu Lys Gly
        115                 120                 125

Val Phe Tyr Met Pro Gly Val Met Thr Pro Thr Glu Leu Val Lys Ala
    130                 135                 140

Met Lys Leu Gly His Thr Ile Leu Lys Leu Phe Pro Gly Glu Val Val
145                 150                 155                 160

Gly Pro Gln Phe Val Lys Ala Met Lys Gly Pro Phe Pro Asn Val Lys
                165                 170                 175

Phe Val Pro Thr Gly Gly Val Asn Leu Asp Asn Val Cys Glu Trp Phe
            180                 185                 190

Lys Ala Gly Val Leu Ala Val Gly Val Gly Ser Ala Leu Val Lys Gly
        195                 200                 205

Thr Pro Val Glu Val Ala Glu Lys Ala Lys Ala Phe Val Glu Lys Ile
    210                 215                 220

Arg Gly Cys Thr Glu Gln Lys Leu Ile Ser Glu Glu Asp Leu Gln Ser
225                 230                 235                 240

Arg Pro Glu Pro Thr Ala Pro Pro Glu Glu Ser Phe Arg Ser Gly Val
                245                 250                 255

Glu Thr Thr Thr Pro Pro Gln Lys Gln Glu Pro Ile Asp Lys Glu Leu
            260                 265                 270

Tyr Pro Leu Thr Ser Leu Arg Ser Leu Phe Gly Asn Asp Pro Ser Ser
        275                 280                 285

Gln
```

<210> SEQ ID NO 235
<211> LENGTH: 278
<212> TYPE: PRT

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (270)..(278)
<223> OTHER INFORMATION: Myc tag-optionally absent

<400> SEQUENCE: 235
```

Met Gly Cys Ile Lys Ser Lys Arg Lys Asp Asn Leu Asn Leu Gln Ser
1               5                   10                  15

Arg Pro Glu Pro Thr Ala Pro Pro Glu Ser Phe Arg Ser Gly Val
            20                  25                  30

Glu Thr Thr Thr Pro Pro Gln Lys Gln Glu Pro Ile Asp Lys Glu Leu
            35                  40                  45

Tyr Pro Leu Thr Ser Leu Arg Ser Leu Phe Gly Asn Asp Pro Ser Ser
        50                  55                  60

Gln Lys Ile Glu Glu Leu Phe Lys Lys His Lys Ile Val Ala Val Leu
65                  70                  75                  80

Arg Ala Asn Ser Val Glu Gly Ala Lys Lys Ala Leu Ala Val Phe
                85                  90                  95

Leu Gly Gly Val His Leu Ile Glu Ile Thr Phe Thr Val Pro Asp Ala
                100                 105                 110

Asp Thr Val Ile Lys Glu Leu Ser Phe Leu Lys Glu Met Gly Ala Ile
                115                 120                 125

Ile Gly Ala Gly Thr Val Thr Ser Val Glu Gln Cys Arg Lys Ala Val
130                 135                 140

Glu Ser Gly Ala Glu Phe Ile Val Ser Pro His Leu Asp Glu Glu Ile
145                 150                 155                 160

Ser Gln Phe Cys Lys Glu Lys Gly Val Phe Tyr Met Pro Gly Val Met
                165                 170                 175

Thr Pro Thr Glu Leu Val Lys Ala Met Lys Leu Gly His Thr Ile Leu
                180                 185                 190

Lys Leu Phe Pro Gly Glu Val Val Gly Pro Gln Phe Val Lys Ala Met
                195                 200                 205

Lys Gly Pro Phe Pro Asn Val Lys Phe Val Pro Thr Gly Gly Val Asn
                210                 215                 220

Leu Asp Asn Val Cys Glu Trp Phe Lys Ala Gly Val Leu Ala Val Gly
225                 230                 235                 240

Val Gly Ser Ala Leu Val Lys Gly Thr Pro Val Glu Val Ala Glu Lys
                245                 250                 255

Ala Lys Ala Phe Val Glu Lys Ile Arg Gly Cys Thr Glu Gln Lys Leu
                260                 265                 270

Ile Ser Glu Glu Asp Leu
        275

```
<210> SEQ ID NO 236
<211> LENGTH: 399
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
```

<220> FEATURE:
<221> NAME/KEY: MISC_FEATURE
<222> LOCATION: (340)..(348)
<223> OTHER INFORMATION: Myc tag-optionally absent

<400> SEQUENCE: 236

```
Met His Gly Leu Gln Asp Asp Pro Asp Leu Gln Ala Leu Leu Lys Gly
1               5                   10                  15

Ser Gln Leu Leu Lys Val Lys Ser Ser Trp Arg Arg Glu Arg Phe
            20                  25                  30

Tyr Lys Leu Gln Glu Asp Cys Lys Thr Ile Trp Gln Glu Ser Arg Lys
            35                  40                  45

Val Met Arg Ser Pro Glu Ser Gln Leu Phe Ser Ile Glu Asp Ile Gln
50                  55                  60

Glu Val Arg Met Gly His Arg Thr Gly Leu Glu Lys Phe Ala Arg
65                  70                  75                  80

Asp Ile Pro Glu Asp Arg Cys Phe Ser Ile Val Phe Lys Asp Gln Arg
                85                  90                  95

Asn Thr Leu Asp Leu Ile Ala Pro Ser Pro Ala Asp Ala Gln His Trp
            100                 105                 110

Val Gln Gly Leu Arg Lys Ile Ile His His Ser Gly Ser Met Asp Gln
        115                 120                 125

Arg Gln Lys Gly Ser Gly Ser Lys Ile Glu Glu Leu Phe Lys Lys His
130                 135                 140

Lys Ile Val Ala Val Leu Arg Ala Asn Ser Val Glu Ala Lys Lys
145                 150                 155                 160

Lys Ala Leu Ala Val Phe Leu Gly Gly Val His Leu Ile Glu Ile Thr
                165                 170                 175

Phe Thr Val Pro Asp Ala Asp Thr Val Ile Lys Glu Leu Ser Phe Leu
            180                 185                 190

Lys Glu Met Gly Ala Ile Ile Gly Ala Gly Thr Val Thr Ser Val Glu
        195                 200                 205

Gln Cys Arg Lys Ala Val Glu Ser Gly Ala Glu Phe Ile Val Ser Pro
210                 215                 220

His Leu Asp Glu Glu Ile Ser Gln Phe Cys Lys Glu Lys Gly Val Phe
225                 230                 235                 240

Tyr Met Pro Gly Val Met Thr Pro Thr Glu Leu Val Lys Ala Met Lys
                245                 250                 255

Leu Gly His Thr Ile Leu Lys Leu Phe Pro Gly Glu Val Val Gly Pro
            260                 265                 270

Gln Phe Val Lys Ala Met Lys Gly Pro Phe Pro Asn Val Lys Phe Val
        275                 280                 285

Pro Thr Gly Gly Val Asn Leu Asp Asn Val Cys Glu Trp Phe Lys Ala
290                 295                 300

Gly Val Leu Ala Val Gly Val Gly Ser Ala Leu Val Lys Gly Thr Pro
305                 310                 315                 320

Val Glu Val Ala Glu Lys Ala Lys Ala Phe Val Glu Lys Ile Arg Gly
                325                 330                 335

Cys Thr Glu Gln Lys Leu Ile Ser Glu Glu Asp Leu Gln Ser Arg Pro
            340                 345                 350

Glu Pro Thr Ala Pro Pro Glu Glu Ser Phe Arg Ser Gly Val Glu Thr
        355                 360                 365

Thr Thr Pro Pro Gln Lys Gln Glu Pro Ile Asp Lys Glu Leu Tyr Pro
370                 375                 380
```

```
Leu Thr Ser Leu Arg Ser Leu Phe Gly Asn Asp Pro Ser Ser Gln
385                 390                 395
```

<210> SEQ ID NO 237
<211> LENGTH: 368
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (230)..(238)
<223> OTHER INFORMATION: Myc tag-optionally absent

<400> SEQUENCE: 237

```
Met Arg Arg Val Ile Leu Pro Thr Ala Pro Glu Tyr Met Glu Ala
1               5                   10                  15

Ile Tyr Pro Val Arg Gly Ser Gly Ser Lys Ile Glu Glu Leu Phe Lys
                20                  25                  30

Lys His Lys Ile Val Ala Val Leu Arg Ala Asn Ser Val Glu Glu Ala
                35                  40                  45

Lys Lys Lys Ala Leu Ala Val Phe Leu Gly Gly Val His Leu Ile Glu
50                  55                  60

Ile Thr Phe Thr Val Pro Asp Ala Asp Thr Val Ile Lys Glu Leu Ser
65                  70                  75                  80

Phe Leu Lys Glu Met Gly Ala Ile Ile Gly Ala Gly Thr Val Thr Ser
                85                  90                  95

Val Glu Gln Cys Arg Lys Ala Val Glu Ser Gly Ala Glu Phe Ile Val
                100                 105                 110

Ser Pro His Leu Asp Glu Glu Ile Ser Gln Phe Cys Lys Glu Lys Gly
                115                 120                 125

Val Phe Tyr Met Pro Gly Val Met Thr Pro Thr Glu Leu Val Lys Ala
                130                 135                 140

Met Lys Leu Gly His Thr Ile Leu Lys Leu Phe Pro Gly Glu Val Val
145                 150                 155                 160

Gly Pro Gln Phe Val Lys Ala Met Lys Gly Pro Phe Pro Asn Val Lys
                165                 170                 175

Phe Val Pro Thr Gly Gly Val Asn Leu Asp Asn Val Cys Glu Trp Phe
                180                 185                 190

Lys Ala Gly Val Leu Ala Val Gly Val Gly Ser Ala Leu Val Lys Gly
                195                 200                 205

Thr Pro Val Glu Val Ala Glu Lys Ala Lys Ala Phe Val Glu Lys Ile
                210                 215                 220

Arg Gly Cys Thr Glu Gln Lys Leu Ile Ser Glu Glu Asp Leu His Gly
225                 230                 235                 240

Leu Gln Asp Asp Pro Asp Leu Gln Ala Leu Leu Lys Gly Ser Gln Leu
                245                 250                 255

Leu Lys Val Lys Ser Ser Ser Trp Arg Arg Glu Arg Phe Tyr Lys Leu
                260                 265                 270

Gln Glu Asp Cys Lys Thr Ile Trp Gln Glu Ser Arg Lys Val Met Arg
                275                 280                 285

Ser Pro Glu Ser Gln Leu Phe Ser Ile Glu Asp Ile Gln Glu Val Arg
                290                 295                 300

Met Gly His Arg Thr Glu Gly Leu Glu Lys Phe Ala Arg Asp Ile Pro
```

```
            305                 310                 315                 320
Glu Asp Arg Cys Phe Ser Ile Val Phe Lys Asp Gln Arg Asn Thr Leu
                325                 330                 335
Asp Leu Ile Ala Pro Ser Pro Ala Asp Ala Gln His Trp Val Gln Gly
                340                 345                 350
Leu Arg Lys Ile Ile His His Ser Gly Ser Met Asp Gln Arg Gln Lys
                355                 360                 365

<210> SEQ ID NO 238
<211> LENGTH: 400
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (392)..(400)
<223> OTHER INFORMATION: Myc tag-optionally absent

<400> SEQUENCE: 238

Met Leu Gln Ser Arg Pro Glu Pro Thr Ala Pro Pro Glu Glu Ser Phe
1               5                   10                  15
Arg Ser Gly Val Glu Thr Thr Thr Pro Pro Gln Lys Gln Glu Pro Ile
                20                  25                  30
Asp Lys Glu Leu Tyr Pro Leu Thr Ser Leu Arg Ser Leu Phe Gly Asn
                35                  40                  45
Asp Pro Ser Ser Gln His Gly Leu Gln Asp Asp Pro Asp Leu Gln Ala
            50                  55                  60
Leu Leu Lys Gly Ser Gln Leu Leu Lys Val Lys Ser Ser Trp Arg
65                  70                  75                  80
Arg Glu Arg Phe Tyr Lys Leu Gln Glu Asp Cys Lys Thr Ile Trp Gln
                85                  90                  95
Glu Ser Arg Lys Val Met Arg Ser Pro Glu Ser Gln Leu Phe Ser Ile
                100                 105                 110
Glu Asp Ile Gln Glu Val Arg Met Gly His Arg Thr Glu Gly Leu Glu
            115                 120                 125
Lys Phe Ala Arg Asp Ile Pro Glu Asp Arg Cys Phe Ser Ile Val Phe
            130                 135                 140
Lys Asp Gln Arg Asn Thr Leu Asp Leu Ile Ala Pro Ser Pro Ala Asp
145                 150                 155                 160
Ala Gln His Trp Val Gln Gly Leu Arg Lys Ile Ile His His Ser Gly
                165                 170                 175
Ser Met Asp Gln Arg Gln Lys Gly Ser Gly Ser Lys Ile Glu Glu Leu
                180                 185                 190
Phe Lys Lys His Lys Ile Val Ala Val Leu Arg Ala Asn Ser Val Glu
                195                 200                 205
Glu Ala Lys Lys Lys Ala Leu Ala Val Phe Leu Gly Gly Val His Leu
            210                 215                 220
Ile Glu Ile Thr Phe Thr Val Pro Asp Ala Asp Thr Val Ile Lys Glu
225                 230                 235                 240
Leu Ser Phe Leu Lys Glu Met Gly Ala Ile Ile Gly Ala Gly Thr Val
                245                 250                 255
Thr Ser Val Glu Gln Cys Arg Lys Ala Val Glu Ser Gly Ala Glu Phe
                260                 265                 270
```

```
Ile Val Ser Pro His Leu Asp Glu Glu Ile Ser Gln Phe Cys Lys Glu
        275                 280                 285

Lys Gly Val Phe Tyr Met Pro Gly Val Met Thr Pro Thr Glu Leu Val
290                 295                 300

Lys Ala Met Lys Leu Gly His Thr Ile Leu Lys Leu Phe Pro Gly Glu
305                 310                 315                 320

Val Val Gly Pro Gln Phe Val Lys Ala Met Lys Gly Pro Phe Pro Asn
                325                 330                 335

Val Lys Phe Val Pro Thr Gly Gly Val Asn Leu Asp Asn Val Cys Glu
                340                 345                 350

Trp Phe Lys Ala Gly Val Leu Ala Val Gly Val Gly Ser Ala Leu Val
                355                 360                 365

Lys Gly Thr Pro Val Glu Val Ala Glu Lys Ala Lys Ala Phe Val Glu
370                 375                 380

Lys Ile Arg Gly Cys Thr Glu Gln Lys Leu Ile Ser Glu Glu Asp Leu
385                 390                 395                 400

<210> SEQ ID NO 239
<211> LENGTH: 396
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (388)..(396)
<223> OTHER INFORMATION: Myc tag-optionally absent

<400> SEQUENCE: 239

Met His Gly Leu Gln Asp Asp Pro Asp Leu Gln Ala Leu Leu Lys Gly
1               5                   10                  15

Ser Gln Leu Leu Lys Val Lys Ser Ser Ser Trp Arg Arg Glu Arg Phe
                20                  25                  30

Tyr Lys Leu Gln Glu Asp Cys Lys Thr Ile Trp Gln Glu Ser Arg Lys
            35                  40                  45

Val Met Arg Ser Pro Glu Ser Gln Leu Phe Ser Ile Glu Asp Ile Gln
50                  55                  60

Glu Val Arg Met Gly His Arg Thr Gly Leu Glu Lys Phe Ala Arg
65                  70                  75                  80

Asp Ile Pro Glu Asp Arg Cys Phe Ser Ile Val Phe Lys Asp Gln Arg
                85                  90                  95

Asn Thr Leu Asp Leu Ile Ala Pro Ser Pro Ala Asp Ala Gln His Trp
            100                 105                 110

Val Gln Gly Leu Arg Lys Ile Ile His His Ser Gly Ser Met Asp Gln
        115                 120                 125

Arg Gln Lys Leu Gln Ser Arg Pro Glu Pro Thr Ala Pro Pro Glu Glu
    130                 135                 140

Ser Phe Arg Ser Gly Val Glu Thr Thr Thr Pro Pro Gln Lys Gln Glu
145                 150                 155                 160

Pro Ile Asp Lys Glu Leu Tyr Pro Leu Thr Ser Leu Arg Ser Leu Phe
                165                 170                 175

Gly Asn Asp Pro Ser Ser Gln Lys Ile Glu Glu Leu Phe Lys Lys His
            180                 185                 190
```

```
Lys Ile Val Ala Val Leu Arg Ala Asn Ser Val Glu Glu Ala Lys Lys
            195                 200                 205

Lys Ala Leu Ala Val Phe Leu Gly Gly Val His Leu Ile Glu Ile Thr
    210                 215                 220

Phe Thr Val Pro Asp Ala Asp Thr Val Ile Lys Glu Leu Ser Phe Leu
225                 230                 235                 240

Lys Glu Met Gly Ala Ile Ile Gly Ala Gly Thr Val Thr Ser Val Glu
                245                 250                 255

Gln Cys Arg Lys Ala Val Glu Ser Ala Glu Phe Ile Val Ser Pro
            260                 265                 270

His Leu Asp Glu Glu Ile Ser Gln Phe Cys Lys Glu Lys Gly Val Phe
    275                 280                 285

Tyr Met Pro Gly Val Met Thr Pro Thr Glu Leu Val Lys Ala Met Lys
290                 295                 300

Leu Gly His Thr Ile Leu Lys Leu Phe Pro Gly Glu Val Val Gly Pro
305                 310                 315                 320

Gln Phe Val Lys Ala Met Lys Gly Pro Phe Pro Asn Val Lys Phe Val
                325                 330                 335

Pro Thr Gly Gly Val Asn Leu Asp Asn Val Cys Glu Trp Phe Lys Ala
            340                 345                 350

Gly Val Leu Ala Val Gly Val Gly Ser Ala Leu Val Lys Gly Thr Pro
    355                 360                 365

Val Glu Val Ala Glu Lys Ala Lys Ala Phe Val Glu Lys Ile Arg Gly
370                 375                 380

Cys Thr Glu Gln Lys Leu Ile Ser Glu Glu Asp Leu
385                 390                 395

<210> SEQ ID NO 240
<211> LENGTH: 395
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (206)..(214)
<223> OTHER INFORMATION: Myc tag-optionally absent

<400> SEQUENCE: 240

Met Lys Ile Glu Glu Leu Phe Lys Lys His Lys Ile Val Ala Val Leu
1               5                   10                  15

Arg Ala Asn Ser Val Glu Glu Ala Lys Lys Lys Ala Leu Ala Val Phe
            20                  25                  30

Leu Gly Gly Val His Leu Ile Glu Ile Thr Phe Thr Val Pro Asp Ala
        35                  40                  45

Asp Thr Val Ile Lys Glu Leu Ser Phe Leu Lys Glu Met Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Thr Ile Leu
```

```
            115                 120                 125
Lys Leu Phe Pro Gly Glu Val Gly Pro Gln Phe Val Lys Ala Met
    130                 135                 140

Lys Gly Pro Phe Pro Asn Val Lys Phe Val Pro Thr Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Pro Val Glu Val Ala Glu Lys
            180                 185                 190

Ala Lys Ala Phe Val Glu Lys Ile Arg Gly Cys Thr Glu Gln Lys Leu
            195                 200                 205

Ile Ser Glu Glu Asp Leu Gln Ser Arg Pro Glu Pro Thr Ala Pro Pro
    210                 215                 220

Glu Glu Ser Phe Arg Ser Gly Val Glu Thr Thr Thr Pro Pro Gln Lys
225                 230                 235                 240

Gln Glu Pro Ile Asp Lys Glu Leu Tyr Pro Leu Thr Ser Leu Arg Ser
                245                 250                 255

Leu Phe Gly Asn Asp Pro Ser Ser Gln His Gly Leu Gln Asp Asp Pro
                260                 265                 270

Asp Leu Gln Ala Leu Leu Lys Gly Ser Gln Leu Leu Lys Val Lys Ser
            275                 280                 285

Ser Ser Trp Arg Arg Glu Arg Phe Tyr Lys Leu Gln Glu Asp Cys Lys
    290                 295                 300

Thr Ile Trp Gln Glu Ser Arg Lys Val Met Arg Ser Pro Glu Ser Gln
305                 310                 315                 320

Leu Phe Ser Ile Glu Asp Ile Gln Glu Val Arg Met Gly His Arg Thr
                325                 330                 335

Glu Gly Leu Glu Lys Phe Ala Arg Asp Ile Pro Glu Asp Arg Cys Phe
            340                 345                 350

Ser Ile Val Phe Lys Asp Gln Arg Asn Thr Leu Asp Leu Ile Ala Pro
            355                 360                 365

Ser Pro Ala Asp Ala Gln His Trp Val Gln Gly Leu Arg Lys Ile Ile
    370                 375                 380

His His Ser Gly Ser Met Asp Gln Arg Gln Lys
385                 390                 395

<210> SEQ ID NO 241
<211> LENGTH: 251
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 241

Met Gly Ala Arg Ala Ser Gly Lys Ser Ser Gly Ser Asp Ser
1               5                   10                  15

Gly Ser Lys Ile Glu Glu Leu Phe Lys Lys His Lys Ile Val Ala Val
            20                  25                  30

Leu Arg Ala Asn Ser Val Glu Glu Ala Lys Lys Lys Ala Leu Ala Val
            35                  40                  45
```

```
Phe Leu Gly Gly Val His Leu Ile Glu Ile Thr Phe Thr Val Pro Asp
         50                  55                  60

Ala Asp Thr Val Ile Lys Glu Leu Ser Phe Leu Lys Glu Met Gly Ala
 65                  70                  75                  80

Ile Ile Gly Ala Gly Thr Val Thr Ser Val Glu Gln Cys Arg Lys Ala
                 85                  90                  95

Val Glu Ser Gly Ala Glu Phe Ile Val Ser Pro His Leu Asp Glu Glu
                100                 105                 110

Ile Ser Gln Phe Cys Lys Glu Lys Gly Val Phe Tyr Met Pro Gly Val
            115                 120                 125

Met Thr Pro Thr Glu Leu Val Lys Ala Met Lys Leu Gly His Thr Ile
130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175

Asn Leu Asp Asn Val Cys Glu Trp Phe Lys Ala Gly Val Leu Ala Val
                180                 185                 190

Gly Val Gly Ser Ala Leu Val Lys Gly Thr Pro Val Glu Val Ala Glu
            195                 200                 205

Lys Ala Lys Ala Phe Val Glu Lys Ile Arg Gly Cys Thr Glu Gln Lys
210                 215                 220

Leu Ile Ser Glu Glu Asp Leu Arg Arg Val Ile Leu Pro Thr Ala Pro
225                 230                 235                 240

Pro Glu Tyr Met Glu Ala Ile Tyr Pro Val Arg
                245                 250

<210> SEQ ID NO 242
<211> LENGTH: 282
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 242

Met Gly Ala Arg Ala Ser Gly Ser Lys Ser Gly Ser Gly Ser Asp Ser
 1               5                  10                  15

Gly Ser Lys Ile Glu Glu Leu Phe Lys Lys His Lys Ile Val Ala Val
                20                  25                  30

Leu Arg Ala Asn Ser Val Glu Glu Ala Lys Lys Lys Ala Leu Ala Val
            35                  40                  45

Phe Leu Gly Gly Val His Leu Ile Glu Ile Thr Phe Thr Val Pro Asp
         50                  55                  60

Ala Asp Thr Val Ile Lys Glu Leu Ser Phe Leu Lys Glu Met Gly Ala
 65                  70                  75                  80

Ile Ile Gly Ala Gly Thr Val Thr Ser Val Glu Gln Cys Arg Lys Ala
                 85                  90                  95

Val Glu Ser Gly Ala Glu Phe Ile Val Ser Pro His Leu Asp Glu Glu
                100                 105                 110
```

```
Ile Ser Gln Phe Cys Lys Glu Lys Gly Val Phe Tyr Met Pro Gly Val
            115                 120                 125

Met Thr Pro Thr Glu Leu Val Lys Ala Met Lys Leu Gly His Thr Ile
        130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175

Asn Leu Asp Asn Val Cys Glu Trp Phe Lys Ala Gly Val Leu Ala Val
            180                 185                 190

Gly Val Gly Ser Ala Leu Val Lys Gly Thr Pro Val Glu Val Ala Glu
        195                 200                 205

Lys Ala Lys Ala Phe Val Glu Lys Ile Arg Gly Cys Thr Glu Gln Lys
210                 215                 220

Leu Ile Ser Glu Glu Asp Leu Pro Ile Gln Gln Lys Ser Gln His Asn
225                 230                 235                 240

Lys Ser Val Val Gln Glu Thr Pro Gln Thr Gln Asn Leu Tyr Pro Asp
                245                 250                 255

Leu Ser Glu Ile Lys Lys Glu Tyr Asn Val Lys Glu Lys Asp Gln Val
            260                 265                 270

Glu Asp Leu Asn Leu Asp Ser Leu Trp Glu
        275                 280

<210> SEQ ID NO 243
<211> LENGTH: 251
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 243

Met Gly Ala Arg Ala Ser Gly Ser Lys Ser Gly Ser Gly Ser Asp Ser
1               5                   10                  15

Gly Ser Lys Ile Glu Glu Leu Phe Lys Lys His Lys Ile Val Ala Val
            20                  25                  30

Leu Arg Ala Asn Ser Val Glu Glu Ala Lys Lys Lys Ala Leu Ala Val
        35                  40                  45

Phe Leu Gly Gly Val His Leu Ile Glu Ile Thr Phe Thr Val Pro Asp
    50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Gln Cys Arg Lys Ala
                85                  90                  95

Val Glu Ser Gly Ala Glu Phe Ile Val Ser Pro His Leu Asp Glu Glu
                100                 105                 110

Ile Ser Gln Phe Cys Lys Glu Lys Gly Val Phe Tyr Met Pro Gly Val
            115                 120                 125

Met Thr Pro Thr Glu Leu Val Lys Ala Met Lys Leu Gly His Thr Ile
        130                 135                 140

Leu Lys Leu Phe Pro Gly Glu Val Val Gly Pro Gln Phe Val Lys Ala
```

```
145                 150                 155                 160
Met Lys Gly Pro Phe Pro Asn Val Lys Phe Val Pro Thr Gly Gly Val
                165                 170                 175

Asn Leu Asp Asn Val Cys Glu Trp Phe Lys Ala Gly Val Leu Ala Val
            180                 185                 190

Gly Val Gly Ser Ala Leu Val Lys Gly Thr Pro Val Glu Val Ala Glu
        195                 200                 205

Lys Ala Lys Ala Phe Val Glu Lys Ile Arg Gly Cys Thr Glu Gln Lys
    210                 215                 220

Leu Ile Ser Glu Glu Asp Leu Asn Pro Arg Gln Ser Ile Lys Ala Phe
225                 230                 235                 240

Pro Ile Val Ile Asn Ser Asp Gly Gly Glu Lys
                245                 250

<210> SEQ ID NO 244
<211> LENGTH: 305
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 244

Met Gly Ala Arg Ala Ser Gly Ser Lys Ser Gly Ser Gly Ser Asp Ser
1               5                   10                  15

Gly Ser Lys Ile Glu Glu Leu Phe Lys Lys His Lys Ile Val Ala Val
                20                  25                  30

Leu Arg Ala Asn Ser Val Glu Glu Ala Lys Lys Lys Ala Leu Ala Val
            35                  40                  45

Phe Leu Gly Gly Val His Leu Ile Glu Ile Thr Phe Thr Val Pro Asp
        50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
        115                 120                 125

Met Thr Pro Thr Glu Leu Val Lys Ala Met Lys Leu Gly His Thr Ile
130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175

Asn Leu Asp Asn Val Cys Glu Trp Phe Lys Ala Gly Val Leu Ala Val
            180                 185                 190

Gly Val Gly Ser Ala Leu Val Lys Gly Thr Pro Val Glu Val Ala Glu
        195                 200                 205

Lys Ala Lys Ala Phe Val Glu Lys Ile Arg Gly Cys Thr Glu Gln Lys
    210                 215                 220
```

```
Leu Ile Ser Glu Glu Asp Leu Gly Ser Gly Ser Gly Asp Gly Gly Arg
225                 230                 235                 240

Gly Ser Arg Gly Gly Asp Gly Ser Gly Gly Ser Ser Gly Leu Gln Ser
            245                 250                 255

Arg Pro Glu Pro Thr Ala Pro Pro Glu Glu Ser Phe Arg Ser Gly Val
        260                 265                 270

Glu Thr Thr Thr Pro Pro Gln Lys Gln Glu Pro Ile Asp Lys Glu Leu
        275                 280                 285

Tyr Pro Leu Thr Ser Leu Arg Ser Leu Phe Gly Asn Asp Pro Ser Ser
        290                 295                 300

Gln
305

<210> SEQ ID NO 245
<211> LENGTH: 304
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 245

Met Gly Ala Arg Ala Ser Gly Ser Lys Ser Gly Ser Gly Ser Asp Ser
1               5                   10                  15

Gly Ser Lys Ile Glu Glu Leu Phe Lys Lys His Lys Ile Val Ala Val
            20                  25                  30

Leu Arg Ala Asn Ser Val Glu Glu Ala Lys Lys Lys Ala Leu Ala Val
        35                  40                  45

Phe Leu Gly Gly Val His Leu Ile Glu Ile Thr Phe Thr Val Pro Asp
    50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
        115                 120                 125

Met Thr Pro Thr Glu Leu Val Lys Ala Met Lys Leu Gly His Thr Ile
    130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175

Asn Leu Asp Asn Val Cys Glu Trp Phe Lys Ala Gly Val Leu Ala Val
            180                 185                 190

Gly Val Gly Ser Ala Leu Val Lys Gly Thr Pro Val Glu Val Ala Glu
        195                 200                 205

Lys Ala Lys Ala Phe Val Glu Lys Ile Arg Gly Cys Thr Glu Gln Lys
    210                 215                 220
```

```
Leu Ile Ser Glu Glu Asp Leu Gly Ser Gly Ser Gly Asp Gly Gly Arg
225                 230                 235                 240

Gly Ser Arg Gly Gly Asp Gly Ser Gly Gly Ser Ser Gly Pro Ile Gln
            245                 250                 255

Gln Lys Ser Gln His Asn Lys Ser Val Val Gln Glu Thr Pro Gln Thr
        260                 265                 270

Gln Asn Leu Tyr Pro Asp Leu Ser Glu Ile Lys Lys Glu Tyr Asn Val
    275                 280                 285

Lys Glu Lys Asp Gln Val Glu Asp Leu Asn Leu Asp Ser Leu Trp Glu
290                 295                 300
```

<210> SEQ ID NO 246
<211> LENGTH: 273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 246

```
Met Gly Ala Arg Ala Ser Gly Ser Lys Ser Gly Ser Gly Ser Asp Ser
1               5                   10                  15

Gly Ser Lys Ile Glu Glu Leu Phe Lys Lys His Lys Ile Val Ala Val
            20                  25                  30

Leu Arg Ala Asn Ser Val Glu Glu Ala Lys Lys Lys Ala Leu Ala Val
        35                  40                  45

Phe Leu Gly Gly Val His Leu Ile Glu Ile Thr Phe Thr Val Pro Asp
    50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
        115                 120                 125

Met Thr Pro Thr Glu Leu Val Lys Ala Met Lys Leu Gly His Thr Ile
    130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175

Asn Leu Asp Asn Val Cys Glu Trp Phe Lys Ala Gly Val Leu Ala Val
            180                 185                 190

Gly Val Gly Ser Ala Leu Val Lys Gly Thr Pro Val Glu Val Ala Glu
        195                 200                 205

Lys Ala Lys Ala Phe Val Glu Lys Ile Arg Gly Cys Thr Glu Gln Lys
    210                 215                 220

Leu Ile Ser Glu Glu Asp Leu Gly Ser Gly Ser Gly Asp Gly Gly Arg
225                 230                 235                 240

Gly Ser Arg Gly Gly Asp Gly Ser Gly Gly Ser Ser Gly Asn Pro Arg
```

245                 250                 255

Gln Ser Ile Lys Ala Phe Pro Ile Val Ile Asn Ser Asp Gly Gly Glu
            260                 265                 270

Lys

<210> SEQ ID NO 247
<211> LENGTH: 263
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 247

Met Gly Ala Arg Ala Ser Gly Ser Lys Ser Gly Ser Gly Ser Asp Ser
1               5                   10                  15

Gly Ser Lys Ile Glu Glu Leu Phe Lys Lys His Lys Ile Val Ala Val
            20                  25                  30

Leu Arg Ala Asn Ser Val Glu Glu Ala Lys Lys Lys Ala Leu Ala Val
        35                  40                  45

Phe Leu Gly Gly Val His Leu Ile Glu Ile Thr Phe Thr Val Pro Asp
    50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
        115                 120                 125

Met Thr Pro Thr Glu Leu Val Lys Ala Met Lys Leu Gly His Thr Ile
    130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175

Asn Leu Asp Asn Val Cys Glu Trp Phe Lys Ala Gly Val Leu Ala Val
            180                 185                 190

Gly Val Gly Ser Ala Leu Val Lys Gly Thr Pro Val Glu Val Ala Glu
        195                 200                 205

Lys Ala Lys Ala Phe Val Glu Lys Ile Arg Gly Cys Thr Glu Gln Lys
    210                 215                 220

Leu Ile Ser Glu Glu Asp Leu Gly Ser Gly Gly Asp Gly Gly Arg
225                 230                 235                 240

Gly Ser Arg Gly Gly Asp Gly Ser Gly Gly Ser Gly Pro Thr Ala
                245                 250                 255

Pro Pro Glu Tyr Gly Gly Ser
            260

<210> SEQ ID NO 248
<211> LENGTH: 260

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 248
```

| Met | Gly | Ala | Arg | Ala | Ser | Gly | Ser | Lys | Ser | Gly | Ser | Gly | Ser | Asp | Ser |
|---|---|---|---|---|---|---|---|---|---|---|---|---|---|---|---|
| 1 | | | | 5 | | | | | 10 | | | | | 15 | |

Gly Ser Lys Ile Glu Glu Leu Phe Lys His Lys Ile Val Ala Val
                 20                    25                    30

Leu Arg Ala Asn Ser Val Glu Ala Lys Lys Ala Leu Ala Val
           35                    40                    45

Phe Leu Gly Gly Val His Leu Ile Glu Ile Thr Phe Thr Val Pro Asp
     50                       55                    60

Ala Asp Thr Val Ile Lys Glu Leu Ser Phe Leu Lys Glu Met Gly Ala
65                    70                    75                    80

Ile Ile Gly Ala Gly Thr Val Thr Ser Val Glu Gln Cys Arg Lys Ala
           85                    90                    95

Val Glu Ser Gly Ala Glu Phe Ile Val Ser Pro His Leu Asp Glu Glu
             100                   105                  110

Ile Ser Gln Phe Cys Lys Glu Lys Gly Val Phe Tyr Met Pro Gly Val
           115                   120                  125

Met Thr Pro Thr Glu Leu Val Lys Ala Met Lys Leu Gly His Thr Ile
         130                   135                  140

Leu Lys Leu Phe Pro Gly Glu Val Val Gly Pro Gln Phe Val Lys Ala
145                  150                  155              160

Met Lys Gly Pro Phe Pro Asn Val Lys Phe Val Pro Thr Gly Gly Val
               165                170                175

Asn Leu Asp Asn Val Cys Glu Trp Phe Lys Ala Gly Val Leu Ala Val
         180                   185                  190

Gly Val Gly Ser Ala Leu Val Lys Gly Thr Pro Val Glu Val Ala Glu
         195                   200                  205

Lys Ala Lys Ala Phe Val Glu Lys Ile Arg Gly Cys Thr Glu Gln Lys
       210                   215                  220

Leu Ile Ser Glu Glu Asp Leu Gly Ser Gly Ser Gly Asp Gly Gly Arg
225                  230                  235              240

Gly Ser Arg Gly Gly Asp Gly Ser Gly Gly Ser Ser Gly Pro Thr Ala
               245                250                255

Pro Gly Gly Ser
         260

```
<210> SEQ ID NO 249
<211> LENGTH: 262
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
```

```
<222> LOCATION: (223)..(231)
<223> OTHER INFORMATION: Myc tag-optionally absent

<400> SEQUENCE: 249

Met Gly Ala Arg Ala Ser Gly Ser Lys Ser Gly Ser Gly Ser Asp Ser
1               5                   10                  15

Gly Ser Lys Ile Glu Glu Leu Phe Lys Lys His Lys Ile Val Ala Val
                20                  25                  30

Leu Arg Ala Asn Ser Val Glu Glu Ala Lys Lys Lys Ala Leu Ala Val
            35                  40                  45

Phe Leu Gly Gly Val His Leu Ile Glu Ile Thr Phe Thr Val Pro Asp
50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Gln Cys Arg Lys Ala
                85                  90                  95

Val Glu Ser Gly Ala Glu Phe Ile Val Ser Pro His Leu Asp Glu Glu
                100                 105                 110

Ile Ser Gln Phe Cys Lys Glu Lys Gly Val Phe Tyr Met Pro Gly Val
            115                 120                 125

Met Thr Pro Thr Glu Leu Val Lys Ala Met Lys Leu Gly His Thr Ile
130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175

Asn Leu Asp Asn Val Cys Glu Trp Phe Lys Ala Gly Val Leu Ala Val
            180                 185                 190

Gly Val Gly Ser Ala Leu Val Lys Gly Thr Pro Val Glu Val Ala Glu
        195                 200                 205

Lys Ala Lys Ala Phe Val Glu Lys Ile Arg Gly Cys Thr Glu Gln Lys
210                 215                 220

Leu Ile Ser Glu Glu Asp Leu Gly Ser Gly Ser Gly Asp Gly Gly Arg
225                 230                 235                 240

Gly Ser Arg Gly Gly Asp Gly Ser Gly Ser Ser Gly Tyr Pro Leu
                245                 250                 255

Thr Ser Leu Gly Gly Ser
            260

<210> SEQ ID NO 250
<211> LENGTH: 260
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 250

Met Gly Ala Arg Ala Ser Gly Ser Lys Ser Gly Ser Gly Ser Asp Ser
1               5                   10                  15

Gly Ser Lys Ile Glu Glu Leu Phe Lys Lys His Lys Ile Val Ala Val
                20                  25                  30
```

```
Leu Arg Ala Asn Ser Val Glu Glu Ala Lys Lys Lys Ala Leu Ala Val
            35                  40                  45

Phe Leu Gly Gly Val His Leu Ile Glu Ile Thr Phe Thr Val Pro Asp
     50                  55                  60

Ala Asp Thr Val Ile Lys Glu Leu Ser Phe Leu Lys Glu Met Gly Ala
 65                  70                  75                  80

Ile Ile Gly Ala Gly Thr Val Thr Ser Val Glu Gln Cys Arg Lys Ala
                 85                  90                  95

Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
        115                 120                 125

Met Thr Pro Thr Glu Leu Val Lys Ala Met Lys Leu Gly His Thr Ile
    130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175

Asn Leu Asp Asn Val Cys Glu Trp Phe Lys Ala Gly Val Leu Ala Val
            180                 185                 190

Gly Val Gly Ser Ala Leu Val Lys Gly Thr Pro Val Glu Val Ala Glu
        195                 200                 205

Lys Ala Lys Ala Phe Val Glu Lys Ile Arg Gly Cys Thr Glu Gln Lys
    210                 215                 220

Leu Ile Ser Glu Glu Asp Leu Gly Ser Gly Gly Asp Gly Gly Arg
225                 230                 235                 240

Gly Ser Arg Gly Gly Asp Gly Ser Gly Gly Ser Ser Gly Tyr Pro Asp
                245                 250                 255

Leu Gly Gly Ser
            260

<210> SEQ ID NO 251
<211> LENGTH: 260
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 251

Met Gly Ala Arg Ala Ser Gly Ser Lys Ser Gly Ser Gly Ser Asp Ser
 1               5                  10                  15

Gly Ser Lys Ile Glu Glu Leu Phe Lys Lys His Lys Ile Val Ala Val
             20                  25                  30

Leu Arg Ala Asn Ser Val Glu Glu Ala Lys Lys Lys Ala Leu Ala Val
            35                  40                  45

Phe Leu Gly Gly Val His Leu Ile Glu Ile Thr Phe Thr Val Pro Asp
     50                  55                  60

Ala Asp Thr Val Ile Lys Glu Leu Ser Phe Leu Lys Glu Met Gly Ala
 65                  70                  75                  80
```

```
Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
        115                 120                 125

Met Thr Pro Thr Glu Leu Val Lys Ala Met Lys Leu Gly His Thr Ile
130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175

Asn Leu Asp Asn Val Cys Glu Trp Phe Lys Ala Gly Val Leu Ala Val
            180                 185                 190

Gly Val Gly Ser Ala Leu Val Lys Gly Thr Pro Val Glu Val Ala Glu
        195                 200                 205

Lys Ala Lys Ala Phe Val Glu Lys Ile Arg Gly Cys Thr Glu Gln Lys
210                 215                 220

Leu Ile Ser Glu Glu Asp Leu Gly Ser Gly Gly Asp Gly Arg
225                 230                 235                 240

Gly Ser Arg Gly Gly Asp Gly Ser Gly Gly Ser Ser Gly Phe Pro Ile
                245                 250                 255

Val Gly Gly Ser
            260

<210> SEQ ID NO 252
<211> LENGTH: 375
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (237)..(245)
<223> OTHER INFORMATION: Myc tag-optionally absent

<400> SEQUENCE: 252

Met Leu Gln Ser Arg Pro Glu Pro Thr Ala Pro Glu Glu Ser Phe
1               5                   10                  15

Arg Ser Gly Val Glu Thr Thr Thr Pro Pro Gln Lys Gln Glu Pro Ile
            20                  25                  30

Asp Lys Glu Leu Tyr Pro Leu Thr Ser Leu Arg Ser Leu Phe Gly Asn
        35                  40                  45

Asp Pro Ser Ser Gln Ser Gln Ala Ile Gly Ile Leu Glu Leu Thr Ser
    50                  55                  60

Ile Ala Ala Gly Met Glu Leu Gly Asp Ala Met Leu Lys Ser Ala Asn
65                  70                  75                  80

Val Asp Leu Leu Val Ser Lys Thr Ile Ser Pro Gly Lys Phe Leu Leu
                85                  90                  95

Met Leu Gly Gly Asp Ile Gly Ala Ile Gln Gln Ala Ile Glu Thr Gly
            100                 105                 110

Thr Ser Gln Ala Gly Glu Leu Leu Val Asp Ser Leu Val Leu Ala Asn
        115                 120                 125

Ile His Pro Ser Val Leu Pro Ala Ile Ser Gly Leu Asn Ser Val Asp
```

```
                   130                 135                 140
Lys Arg Gln Ala Val Gly Ile Val Glu Thr Trp Ser Val Ala Ala Cys
145                 150                 155                 160

Ile Ser Ala Ala Asp Arg Ala Val Lys Gly Ser Asn Val Thr Leu Val
                165                 170                 175

Arg Val His Met Ala Phe Gly Ile Gly Lys Cys Tyr Met Val Val
                180                 185                 190

Ala Gly Asp Val Ser Asp Val Ala Leu Ala Val Thr Val Ala Ser Ser
                195                 200                 205

Ser Ala Gly Ala Tyr Gly Leu Leu Val Tyr Ala Ser Leu Ile Pro Arg
                210                 215                 220

Pro His Glu Ala Met Trp Arg Gln Met Val Glu Gly Gln Lys Leu Ile
225                 230                 235                 240

Ser Glu Glu Asp Leu His Gly Leu Gln Asp Asp Pro Asp Leu Gln Ala
                245                 250                 255

Leu Leu Lys Gly Ser Gln Leu Leu Lys Val Lys Ser Ser Ser Trp Arg
                260                 265                 270

Arg Glu Arg Phe Tyr Lys Leu Gln Glu Asp Cys Lys Thr Ile Trp Gln
                275                 280                 285

Glu Ser Arg Lys Val Met Arg Ser Pro Glu Ser Gln Leu Phe Ser Ile
                290                 295                 300

Glu Asp Ile Gln Glu Val Arg Met Gly His Arg Thr Glu Gly Leu Glu
305                 310                 315                 320

Lys Phe Ala Arg Asp Ile Pro Glu Asp Arg Cys Phe Ser Ile Val Phe
                325                 330                 335

Lys Asp Gln Arg Asn Thr Leu Asp Leu Ile Ala Pro Ser Pro Ala Asp
                340                 345                 350

Ala Gln His Trp Val Gln Gly Leu Arg Lys Ile Ile His His Ser Gly
                355                 360                 365

Ser Met Asp Gln Arg Gln Lys
                370                 375

<210> SEQ ID NO 253
<211> LENGTH: 634
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (575)..(583)
<223> OTHER INFORMATION: Myc tag-optionally absent

<400> SEQUENCE: 253

Met His Gly Leu Gln Asp Asp Pro Asp Leu Gln Ala Leu Leu Lys Gly
1               5                   10                  15

Ser Gln Leu Leu Lys Val Lys Ser Ser Ser Trp Arg Arg Glu Arg Phe
                20                  25                  30

Tyr Lys Leu Gln Glu Asp Cys Lys Thr Ile Trp Gln Glu Ser Arg Lys
                35                  40                  45

Val Met Arg Ser Pro Glu Ser Gln Leu Phe Ser Ile Glu Asp Ile Gln
                50                  55                  60

Glu Val Arg Met Gly His Arg Thr Glu Gly Leu Glu Lys Phe Ala Arg
65                  70                  75                  80
```

-continued

Asp Ile Pro Glu Asp Arg Cys Phe Ser Ile Val Phe Lys Asp Gln Arg
                85                  90                  95

Asn Thr Leu Asp Leu Ile Ala Pro Ser Pro Ala Asp Ala Gln His Trp
            100                 105                 110

Val Gln Gly Leu Arg Lys Ile Ile His His Ser Gly Ser Met Asp Gln
        115                 120                 125

Arg Gln Lys Lys Gly Glu Glu Leu Phe Thr Gly Val Val Pro Ile Leu
    130                 135                 140

Val Glu Leu Asp Gly Asp Val Asn Gly His Lys Phe Ser Val Arg Gly
145                 150                 155                 160

Glu Gly Glu Gly Asp Ala Thr Asn Gly Lys Leu Thr Leu Lys Phe Ile
                165                 170                 175

Cys Thr Thr Gly Lys Leu Pro Val Pro Trp Pro Thr Leu Val Thr Thr
            180                 185                 190

Leu Thr Tyr Gly Val Gln Cys Phe Ala Arg Tyr Pro Asp His Met Lys
        195                 200                 205

Gln His Asp Phe Phe Lys Ser Ala Met Pro Glu Gly Tyr Val Gln Glu
    210                 215                 220

Arg Thr Ile Ser Phe Lys Asp Asp Gly Thr Tyr Lys Thr Arg Ala Glu
225                 230                 235                 240

Val Lys Phe Glu Gly Asp Thr Leu Val Asn Arg Ile Glu Leu Lys Gly
                245                 250                 255

Ile Asp Phe Lys Glu Asp Gly Asn Ile Leu Gly His Lys Leu Glu Tyr
            260                 265                 270

Asn Phe Asn Ser His Asn Val Tyr Ile Thr Ala Asp Lys Gln Lys Asn
        275                 280                 285

Gly Ile Lys Ala Asn Phe Lys Ile Arg His Asn Val Glu Asp Gly Ser
    290                 295                 300

Val Gln Leu Ala Asp His Tyr Gln Gln Asn Thr Pro Ile Gly Asp Gly
305                 310                 315                 320

Pro Val Leu Leu Pro Asp Asn His Tyr Leu Ser Thr Gln Ser Val Leu
                325                 330                 335

Ser Lys Asp Pro Asn Glu Lys Arg Asp His Met Val Leu Leu Glu Phe
            340                 345                 350

Val Thr Ala Ala Gly Ile Thr His Gly Met Asp Glu Leu Tyr Gly Ser
        355                 360                 365

Gly Ser Lys Ile Glu Glu Leu Phe Lys Lys His Lys Ile Val Ala Val
    370                 375                 380

Leu Arg Ala Asn Ser Val Glu Glu Ala Lys Lys Lys Ala Leu Ala Val
385                 390                 395                 400

Phe Leu Gly Gly Val His Leu Ile Glu Ile Thr Phe Thr Val Pro Asp
                405                 410                 415

Ala Asp Thr Val Ile Lys Glu Leu Ser Phe Leu Lys Glu Met Gly Ala
            420                 425                 430

Ile Ile Gly Ala Gly Thr Val Thr Ser Val Glu Gln Cys Arg Lys Ala
        435                 440                 445

Val Glu Ser Gly Ala Glu Phe Ile Val Ser Pro His Leu Asp Glu Glu
    450                 455                 460

Ile Ser Gln Phe Cys Lys Glu Lys Gly Val Phe Tyr Met Pro Gly Val
465                 470                 475                 480

Met Thr Pro Thr Glu Leu Val Lys Ala Met Lys Leu Gly His Thr Ile
                485                 490                 495

-continued

```
Leu Lys Leu Phe Pro Gly Glu Val Val Gly Pro Gln Phe Val Lys Ala
            500                 505                 510
Met Lys Gly Pro Phe Pro Asn Val Lys Phe Val Pro Thr Gly Gly Val
        515                 520                 525
Asn Leu Asp Asn Val Cys Glu Trp Phe Lys Ala Gly Val Leu Ala Val
    530                 535                 540
Gly Val Gly Ser Ala Leu Val Lys Gly Thr Pro Val Glu Val Ala Glu
545                 550                 555                 560
Lys Ala Lys Ala Phe Val Glu Lys Ile Arg Gly Cys Thr Glu Gln Lys
                565                 570                 575
Leu Ile Ser Glu Glu Asp Leu Gln Ser Arg Pro Glu Pro Thr Ala Pro
            580                 585                 590
Pro Glu Glu Ser Phe Arg Ser Gly Val Glu Thr Thr Thr Pro Pro Gln
        595                 600                 605
Lys Gln Glu Pro Ile Asp Lys Glu Leu Tyr Pro Leu Thr Ser Leu Arg
    610                 615                 620
Ser Leu Phe Gly Asn Asp Pro Ser Ser Gln
625                 630

<210> SEQ ID NO 254
<211> LENGTH: 311
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 254

Met Gly Ala Arg Ala Ser Gly Ser Lys Ser Ser Gly Ser Gly Asp Ser
1               5                   10                  15
Gly Ser Lys Ile Glu Glu Leu Phe Lys Lys His Lys Ile Val Ala Val
            20                  25                  30
Leu Arg Ala Asn Ser Val Glu Glu Ala Lys Lys Lys Ala Leu Ala Val
        35                  40                  45
Phe Leu Gly Gly Val His Leu Ile Glu Ile Thr Phe Thr Val Pro Asp
    50                  55                  60
Ala Asp Thr Val Ile Lys Glu Leu Ser Phe Leu Lys Glu Met Gly Ala
65                  70                  75                  80
Ile Ile Gly Ala Gly Thr Val Thr Ser Val Glu Gln Cys Arg Lys Ala
                85                  90                  95
Val Glu Ser Gly Ala Glu Phe Ile Val Ser Pro His Leu Asp Glu Glu
            100                 105                 110
Ile Ser Gln Phe Cys Lys Glu Lys Gly Val Phe Tyr Met Pro Gly Val
        115                 120                 125
Met Thr Pro Thr Glu Leu Val Lys Ala Met Lys Leu Gly His Thr Ile
    130                 135                 140
Leu Lys Leu Phe Pro Gly Glu Val Val Gly Pro Gln Phe Val Lys Ala
145                 150                 155                 160
Met Lys Gly Pro Phe Pro Asn Val Lys Phe Val Pro Thr Gly Gly Val
                165                 170                 175
Asn Leu Asp Asn Val Cys Glu Trp Phe Lys Ala Gly Val Leu Ala Val
```

```
            180                 185                 190
Gly Val Gly Ser Ala Leu Val Lys Gly Thr Pro Val Glu Val Ala Glu
            195                 200                 205

Lys Ala Lys Ala Phe Val Glu Lys Ile Arg Gly Cys Thr Glu Gln Lys
210                 215                 220

Leu Ile Ser Glu Glu Asp Leu Leu Gln Ser Arg Pro Glu Pro Thr Ala
225                 230                 235                 240

Pro Pro Glu Glu Ser Phe Arg Ser Gly Val Glu Thr Thr Thr Pro Pro
                245                 250                 255

Gln Lys Gln Glu Pro Ile Asp Lys Glu Leu Tyr Pro Leu Thr Ser Leu
            260                 265                 270

Arg Ser Leu Phe Gly Asn Asp Pro Ser Ser Gln Gly Gly Ser Lys Gly
            275                 280                 285

Ser Asp Arg Arg Arg Gly Ser Arg Pro Ser Gly Ala Glu Arg Arg
290                 295                 300

Arg Arg Arg Ala Ala Ala Ala
305                 310

<210> SEQ ID NO 255
<211> LENGTH: 329
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: myc tag-optionally absent

<400> SEQUENCE: 255

Met Gly Ala Arg Ala Ser Gly Ser Lys Ser Gly Ser Gly Ser Asp Ser
1               5                   10                  15

Gly Ser Lys Ile Glu Glu Leu Phe Lys His Lys Ile Val Ala Val
            20                  25                  30

Leu Arg Ala Asn Ser Val Glu Glu Ala Lys Lys Lys Ala Leu Ala Val
            35                  40                  45

Phe Leu Gly Gly Val His Leu Ile Glu Ile Thr Phe Thr Val Pro Asp
        50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
        115                 120                 125

Met Thr Pro Thr Glu Leu Val Lys Ala Met Lys Leu Gly His Thr Ile
130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175

Asn Leu Asp Asn Val Cys Glu Trp Phe Lys Ala Gly Val Leu Ala Val
            180                 185                 190
```

```
Gly Val Gly Ser Ala Leu Val Lys Gly Thr Pro Val Glu Val Ala Glu
            195                 200                 205

Lys Ala Lys Ala Phe Val Lys Ile Arg Gly Cys Thr Glu Gln Lys
210                 215                 220

Leu Ile Ser Glu Glu Asp Leu Leu Gln Ser Arg Pro Glu Pro Thr Ala
225                 230                 235                 240

Pro Pro Glu Glu Ser Phe Arg Ser Gly Val Glu Thr Thr Thr Pro Pro
            245                 250                 255

Gln Lys Gln Glu Pro Ile Asp Lys Glu Leu Tyr Pro Leu Thr Ser Leu
            260                 265                 270

Arg Ser Leu Phe Gly Asn Asp Pro Ser Ser Gln Gly Ser Phe Phe Arg
            275                 280                 285

Glu Asp Leu Ala Phe Leu Gln Gly Lys Ala Arg Glu Leu Gly Gly Ser
            290                 295                 300

Lys Gly Ser Asp Arg Arg Arg Gly Ser Arg Pro Ser Gly Ala Glu
305                 310                 315                 320

Arg Arg Arg Arg Arg Ala Ala Ala Ala
                325

<210> SEQ ID NO 256
<211> LENGTH: 310
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 256

Met Gly Ala Arg Ala Ser Gly Ser Lys Ser Gly Ser Gly Ser Asp Ser
1               5                   10                  15

Gly Ser Lys Met Glu Glu Leu Phe Lys His Lys Ile Val Ala Val
                20                  25                  30

Leu Arg Ala Asn Ser Val Glu Glu Ala Lys Lys Lys Ala Leu Ala Val
            35                  40                  45

Phe Leu Gly Gly Val His Leu Ile Glu Ile Thr Phe Thr Val Pro Asp
    50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
                100                 105                 110

Ile Ser Gln Phe Cys Lys Glu Lys Gly Val Phe Tyr Met Pro Gly Val
            115                 120                 125

Met Thr Pro Thr Glu Leu Val Lys Ala Met Lys Leu Gly His Thr Ile
    130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175
```

```
Asn Leu Lys Asn Val Cys Lys Trp Phe Lys Ala Gly Val Leu Ala Val
            180                 185                 190

Gly Val Gly Lys Ala Leu Val Lys Gly Thr Pro Val Glu Val Ala Lys
        195                 200                 205

Lys Ala Lys Ala Phe Val Lys Lys Ile Arg Gly Cys Thr Glu Gln Lys
    210                 215                 220

Leu Ile Ser Glu Glu Asp Leu Gln Ser Arg Pro Glu Pro Thr Ala Pro
225                 230                 235                 240

Pro Glu Glu Ser Phe Arg Ser Gly Val Glu Thr Thr Thr Pro Pro Gln
                245                 250                 255

Lys Gln Glu Pro Ile Asp Lys Glu Leu Tyr Pro Leu Thr Ser Leu Arg
            260                 265                 270

Ser Leu Phe Gly Asn Asp Pro Ser Ser Gln Gly Gly Ser Lys Gly Ser
        275                 280                 285

Asp Arg Arg Arg Gly Ser Arg Pro Ser Gly Ala Glu Arg Arg Arg
    290                 295                 300

Arg Arg Ala Ala Ala Ala
305                 310

<210> SEQ ID NO 257
<211> LENGTH: 328
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 257

Met Gly Ala Arg Ala Ser Gly Ser Lys Ser Ser Gly Ser Asp Ser
1               5                   10                  15

Gly Ser Lys Met Glu Glu Leu Phe Lys Lys His Lys Ile Val Ala Val
            20                  25                  30

Leu Arg Ala Asn Ser Val Glu Glu Ala Lys Lys Lys Ala Leu Ala Val
        35                  40                  45

Phe Leu Gly Gly Val His Leu Ile Glu Ile Thr Phe Thr Val Pro Asp
    50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
        115                 120                 125

Met Thr Pro Thr Glu Leu Val Lys Ala Met Lys Leu Gly His Thr Ile
    130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175

Asn Leu Lys Asn Val Cys Lys Trp Phe Lys Ala Gly Val Leu Ala Val
```

```
                    180                 185                 190
Gly Val Gly Lys Ala Leu Val Lys Gly Thr Pro Val Glu Val Ala Lys
            195                 200                 205

Lys Ala Lys Ala Phe Val Lys Lys Ile Arg Gly Cys Thr Glu Gln Lys
        210                 215                 220

Leu Ile Ser Glu Glu Asp Leu Gln Ser Arg Pro Glu Pro Thr Ala Pro
225                 230                 235                 240

Pro Glu Glu Ser Phe Arg Ser Gly Val Glu Thr Thr Thr Pro Pro Gln
                245                 250                 255

Lys Gln Glu Pro Ile Asp Lys Glu Leu Tyr Pro Leu Thr Ser Leu Arg
            260                 265                 270

Ser Leu Phe Gly Asn Asp Pro Ser Ser Gln Gly Ser Phe Phe Arg Glu
        275                 280                 285

Asp Leu Ala Phe Leu Gln Gly Lys Ala Arg Glu Leu Gly Gly Ser Lys
    290                 295                 300

Gly Ser Asp Arg Arg Arg Gly Ser Arg Pro Ser Gly Ala Glu Arg
305                 310                 315                 320

Arg Arg Arg Arg Ala Ala Ala Ala
                325

<210> SEQ ID NO 258
<211> LENGTH: 386
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 258

Met Gly Ala Arg Ala Ser Gly Ser Lys Ser Gly Ser Gly Ser Asp Ser
1               5                   10                  15

Gly Ser Lys Ile Glu Glu Leu Phe Lys Lys His Lys Ile Val Ala Val
            20                  25                  30

Leu Arg Ala Asn Ser Val Glu Glu Ala Lys Lys Lys Ala Leu Ala Val
        35                  40                  45

Phe Leu Gly Gly Val His Leu Ile Glu Ile Thr Phe Thr Val Pro Asp
    50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
        115                 120                 125

Met Thr Pro Thr Glu Leu Val Lys Ala Met Lys Leu Gly His Thr Ile
    130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175
```

```
Asn Leu Asp Asn Val Cys Glu Trp Phe Lys Ala Gly Val Leu Ala Val
            180                 185                 190

Gly Val Gly Ser Ala Leu Val Lys Gly Thr Pro Val Glu Val Ala Glu
        195                 200                 205

Lys Ala Lys Ala Phe Val Glu Lys Ile Arg Gly Cys Thr Glu Gln Lys
    210                 215                 220

Leu Ile Ser Glu Glu Asp Leu Leu Gln Ser Arg Pro Glu Pro Thr Ala
225                 230                 235                 240

Pro Pro Glu Glu Ser Phe Arg Ser Gly Val Glu Thr Thr Thr Pro Pro
                245                 250                 255

Gln Lys Gln Glu Pro Ile Asp Lys Glu Leu Tyr Pro Leu Thr Ser Leu
            260                 265                 270

Arg Ser Leu Phe Gly Asn Asp Pro Ser Ser Gln Gly Gly Ser Lys Gly
        275                 280                 285

Ser Ala Val Pro Glu Thr Arg Pro Asn His Thr Ile Tyr Ile Asn Asn
    290                 295                 300

Leu Asn Glu Lys Ile Lys Lys Asp Glu Leu Lys Lys Ser Leu His Ala
305                 310                 315                 320

Ile Phe Ser Arg Phe Gly Gln Ile Leu Asp Ile Leu Val Ser Arg Ser
                325                 330                 335

Leu Lys Met Arg Gly Gln Ala Phe Val Ile Phe Lys Glu Val Ser Ser
            340                 345                 350

Ala Thr Asn Ala Leu Arg Ser Met Gln Gly Phe Pro Phe Tyr Asp Lys
        355                 360                 365

Pro Met Arg Ile Gln Tyr Ala Lys Thr Asp Ser Asp Ile Ile Ala Lys
    370                 375                 380

Met Lys
385

<210> SEQ ID NO 259
<211> LENGTH: 404
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 259

Met Gly Ala Arg Ala Ser Gly Ser Lys Ser Gly Ser Gly Ser Asp Ser
1               5                   10                  15

Gly Ser Lys Ile Glu Glu Leu Phe Lys Lys His Lys Ile Val Ala Val
            20                  25                  30

Leu Arg Ala Asn Ser Val Glu Glu Ala Lys Lys Lys Ala Leu Ala Val
        35                  40                  45

Phe Leu Gly Gly Val His Leu Ile Glu Ile Thr Phe Thr Val Pro Asp
    50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95
```

```
Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
        115                 120                 125

Met Thr Pro Thr Glu Leu Val Lys Ala Met Lys Leu Gly His Thr Ile
    130                 135                 140

Leu Lys Leu Phe Pro Gly Val Val Gly Pro Gln Phe Val Lys Ala
145                 150                 155                 160

Met Lys Gly Pro Phe Pro Asn Val Lys Phe Val Pro Thr Gly Gly Val
                165                 170                 175

Asn Leu Asp Asn Val Cys Glu Trp Phe Lys Ala Gly Val Leu Ala Val
                180                 185                 190

Gly Val Gly Ser Ala Leu Val Lys Gly Thr Pro Val Glu Val Ala Glu
            195                 200                 205

Lys Ala Lys Ala Phe Val Glu Lys Ile Arg Gly Cys Thr Glu Gln Lys
210                 215                 220

Leu Ile Ser Glu Glu Asp Leu Leu Gln Ser Arg Pro Glu Pro Thr Ala
225                 230                 235                 240

Pro Pro Glu Glu Ser Phe Arg Ser Gly Val Glu Thr Thr Thr Pro Pro
                245                 250                 255

Gln Lys Gln Glu Pro Ile Asp Lys Glu Leu Tyr Pro Leu Thr Ser Leu
            260                 265                 270

Arg Ser Leu Phe Gly Asn Asp Pro Ser Ser Gln Gly Ser Phe Phe Arg
        275                 280                 285

Glu Asp Leu Ala Phe Leu Gln Gly Lys Ala Arg Glu Leu Gly Gly Ser
    290                 295                 300

Lys Gly Ser Ala Val Pro Glu Thr Arg Pro Asn His Thr Ile Tyr Ile
305                 310                 315                 320

Asn Asn Leu Asn Glu Lys Ile Lys Lys Asp Glu Leu Lys Lys Ser Leu
                325                 330                 335

His Ala Ile Phe Ser Arg Phe Gly Gln Ile Leu Asp Ile Leu Val Ser
            340                 345                 350

Arg Ser Leu Lys Met Arg Gly Gln Ala Phe Val Ile Phe Lys Glu Val
        355                 360                 365

Ser Ser Ala Thr Asn Ala Leu Arg Ser Met Gln Gly Phe Pro Phe Tyr
    370                 375                 380

Asp Lys Pro Met Arg Ile Gln Tyr Ala Lys Thr Asp Ser Asp Ile Ile
385                 390                 395                 400

Ala Lys Met Lys

<210> SEQ ID NO 260
<211> LENGTH: 385
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 260

Met Gly Ala Arg Ala Ser Gly Ser Lys Ser Gly Ser Gly Ser Asp Ser
1               5                   10                  15
```

Gly Ser Lys Met Glu Glu Leu Phe Lys His Lys Ile Val Ala Val
            20              25              30

Leu Arg Ala Asn Ser Val Glu Ala Lys Lys Lys Ala Leu Ala Val
            35              40              45

Phe Leu Gly Gly Val His Leu Ile Glu Ile Thr Phe Thr Val Pro Asp
 50              55              60

Ala Asp Thr Val Ile Lys Glu Leu Ser Phe Leu Lys Glu Met Gly Ala
 65              70              75              80

Ile Ile Gly Ala Gly Thr Val Thr Ser Val Glu Gln Cys Arg Lys Ala
                85              90              95

Val Glu Ser Gly Ala Glu Phe Ile Val Ser Pro His Leu Asp Glu Glu
            100             105             110

Ile Ser Gln Phe Cys Lys Glu Lys Gly Val Phe Tyr Met Pro Gly Val
            115             120             125

Met Thr Pro Thr Glu Leu Val Lys Ala Met Lys Leu Gly His Thr Ile
 130             135             140

Leu Lys Leu Phe Pro Gly Glu Val Val Gly Pro Gln Phe Val Lys Ala
145             150             155             160

Met Lys Gly Pro Phe Pro Asn Val Lys Phe Val Pro Thr Gly Gly Val
            165             170             175

Asn Leu Lys Asn Val Cys Lys Trp Phe Lys Ala Gly Val Leu Ala Val
            180             185             190

Gly Val Gly Lys Ala Leu Val Lys Gly Thr Pro Val Glu Val Ala Lys
            195             200             205

Lys Ala Lys Ala Phe Val Lys Lys Ile Arg Gly Cys Thr Glu Gln Lys
 210             215             220

Leu Ile Ser Glu Glu Asp Leu Gln Ser Arg Pro Glu Pro Thr Ala Pro
225             230             235             240

Pro Glu Glu Ser Phe Arg Ser Gly Val Glu Thr Thr Thr Pro Pro Gln
            245             250             255

Lys Gln Glu Pro Ile Asp Lys Glu Leu Tyr Pro Leu Thr Ser Leu Arg
            260             265             270

Ser Leu Phe Gly Asn Asp Pro Ser Gln Gly Gly Ser Lys Gly Ser
            275             280             285

Ala Val Pro Glu Thr Arg Pro Asn His Thr Ile Tyr Ile Asn Asn Leu
290             295             300

Asn Glu Lys Ile Lys Lys Asp Glu Leu Lys Lys Ser Leu His Ala Ile
305             310             315             320

Phe Ser Arg Phe Gly Gln Ile Leu Asp Ile Leu Val Ser Arg Ser Leu
            325             330             335

Lys Met Arg Gly Gln Ala Phe Val Ile Phe Lys Glu Val Ser Ser Ala
            340             345             350

Thr Asn Ala Leu Arg Ser Met Gln Gly Phe Pro Phe Tyr Asp Lys Pro
            355             360             365

Met Arg Ile Gln Tyr Ala Lys Thr Asp Ser Asp Ile Ile Ala Lys Met
 370             375             380

Lys
385

<210> SEQ ID NO 261
<211> LENGTH: 403
<212> TYPE: PRT
<213> ORGANISM: Artificial Sequence
<220> FEATURE:

```
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 261

Met Gly Ala Arg Ala Ser Gly Ser Lys Ser Gly Ser Gly Ser Asp Ser
1               5                   10                  15

Gly Ser Lys Met Glu Glu Leu Phe Lys Lys His Lys Ile Val Ala Val
            20                  25                  30

Leu Arg Ala Asn Ser Val Glu Glu Ala Lys Lys Lys Ala Leu Ala Val
        35                  40                  45

Phe Leu Gly Gly Val His Leu Ile Glu Ile Thr Phe Thr Val Pro Asp
    50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
        115                 120                 125

Met Thr Pro Thr Glu Leu Val Lys Ala Met Lys Leu Gly His Thr Ile
130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175

Asn Leu Lys Asn Val Cys Lys Trp Phe Lys Ala Gly Val Leu Ala Val
            180                 185                 190

Gly Val Gly Lys Ala Leu Val Lys Gly Thr Pro Val Glu Val Ala Lys
        195                 200                 205

Lys Ala Lys Ala Phe Val Lys Lys Ile Arg Gly Cys Thr Glu Gln Lys
210                 215                 220

Leu Ile Ser Glu Glu Asp Leu Gln Ser Arg Pro Glu Pro Thr Ala Pro
225                 230                 235                 240

Pro Glu Glu Ser Phe Arg Ser Gly Val Glu Thr Thr Thr Pro Pro Gln
                245                 250                 255

Lys Gln Glu Pro Ile Asp Lys Glu Leu Tyr Pro Leu Thr Ser Leu Arg
            260                 265                 270

Ser Leu Phe Gly Asn Asp Pro Ser Ser Gln Gly Ser Phe Phe Arg Glu
        275                 280                 285

Asp Leu Ala Phe Leu Gln Gly Lys Ala Arg Glu Leu Gly Gly Ser Lys
290                 295                 300

Gly Ser Ala Val Pro Glu Thr Arg Pro Asn His Thr Ile Tyr Ile Asn
305                 310                 315                 320

Asn Leu Asn Glu Lys Ile Lys Lys Asp Glu Leu Lys Lys Ser Leu His
                325                 330                 335

Ala Ile Phe Ser Arg Phe Gly Gln Ile Leu Asp Ile Leu Val Ser Arg
            340                 345                 350

Ser Leu Lys Met Arg Gly Gln Ala Phe Val Ile Phe Lys Glu Val Ser
```

```
                    355                 360                 365

Ser Ala Thr Asn Ala Leu Arg Ser Met Gln Gly Phe Pro Phe Tyr Asp
            370                 375                 380

Lys Pro Met Arg Ile Gln Tyr Ala Lys Thr Asp Ser Asp Ile Ile Ala
385                 390                 395                 400

Lys Met Lys

<210> SEQ ID NO 262
<211> LENGTH: 344
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 262

Met Gly Ala Arg Ala Ser Gly Ser Lys Ser Ser Gly Ser Asp Ser
1               5                   10                  15

Gly Ser Lys Ile Glu Glu Leu Phe Lys Lys His Lys Ile Val Ala Val
            20                  25                  30

Leu Arg Ala Asn Ser Val Glu Glu Ala Lys Lys Lys Ala Leu Ala Val
        35                  40                  45

Phe Leu Gly Gly Val His Leu Ile Glu Ile Thr Phe Thr Val Pro Asp
    50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
        115                 120                 125

Met Thr Pro Thr Glu Leu Val Lys Ala Met Lys Leu Gly His Thr Ile
    130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175

Asn Leu Asp Asn Val Cys Glu Trp Phe Lys Ala Gly Val Leu Ala Val
            180                 185                 190

Gly Val Gly Ser Ala Leu Val Lys Gly Thr Pro Val Glu Val Ala Glu
        195                 200                 205

Lys Ala Lys Ala Phe Val Glu Lys Ile Arg Gly Cys Thr Glu Gln Lys
    210                 215                 220

Leu Ile Ser Glu Glu Asp Leu Leu Gln Ser Arg Pro Glu Pro Thr Ala
225                 230                 235                 240

Pro Pro Glu Glu Ser Phe Arg Ser Gly Val Glu Thr Thr Thr Pro Pro
                245                 250                 255

Gln Lys Gln Glu Pro Ile Asp Lys Glu Leu Tyr Pro Leu Thr Ser Leu
            260                 265                 270
```

```
Arg Ser Leu Phe Gly Asn Asp Pro Ser Ser Gln Gly Ser Lys Gly
        275                 280                 285

Ser Met Gln Lys Gly Asn Phe Arg Asn Gln Arg Lys Thr Val Lys Cys
290                 295                 300

Phe Asn Cys Gly Lys Glu Gly His Ile Ala Lys Asn Cys Arg Ala Pro
305                 310                 315                 320

Arg Lys Lys Gly Cys Trp Lys Cys Gly Lys Glu Gly His Gln Met Lys
                325                 330                 335

Asp Cys Thr Glu Arg Gln Ala Asn
            340

<210> SEQ ID NO 263
<211> LENGTH: 362
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 263

Met Gly Ala Arg Ala Ser Gly Ser Lys Ser Gly Ser Gly Ser Asp Ser
1               5                   10                  15

Gly Ser Lys Ile Glu Glu Leu Phe Lys Lys His Lys Ile Val Ala Val
                20                  25                  30

Leu Arg Ala Asn Ser Val Glu Glu Ala Lys Lys Lys Ala Leu Ala Val
            35                  40                  45

Phe Leu Gly Gly Val His Leu Ile Glu Ile Thr Phe Thr Val Pro Asp
    50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
        115                 120                 125

Met Thr Pro Thr Glu Leu Val Lys Ala Met Lys Leu Gly His Thr Ile
    130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175

Asn Leu Asp Asn Val Cys Glu Trp Phe Lys Ala Gly Val Leu Ala Val
            180                 185                 190

Gly Val Gly Ser Ala Leu Val Lys Gly Thr Pro Val Glu Val Ala Glu
        195                 200                 205

Lys Ala Lys Ala Phe Val Glu Lys Ile Arg Gly Cys Thr Glu Gln Lys
    210                 215                 220

Leu Ile Ser Glu Glu Asp Leu Leu Gln Ser Arg Pro Glu Pro Thr Ala
225                 230                 235                 240

Pro Pro Glu Glu Ser Phe Arg Ser Gly Val Glu Thr Thr Thr Pro Pro
```

-continued

```
                  245                 250                 255
Gln Lys Gln Glu Pro Ile Asp Lys Glu Leu Tyr Pro Leu Thr Ser Leu
            260                 265                 270

Arg Ser Leu Phe Gly Asn Asp Pro Ser Ser Gln Gly Ser Phe Phe Arg
        275                 280                 285

Glu Asp Leu Ala Phe Leu Gln Gly Lys Ala Arg Glu Leu Gly Gly Ser
    290                 295                 300

Lys Gly Ser Met Gln Lys Gly Asn Phe Arg Asn Gln Arg Lys Thr Val
305                 310                 315                 320

Lys Cys Phe Asn Cys Gly Lys Glu Gly His Ile Ala Lys Asn Cys Arg
                325                 330                 335

Ala Pro Arg Lys Lys Gly Cys Trp Lys Cys Gly Lys Glu Gly His Gln
            340                 345                 350

Met Lys Asp Cys Thr Glu Arg Gln Ala Asn
        355                 360
```

<210> SEQ ID NO 264
<211> LENGTH: 343
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 264

```
Met Gly Ala Arg Ala Ser Gly Ser Lys Ser Gly Ser Gly Ser Asp Ser
1               5                   10                  15

Gly Ser Lys Met Glu Glu Leu Phe Lys Lys His Lys Ile Val Ala Val
            20                  25                  30

Leu Arg Ala Asn Ser Val Glu Glu Ala Lys Lys Lys Ala Leu Ala Val
        35                  40                  45

Phe Leu Gly Gly Val His Leu Ile Glu Ile Thr Phe Thr Val Pro Asp
    50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
        115                 120                 125

Met Thr Pro Thr Glu Leu Val Lys Ala Met Lys Leu Gly His Thr Ile
    130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175

Asn Leu Lys Asn Val Cys Lys Trp Phe Lys Ala Gly Val Leu Ala Val
            180                 185                 190

Gly Val Gly Lys Ala Leu Val Lys Gly Thr Pro Val Glu Val Ala Lys
        195                 200                 205
```

```
Lys Ala Lys Ala Phe Val Lys Ile Arg Gly Cys Thr Glu Gln Lys
        210                 215                 220

Leu Ile Ser Glu Glu Asp Leu Gln Ser Arg Pro Glu Pro Thr Ala Pro
225                 230                 235                 240

Pro Glu Glu Ser Phe Arg Ser Gly Val Glu Thr Thr Thr Pro Pro Gln
                245                 250                 255

Lys Gln Glu Pro Ile Asp Lys Glu Leu Tyr Pro Leu Thr Ser Leu Arg
                260                 265                 270

Ser Leu Phe Gly Asn Asp Pro Ser Ser Gln Gly Gly Ser Lys Gly Ser
        275                 280                 285

Met Gln Lys Gly Asn Phe Arg Asn Gln Arg Lys Thr Val Lys Cys Phe
        290                 295                 300

Asn Cys Gly Lys Glu Gly His Ile Ala Lys Asn Cys Arg Ala Pro Arg
305                 310                 315                 320

Lys Lys Gly Cys Trp Lys Cys Gly Lys Glu Gly His Gln Met Lys Asp
                325                 330                 335

Cys Thr Glu Arg Gln Ala Asn
            340

<210> SEQ ID NO 265
<211> LENGTH: 361
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 265

Met Gly Ala Arg Ala Ser Gly Ser Lys Ser Gly Ser Gly Ser Asp Ser
1               5                   10                  15

Gly Ser Lys Met Glu Glu Leu Phe Lys Lys His Lys Ile Val Ala Val
                20                  25                  30

Leu Arg Ala Asn Ser Val Glu Glu Ala Lys Lys Lys Ala Leu Ala Val
            35                  40                  45

Phe Leu Gly Gly Val His Leu Ile Glu Ile Thr Phe Thr Val Pro Asp
    50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
    115                 120                 125

Met Thr Pro Thr Glu Leu Val Lys Ala Met Lys Leu Gly His Thr Ile
130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175
```

```
Asn Leu Lys Asn Val Cys Lys Trp Phe Lys Ala Gly Val Leu Ala Val
            180                 185                 190

Gly Val Gly Lys Ala Leu Val Lys Gly Thr Pro Val Glu Val Ala Lys
        195                 200                 205

Lys Ala Lys Ala Phe Val Lys Lys Ile Arg Gly Cys Thr Glu Gln Lys
    210                 215                 220

Leu Ile Ser Glu Glu Asp Leu Gln Ser Arg Pro Glu Pro Thr Ala Pro
225                 230                 235                 240

Pro Glu Glu Ser Phe Arg Ser Gly Val Glu Thr Thr Thr Pro Pro Gln
                245                 250                 255

Lys Gln Glu Pro Ile Asp Lys Glu Leu Tyr Pro Leu Thr Ser Leu Arg
            260                 265                 270

Ser Leu Phe Gly Asn Asp Pro Ser Ser Gln Gly Ser Phe Phe Arg Glu
        275                 280                 285

Asp Leu Ala Phe Leu Gln Gly Lys Ala Arg Glu Leu Gly Gly Ser Lys
    290                 295                 300

Gly Ser Met Gln Lys Gly Asn Phe Arg Asn Gln Arg Lys Thr Val Lys
305                 310                 315                 320

Cys Phe Asn Cys Gly Lys Glu Gly His Ile Ala Lys Asn Cys Arg Ala
                325                 330                 335

Pro Arg Lys Lys Gly Cys Trp Lys Cys Gly Lys Glu Gly His Gln Met
            340                 345                 350

Lys Asp Cys Thr Glu Arg Gln Ala Asn
        355                 360

<210> SEQ ID NO 266
<211> LENGTH: 303
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc Tag-optionally absent

<400> SEQUENCE: 266

Met Gly Ala Arg Ala Ser Gly Ser Lys Ser Gly Ser Gly Ser Asp Ser
1               5                   10                  15

Gly Ser Lys Ile Glu Glu Leu Phe Lys Lys His Lys Ile Val Ala Val
            20                  25                  30

Leu Arg Ala Asn Ser Val Glu Glu Ala Lys Lys Lys Ala Leu Ala Val
        35                  40                  45

Phe Leu Gly Gly Val His Leu Ile Glu Ile Thr Phe Thr Val Pro Asp
50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
        115                 120                 125

Met Thr Pro Thr Glu Leu Val Lys Ala Met Lys Leu Gly His Thr Ile
```

-continued

```
                130                 135                 140
Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175

Asn Leu Asp Asn Val Cys Glu Trp Phe Lys Ala Gly Val Leu Ala Val
                180                 185                 190

Gly Val Gly Ser Ala Leu Val Lys Gly Thr Pro Val Glu Val Ala Glu
                195                 200                 205

Lys Ala Lys Ala Phe Val Glu Lys Ile Arg Gly Cys Thr Glu Gln Lys
                210                 215                 220

Leu Ile Ser Glu Glu Asp Leu Leu Gln Ser Arg Pro Glu Pro Thr Ala
225                 230                 235                 240

Pro Pro Glu Glu Ser Phe Arg Ser Gly Val Glu Thr Thr Thr Pro Pro
                245                 250                 255

Gln Lys Gln Glu Pro Ile Asp Lys Glu Leu Tyr Pro Leu Thr Ser Leu
                260                 265                 270

Arg Ser Leu Phe Gly Asn Asp Pro Ser Ser Gln Gly Gly Ser Lys Gly
                275                 280                 285

Ser Arg Pro Arg Gly Thr Arg Gly Lys Gly Arg Arg Ile Arg Arg
                290                 295                 300
```

<210> SEQ ID NO 267
<211> LENGTH: 321
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 267

```
Met Gly Ala Arg Ala Ser Gly Ser Lys Ser Gly Ser Gly Ser Asp Ser
1               5                   10                  15

Gly Ser Lys Ile Glu Glu Leu Phe Lys Lys His Lys Ile Val Ala Val
                20                  25                  30

Leu Arg Ala Asn Ser Val Glu Glu Ala Lys Lys Lys Ala Leu Ala Val
                35                  40                  45

Phe Leu Gly Gly Val His Leu Ile Glu Ile Thr Phe Thr Val Pro Asp
50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
                100                 105                 110

Ile Ser Gln Phe Cys Lys Glu Lys Gly Val Phe Tyr Met Pro Gly Val
                115                 120                 125

Met Thr Pro Thr Glu Leu Val Lys Ala Met Lys Leu Gly His Thr Ile
                130                 135                 140

Leu Lys Leu Phe Pro Gly Glu Val Val Gly Pro Gln Phe Val Lys Ala
145                 150                 155                 160
```

```
Met Lys Gly Pro Phe Pro Asn Val Lys Phe Val Pro Thr Gly Gly Val
                165                 170                 175

Asn Leu Asp Asn Val Cys Glu Trp Phe Lys Ala Gly Val Leu Ala Val
            180                 185                 190

Gly Val Gly Ser Ala Leu Val Lys Gly Thr Pro Val Glu Val Ala Glu
        195                 200                 205

Lys Ala Lys Ala Phe Val Glu Lys Ile Arg Gly Cys Thr Glu Gln Lys
    210                 215                 220

Leu Ile Ser Glu Glu Asp Leu Leu Gln Ser Arg Pro Glu Pro Thr Ala
225                 230                 235                 240

Pro Pro Glu Glu Ser Phe Arg Ser Gly Val Thr Thr Thr Pro Pro
                245                 250                 255

Gln Lys Gln Glu Pro Ile Asp Lys Glu Leu Tyr Pro Leu Thr Ser Leu
            260                 265                 270

Arg Ser Leu Phe Gly Asn Asp Pro Ser Ser Gln Gly Ser Phe Phe Arg
        275                 280                 285

Glu Asp Leu Ala Phe Leu Gln Gly Lys Ala Arg Glu Leu Gly Gly Ser
    290                 295                 300

Lys Gly Ser Arg Pro Arg Gly Thr Arg Gly Lys Gly Arg Arg Ile Arg
305                 310                 315                 320

Arg

<210> SEQ ID NO 268
<211> LENGTH: 302
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 268

Met Gly Ala Arg Ala Ser Gly Ser Lys Ser Gly Ser Gly Ser Asp Ser
1               5                   10                  15

Gly Ser Lys Met Glu Glu Leu Phe Lys Lys His Lys Ile Val Ala Val
                20                  25                  30

Leu Arg Ala Asn Ser Val Glu Glu Ala Lys Lys Lys Ala Leu Ala Val
            35                  40                  45

Phe Leu Gly Gly Val His Leu Ile Glu Ile Thr Phe Thr Val Pro Asp
        50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
        115                 120                 125

Met Thr Pro Thr Glu Leu Val Lys Ala Met Lys Leu Gly His Thr Ile
    130                 135                 140

Leu Lys Leu Phe Pro Gly Glu Val Val Gly Pro Gln Phe Val Lys Ala
```

| | | | | |
|---|---|---|---|---|
| 145 | 150 | 155 | 160 | |

Met Lys Gly Pro Phe Pro Asn Val Lys Phe Val Pro Thr Gly Val
                165                 170                 175

Asn Leu Lys Asn Val Cys Lys Trp Phe Lys Ala Gly Val Leu Ala Val
                180                 185                 190

Gly Val Gly Lys Ala Leu Val Lys Gly Thr Pro Val Glu Val Ala Lys
                195                 200                 205

Lys Ala Lys Ala Phe Val Lys Lys Ile Arg Gly Cys Thr Glu Gln Lys
210                 215                 220

Leu Ile Ser Glu Glu Asp Leu Gln Ser Arg Pro Glu Pro Thr Ala Pro
225                 230                 235                 240

Pro Glu Glu Ser Phe Arg Ser Gly Val Glu Thr Thr Thr Pro Pro Gln
                245                 250                 255

Lys Gln Glu Pro Ile Asp Lys Glu Leu Tyr Pro Leu Thr Ser Leu Arg
                260                 265                 270

Ser Leu Phe Gly Asn Asp Pro Ser Ser Gln Gly Gly Ser Lys Gly Ser
                275                 280                 285

Arg Pro Arg Gly Thr Arg Gly Lys Gly Arg Arg Ile Arg Arg
                290                 295                 300

<210> SEQ ID NO 269
<211> LENGTH: 320
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: Myc tag-optionally absent

<400> SEQUENCE: 269

Met Gly Ala Arg Ala Ser Gly Ser Lys Ser Gly Ser Gly Ser Asp Ser
1               5                   10                  15

Gly Ser Lys Met Glu Glu Leu Phe Lys Lys His Lys Ile Val Ala Val
                20                  25                  30

Leu Arg Ala Asn Ser Val Glu Glu Ala Lys Lys Lys Ala Leu Ala Val
                35                  40                  45

Phe Leu Gly Gly Val His Leu Ile Glu Ile Thr Phe Thr Val Pro Asp
50                  55                  60

Ala Asp Thr Val Ile Lys Glu Leu Ser Phe Leu Lys Glu Met Gly Ala
65                  70                  75                  80

Ile Ile Gly Ala Gly Thr Val Thr Ser Val Glu Gln Cys Arg Lys Ala
                85                  90                  95

Val Glu Ser Gly Ala Glu Phe Ile Val Ser Pro His Leu Asp Glu Glu
                100                 105                 110

Ile Ser Gln Phe Cys Lys Glu Lys Gly Val Phe Tyr Met Pro Gly Val
                115                 120                 125

Met Thr Pro Thr Glu Leu Val Lys Ala Met Lys Leu Gly His Thr Ile
                130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175

```
Asn Leu Lys Asn Val Cys Lys Trp Phe Lys Ala Gly Val Leu Ala Val
            180                 185                 190

Gly Val Gly Lys Ala Leu Val Lys Gly Thr Pro Val Glu Val Ala Lys
        195                 200                 205

Lys Ala Lys Ala Phe Val Lys Lys Ile Arg Gly Cys Thr Glu Gln Lys
    210                 215                 220

Leu Ile Ser Glu Glu Asp Leu Gln Ser Arg Pro Glu Pro Thr Ala Pro
225                 230                 235                 240

Pro Glu Glu Ser Phe Arg Ser Gly Val Glu Thr Thr Thr Pro Pro Gln
                245                 250                 255

Lys Gln Glu Pro Ile Asp Lys Glu Leu Tyr Pro Leu Thr Ser Leu Arg
            260                 265                 270

Ser Leu Phe Gly Asn Asp Pro Ser Ser Gln Gly Ser Phe Phe Arg Glu
        275                 280                 285

Asp Leu Ala Phe Leu Gln Gly Lys Ala Arg Glu Leu Gly Gly Ser Lys
    290                 295                 300

Gly Ser Arg Pro Arg Gly Thr Arg Gly Lys Gly Arg Arg Ile Arg Arg
305                 310                 315                 320

<210> SEQ ID NO 270
<211> LENGTH: 207
<212> TYPE: PRT
<213> ORGANISM: Artificial Sequence
<220> FEATURE:
<223> OTHER INFORMATION: Synthetic

<400> SEQUENCE: 270

Met Glu Gly Met Asp Pro Leu Ala Val Leu Ala Glu Ser Arg Leu Leu
1               5                   10                  15

Pro Leu Leu Thr Val Arg Gly Gly Glu Asp Leu Ala Gly Leu Ala Thr
            20                  25                  30

Val Leu Glu Leu Met Gly Val Gly Ala Leu Glu Ile Thr Leu Arg Thr
        35                  40                  45

Glu Lys Gly Leu Glu Ala Leu Lys Ala Leu Arg Lys Ser Gly Leu Leu
    50                  55                  60

Leu Gly Ala Gly Thr Val Arg Ser Pro Lys Glu Ala Glu Ala Ala Leu
65                  70                  75                  80

Glu Ala Gly Ala Ala Phe Leu Val Ser Pro Gly Leu Leu Glu Glu Val
                85                  90                  95

Ala Ala Leu Ala Gln Ala Arg Gly Val Pro Tyr Leu Pro Gly Val Leu
            100                 105                 110

Thr Pro Thr Glu Val Glu Arg Ala Leu Ala Leu Gly Leu Ser Ala Leu
        115                 120                 125

Lys Phe Phe Pro Ala Glu Pro Phe Gln Gly Val Arg Val Leu Arg Ala
    130                 135                 140

Tyr Ala Glu Val Phe Pro Glu Val Arg Phe Leu Pro Thr Gly Gly Ile
145                 150                 155                 160

Lys Glu Glu His Leu Pro His Tyr Ala Ala Leu Pro Asn Leu Leu Ala
                165                 170                 175

Val Gly Gly Ser Trp Leu Leu Gln Gly Asp Leu Ala Ala Val Met Lys
            180                 185                 190

Lys Val Lys Ala Ala Lys Ala Leu Leu Ser Pro Gln Ala Pro Gly
        195                 200                 205

<210> SEQ ID NO 271
```

<211> LENGTH: 156
<212> TYPE: PRT
<213> ORGANISM: Artificial Sequence
<220> FEATURE:
<223> OTHER INFORMATION: Synthetic

<400> SEQUENCE: 271

```
Met Thr Lys Lys Val Gly Ile Val Asp Thr Thr Phe Ala Arg Val Asp
1               5                   10                  15

Met Ala Glu Ala Ala Ile Arg Thr Leu Lys Ala Leu Ser Pro Asn Ile
                20                  25                  30

Lys Ile Ile Arg Lys Thr Val Pro Gly Ile Lys Asp Leu Pro Val Ala
            35                  40                  45

Cys Lys Lys Leu Leu Glu Glu Glu Gly Cys Asp Ile Val Met Ala Leu
        50                  55                  60

Gly Met Pro Gly Lys Ala Glu Lys Asp Lys Val Cys Ala His Glu Ala
65                  70                  75                  80

Ser Leu Gly Leu Met Leu Ala Gln Leu Met Thr Asn Lys His Ile Ile
                85                  90                  95

Glu Val Phe Val His Glu Asp Glu Ala Lys Asp Asp Glu Leu Asp
                100                 105                 110

Ile Leu Ala Leu Val Arg Ala Ile Glu His Ala Ala Asn Val Tyr Tyr
            115                 120                 125

Leu Leu Phe Lys Pro Glu Tyr Leu Thr Arg Met Ala Gly Lys Gly Leu
        130                 135                 140

Arg Gln Gly Arg Glu Asp Ala Gly Pro Ala Arg Glu
145                 150                 155
```

<210> SEQ ID NO 272
<211> LENGTH: 156
<212> TYPE: PRT
<213> ORGANISM: Artificial Sequence
<220> FEATURE:
<223> OTHER INFORMATION: Synthetic

<400> SEQUENCE: 272

```
Met Thr Lys Lys Val Gly Ile Val Asp Thr Thr Phe Ala Arg Val Asp
1               5                   10                  15

Met Ala Ser Ala Ala Ile Leu Thr Leu Lys Met Glu Ser Pro Asn Ile
                20                  25                  30

Lys Ile Ile Arg Lys Thr Val Pro Gly Ile Lys Asp Leu Pro Val Ala
            35                  40                  45

Cys Lys Lys Leu Leu Glu Glu Glu Gly Cys Asp Ile Val Met Ala Leu
        50                  55                  60

Gly Met Pro Gly Lys Ala Glu Lys Asp Lys Val Cys Ala His Glu Ala
65                  70                  75                  80

Ser Leu Gly Leu Met Leu Ala Gln Leu Met Thr Asn Lys His Ile Ile
                85                  90                  95

Glu Val Phe Val His Glu Asp Glu Ala Lys Asp Ala Glu Leu Lys
                100                 105                 110

Ile Leu Ala Ala Arg Arg Ala Ile Glu His Ala Leu Asn Val Tyr Tyr
            115                 120                 125

Leu Leu Phe Lys Pro Glu Tyr Leu Thr Arg Met Ala Gly Lys Gly Leu
        130                 135                 140

Arg Gln Gly Phe Glu Asp Ala Gly Pro Ala Arg Glu
145                 150                 155
```

```
<210> SEQ ID NO 273
<211> LENGTH: 209
<212> TYPE: PRT
<213> ORGANISM: Artificial Sequence
<220> FEATURE:
<223> OTHER INFORMATION: Synthetic

<400> SEQUENCE: 273

Met Ser Thr Ile Asn Asn Gln Leu Lys Ala Leu Lys Val Ile Pro Val
1               5                   10                  15

Ile Ala Ile Asp Asn Ala Glu Asp Ile Ile Pro Leu Gly Lys Val Leu
            20                  25                  30

Ala Glu Asn Gly Leu Pro Ala Ala Glu Ile Thr Phe Arg Ser Ser Ala
        35                  40                  45

Ala Val Lys Ala Ile Met Leu Leu Arg Ser Ala Gln Pro Glu Met Leu
    50                  55                  60

Ile Gly Ala Gly Thr Ile Leu Asn Gly Val Gln Ala Leu Ala Ala Lys
65                  70                  75                  80

Glu Ala Gly Ala Thr Phe Val Val Ser Pro Gly Phe Asn Pro Asn Thr
                85                  90                  95

Val Arg Ala Cys Gln Ile Ile Gly Ile Asp Ile Val Pro Gly Val Asn
            100                 105                 110

Asn Pro Ser Thr Val Glu Ala Ala Leu Glu Met Gly Leu Thr Thr Leu
        115                 120                 125

Lys Phe Phe Pro Ala Glu Ala Ser Gly Gly Ile Ser Met Val Lys Ser
    130                 135                 140

Leu Val Gly Pro Tyr Gly Asp Ile Arg Leu Met Pro Thr Gly Gly Ile
145                 150                 155                 160

Thr Pro Ser Asn Ile Asp Asn Tyr Leu Ala Ile Pro Gln Val Leu Ala
                165                 170                 175

Cys Gly Gly Thr Trp Met Val Asp Lys Lys Leu Val Thr Asn Gly Glu
            180                 185                 190

Trp Asp Glu Ile Ala Arg Leu Thr Arg Glu Ile Val Glu Gln Val Asn
        195                 200                 205

Pro

<210> SEQ ID NO 274
<211> LENGTH: 114
<212> TYPE: PRT
<213> ORGANISM: Artificial Sequence
<220> FEATURE:
<223> OTHER INFORMATION: Synthetic

<400> SEQUENCE: 274

Met Pro Ile Phe Thr Leu Asn Thr Asn Ile Lys Ala Thr Asp Val Pro
1               5                   10                  15

Ser Asp Phe Leu Ser Leu Thr Ser Arg Leu Val Gly Leu Ile Leu Ser
            20                  25                  30

Lys Pro Gly Ser Tyr Val Ala Val His Ile Asn Thr Asp Gln Gln Leu
        35                  40                  45

Ser Phe Gly Gly Ser Thr Asn Pro Ala Ala Phe Gly Thr Leu Met Ser
    50                  55                  60

Ile Gly Gly Ile Glu Pro Ser Lys Asn Arg Asp His Ser Ala Val Leu
65                  70                  75                  80

Phe Asp His Leu Asn Ala Met Leu Gly Ile Pro Lys Asn Arg Met Tyr
                85                  90                  95

Ile His Phe Val Asn Leu Asn Gly Asp Asp Val Gly Trp Asn Gly Thr
```

Thr Phe

<210> SEQ ID NO 275
<211> LENGTH: 157
<212> TYPE: PRT
<213> ORGANISM: Artificial Sequence
<220> FEATURE:
<223> OTHER INFORMATION: Synthetic

<400> SEQUENCE: 275

Met Asn Gln His Ser His Lys Asp Tyr Glu Thr Val Arg Ile Ala Val
1               5                   10                  15

Val Arg Ala Arg Trp His Ala Asp Ile Val Asp Ala Cys Val Glu Ala
            20                  25                  30

Phe Glu Ile Ala Met Ala Ala Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asp Gly Met Met Asn Val Gln Leu Ser Thr Gly Val Pro Val Leu Ser
            100                 105                 110

Ala Val Leu Thr Pro His Arg Tyr Arg Asp Ser Ala Glu His His Arg
        115                 120                 125

Phe Phe Ala Ala His Phe Ala Val Lys Gly Val Glu Ala Ala Arg Ala
    130                 135                 140

Cys Ile Glu Ile Leu Ala Ala Arg Glu Lys Ile Ala Ala
145                 150                 155

<210> SEQ ID NO 276
<211> LENGTH: 205
<212> TYPE: PRT
<213> ORGANISM: Artificial Sequence
<220> FEATURE:
<223> OTHER INFORMATION: Synthetic

<400> SEQUENCE: 276

Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
            20                  25                  30

Ala Gly Gly Val His Leu Ile Glu Ile Thr Phe Thr Val Pro Asp Ala
        35                  40                  45

Asp Thr Val Ile Lys Ala Leu Ser Val Leu Lys Glu Lys Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Thr Ile Leu
        115                 120                 125

Lys Leu Phe Pro Gly Glu Val Val Gly Pro Gln Phe Val Lys Ala Met 130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Pro Asp Glu Val Arg Glu Lys
                180                 185                 190

Ala Lys Ala Phe Val Glu Lys Ile Arg Gly Cys Thr Glu
        195                 200                 205

<210> SEQ ID NO 277
<211> LENGTH: 157
<212> TYPE: PRT
<213> ORGANISM: Artificial Sequence
<220> FEATURE:
<223> OTHER INFORMATION: Synthetic

<400> SEQUENCE: 277

Met Asn Gln His Ser His Lys Asp Tyr Glu Thr Val Arg Ile Ala Val
1               5                   10                  15

Val Arg Ala Arg Trp His Ala Glu Ile Val Asp Ala Cys Val Ser Ala
                20                  25                  30

Phe Glu Ala Ala Met Ala Asp Ile Gly Gly Asp Arg Phe Ala Val Asp
            35                  40                  45

Val Phe Asp Val Pro Gly Ala Tyr Glu Ile Pro His Ala Arg Thr
        50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asp Gly Met Met Asn Val Gln Leu Ser Thr Gly Val Pro Val Leu Ser
            100                 105                 110

Ala Val Leu Thr Pro His Arg Tyr Arg Asp Ser Asp Ala His Thr Leu
        115                 120                 125

Leu Phe Leu Ala Leu Phe Ala Val Lys Gly Met Glu Ala Ala Arg Ala
    130                 135                 140

Cys Val Glu Ile Leu Ala Ala Arg Glu Lys Ile Ala Ala
145                 150                 155

<210> SEQ ID NO 278
<211> LENGTH: 177
<212> TYPE: PRT
<213> ORGANISM: Artificial Sequence
<220> FEATURE:
<223> OTHER INFORMATION: Synthetic

<400> SEQUENCE: 278

Met Phe Thr Lys Ser Gly Asp Asp Gly Asn Thr Asn Val Ile Asn Lys
1               5                   10                  15

Arg Val Gly Lys Asp Ser Pro Leu Val Asn Phe Leu Gly Asp Leu Asp
                20                  25                  30

Glu Leu Asn Ser Phe Ile Gly Phe Ala Ile Ser Lys Ile Pro Trp Glu
            35                  40                  45

Asp Met Lys Lys Asp Leu Glu Arg Val Gln Val Glu Leu Phe Glu Ile
        50                  55                  60

Gly Glu Asp Leu Ser Thr Gln Ser Ser Lys Lys Ile Asp Glu Ser
65                  70                  75                  80

Tyr Val Leu Trp Leu Leu Ala Thr Ala Ile Tyr Arg Ile Glu Ser
            85                  90                  95

Gly Pro Val Lys Leu Phe Val Ile Pro Gly Gly Ser Glu Glu Ala Ser
                100                 105                 110

Val Leu His Val Thr Arg Ser Val Ala Arg Arg Val Glu Arg Asn Ala
            115                 120                 125

Val Lys Tyr Thr Lys Glu Leu Pro Glu Ile Asn Arg Met Ile Ile Val
            130                 135                 140

Tyr Leu Asn Arg Leu Ser Ser Leu Leu Phe Ala Met Ala Leu Val Ala
145                 150                 155                 160

Asn Lys Arg Arg Asn Gln Ser Glu Lys Ile Tyr Glu Ile Gly Lys Ser
                165                 170                 175

Trp

<210> SEQ ID NO 279
<211> LENGTH: 157
<212> TYPE: PRT
<213> ORGANISM: Artificial Sequence
<220> FEATURE:
<223> OTHER INFORMATION: Synthetic

<400> SEQUENCE: 279

Met Asn Gln His Ser His Lys Asp Tyr Glu Thr Val Arg Ile Ala Val
1               5                   10                  15

Val Arg Ala Arg Trp His Ala Asp Ile Val Asp Gln Cys Val Arg Ala
            20                  25                  30

Phe Glu Glu Ala Met Ala Asp Ala Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asp Gly Met Met Asn Val Gln Leu Ser Thr Gly Val Pro Val Leu Ser
            100                 105                 110

Ala Val Leu Thr Pro His Arg Tyr Arg Ser Ser Arg Glu His His Glu
            115                 120                 125

Phe Phe Arg Glu His Phe Met Val Lys Gly Val Glu Ala Ala Ala Ala
        130                 135                 140

Cys Ile Thr Ile Leu Ala Ala Arg Glu Lys Ile Ala Ala
145                 150                 155

<210> SEQ ID NO 280
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 280

Met Gly Ala Arg Ala Ser
1               5

<210> SEQ ID NO 281

```
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 281

Met Gly Ala Gln Phe Ser
1               5

<210> SEQ ID NO 282
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 282

Met Gly Ser Ser Lys Ser
1               5

<210> SEQ ID NO 283
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 283

Met Gly Lys Gln Asn Ser
1               5

<210> SEQ ID NO 284
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 284

Met Gly Cys Ile Lys Ser Lys Arg Lys Asp Asn Leu Asn
1               5                   10

<210> SEQ ID NO 285
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 285
```

Met Gly Cys Thr Leu Ser Ala Glu Glu Arg Ala Ala Leu
1               5                   10

<210> SEQ ID NO 286
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 286

Met Leu Cys Cys Met Arg Arg Thr Lys Gln Val Glu Lys
1               5                   10

<210> SEQ ID NO 287
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 287

Met Asp Cys Leu Cys Ile Val Thr Thr Lys Lys Tyr Arg
1               5                   10

<210> SEQ ID NO 288
<211> LENGTH: 13
<212> TYPE: PRT
<213> ORGANISM: Artificial Sequence
<220> FEATURE:
<223> OTHER INFORMATION: Synthetic

<400> SEQUENCE: 288

Lys Lys Lys Lys Lys Ser Lys Thr Lys Cys Val Ile Met
1               5                   10

<210> SEQ ID NO 289
<211> LENGTH: 13
<212> TYPE: PRT
<213> ORGANISM: Artificial Sequence
<220> FEATURE:
<223> OTHER INFORMATION: Synthetic

<400> SEQUENCE: 289

Asp Met Lys Lys His Arg Cys Lys Cys Cys Ser Ile Met
1               5                   10

<210> SEQ ID NO 290
<211> LENGTH: 13
<212> TYPE: PRT
<213> ORGANISM: Artificial Sequence
<220> FEATURE:
<223> OTHER INFORMATION: Synthetic

<400> SEQUENCE: 290

Ala Gln Arg Gln Lys Lys Arg Arg Leu Cys Leu Leu Leu
1               5                   10

<210> SEQ ID NO 291

```
<211> LENGTH: 13
<212> TYPE: PRT
<213> ORGANISM: Artificial Sequence
<220> FEATURE:
<223> OTHER INFORMATION: Synthetic

<400> SEQUENCE: 291

Ala Gln Glu Phe Ile His Gln Phe Leu Cys Asn Pro Leu
1               5                   10

<210> SEQ ID NO 292
<211> LENGTH: 130
<212> TYPE: PRT
<213> ORGANISM: Artificial Sequence
<220> FEATURE:
<223> OTHER INFORMATION: Synthetic

<400> SEQUENCE: 292

His Gly Leu Gln Asp Asp Pro Asp Leu Gln Ala Leu Leu Lys Gly Ser
1               5                   10                  15

Gln Leu Leu Lys Val Lys Ser Ser Ser Trp Arg Arg Glu Arg Phe Tyr
            20                  25                  30

Lys Leu Gln Glu Asp Cys Lys Thr Ile Trp Gln Glu Ser Arg Lys Val
        35                  40                  45

Met Arg Ser Pro Glu Ser Gln Leu Phe Ser Ile Glu Asp Ile Gln Glu
    50                  55                  60

Val Arg Met Gly His Arg Thr Glu Gly Leu Glu Lys Phe Ala Arg Asp
65                  70                  75                  80

Ile Pro Glu Asp Arg Cys Phe Ser Ile Val Phe Lys Asp Gln Arg Asn
                85                  90                  95

Thr Leu Asp Leu Ile Ala Pro Ser Pro Ala Asp Ala Gln His Trp Val
            100                 105                 110

Gln Gly Leu Arg Lys Ile Ile His Ser Gly Ser Met Asp Gln Arg
        115                 120                 125

Gln Lys
    130

<210> SEQ ID NO 293
<211> LENGTH: 52
<212> TYPE: PRT
<213> ORGANISM: Artificial Sequence
<220> FEATURE:
<223> OTHER INFORMATION: Synthetic

<400> SEQUENCE: 293

Pro His Arg Phe Lys Val His Asn Tyr Met Ser Pro Thr Phe Cys Asp
1               5                   10                  15

His Cys Gly Ser Leu Leu Trp Gly Leu Val Lys Gln Gly Leu Lys Cys
            20                  25                  30

Glu Asp Cys Gly Met Asn Val His His Lys Cys Arg Glu Lys Val Ala
        35                  40                  45

Asn Leu Cys Gly
    50

<210> SEQ ID NO 294
<211> LENGTH: 126
<212> TYPE: PRT
<213> ORGANISM: Artificial Sequence
<220> FEATURE:
<223> OTHER INFORMATION: Synthetic

<400> SEQUENCE: 294
```

```
Gly Ala Val Lys Leu Ser Val Ser Tyr Arg Asn Gly Thr Leu Phe Ile
1               5                   10                  15

Met Val Met His Ile Lys Asp Leu Val Thr Glu Asp Gly Ala Asp Pro
            20                  25                  30

Asn Pro Tyr Val Lys Thr Tyr Leu Leu Pro Asp Thr His Lys Thr Ser
        35                  40                  45

Lys Arg Lys Thr Lys Ile Ser Arg Lys Thr Arg Asn Pro Thr Phe Asn
50                  55                  60

Glu Met Leu Val Tyr Ser Gly Tyr Ser Lys Glu Thr Leu Arg Gln Arg
65                  70                  75                  80

Glu Leu Gln Leu Ser Val Leu Ser Ala Glu Ser Leu Arg Glu Asn Phe
                85                  90                  95

Phe Leu Gly Gly Ile Thr Leu Pro Leu Lys Asp Phe Asn Leu Ser Lys
            100                 105                 110

Glu Thr Val Lys Trp Tyr Gln Leu Thr Ala Ala Thr Tyr Leu
            115                 120                 125

<210> SEQ ID NO 295
<211> LENGTH: 148
<212> TYPE: PRT
<213> ORGANISM: Artificial Sequence
<220> FEATURE:
<223> OTHER INFORMATION: Synthetic

<400> SEQUENCE: 295

Ala Val Ala Gln Gln Leu Arg Ala Glu Ser Asp Phe Glu Gln Leu Pro
1               5                   10                  15

Asp Asp Val Ala Ile Ser Ala Asn Ile Ala Asp Ile Glu Glu Lys Arg
            20                  25                  30

Gly Phe Thr Ser His Phe Val Phe Val Ile Glu Val Lys Thr Lys Gly
        35                  40                  45

Gly Ser Lys Tyr Leu Ile Tyr Arg Arg Tyr Arg Gln Phe His Ala Leu
50                  55                  60

Gln Ser Lys Leu Glu Glu Arg Phe Gly Pro Asp Ser Lys Ser Ser Ala
65                  70                  75                  80

Leu Ala Cys Thr Leu Pro Thr Leu Pro Ala Lys Val Tyr Val Gly Val
                85                  90                  95

Lys Gln Glu Ile Ala Glu Met Arg Ile Pro Ala Leu Asn Ala Tyr Met
            100                 105                 110

Lys Ser Leu Leu Ser Leu Pro Val Trp Val Leu Met Asp Glu Asp Val
            115                 120                 125

Arg Ile Phe Phe Tyr Gln Ser Pro Tyr Asp Ser Glu Gln Val Pro Gln
            130                 135                 140

Ala Leu Arg Arg
145

<210> SEQ ID NO 296
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 296
```

```
Met Gly Cys Ile Lys Ser Lys Gly Lys Asp Ser Leu Ser
1               5                   10
```

<210> SEQ ID NO 297
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 297

```
Met Gly Cys Ile Asn Ser Lys Arg Lys Asp
1               5                   10
```

<210> SEQ ID NO 298
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 298

```
Met Gly Ser Ser Lys Ser Lys Pro Lys Asp Pro Ser Gln Arg Arg Arg
1               5                   10                  15
```

<210> SEQ ID NO 299
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 299

```
Met Gly Cys Ile Lys Ser Lys Glu Asp Lys Gly Pro Ala Met Lys Tyr
1               5                   10                  15
```

<210> SEQ ID NO 300
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (3)..(5)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is T or S

<400> SEQUENCE: 300

```
Met Gly Xaa Xaa Xaa Xaa
1               5
```

<210> SEQ ID NO 301
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is any amino acid

<400> SEQUENCE: 301

Tyr Pro Xaa Leu
1

<210> SEQ ID NO 302
<211> LENGTH: 6
<212> TYPE: PRT
<213> ORGANISM: Artificial Sequence
<220> FEATURE:
<223> OTHER INFORMATION: Synthetic

<400> SEQUENCE: 302

Tyr Pro Leu Thr Ser Leu
1               5

<210> SEQ ID NO 303
<211> LENGTH: 4
<212> TYPE: PRT
<213> ORGANISM: Artificial Sequence
<220> FEATURE:
<223> OTHER INFORMATION: Synthetic

<400> SEQUENCE: 303

Pro Thr Ala Pro
1

<210> SEQ ID NO 304
<211> LENGTH: 205
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 304

Met Lys Ile Glu Glu Leu Phe Lys Lys His Lys Ile Val Ala Val Leu
1               5                   10                  15

Arg Ala Asn Ser Val Glu Glu Ala Lys Lys Lys Ala Leu Ala Val Phe
            20                  25                  30

Leu Gly Gly Val His Leu Ile Glu Ile Thr Phe Thr Val Pro Asp Ala
        35                  40                  45

Asp Thr Val Ile Lys Glu Leu Ser Phe Leu Lys Glu Met Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Thr Ile Leu

```
                115                 120                 125
Lys Leu Phe Pro Gly Glu Val Gly Pro Gln Phe Val Lys Ala Met
        130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Pro Val Glu Val Ala Glu Lys
            180                 185                 190

Ala Lys Ala Phe Val Glu Lys Ile Arg Gly Cys Thr Glu
        195                 200                 205

<210> SEQ ID NO 305
<211> LENGTH: 18
<212> TYPE: PRT
<213> ORGANISM: Artificial Sequence
<220> FEATURE:
<223> OTHER INFORMATION: Synthetic

<400> SEQUENCE: 305

Arg Lys Ser Pro Thr Pro Ser Ala Pro Val Pro Leu Thr Glu Pro Ala
1               5                   10                  15

Ala Gln

<210> SEQ ID NO 306
<211> LENGTH: 62
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 306

Met Ser Leu Tyr Pro Ser Leu Glu Asp Leu Lys Val Asp Lys Val Ile
1               5                   10                  15

Gln Ala Gln Thr Ala Phe Ser Ala Asn Pro Ala Asn Pro Ala Ile Leu
            20                  25                  30

Ser Glu Ala Ser Ala Pro Ile Pro His Asp Gly Asn Leu Tyr Pro Arg
        35                  40                  45

Leu Tyr Pro Glu Leu Ser Gln Tyr Met Gly Leu Ser Leu Asn
    50                  55                  60

<210> SEQ ID NO 307
<211> LENGTH: 511
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 307

Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
```

```
                35                  40                  45
His Asn Asp Leu Ile Gly Thr Ala Leu Gln Val Lys Met Pro Lys Ser
 50                  55                  60

His Lys Ala Ile Gln Ala Asp Gly Trp Met Cys His Ala Ser Lys Trp
 65                  70                  75                  80

Val Thr Thr Cys Asp Phe Arg Trp Tyr Gly Pro Lys Tyr Ile Thr His
                 85                  90                  95

Ser Ile Arg Ser Phe Thr Pro Ser Val Glu Gln Cys Lys Glu Ser Ile
                100                 105                 110

Glu Gln Thr Lys Gln Gly Thr Trp Leu Asn Pro Gly Phe Pro Pro Gln
                115                 120                 125

Ser Cys Gly Tyr Ala Thr Val Thr Asp Ala Glu Ala Val Ile Val Gln
                130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Tyr Ile Cys Pro Thr
                165                 170                 175

Val His Asn Ser Thr Thr Trp His Ser Asp Tyr Lys Val Lys Gly Leu
                180                 185                 190

Cys Asp Ser Asn Leu Ile Ser Met Asp Ile Thr Phe Phe Ser Glu Asp
                195                 200                 205

Gly Glu Leu Ser Ser Leu Gly Lys Glu Gly Thr Gly Phe Arg Ser Asn
210                 215                 220

Tyr Phe Ala Tyr Glu Thr Gly Gly Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
                260                 265                 270

Ser Ser Ile Ser Ala Pro Ser Gln Thr Ser Val Asp Val Ser Leu Ile
                275                 280                 285

Gln Asp Val Glu Arg Ile Leu Asp Tyr Ser Leu Cys Gln Glu Thr Trp
                290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
                340                 345                 350

Ala Pro Ile Leu Ser Arg Met Val Gly Met Ile Ser Gly Thr Thr Thr
                355                 360                 365

Glu Arg Glu Leu Trp Asp Asp Trp Ala Pro Tyr Glu Asp Val Glu Ile
                370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
                420                 425                 430

Leu Pro Asp Asp Glu Ser Leu Phe Phe Gly Asp Thr Gly Leu Ser Lys
                435                 440                 445

Asn Pro Ile Glu Leu Val Glu Gly Trp Phe Ser Ser Trp Lys Ser Ser
                450                 455                 460
```

```
Ile Ala Ser Phe Phe Phe Ile Ile Gly Leu Ile Ile Gly Leu Phe Leu
465                 470                 475                 480

Val Leu Arg Val Gly Ile His Leu Cys Ile Lys Leu Lys His Thr Lys
                485                 490                 495

Lys Arg Gln Ile Tyr Thr Asp Ile Glu Met Asn Arg Leu Gly Lys
            500                 505                 510

<210> SEQ ID NO 308
<211> LENGTH: 665
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 308

Met Ala Arg Ser Thr Leu Ser Lys Pro Leu Lys Asn Lys Val Asn Pro
1               5                   10                  15

Arg Gly Pro Leu Ile Pro Leu Ile Leu Leu Met Leu Arg Gly Val Ser
                20                  25                  30

Thr Ala Ser Pro Gly Ser Ser Pro His Gln Val Tyr Asn Ile Thr Trp
            35                  40                  45

Glu Val Thr Asn Gly Asp Arg Glu Thr Val Trp Ala Thr Ser Gly Asn
    50                  55                  60

His Pro Leu Trp Thr Trp Trp Pro Asp Leu Thr Pro Asp Leu Cys Met
65                  70                  75                  80

Leu Ala His His Gly Pro Ser Tyr Trp Gly Leu Glu Tyr Gln Ser Pro
                85                  90                  95

Phe Ser Ser Pro Pro Gly Pro Pro Cys Cys Ser Gly Ser Ser Pro
                100                 105                 110

Gly Cys Ser Arg Asp Cys Glu Glu Pro Leu Thr Ser Leu Thr Pro Arg
                115                 120                 125

Cys Asn Thr Ala Trp Asn Arg Leu Lys Leu Asp Gln Thr Thr His Lys
130                 135                 140

Ser Asn Glu Gly Phe Tyr Val Cys Pro Gly Pro His Arg Pro Arg Glu
145                 150                 155                 160

Ser Lys Ser Cys Gly Gly Pro Asp Ser Phe Tyr Cys Ala Tyr Trp Gly
                165                 170                 175

Cys Glu Thr Thr Gly Arg Ala Tyr Trp Lys Pro Ser Ser Ser Trp Asp
                180                 185                 190

Phe Ile Thr Val Asn Asn Asn Leu Thr Ser Asp Gln Ala Val Gln Val
                195                 200                 205

Cys Lys Asp Asn Lys Trp Cys Asn Pro Leu Val Ile Arg Phe Thr Asp
210                 215                 220

Ala Gly Arg Arg Val Thr Ser Trp Thr Thr Gly His Tyr Trp Gly Leu
225                 230                 235                 240

Arg Leu Tyr Val Ser Gly Gln Asp Pro Gly Leu Thr Phe Gly Ile Arg
                245                 250                 255

Leu Arg Tyr Gln Asn Leu Gly Pro Arg Val Pro Ile Gly Pro Asn Pro
                260                 265                 270

Val Leu Ala Asp Gln Gln Pro Leu Ser Lys Pro Lys Pro Val Lys Ser
                275                 280                 285

Pro Ser Val Thr Lys Pro Pro Ser Gly Thr Pro Leu Ser Pro Thr Gln
```

```
                290                 295                 300
Leu Pro Pro Ala Gly Thr Glu Asn Arg Leu Leu Asn Leu Val Asp Gly
305                 310                 315                 320

Ala Tyr Gln Ala Leu Asn Leu Thr Ser Pro Asp Lys Thr Gln Glu Cys
                325                 330                 335

Trp Leu Cys Leu Val Ala Gly Pro Pro Tyr Tyr Glu Gly Val Ala Val
                340                 345                 350

Leu Gly Thr Tyr Ser Asn His Thr Ser Ala Pro Ala Asn Cys Ser Val
                355                 360                 365

Ala Ser Gln His Lys Leu Thr Leu Ser Glu Val Thr Gly Gln Gly Leu
370                 375                 380

Cys Ile Gly Ala Val Pro Lys Thr His Gln Ala Leu Cys Asn Thr Thr
385                 390                 395                 400

Gln Thr Ser Ser Arg Gly Ser Tyr Tyr Leu Val Ala Pro Thr Gly Thr
                405                 410                 415

Met Trp Ala Cys Ser Thr Gly Leu Thr Pro Cys Ile Ser Thr Thr Ile
                420                 425                 430

Leu Asn Leu Thr Thr Asp Tyr Cys Val Leu Val Glu Leu Trp Pro Arg
                435                 440                 445

Val Thr Tyr His Ser Pro Ser Tyr Val Tyr Gly Leu Phe Glu Arg Ser
                450                 455                 460

Asn Arg His Lys Arg Glu Pro Val Ser Leu Thr Leu Ala Leu Leu Leu
465                 470                 475                 480

Gly Gly Leu Thr Met Gly Gly Ile Ala Ala Gly Ile Gly Thr Gly Thr
                485                 490                 495

Thr Ala Leu Met Ala Thr Gln Gln Phe Gln Gln Leu Gln Ala Ala Val
                500                 505                 510

Gln Asp Asp Leu Arg Glu Val Glu Lys Ser Ile Ser Asn Leu Glu Lys
                515                 520                 525

Ser Leu Thr Ser Leu Ser Glu Val Val Leu Gln Asn Arg Arg Gly Leu
                530                 535                 540

Asp Leu Leu Phe Leu Lys Glu Gly Gly Leu Cys Ala Ala Leu Lys Glu
545                 550                 555                 560

Glu Cys Cys Phe Tyr Ala Asp His Thr Gly Leu Val Arg Asp Ser Met
                565                 570                 575

Ala Lys Leu Arg Glu Arg Leu Asn Gln Arg Gln Lys Leu Phe Glu Ser
                580                 585                 590

Thr Gln Gly Trp Phe Glu Gly Leu Phe Asn Arg Ser Pro Trp Phe Thr
                595                 600                 605

Thr Leu Ile Ser Thr Ile Met Gly Pro Leu Ile Val Leu Leu Met Ile
                610                 615                 620

Leu Leu Phe Gly Pro Cys Ile Leu Asn Arg Leu Val Gln Phe Val Lys
625                 630                 635                 640

Asp Arg Ile Ser Val Val Gln Ala Leu Val Leu Thr Gln Gln Tyr His
                645                 650                 655

Gln Leu Lys Pro Ile Glu Tyr Glu Pro
                660                 665

<210> SEQ ID NO 309
<211> LENGTH: 654
<212> TYPE: PRT
<213> ORGANISM: Artificial Sequence
<220> FEATURE:
<223> OTHER INFORMATION: Synthetic
<220> FEATURE:
```

<221> NAME/KEY: MISC_FEATURE
<222> LOCATION: (1)..(1)
<223> OTHER INFORMATION: optionally absent

<400> SEQUENCE: 309

Met Ala Arg Ser Thr Leu Ser Lys Pro Pro Gln Asp Lys Ile Asn Pro
1               5                   10                  15

Trp Lys Pro Leu Ile Val Met Gly Val Leu Leu Gly Val Gly Met Ala
            20                  25                  30

Glu Ser Pro His Gln Val Phe Asn Val Thr Trp Arg Val Thr Asn Leu
        35                  40                  45

Met Thr Gly Arg Thr Ala Asn Ala Thr Ser Leu Leu Gly Thr Val Gln
50                  55                  60

Asp Ala Phe Pro Lys Leu Tyr Phe Asp Leu Cys Asp Leu Val Gly Glu
65                  70                  75                  80

Glu Trp Asp Pro Ser Asp Gln Glu Pro Tyr Val Gly Tyr Gly Cys Lys
                85                  90                  95

Tyr Pro Ala Gly Arg Gln Arg Thr Arg Thr Phe Asp Phe Tyr Val Cys
            100                 105                 110

Pro Gly His Thr Val Lys Ser Gly Cys Gly Gly Pro Gly Glu Gly Tyr
        115                 120                 125

Cys Gly Lys Trp Gly Cys Glu Thr Thr Gly Gln Ala Tyr Trp Lys Pro
130                 135                 140

Thr Ser Ser Trp Asp Leu Ile Ser Leu Lys Arg Gly Asn Thr Pro Trp
145                 150                 155                 160

Asp Thr Gly Cys Ser Lys Val Ala Cys Gly Pro Cys Tyr Asp Leu Ser
                165                 170                 175

Lys Val Ser Asn Ser Phe Gln Gly Ala Thr Arg Gly Gly Arg Cys Asn
            180                 185                 190

Pro Leu Val Leu Glu Phe Thr Asp Ala Gly Lys Lys Ala Asn Trp Asp
        195                 200                 205

Gly Pro Lys Ser Trp Gly Leu Arg Leu Tyr Arg Thr Gly Thr Asp Pro
210                 215                 220

Ile Thr Met Phe Ser Leu Thr Arg Gln Val Leu Asn Val Gly Pro Arg
225                 230                 235                 240

Val Pro Ile Gly Pro Asn Pro Val Leu Pro Asp Gln Arg Leu Pro Ser
                245                 250                 255

Ser Pro Ile Glu Ile Val Pro Ala Pro Gln Pro Ser Pro Leu Asn
            260                 265                 270

Thr Ser Tyr Pro Pro Ser Thr Thr Ser Thr Pro Ser Thr Ser Pro Thr
        275                 280                 285

Ser Pro Ser Val Pro Gln Pro Pro Gly Thr Gly Asp Arg Leu Leu
290                 295                 300

Ala Leu Val Lys Gly Ala Tyr Gln Ala Leu Asn Leu Thr Asn Pro Asp
305                 310                 315                 320

Lys Thr Gln Glu Cys Trp Leu Cys Leu Val Ser Gly Pro Pro Tyr Tyr
                325                 330                 335

Glu Gly Val Ala Val Val Gly Thr Tyr Thr Asn His Ser Thr Ala Pro
            340                 345                 350

Ala Asn Cys Thr Ala Thr Ser Gln His Lys Leu Thr Leu Ser Glu Val
        355                 360                 365

Thr Gly Gln Gly Leu Cys Met Gly Ala Val Pro Lys Thr His Gln Ala
370                 375                 380

Leu Cys Asn Thr Thr Gln Ser Ala Gly Ser Gly Ser Tyr Tyr Leu Ala

```
                385                 390                 395                 400
Ala Pro Ala Gly Thr Met Trp Ala Cys Ser Thr Gly Leu Thr Pro Cys
                405                 410                 415

Leu Ser Thr Thr Val Leu Asn Leu Thr Thr Asp Tyr Cys Val Leu Val
            420                 425                 430

Glu Leu Trp Pro Arg Val Ile Tyr His Ser Pro Asp Tyr Met Tyr Gly
        435                 440                 445

Gln Leu Glu Gln Arg Thr Lys Tyr Lys Arg Glu Pro Val Ser Leu Thr
    450                 455                 460

Leu Ala Leu Leu Leu Gly Gly Leu Thr Met Gly Gly Ile Ala Ala Gly
465                 470                 475                 480

Ile Gly Thr Gly Thr Thr Ala Leu Ile Lys Thr Gln Gln Phe Glu Gln
                485                 490                 495

Leu His Ala Ala Ile Gln Thr Asp Leu Asn Glu Val Glu Lys Ser Ile
            500                 505                 510

Thr Asn Leu Glu Lys Ser Leu Thr Ser Leu Ser Glu Val Val Leu Gln
        515                 520                 525

Asn Arg Arg Gly Leu Asp Leu Leu Phe Leu Lys Glu Gly Gly Leu Cys
    530                 535                 540

Ala Ala Leu Lys Glu Glu Cys Cys Phe Tyr Ala Asp His Thr Gly Leu
545                 550                 555                 560

Val Arg Asp Ser Met Ala Lys Leu Arg Glu Arg Leu Asn Gln Arg Gln
                565                 570                 575

Lys Leu Phe Glu Thr Gly Gln Gly Trp Phe Glu Gly Leu Phe Asn Arg
            580                 585                 590

Ser Pro Trp Phe Thr Thr Leu Ile Ser Thr Ile Met Gly Pro Leu Ile
        595                 600                 605

Val Leu Leu Leu Ile Leu Leu Phe Gly Pro Cys Ile Leu Asn Arg Leu
    610                 615                 620

Val Gln Phe Val Lys Asp Arg Ile Ser Val Val Gln Ala Leu Val Leu
625                 630                 635                 640

Thr Gln Gln Tyr His Gln Leu Lys Pro Ile Glu Tyr Glu Pro
                645                 650

<210> SEQ ID NO 310
<211> LENGTH: 981
<212> TYPE: PRT
<213> ORGANISM: Artificial Sequence
<220> FEATURE:
<223> OTHER INFORMATION: Synthetic

<400> SEQUENCE: 310

Ser Ala Ala Pro Leu Val Thr Ala Met Cys Leu Leu Gly Asn Val Ser
1               5                   10                  15

Phe Pro Cys Asp Arg Pro Pro Thr Cys Tyr Thr Arg Glu Pro Ser Arg
                20                  25                  30

Ala Leu Asp Ile Leu Glu Glu Asn Val Asn His Glu Ala Tyr Asp Thr
            35                  40                  45

Leu Leu Asn Ala Ile Leu Arg Cys Gly Ser Ser Gly Arg Ser Lys Arg
        50                  55                  60

Ser Val Ile Asp Asp Phe Thr Leu Thr Ser Pro Tyr Leu Gly Thr Cys
65                  70                  75                  80

Ser Tyr Cys His His Thr Val Pro Cys Phe Ser Pro Val Lys Ile Glu
                85                  90                  95

Gln Val Trp Asp Glu Ala Asp Asp Asn Thr Ile Arg Ile Gln Thr Ser
```

```
                100                 105                 110
Ala Gln Phe Gly Tyr Asp Gln Ser Gly Ala Ala Ser Ala Asn Lys Tyr
            115                 120                 125

Arg Tyr Met Ser Leu Lys Gln Asp His Thr Val Lys Glu Gly Thr Met
        130                 135                 140

Asp Asp Ile Lys Ile Ser Thr Ser Gly Pro Cys Arg Arg Leu Ser Tyr
145                 150                 155                 160

Lys Gly Tyr Phe Leu Leu Ala Lys Cys Pro Pro Gly Asp Ser Val Thr
                165                 170                 175

Val Ser Ile Val Ser Ser Asn Ser Ala Thr Ser Cys Thr Leu Ala Arg
            180                 185                 190

Lys Ile Lys Pro Lys Phe Val Gly Arg Glu Lys Tyr Asp Leu Pro Pro
        195                 200                 205

Val His Gly Lys Lys Ile Pro Cys Thr Val Tyr Asp Arg Leu Lys Glu
    210                 215                 220

Thr Thr Ala Gly Tyr Ile Thr Met His Arg Pro Arg Pro His Ala Tyr
225                 230                 235                 240

Thr Ser Tyr Leu Glu Glu Ser Ser Gly Lys Val Tyr Ala Lys Pro Pro
                245                 250                 255

Ser Gly Lys Asn Ile Thr Tyr Glu Cys Lys Cys Gly Asp Tyr Lys Thr
            260                 265                 270

Gly Thr Val Ser Thr Arg Thr Glu Ile Thr Gly Cys Thr Ala Ile Lys
        275                 280                 285

Gln Cys Val Ala Tyr Lys Ser Asp Gln Thr Lys Trp Val Phe Asn Ser
    290                 295                 300

Pro Asp Leu Ile Arg His Asp Asp His Thr Ala Gln Gly Lys Leu His
305                 310                 315                 320

Leu Pro Phe Lys Leu Ile Pro Ser Thr Cys Met Val Pro Val Ala His
                325                 330                 335

Ala Pro Asn Val Ile His Gly Phe Lys His Ile Ser Leu Gln Leu Asp
            340                 345                 350

Thr Asp His Leu Thr Leu Leu Thr Thr Arg Arg Leu Gly Ala Asn Pro
        355                 360                 365

Glu Pro Thr Thr Glu Trp Ile Val Gly Lys Thr Val Arg Asn Phe Thr
    370                 375                 380

Val Asp Arg Asp Gly Leu Glu Tyr Ile Trp Gly Asn His Glu Pro Val
385                 390                 395                 400

Arg Val Tyr Ala Gln Glu Ser Ala Pro Gly Asp Pro His Gly Trp Pro
                405                 410                 415

His Glu Ile Val Gln His Tyr Tyr His Arg His Pro Val Tyr Thr Ile
            420                 425                 430

Leu Ala Val Ala Ser Ala Thr Val Ala Met Met Ile Gly Val Thr Val
        435                 440                 445

Ala Val Leu Cys Ala Cys Lys Ala Arg Arg Glu Cys Leu Thr Pro Tyr
    450                 455                 460

Ala Leu Ala Pro Asn Ala Val Ile Pro Thr Ser Leu Ala Leu Leu Cys
465                 470                 475                 480

Cys Val Arg Ser Ala Asn Ala Glu Thr Phe Thr Glu Thr Met Ser Tyr
                485                 490                 495

Leu Trp Ser Asn Ser Gln Pro Phe Phe Trp Val Gln Leu Cys Ile Pro
            500                 505                 510

Leu Ala Ala Phe Ile Val Leu Met Arg Cys Cys Ser Cys Cys Leu Pro
        515                 520                 525
```

```
Phe Leu Val Val Ala Gly Ala Tyr Leu Ala Lys Val Asp Ala Tyr Glu
    530                 535                 540

His Ala Thr Thr Val Pro Asn Val Pro Gln Ile Pro Tyr Lys Ala Leu
545                 550                 555                 560

Val Glu Arg Ala Gly Tyr Ala Pro Leu Asn Leu Glu Ile Thr Val Met
                565                 570                 575

Ser Ser Glu Val Leu Pro Ser Thr Asn Gln Glu Tyr Ile Thr Cys Lys
            580                 585                 590

Phe Thr Thr Val Val Pro Ser Pro Lys Ile Lys Cys Cys Gly Ser Leu
        595                 600                 605

Glu Cys Gln Pro Ala Ala His Ala Asp Tyr Thr Cys Lys Val Phe Gly
    610                 615                 620

Gly Val Tyr Pro Phe Met Trp Gly Gly Ala Gln Cys Phe Cys Asp Ser
625                 630                 635                 640

Glu Asn Ser Gln Met Ser Glu Ala Tyr Val Glu Leu Ser Ala Asp Cys
                645                 650                 655

Ala Ser Asp His Ala Gln Ala Ile Lys Val His Thr Ala Ala Met Lys
            660                 665                 670

Val Gly Leu Arg Ile Val Tyr Gly Asn Thr Thr Ser Phe Leu Asp Val
        675                 680                 685

Tyr Val Asn Gly Val Thr Pro Gly Thr Ser Lys Asp Leu Lys Val Ile
    690                 695                 700

Ala Gly Pro Ile Ser Ala Ser Phe Thr Pro Phe Asp His Lys Val Val
705                 710                 715                 720

Ile His Arg Gly Leu Val Tyr Asn Tyr Asp Phe Pro Glu Tyr Gly Ala
                725                 730                 735

Met Lys Pro Gly Ala Phe Gly Asp Ile Gln Ala Thr Ser Leu Thr Ser
            740                 745                 750

Lys Asp Leu Ile Ala Ser Thr Asp Ile Arg Leu Leu Lys Pro Ser Ala
        755                 760                 765

Lys Asn Val His Val Pro Tyr Thr Gln Ala Ser Ser Gly Phe Glu Met
    770                 775                 780

Trp Lys Asn Asn Ser Gly Arg Pro Leu Gln Glu Thr Ala Pro Phe Gly
785                 790                 795                 800

Cys Lys Ile Ala Val Asn Pro Leu Arg Ala Val Asp Cys Ser Tyr Gly
                805                 810                 815

Asn Ile Pro Ile Ser Ile Asp Ile Pro Asn Ala Ala Phe Ile Arg Thr
            820                 825                 830

Ser Asp Ala Pro Leu Val Ser Thr Val Lys Cys Glu Val Ser Glu Cys
        835                 840                 845

Thr Tyr Ser Ala Asp Phe Gly Gly Met Ala Thr Leu Gln Tyr Val Ser
    850                 855                 860

Asp Arg Glu Gly Gln Cys Pro Val His Ser His Ser Ser Thr Ala Thr
865                 870                 875                 880

Leu Gln Glu Ser Thr Val His Val Leu Glu Lys Gly Ala Val Thr Val
                885                 890                 895

His Phe Ser Thr Ala Ser Pro Gln Ala Asn Phe Ile Val Ser Leu Cys
            900                 905                 910

Gly Lys Lys Thr Thr Cys Asn Ala Glu Cys Lys Pro Pro Ala Asp His
        915                 920                 925

Ile Val Ser Thr Pro His Lys Asn Asp Gln Glu Phe Gln Ala Ala Ile
    930                 935                 940
```

```
Ser Lys Thr Ser Trp Ser Trp Leu Phe Ala Leu Phe Gly Gly Ala Ser
945                 950                 955                 960

Ser Leu Leu Ile Ile Gly Leu Met Ile Phe Ala Cys Ser Met Met Leu
                965                 970                 975

Thr Ser Thr Arg Arg
            980

<210> SEQ ID NO 311
<211> LENGTH: 676
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 311

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
            35                  40                  45

Asp Lys Leu Val Cys Arg Asp Lys Leu Ser Ser Thr Asn Gln Leu Arg
50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
290                 295                 300
```

```
Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
                325                 330                 335

Glu Asp His Lys Ile Met Ala Ser Glu Asn Ser Ser Ala Met Val Gln
            340                 345                 350

Val His Ser Gln Gly Arg Glu Ala Ala Val Ser His Leu Thr Thr Leu
        355                 360                 365

Ala Thr Ile Ser Thr Ser Pro Gln Ser Leu Thr Thr Lys Pro Gly Pro
370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
                405                 410                 415

Ala Ser Asp Thr Pro Ser Ala Thr Thr Ala Ala Gly Pro Pro Lys Ala
            420                 425                 430

Glu Asn Thr Asn Thr Ser Lys Ser Thr Asp Phe Leu Asp Pro Ala Thr
        435                 440                 445

Thr Thr Ser Pro Gln Asn His Ser Glu Thr Ala Gly Asn Asn Asn Thr
450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Ile
530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
        675

<210> SEQ ID NO 312
<211> LENGTH: 853
<212> TYPE: PRT
<213> ORGANISM: Artificial Sequence
<220> FEATURE:
```

-continued

```
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 312

Met Arg Val Lys Glu Lys Tyr Gln His Leu Trp Arg Trp Gly Trp Lys
1               5                   10                  15

Trp Gly Ile Met Leu Leu Gly Ile Leu Met Ile Cys Ser Ala Thr Glu
            20                  25                  30

Asn Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Cys Ala Thr His Ala Cys Val Pro Thr Asp Pro Asn
65                  70                  75                  80

Pro Gln Glu Val Ile Leu Val Asn Val Thr Glu Asn Phe Asp Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Asn
        115                 120                 125

Leu Lys Cys Thr Asp Leu Lys Asn Asp Thr Asn Thr Asn Ser Ser Asn
130                 135                 140

Gly Arg Met Ile Met Glu Lys Gly Glu Ile Lys Asn Cys Ser Phe Asn
145                 150                 155                 160

Ile Ser Thr Ser Ile Arg Asn Lys Val Gln Lys Glu Tyr Ala Phe Phe
                165                 170                 175

Tyr Lys Leu Asp Ile Arg Pro Ile Asp Asn Thr Thr Tyr Arg Leu Ile
            180                 185                 190

Ser Cys Asn Thr Ser Val Ile Thr Gln Ala Cys Pro Lys Val Ser Phe
        195                 200                 205

Glu Pro Ile Pro Ile His Tyr Cys Ala Pro Ala Gly Phe Ala Ile Leu
    210                 215                 220

Lys Cys Asn Asp Lys Thr Phe Asn Gly Thr Gly Pro Cys Thr Asn Val
225                 230                 235                 240

Ser Thr Val Gln Cys Thr His Gly Ile Arg Pro Val Val Ser Thr Gln
                245                 250                 255

Leu Leu Leu Asn Gly Ser Leu Ala Glu Glu Glu Gly Val Ile Arg Ser
            260                 265                 270

Ala Asn Phe Thr Asp Asn Ala Lys Thr Ile Ile Val Gln Leu Asn Thr
        275                 280                 285

Ser Val Glu Ile Asn Cys Thr Arg Pro Asn Asn Asn Thr Arg Lys Ser
    290                 295                 300

Ile Arg Ile Gln Arg Gly Pro Gly Arg Ala Phe Val Thr Ile Gly Lys
305                 310                 315                 320

Ile Gly Asn Met Arg Gln Ala His Cys Asn Ile Ser Arg Ala Lys Trp
                325                 330                 335

Met Ser Thr Leu Lys Gln Ile Ala Ser Lys Leu Arg Glu Gln Phe Gly
            340                 345                 350

Asn Asn Lys Thr Val Ile Phe Lys Gln Ser Ser Gly Gly Asp Pro Glu
        355                 360                 365

Ile Val Thr His Ser Phe Asn Cys Gly Gly Glu Phe Phe Tyr Cys Asn
    370                 375                 380
```

```
Ser Thr Gln Leu Phe Asn Ser Thr Trp Phe Asn Ser Thr Trp Ser Thr
385                 390                 395                 400

Glu Gly Ser Asn Asn Thr Glu Gly Ser Asp Thr Ile Thr Leu Pro Cys
            405                 410                 415

Arg Ile Lys Gln Phe Ile Asn Met Trp Gln Glu Val Gly Lys Ala Met
        420                 425                 430

Tyr Ala Pro Pro Ile Ser Gly Gln Ile Arg Cys Ser Ser Asn Ile Thr
            435                 440                 445

Gly Leu Leu Leu Thr Arg Asp Gly Gly Lys Asn Thr Asn Glu Ser Glu
        450                 455                 460

Val Phe Arg Pro Gly Gly Gly Asp Met Arg Asp Asn Trp Arg Ser Glu
465                 470                 475                 480

Leu Tyr Lys Tyr Lys Val Val Lys Ile Glu Thr Leu Gly Val Ala Pro
            485                 490                 495

Thr Lys Ala Lys Arg Arg Val Val Gln Arg Glu Lys Arg Ala Val Gly
        500                 505                 510

Ile Gly Ala Leu Phe Leu Gly Phe Leu Gly Ala Ala Gly Ser Thr Met
        515                 520                 525

Gly Ala Ala Ser Met Thr Leu Thr Val Gln Ala Arg Gln Leu Leu Ser
530                 535                 540

Gly Ile Val Gln Gln Gln Asn Asn Leu Leu Arg Ala Ile Glu Ala Gln
545                 550                 555                 560

Gln His Leu Leu Gln Leu Thr Val Trp Gly Ile Lys Gln Leu Gln Ala
            565                 570                 575

Arg Ile Leu Ala Val Glu Arg Tyr Leu Lys Asp Gln Gln Leu Leu Gly
        580                 585                 590

Ile Trp Gly Cys Ser Gly Lys Leu Ile Cys Thr Thr Ala Val Pro Trp
        595                 600                 605

Asn Ala Ser Trp Ser Asn Lys Ser Leu Glu Gln Phe Trp Asn Asn Met
        610                 615                 620

Thr Trp Met Glu Trp Asp Arg Glu Ile Asn Asn Tyr Thr Ser Leu Ile
625                 630                 635                 640

His Ser Leu Ile Asp Glu Ser Gln Asn Gln Gln Glu Lys Asn Glu Gln
            645                 650                 655

Glu Leu Leu Glu Leu Asp Lys Trp Ala Ser Leu Trp Asn Trp Phe Asn
            660                 665                 670

Ile Thr Asn Trp Leu Trp Tyr Ile Lys Ile Phe Ile Met Ile Val Gly
        675                 680                 685

Gly Leu Val Gly Leu Arg Ile Val Phe Ala Val Leu Ser Ile Val Asn
        690                 695                 700

Arg Val Arg Gln Gly Tyr Ser Pro Leu Ser Phe Gln Thr His Leu Pro
705                 710                 715                 720

Asn Arg Gly Gly Pro Asp Arg Pro Glu Gly Ile Glu Glu Glu Gly Gly
            725                 730                 735

Glu Arg Asp Arg Asp Arg Ser Val Arg Leu Val Asn Gly Ser Leu Ala
            740                 745                 750

Leu Ile Trp Asp Asp Leu Arg Ser Leu Cys Leu Phe Ser Tyr His Arg
        755                 760                 765

Leu Arg Asp Leu Leu Leu Ile Val Thr Arg Ile Val Glu Leu Leu Gly
        770                 775                 780

Arg Arg Gly Trp Glu Ala Leu Lys Tyr Trp Trp Asn Leu Leu Gln Tyr
785                 790                 795                 800
```

```
Trp Ser Gln Glu Leu Lys Asn Ser Ala Val Ser Leu Leu Asn Ala Thr
                805                 810                 815

Ala Ile Ala Val Ala Glu Gly Thr Asp Arg Val Ile Glu Val Val Gln
            820                 825                 830

Gly Ala Tyr Arg Ala Ile Arg His Ile Pro Arg Arg Ile Arg Gln Gly
        835                 840                 845

Leu Glu Arg Ile Leu
        850

<210> SEQ ID NO 313
<211> LENGTH: 574
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 313

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Pro Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285
```

```
Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Ile Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Met Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 314
<211> LENGTH: 1255
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 314

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
```

```
            50                  55                  60
Asn Val Thr Gly Phe His Thr Ile Asn His Thr Phe Gly Asn Pro Val
 65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
                    100                 105                 110

Ser Val Ile Ile Ile Asn Asn Ser Thr Asn Val Val Ile Arg Ala Cys
                115                 120                 125

Asn Phe Glu Leu Cys Asp Asn Pro Phe Phe Ala Val Ser Lys Pro Met
            130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
                180                 185                 190

Phe Leu Tyr Val Tyr Lys Gly Tyr Gln Pro Ile Asp Val Val Arg Asp
                195                 200                 205

Leu Pro Ser Gly Phe Asn Thr Leu Lys Pro Ile Phe Lys Leu Pro Leu
210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Tyr Phe Val Gly Tyr
                    245                 250                 255

Leu Lys Pro Thr Thr Phe Met Leu Lys Tyr Asp Glu Asn Gly Thr Ile
                260                 265                 270

Thr Asp Ala Val Asp Cys Ser Gln Asn Pro Leu Ala Glu Leu Lys Cys
                275                 280                 285

Ser Val Lys Ser Phe Glu Ile Asp Lys Gly Ile Tyr Gln Thr Ser Asn
                290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
                340                 345                 350

Ser Val Leu Tyr Asn Ser Thr Phe Phe Ser Thr Phe Lys Cys Tyr Gly
                355                 360                 365

Val Ser Ala Thr Lys Leu Asn Asp Leu Cys Phe Ser Asn Val Tyr Ala
                370                 375                 380

Asp Ser Phe Val Val Lys Gly Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
                420                 425                 430

Thr Gly Asn Tyr Asn Tyr Lys Tyr Arg Tyr Leu Arg His Gly Lys Leu
                435                 440                 445

Arg Pro Phe Glu Arg Asp Ile Ser Asn Val Pro Phe Ser Pro Asp Gly
            450                 455                 460

Lys Pro Cys Thr Pro Pro Ala Leu Asn Cys Tyr Trp Pro Leu Asn Asp
465                 470                 475                 480
```

-continued

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

```
Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile Arg Ala Ser Ala Asn Leu Ala Ala
        995                 1000                1005

Thr Lys Met Ser Glu Cys Val Leu Gly Gln Ser Lys Arg Val Asp
    1010                1015                1020

Phe Cys Gly Lys Gly Tyr His Leu Met Ser Phe Pro Gln Ala Ala
    1025                1030                1035

Pro His Gly Val Val Phe Leu His Val Thr Tyr Val Pro Ser Gln
    1040                1045                1050

Glu Arg Asn Phe Thr Thr Ala Pro Ala Ile Cys His Glu Gly Lys
    1055                1060                1065

Ala Tyr Phe Pro Arg Glu Gly Val Phe Val Phe Asn Gly Thr Ser
    1070                1075                1080

Trp Phe Ile Thr Gln Arg Asn Phe Phe Ser Pro Gln Ile Ile Thr
    1085                1090                1095

Thr Asp Asn Thr Phe Val Ser Gly Asn Cys Asp Val Val Ile Gly
    1100                1105                1110

Ile Ile Asn Asn Thr Val Tyr Asp Pro Leu Gln Pro Glu Leu Asp
    1115                1120                1125

Ser Phe Lys Glu Glu Leu Asp Lys Tyr Phe Lys Asn His Thr Ser
    1130                1135                1140

Pro Asp Val Asp Leu Gly Asp Ile Ser Gly Ile Asn Ala Ser Val
    1145                1150                1155

Val Asn Ile Gln Lys Glu Ile Asp Arg Leu Asn Glu Val Ala Lys
    1160                1165                1170

Asn Leu Asn Glu Ser Leu Ile Asp Leu Gln Glu Leu Gly Lys Tyr
    1175                1180                1185

Glu Gln Tyr Ile Lys Trp Pro Trp Tyr Val Trp Leu Gly Phe Ile
    1190                1195                1200

Ala Gly Leu Ile Ala Ile Val Met Val Thr Ile Leu Leu Cys Cys
    1205                1210                1215

Met Thr Ser Cys Cys Ser Cys Leu Lys Gly Ala Cys Ser Cys Gly
    1220                1225                1230

Ser Cys Cys Lys Phe Asp Glu Asp Asp Ser Glu Pro Val Leu Lys
    1235                1240                1245

Gly Val Lys Leu His Tyr Thr
    1250                1255

<210> SEQ ID NO 315
<211> LENGTH: 566
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (1)..(1)
<223> OTHER INFORMATION: optionally absent

<400> SEQUENCE: 315

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Ile His His Pro Ser Thr Asn Gln Glu Gln Thr
        195                 200                 205

Ser Leu Tyr Val Gln Ala Ser Gly Arg Val Thr Val Ser Thr Arg Arg
    210                 215                 220

Ser Gln Gln Thr Ile Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Arg Ser Asp Ala
        275                 280                 285

Pro Ile Asp Thr Cys Ile Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
    370                 375                 380
```

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
            405                 410                 415

Glu Val Glu Gly Arg Ile Gln Asp Leu Glu Lys Tyr Val Glu Asp Thr
        420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
        450                 455                 460

Glu Lys Thr Arg Arg Gln Leu Arg Glu Asn Ala Glu Glu Met Gly Asn
465                 470                 475                 480

Gly Cys Phe Lys Ile Tyr His Lys Cys Asp Asn Ala Cys Ile Glu Ser
            485                 490                 495

Ile Arg Asn Gly Thr Tyr Asp His Asp Val Tyr Arg Asp Glu Ala Leu
        500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
        530                 535                 540

Val Val Leu Leu Gly Phe Ile Met Trp Ala Cys Gln Arg Gly Asn Ile
545                 550                 555                 560

Arg Cys Asn Ile Cys Ile
            565

<210> SEQ ID NO 316
<211> LENGTH: 4
<212> TYPE: PRT
<213> ORGANISM: Artificial Sequence
<220> FEATURE:
<223> OTHER INFORMATION: Synthetic

<400> SEQUENCE: 316

Ala Ala Ala Ala
1

<210> SEQ ID NO 317
<211> LENGTH: 263
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (204)..(212)
<223> OTHER INFORMATION: optionally absent

<400> SEQUENCE: 317

Met Glu Glu Leu Phe Lys Lys His Lys Ile Val Ala Val Leu Arg Ala
1               5                   10                  15

Asn Ser Val Glu Glu Ala Lys Lys Lys Ala Leu Ala Val Phe Leu Gly
            20                  25                  30

Gly Val His Leu Ile Glu Ile Thr Phe Thr Val Pro Asp Ala Asp Thr
        35                  40                  45

Val Ile Lys Glu Leu Ser Phe Leu Lys Glu Met Gly Ala Ile Ile Gly
    50                  55                  60

```
Ala Gly Thr Val Thr Ser Val Glu Gln Cys Arg Lys Ala Val Glu Ser
 65                  70                  75                  80

Gly Ala Glu Phe Ile Val Ser Pro His Leu Asp Glu Glu Ile Ser Gln
             85                  90                  95

Phe Cys Lys Glu Lys Gly Val Phe Tyr Met Pro Gly Val Met Thr Pro
            100                 105                 110

Thr Glu Leu Val Lys Ala Met Lys Leu Gly His Thr Ile Leu Lys Leu
            115                 120                 125

Phe Pro Gly Glu Val Val Gly Pro Gln Phe Val Lys Ala Met Lys Gly
130                 135                 140

Pro Phe Pro Asn Val Lys Phe Val Pro Thr Gly Gly Val Asn Leu Asp
145                 150                 155                 160

Asn Val Cys Glu Trp Phe Lys Ala Gly Val Leu Ala Val Gly Val Gly
            165                 170                 175

Ser Ala Leu Val Lys Gly Thr Pro Val Glu Val Ala Glu Lys Ala Lys
            180                 185                 190

Ala Phe Val Glu Lys Ile Arg Gly Cys Thr Glu Gln Lys Leu Ile Ser
            195                 200                 205

Glu Glu Asp Leu Gln Ser Arg Pro Glu Pro Thr Ala Pro Pro Glu Glu
210                 215                 220

Ser Phe Arg Ser Gly Val Glu Thr Thr Thr Pro Pro Gln Lys Gln Glu
225                 230                 235                 240

Pro Ile Asp Lys Glu Leu Tyr Pro Leu Thr Ser Leu Arg Ser Leu Phe
            245                 250                 255

Gly Asn Asp Pro Ser Ser Gln
            260

<210> SEQ ID NO 318
<211> LENGTH: 282
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (223)..(231)
<223> OTHER INFORMATION: optionally absent

<400> SEQUENCE: 318

Met Gly Ala Arg Ala Ser Gly Ser Lys Ser Gly Ser Gly Ser Asp Ser
  1               5                  10                  15

Gly Ser Lys Met Glu Glu Leu Phe Lys Lys His Lys Ile Val Ala Val
             20                  25                  30

Leu Arg Ala Asn Ser Val Glu Glu Ala Lys Lys Lys Ala Leu Ala Val
         35                  40                  45

Phe Leu Gly Gly Val His Leu Ile Glu Ile Thr Phe Thr Val Pro Asp
     50                  55                  60

Ala Asp Thr Val Ile Lys Glu Leu Ser Phe Leu Lys Glu Met Gly Ala
 65                  70                  75                  80

Ile Ile Gly Ala Gly Thr Val Thr Ser Val Glu Gln Cys Arg Lys Ala
             85                  90                  95

Val Glu Ser Gly Ala Glu Phe Ile Val Ser Pro His Leu Asp Glu Glu
            100                 105                 110

Ile Ser Gln Phe Cys Lys Glu Lys Gly Val Phe Tyr Met Pro Gly Val
```

```
            115                 120                 125
Met Thr Pro Thr Glu Leu Val Lys Ala Met Lys Leu Gly His Thr Ile
    130                 135                 140

Leu Lys Leu Phe Pro Gly Glu Val Val Gly Pro Gln Phe Val Lys Ala
145                 150                 155                 160

Met Lys Gly Pro Phe Pro Asn Val Lys Phe Val Pro Thr Gly Gly Val
                165                 170                 175

Asn Leu Asp Asn Val Cys Glu Trp Phe Lys Ala Gly Val Leu Ala Val
            180                 185                 190

Gly Val Gly Ser Ala Leu Val Lys Gly Thr Pro Val Glu Val Ala Glu
        195                 200                 205

Lys Ala Lys Ala Phe Val Glu Lys Ile Arg Gly Cys Thr Glu Gln Lys
    210                 215                 220

Leu Ile Ser Glu Glu Asp Leu Gln Ser Arg Pro Glu Pro Thr Ala Pro
225                 230                 235                 240

Pro Glu Glu Ser Phe Arg Ser Gly Val Glu Thr Thr Thr Pro Pro Gln
                245                 250                 255

Lys Gln Glu Pro Ile Asp Lys Glu Leu Tyr Pro Leu Thr Ser Leu Arg
            260                 265                 270

Ser Ala Ala Gly Asn Asp Pro Ser Ser Gln
        275                 280

<210> SEQ ID NO 319
<211> LENGTH: 20
<212> TYPE: DNA
<213> ORGANISM: Artificial Sequence
<220> FEATURE:
<223> OTHER INFORMATION: Synthetic

<400> SEQUENCE: 319
catactgttg gttgctaggc                                              20

<210> SEQ ID NO 320
<211> LENGTH: 24
<212> TYPE: DNA
<213> ORGANISM: Artificial Sequence
<220> FEATURE:
<223> OTHER INFORMATION: Synthetic

<400> SEQUENCE: 320
gctgtgacga taacgttgta gatg                                         24

<210> SEQ ID NO 321
<211> LENGTH: 20
<212> TYPE: DNA
<213> ORGANISM: Artificial Sequence
<220> FEATURE:
<223> OTHER INFORMATION: Synthetic

<400> SEQUENCE: 321
ggacgatggg catgaaactg                                              20

<210> SEQ ID NO 322
<211> LENGTH: 20
<212> TYPE: DNA
<213> ORGANISM: Artificial Sequence
<220> FEATURE:
<223> OTHER INFORMATION: Synthetic

<400> SEQUENCE: 322
taggattact gctcggtgac                                              20
```

<210> SEQ ID NO 323
<211> LENGTH: 20
<212> TYPE: PRT
<213> ORGANISM: Artificial Sequence
<220> FEATURE:
<223> OTHER INFORMATION: Synthetic

<400> SEQUENCE: 323

Cys Cys Ala Ala Ala Thr Ala Gly Gly Ala Thr Gly Thr Gly Thr Gly
1               5                   10                  15

Cys Gly Ala Cys
            20

<210> SEQ ID NO 324
<211> LENGTH: 26
<212> TYPE: DNA
<213> ORGANISM: Artificial Sequence
<220> FEATURE:
<223> OTHER INFORMATION: Synthetic

<400> SEQUENCE: 324
ccacaaagac attggaacac tatacc                                            26

<210> SEQ ID NO 325
<211> LENGTH: 24
<212> TYPE: DNA
<213> ORGANISM: Artificial Sequence
<220> FEATURE:
<223> OTHER INFORMATION: Synthetic

<400> SEQUENCE: 325
gctgtgacga taacgttgta gatg                                              24

<210> SEQ ID NO 326
<211> LENGTH: 26
<212> TYPE: DNA
<213> ORGANISM: Artificial Sequence
<220> FEATURE:
<223> OTHER INFORMATION: Synthetic

<400> SEQUENCE: 326
ccttatctgc ttcctagtcc tgtatg                                            26

<210> SEQ ID NO 327
<211> LENGTH: 20
<212> TYPE: DNA
<213> ORGANISM: Artificial Sequence
<220> FEATURE:
<223> OTHER INFORMATION: Synthetic

<400> SEQUENCE: 327
ggacgatggg catgaaactg                                                   20

<210> SEQ ID NO 328
<211> LENGTH: 532
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent
<220> FEATURE:
<221> NAME/KEY: MISC_FEATURE
<222> LOCATION: (3)..(11)

<223> OTHER INFORMATION: optionally absent

<400> SEQUENCE: 328

```
Met Glu Gln Lys Leu Ile Ser Glu Glu Asp Leu Gln Pro Trp His Gly
1               5                   10                  15

Lys Ala Met Gln Arg Ala Ser Glu Ala Gly Ala Thr Ala Pro Lys Ala
            20                  25                  30

Ser Ala Arg Asn Ala Arg Gly Ala Pro Met Asp Pro Thr Glu Ser Pro
        35                  40                  45

Ala Ala Pro Glu Ala Ala Leu Pro Lys Ala Gly Lys Phe Gly Pro Ala
    50                  55                  60

Arg Lys Ser Gly Ser Arg Gln Lys Lys Ser Ala Pro Asp Thr Gln Glu
65                  70                  75                  80

Arg Pro Pro Val Arg Ala Thr Gly Ala Arg Ala Lys Lys Ala Pro Gln
                85                  90                  95

Arg Ala Gln Asp Thr Gln Pro Ser Asp Ala Thr Ser Ala Pro Gly Ala
            100                 105                 110

Glu Gly Leu Glu Pro Pro Ala Ala Arg Glu Pro Ala Leu Ser Arg Ala
        115                 120                 125

Gly Ser Cys Arg Gln Arg Gly Ala Arg Cys Ser Thr Lys Pro Arg Pro
130                 135                 140

Pro Pro Gly Pro Trp Asp Val Pro Ser Pro Gly Leu Pro Val Ser Ala
145                 150                 155                 160

Pro Ile Leu Val Arg Arg Asp Ala Ala Pro Gly Ala Ser Lys Leu Arg
                165                 170                 175

Ala Val Leu Glu Lys Leu Lys Leu Ser Arg Asp Asp Ile Ser Thr Ala
            180                 185                 190

Ala Gly Met Val Lys Gly Val Val Asp His Leu Leu Leu Arg Leu Lys
        195                 200                 205

Cys Asp Ser Ala Phe Arg Gly Val Gly Leu Leu Asn Thr Gly Ser Tyr
210                 215                 220

Tyr Glu His Val Lys Ile Ser Ala Pro Asn Glu Phe Asp Val Met Phe
225                 230                 235                 240

Lys Leu Glu Val Pro Arg Ile Gln Leu Glu Glu Tyr Ser Asn Thr Arg
                245                 250                 255

Ala Tyr Tyr Phe Val Lys Phe Lys Arg Asn Pro Lys Glu Asn Pro Leu
            260                 265                 270

Ser Gln Phe Leu Glu Gly Glu Ile Leu Ser Ala Ser Lys Met Leu Ser
        275                 280                 285

Lys Phe Arg Lys Ile Ile Lys Glu Glu Ile Asn Asp Ile Lys Asp Thr
290                 295                 300

Asp Val Ile Met Lys Arg Lys Arg Gly Gly Ser Pro Ala Val Thr Leu
305                 310                 315                 320

Leu Ile Ser Glu Lys Ile Ser Val Asp Ile Thr Leu Ala Leu Glu Ser
                325                 330                 335

Lys Ser Ser Trp Pro Ala Ser Thr Gln Glu Gly Leu Arg Ile Gln Asn
            340                 345                 350

Trp Leu Ser Ala Lys Val Arg Lys Gln Leu Arg Leu Lys Pro Phe Tyr
        355                 360                 365

Leu Val Pro Lys His Ala Lys Glu Gly Asn Gly Phe Gln Glu Glu Thr
370                 375                 380

Trp Arg Leu Ser Phe Ser His Ile Glu Lys Glu Ile Leu Asn Asn His
385                 390                 395                 400
```

-continued

```
Gly Lys Ser Lys Thr Cys Cys Glu Asn Lys Glu Glu Lys Cys Cys Arg
            405                 410                 415

Lys Asp Cys Leu Lys Leu Met Lys Tyr Leu Leu Glu Gln Leu Lys Glu
            420                 425                 430

Arg Phe Lys Asp Lys Lys His Leu Asp Lys Phe Ser Ser Tyr His Val
            435                 440                 445

Lys Thr Ala Phe Phe His Val Cys Thr Gln Asn Pro Gln Asp Ser Gln
    450                 455                 460

Trp Asp Arg Lys Asp Leu Gly Leu Cys Phe Asp Asn Cys Val Thr Tyr
465                 470                 475                 480

Phe Leu Gln Cys Leu Arg Thr Glu Lys Leu Glu Asn Tyr Phe Ile Pro
            485                 490                 495

Glu Phe Asn Leu Phe Ser Ser Asn Leu Ile Asp Lys Arg Ser Lys Glu
            500                 505                 510

Phe Leu Thr Lys Gln Ile Glu Tyr Glu Arg Asn Asn Glu Phe Pro Val
            515                 520                 525

Phe Asp Glu Phe
    530
```

POLYPEPTIDE ASSEMBLIES AND METHODS FOR THE PRODUCTION THEREOF

CROSS REFERENCE

This application is a continuation of U.S. patent application Ser. No. 15/541,201 filed Jun. 30, 2017, which is a U.S. national phase of International Application No. PCT/US2016/020090 filed Feb. 29, 2016, which claims priority to U.S. Provisional Application No. 62/126,331 filed Feb. 27, 2015, all of which are incorporated by reference herein in their entirety.

FEDERAL FUNDING STATEMENT

This invention was made with government support under W911NF1410162 awarded by the Defense Advanced Research Projects Agency (DARPA), and under RO1 AI 051174 and P50 GM082545 awarded by the National Institutes of Health. The government has certain rights in the invention.

SUMMARY OF THE INVENTION

In one aspect, the invention provides multimeric assemblies, comprising a plurality of oligomeric substructures, wherein each oligomeric substructure comprises a plurality of proteins that self-interact around at least one axis of rotational symmetry, wherein each protein comprises:

(a) one or more polypeptide-polypeptide interface ("O interface");

(b) one or more polypeptide domain that is capable of effecting membrane scission and release of an enveloped multimeric assembly from a cell by recruiting the ESCRT machinery to the site of budding by binding directly or indirectly to one or more ESCRT or ESCRT-associated proteins ("L domain");

wherein the multimeric assembly comprises one or more polypeptide domain that is capable of interacting with a lipid bilayer ("M domain");

wherein the M domain, L domain, and O interface are not each present in a single naturally occurring protein, wherein the plurality of oligomeric substructures interact with each other at the one or more O interfaces.

In various embodiments, each oligomeric structure comprises one or more M domain, or wherein each protein comprises one or more M domain. In another embodiment, the one or more O interfaces orient the plurality of oligomeric substructures such that their symmetry axes are aligned with symmetry axes of the same kind in a designated mathematical symmetry group. In a further embodiment, the one or more O interfaces of each oligomeric substructure are identical. In another embodiment, the one or more M domains are capable of non-covalently interacting with a lipid bilayer. In a further embodiment, the one or more L domains are capable of non-covalently interacting with one or more proteins in the ESCRT pathway. In one embodiment, the one or more M domains comprise a polypeptide having an acylation motif (including but not limited to N-terminal myristoylation motifs, palmitoylation motifs, farnesylation motifs, and geranylgeranylation motifs), a polar headgroup-binding domain (including but not limited to those described herein and in the attached appendices), envelope proteins of enveloped viruses, membrane protein transporters, membrane protein channels, B-cell receptors, T-cell receptors, transmembrane antigens of human pathogens, growth factors receptors, G-protein coupled receptors (GPCRs), complement regulatory proteins including but not limited to CD55, CD59, and transmembrane protein domains. In a further embodiment, the one or more M domains are selected from the group consisting of SEQ ID NOS: 52-151 and 280-300. In another embodiment, the one or more O interfaces are non-naturally occurring. In a further embodiment, the one or more O interfaces comprise or consist of the amino acid sequence of SEQ ID NO:1-5, 7-9, 20, or 304. In a still further embodiment, the one or more L domains comprise a linear amino acid sequence motif selected from the group consisting of SEQ ID NOS: 152-197 or 305-306, or overlapping combinations thereof.

In one embodiment, the multimeric assemblies further comprise a packaging moiety. Such packaging moieties may comprise a cysteine residue or a non-canonical amino acid residue on one or more of the L, O, and M domains; a polypeptide that interacts with a cargo of interest, or comprises an amino acid sequence selected from the group consisting of SEQ ID NOS:186 and 198-201.

In a further embodiment, the multimeric assemblies further comprise a cargo interacting with the packaging moiety, or present in the plurality of proteins as a further domain when the cargo is a polypeptide. In one embodiment, the cargo is selected from the group consisting of proteins, nucleic acids, and small organic compounds. In a further embodiment, the cargo may comprise a polypeptide or polynucleotide selected from the group consisting of SEQ ID NOS:202-219. In a still further embodiment, each protein in the plurality of proteins comprises or consists of the amino acid sequence of SEQ ID NOS:227-269.

In another embodiment, the multimeric assembly of any embodiment or combination of embodiments of the invention further comprises a lipid bilayer enveloping the multimeric assembly, wherein one or more of the M domains may be bound to the lipid bilayer. In one embodiment, the assembly further comprises one or more transmembrane protein or membrane-anchored protein embedded in the lipid bilayer. In various non-limiting embodiments, the transmembrane or membrane-anchored protein is selected from the group consisting of the envelope proteins of enveloped viruses, membrane protein transporters, membrane protein channels, B-cell receptors, T-cell receptors, transmembrane antigens of human pathogens, growth factors receptors, G-protein coupled receptors (GPCRs), complement regulatory proteins including but not limited to CD55 and CD59. In a further embodiment, the lipid-enveloped assembly comprises a cargo, wherein the cargo is not bound to the multimeric assembly, such as a protein, nucleic acid, lipid, or small molecule.

In another aspect, the invention provides recombinant polypeptides comprising (a) a polypeptide domain that is capable of interacting with a lipid bilayer ("M domain");

(b) a polypeptide-polypeptide interface ("O interface"); and (c) a polypeptide domain that is capable of effecting membrane scission and release of an enveloped multimeric assembly from a cell by recruiting the ESCRT machinery to the site of budding by binding to one or more proteins in the eukaryotic ESCRT complex ("L domain");

wherein the M domain, the L domain, and the O interface are not each present in a single naturally occurring protein.

In one embodiment, the M domain is capable of non-covalently interacting with a lipid bilayer. In another embodiment, the L domain is capable of non-covalently interacting with one or more proteins in the ESCRT machinery or proteins known to recruit the ESCRT machinery to the site of budding by binding to one or more ESCRT proteins directly or indirectly. In a further embodiment, the M domain comprises a polypeptide having an acylation motif (including but not limited to N-terminal myristoylation motifs, palmitoylation motifs, farnesylation motifs, and geranylgeranylation motifs), a polar headgroup-binding domains (including but not limited to the polar headgroup-binding domains disclosed herein and in the attached appendices), envelope proteins of enveloped viruses, membrane protein transporters, membrane protein channels, B-cell receptors, T-cell receptors, transmembrane antigens of human pathogens, growth factors receptors, G-protein coupled receptors (GPCRs), complement regulatory proteins including but not limited to CD55, CD59, and transmembrane protein domains. In another embodiment of the polypeptides, M domain comprises the amino acid sequence of SEQ ID NOS:52-151 or 280-300. In a further embodiment of the polypeptides, the O interface comprises a non-natural polypeptide, including but not limited to a polypeptide comprising or consisting of SEQ ID NO:1-5, 7-9, 20, or 304. In another embodiment of the polypeptides, the L domains comprise a linear amino acid sequence motif selected from the group consisting of SEQ ID NOS: 152-197 or 305-306, or overlapping combinations thereof. In a further embodiment, the polypeptides further comprising a packaging moiety, including but not limited to a cysteine residue or a non-canonical amino acid residue on one or more of the L, O, and M domains; a polypeptide that interacts with a cargo of interest, or comprises an amino acid sequence selected from the group consisting of SEQ ID NOS:186 and 198-201.

In a further aspect, the invention provides recombinant polypeptides comprising an amino acid sequence at least 75% identical over its full length to SEQ ID NO:20 or 304, wherein the polypeptide includes at least 1, 2, 3, 4, 5, or more amino acid substitutions compared to SEQ NO:21.

In another aspect, the invention provides recombinant nucleic acid encoding the recombinant polypeptide of any embodiment or combination of embodiment of the invention. In a further aspect, the invention provides recombinant expression vectors comprising the recombinant nucleic acid of any embodiment or combination of embodiments operatively linked to a promoter.

In a further aspect, the invention provides recombinant host cells comprising the recombinant expression vector of any embodiment or combination of embodiments of the invention. In one embodiment, the host cell comprises two or more recombinant vectors including:

(a) a first recombinant expression vector of any embodiment of the invention; and (b) a second recombinant expression vector comprising a recombinant nucleic acid encoding one or more transmembrane proteins or membrane-anchored proteins operatively linked to a promoter. In one embodiment, the second expression vector encodes a transmembrane or membrane-anchored protein is selected from the group consisting of the envelope proteins of enveloped viruses, membrane protein transporters, membrane protein channels, B-cell receptors, T-cell receptors, transmembrane antigens of human pathogens, growth factors receptors, G-protein coupled receptors (GPCRs), complement regulatory proteins including but not limited to CD55 and CD59. In a further embodiment, the host cell further comprises a third recombinant expression vector, wherein the third recombinant expression vector comprises a recombinant nucleic acid encoding cyclic GMP-AMP synthase (cGAS) protein operatively linked to a promoter. In a further embodiment, the third recombinant expression vector comprises a recombinant nucleic acid encoding a polypeptide or polynucleotide cargo operatively linked to a promoter.

In another aspect, the invention provides methods for producing a multimeric assembly according to any embodiment or combination of embodiments of the invention, comprising culturing the recombinant host cells of any embodiment or combination of embodiments of the invention under conditions suitable to promote expression of the encoded recombinant polypeptide, wherein the recombinant host cell is a eukaryotic host cell, wherein expression of the encoded recombinant polypeptide in the eukaryotic host cell results in (a) production of the multimeric assembly, and (b) interaction of one or more of the M domains of the multimeric assembly with the lipid bilayer membrane of the eukaryotic host cell, and wherein attachment of the one or more M domains of the multimeric assembly to the lipid bilayer membrane of the eukaryotic host cell results in the multimeric assembly being enveloped by eukaryotic host-derived lipid bilayer membrane, followed by recruitment of the ESCRT machinery to the site of budding by the L domains of the multimeric assembly, which releases the enveloped multimeric assembly from the eukaryotic host cell by catalyzing membrane scission.

DESCRIPTION OF THE FIGURES

FIG. 1. Schematic of enveloped multimeric assembly budding and release. Multimeric assemblies of the invention, comprising oligomeric substructure that each comprise a plurality of proteins having M, O, and L domains, are shown forming a membrane-enveloped bud at a cellular membrane. Recruitment of the host cell ESCRT machinery to the site of budding results in fission of the membrane neck that connects the budding membrane to the cellular membrane, thereby releasing the enveloped multimeric assembly from the cell.

FIG. 2. Size-exclusion chromatography of I3-01, I3-01 (L33R), and 1wa3-wt. Chromatograms of the three proteins obtained using a Superose 6 10/300 GL column (GE Healthcare) are overlaid; the absorbance signal (y-axis) has been normalized so that each peak is of equal height. I3-01 eluted earlier than I3-01(L33R) and 1wa3-wt, indicating assembly to a higher oligomerization state. The elution volume of I3-01 corresponded to that expected for the designed 60-subunit assembly.

FIG. 3. Cryo-electron micrograph of I3-01 multimeric assemblies. Purified I3-01 was visualized by cryo-electron microscopy. A field of monodisperse icosahedral assemblies roughly 25 nm in diameter that closely match the computational design model was observed, confirming that the protein forms the designed multimeric assemblies. Scale bar is 50 nm.

FIG. 4. Analysis of I3-01, EPN-01, and EPN-01 variants by the budding assay. Western blots of the cell lysates and pelleted culture supernatants are shown for various constructs (indicated by the column labels at the top of the blot). I3-01, which lacks M and L domains, was expressed in the cells as demonstrated by its presence in the cell lysates, but was not detected in the pelleted culture supernatants due to its inability to be released from cells. In contrast, EPN-01 was efficiently released from cells and pelleted through a 20% sucrose cushion. A very faint band for EPN-01(ΔPTAP) in the pelleted culture supernatant demonstrates that its ability to bud and be released from cells was severely reduced relative to that of EPN-01. The other EPN-01 mutants were undetectable in the pelleted culture supernatants in this particular experiment. Glyceraldehyde 3-phosphate dehydrogenase (GAPDH) was used as a loading control.

Figure 5:
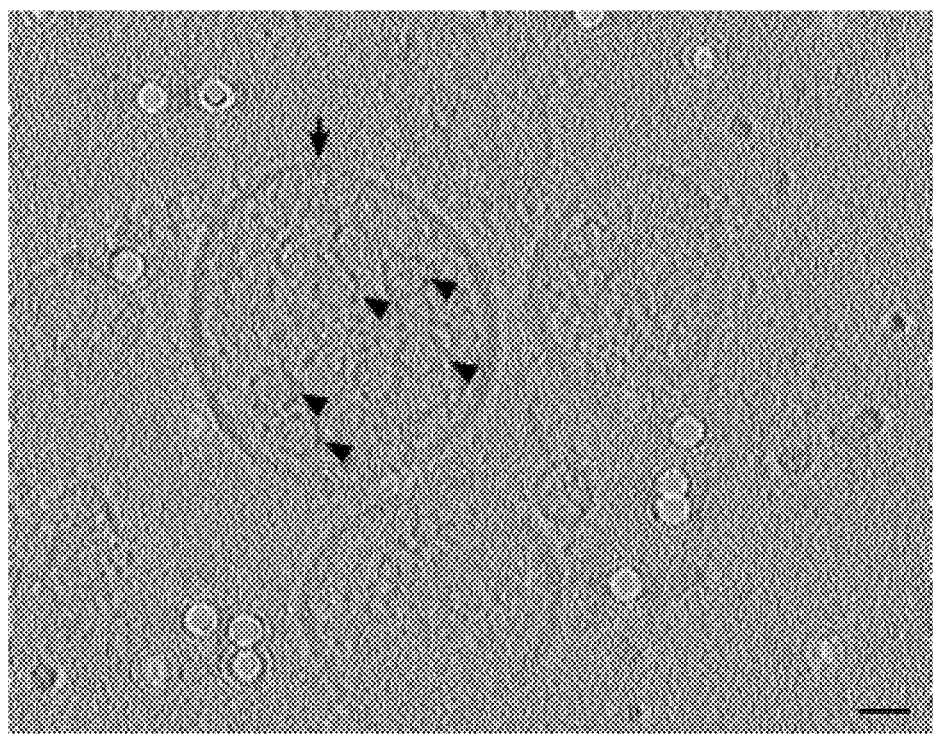

FIG. 5. Visualization of Myr-I3-01-myc-p6 enveloped multimeric assemblies by electron cryo-tomography. A representative image from an electron cryo-tomogram of Myr-I3-01-myc-p6 enveloped multimeric assemblies is shown. The image revealed multiple cage-like Myr-I3-01-myc-p6 multimeric assemblies approximately 25 nm in diameter (indicated by arrowheads) inside a larger membrane envelope (indicated by the arrow). Additional unmarked enveloped multimeric assemblies can be seen in the image. Scale bar is 25 nm.

Figure 6:

FIG. 6. Analysis of EPN-49, EPN-50, and EPN-51 by the protease assay. Western blots of various EPN-49, EPN-50, and EPN-51 samples are shown. All three proteins express as shown by the bands observed in the cell pellet samples. The lack of bands for EPN-50 and EPN-51 in any of the pelleted culture supernatant samples indicated that these proteins are not released from cells as enveloped multimeric assemblies. EPN-51, in contrast, is released into the culture supernatant as an enveloped multimeric assembly. Incubation of EPN-51 enveloped multimeric assemblies with trypsin revealed that the membrane envelope protected the protein from degradation. When the membrane envelope was disrupted by the addition of Triton X-100, trypsin gained access to the protein and degraded it, as shown by the absence of a band in this lane. The experiment indicates that in the absence of detergent, the membrane envelope of the enveloped multimeric assemblies was intact and provided a protective barrier that prevented access of trypsin to the protein.

Figure 7:
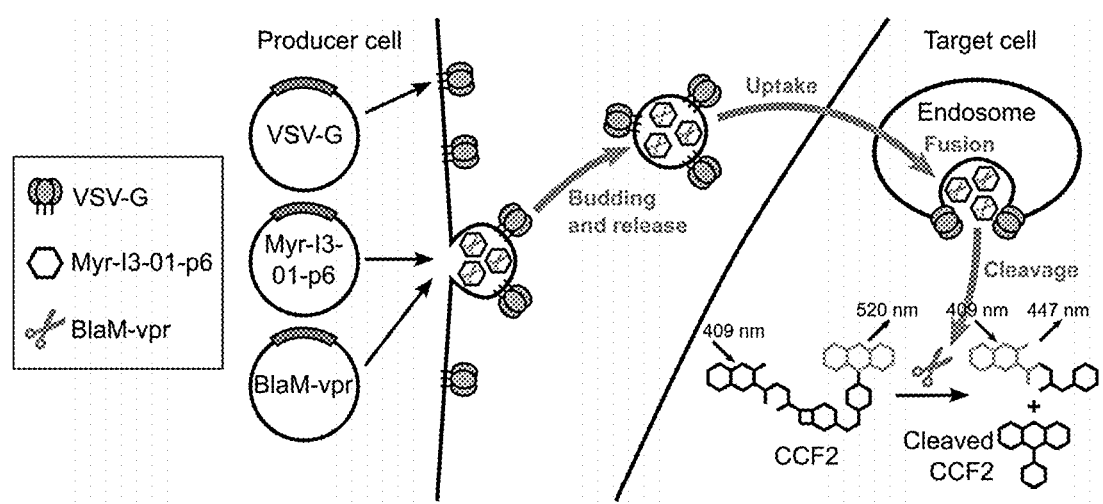

FIG. 7. Schematic of the beta lactamase (BlaM) delivery assay. The image depicts the production of BlaM-packaging, VSV-G-bearing enveloped multimeric assemblies that deliver the BlaM-vpr fusion protein to the cytoplasm of recipient or target cells. Plasmids encoding VSV-G, Myr-I3-01-myc-p6, and BlaM-vpr are co-transfected into a "producer" cell. Production of the three proteins results in the budding and release of enveloped multimeric assemblies that contain the BlaM-vpr cargo within the lumen of their membrane envelopes and VSV-G as a transmembrane protein within the membrane envelope itself. The VSV-G facilitates uptake in the target cell and fusion of the enveloped multimeric assembly membrane with cellular (e.g., endosomal) membranes. Membrane fusion results in the delivery of the packaged BlaM-vpr cargo to the cytoplasm of the target cell, where it cleaves the CCF2 dye, resulting in a change in fluorescence emission from 520 nm to 447 nm that can easily be monitored using a variety of instruments.

Figure 8:
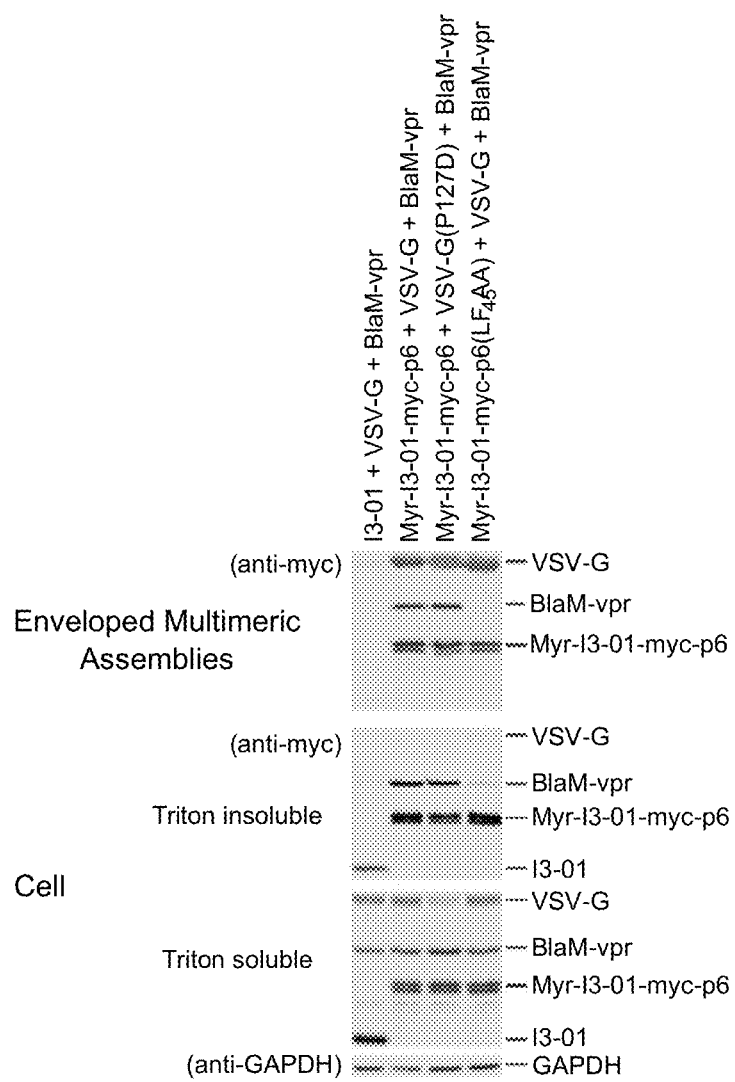

FIG. 8. Analysis of BlaM delivery assay samples by Western blot. Western blots of various enveloped multimeric assemblies and corresponding cell lysates are shown. The proteins expressed in four separate co-transfections are indicated by the column labels at the top of the blot. The first column in the blot reveals that all three proteins—VSV-G, I3-01, and BlaM-vpr—were expressed in the cells but failed to be released into the culture supernatants due to the lack of M and L domains in I3-01. The second and third columns demonstrate that when Myr-I3-01-myc-p6 was expressed instead of I3-01, all three proteins—VSV-G or VSV-G (P127D), BlaM-vpr, and Myr-I3-01-myc-p6—were released into the cell culture supernatant as enveloped multimeric assemblies. The fourth column shows that mutation of the vpr binding site in the packaging moiety of Myr-I3-01-myc-p6 [Myr-I3-01-myc-p6($LF_{45}AA$)] severely reduced the amount of BlaM-vpr cargo packaged in the enveloped multimeric assemblies. GAPDH was used as a loading control.

Figure 9:
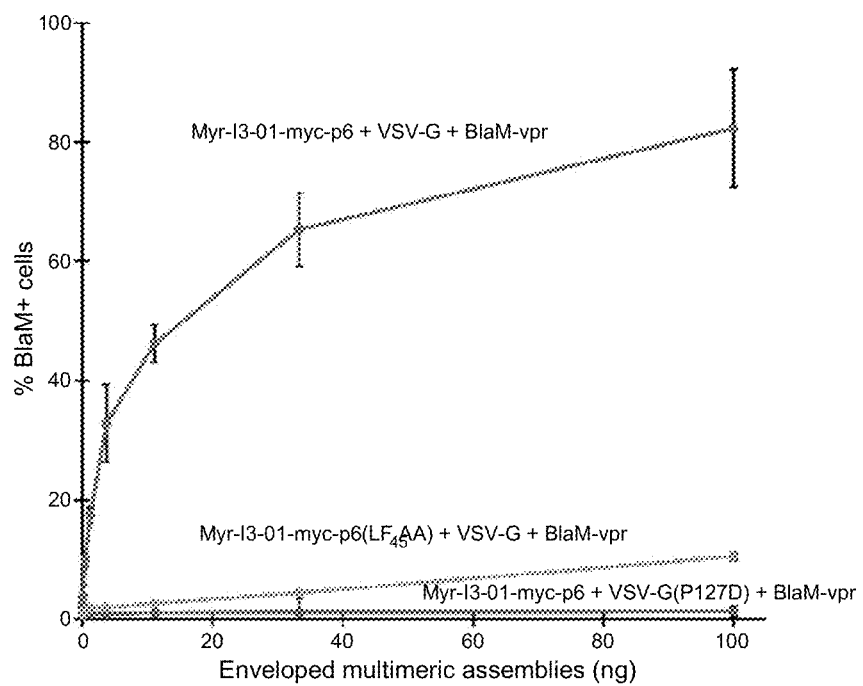

FIG. 9. Cytoplasmic delivery of BlaM-vpr by enveloped multimeric assemblies. The percentage of BlaM-positive (BlaM+) cells in a sample (measured by flow cytometry) is plotted as a function of the amount of enveloped multimeric assemblies administered to the cells. The three set of points correspond to the three enveloped multimeric assemblies analyzed by Western blot in FIG. 8. Enveloped multimeric assemblies produced by co-transfection of plasmids encoding Myr-I3-01-myc-p6, VSV-G, and BlaM-vpr yielded efficient, dose-dependent delivery of BlaM-vpr to the cytoplasm of recipient cells. The enveloped multimeric assemblies in which Blam-vpr cargo packaging was disrupted by mutation of the packaging moiety [Myr-I3-01-myc-p6($LF_{45}AA$)+VSV-G+BlaM-vpr]yielded severely reduced BlaM-vpr delivery. Finally, the enveloped multimeric assemblies bearing a VSV-G mutant incapable of effecting membrane fusion [Myr-I3-01-myc-p6+VSV-G (P127D)+BlaM-vpr] yielded no detectable BlaM delivery, demonstrating that cytoplasmic delivery is required in order to observe cleavage of the fluorescent substrate.

Figure 10:
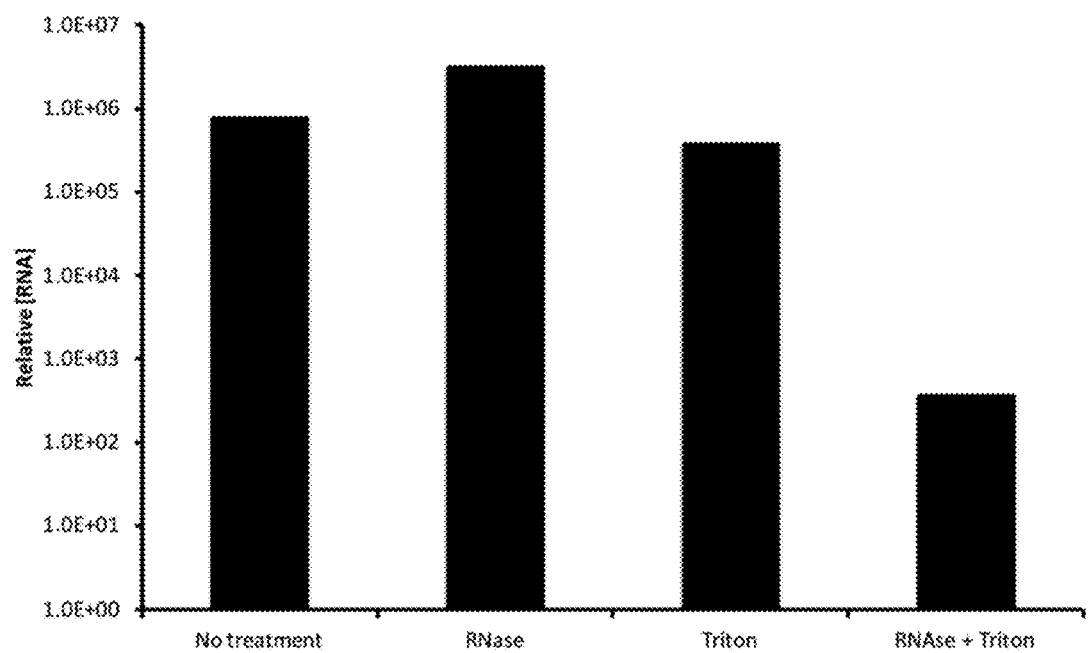

FIG. 10. Protection of packaged mRNA cargoes from RNase by enveloped multimeric assemblies. Relative levels of mRNA cargoes as measured by RT-qPCR are shown. The enveloped multimeric assemblies were incubated in various conditions prior to RT-qPCR analysis. In the "no treatment" sample, the enveloped multimeric assemblies were incubated in phosphate buffered saline only; this sample provides a baseline measurement of packaged mRNA cargoes. The "RNase" sample was incubated with 20 µg/uL of RNase A for 10 minutes; no degradation of the packaged mRNA cargoes was observed because the membrane envelope of the enveloped multimeric assemblies provides an effective barrier preventing access of RNase to the cargoes. Incubation of the enveloped multimeric assemblies with 1% Triton X-100 for 10 minutes ("Triton") had no effect on mRNA cargo stability as expected. Incubation of the enveloped multimeric assemblies with 20 µg/uL of RNase A and 1% Triton X-100 for 10 minutes resulted in a more than 1,000-fold reduction in the amount of intact mRNA cargoes due to disruption of the membrane envelope, allowing access of RNase to the cargoes.

Figure 11:
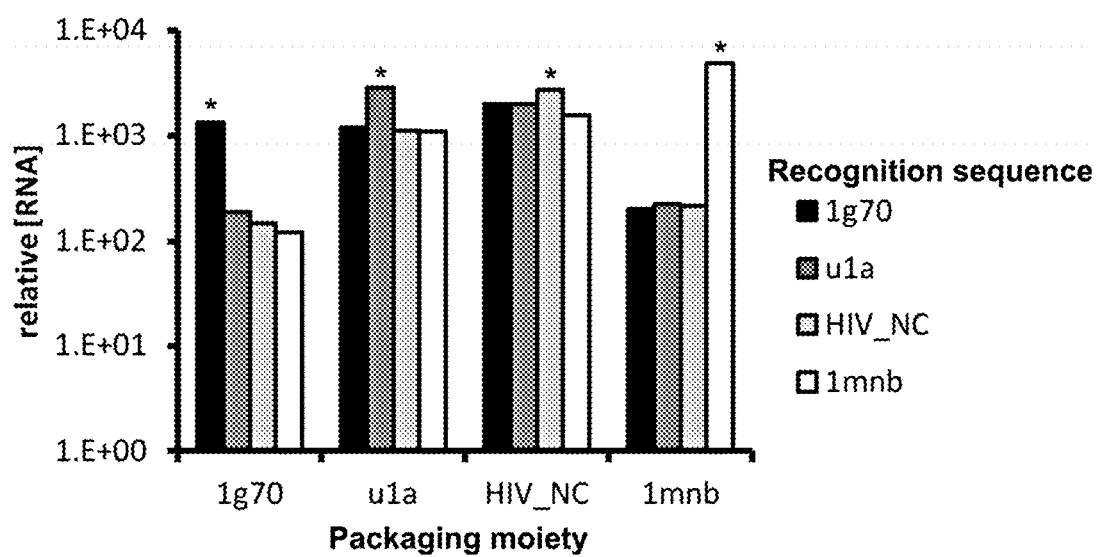

FIG. 11. All-against-all comparison of mRNA packaging moieties and recognition sequences. The relative levels of packaged mRNA cargoes in various enveloped multimeric assemblies as measured by RT-qPCR are shown. 16 different enveloped multimeric assemblies were produced by co-transfection of a plasmid encoding a protein comprising one of four RNA packaging domains (indicated on the x axis) and a plasmid encoding an mRNA cargo comprising one of four recognition sequences (indicated by the legend). The data show that each packaging domain packaged more of the cargo comprising the cognate recognition sequence (bars indicated by *) than non-cognate recognition sequences, and suggest that the 1g70 and 1mnb packaging moiety/recognition sequences pairs may provide the greatest packaging specificity.

Figure 12:
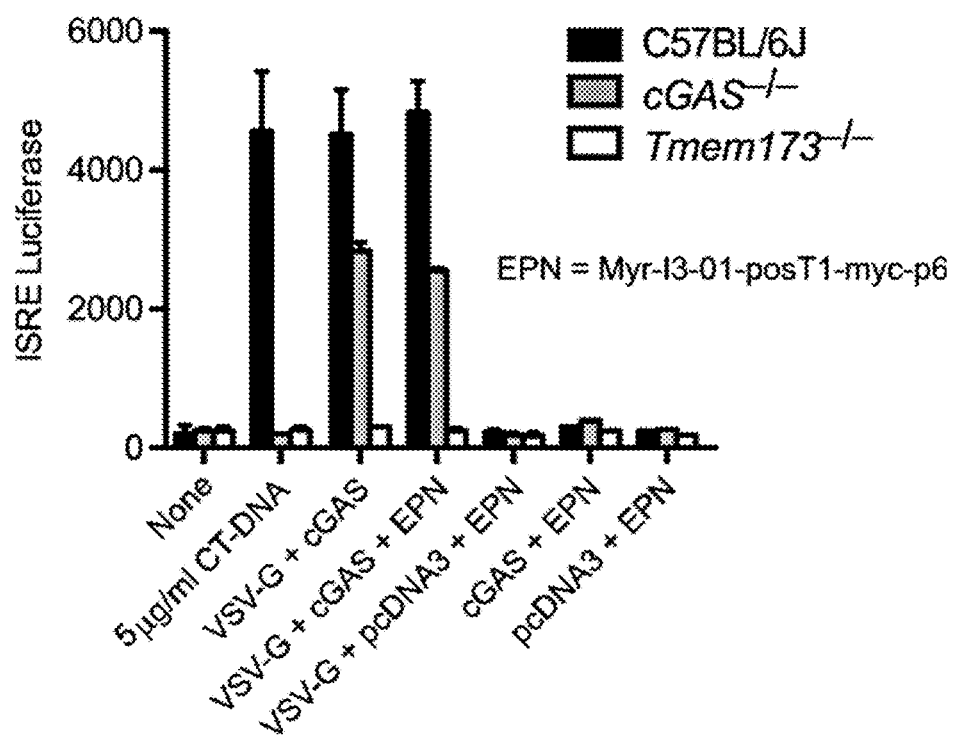

FIG. 12. Cytoplasmic delivery of packaged cyclic GMP-AMP (cGAMP) by enveloped multimeric assemblies. Luciferase activities from lysed reporter cells after treatment with supernatants from macrophages stimulated with various enveloped multimeric assemblies are shown. Bars of different colors indicate activity measured using macrophages derived from wild-type (C57BL/6J), cGAS-deficient (cGAS−/−) or STING-deficient (Tmem173−/−) mice. The data show that enveloped multimeric assemblies packaging cGAMP and pseudotyped with VSV-G (VSV-G+cGAS+ EPN) induced an interferon response in macrophages that is dependent on STING but independent of cGAS. VSV-G-induced extracellular vesicles were also capable of packaging and delivering cGAMP (VSV-G+cGAS), while several negative controls in which various plasmids were omitted from the co-transfections yielded no activity. Calf-thymus DNA (CT-DNA) transfected into the macrophages was used as a positive control.

Figure 13:
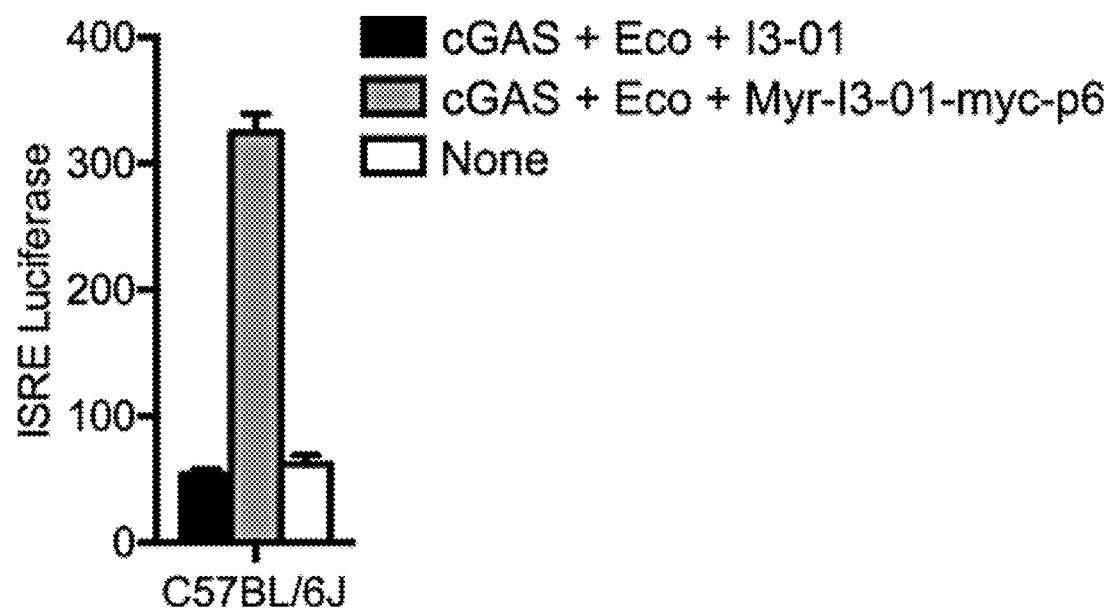

FIG. 13. Enveloped multimeric assemblies are required for cGAMP delivery using the ecotropic envelope protein from Moloney Murine Leukemia Virus (Eco). Supernatants from cells expressing cGAS+Eco+Myr-I3-01-myc-p6 enveloped multimeric assemblies induced an interferon response in macrophages from wild-type (C57BL/6J) mice. Supernatants from cells in which Myr-I3-01-myc-p6 was substituted with I3-01, which does not result in the production of enveloped multimeric assemblies, failed to induce an interferon response.

DETAILED DESCRIPTION OF THE INVENTION

All references cited are herein incorporated by reference in their entirety. As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In a first aspect, the present invention provides multimeric assemblies, comprising a plurality of oligomeric substructures, wherein each oligomeric substructure comprises a plurality of proteins that self-interact around at least one axis of rotational symmetry, wherein each protein comprises:

(a) one or more polypeptide-polypeptide interface ("O interface");

(b) one or more polypeptide domain that is capable of effecting membrane scission and release of an enveloped multimeric assembly from a cell by recruiting the ESCRT machinery to the site of budding by binding directly or indirectly to one or more ESCRT or ESCRT-associated proteins ("L domain");

wherein the multimeric assembly comprises one or more polypeptide domain that is capable of interacting with a lipid bilayer ("M domain");

and wherein the M domain, L domain, and O interface are not each present in a single naturally occurring protein, wherein the plurality of oligomeric substructures interact with each other at the one or more O interfaces.

FIG. 1 shows an exemplary embodiment of a multimeric assembly of this first aspect of the invention.

The multimeric assemblies of each aspect of the invention can be used for any suitable purpose, including but not limited to delivery vehicles or vaccines, as the multimeric assemblies can encapsulate molecules of interest and/or the proteins can be modified to bind to molecules of interest (diagnostics, therapeutics, antigens, adjuvants, nucleic acids, detectable molecules for imaging and other applications, etc.).

The multimeric assemblies of the invention are synthetic, in that they are not naturally occurring. The proteins that make up the multimeric assembly are non-naturally occurring proteins that can be produced by any suitable means, including recombinant production or chemical synthesis. In this first aspect, each member of the plurality of proteins is identical to each other. There are no specific primary amino acid sequence requirements for the proteins. As described in detail herein, the inventors disclose methods for designing the multimeric assemblies of the invention, where the multimeric assemblies are not dependent on specific primary amino acid sequences of the protein that makes up the oligomeric substructures that interact to form the multimeric assemblies of the invention. As will be understood by those of skill in the art, the design methods of the invention can produce a wide variety of multimeric assemblies made of a wide variety of subunit proteins, and the methods are in no way limited to the subunit proteins disclosed herein.

As used herein, a "plurality" means at least two; in various embodiments, there are at least 2, 3, 4, 5, 6 or more proteins in the first oligomeric substructure. In one exemplary embodiment, the oligomeric substructure comprises a trimer of the protein.

The proteins of any aspect of the invention may be of any suitable length for a given purpose of the resulting multimeric assemblies. In one embodiment, the protein is typically between 30-250 amino acids in length. In various further embodiments, the protein is between 30-225, 30-200, 30-175, 50-250, 50-225, 50-200, 50-175, 75-250, 75-225, 75-200, 75-175, 100-250, 100-225, 100-200, 100-175, 125-250, 125-225, 125-200, 125-175, 150-250, 150-225, 150-200, and 150-175 amino acids in length.

The plurality of proteins self-interact to form a oligomeric substructure, where each oligomeric substructure may comprise at least one axis of rotational symmetry. As will be understood by those of skill in the art, the self-interaction is a non-covalent protein-protein interaction. Any suitable non-covalent interaction(s) can drive self-interaction of the proteins to form the oligomeric substructure, including but not limited to one or more of electrostatic interactions, π-effects, van der Waals forces, hydrogen bonding, and hydrophobic effects. The self-interaction in the oligomeric substructure may be natural or synthetic in origin; that is, the synthetic proteins making up the multimeric assemblies of the invention may be synthetic variations of natural proteins that self-interact to form oligomeric substructures, or they may be fully synthetic proteins that have no amino acid sequence relationships to known natural proteins.

As used herein, "at least one axis of rotational symmetry" means at least one axis of symmetry around which the oligomeric substructure can be rotated without changing the appearance of the substructure. In one embodiment, the oligomeric substructure has cyclic symmetry, meaning rotation about a single axis (for example, a three-fold axis in the case of a trimeric protein; generally, oligomeric substructures with n subunits and cyclic symmetry will have n-fold rotational symmetry, sometimes denoted as Cn symmetry). In other embodiments, the oligomeric substructure possesses symmetries comprising multiple rotational symmetry axes, including but not limited to dihedral symmetry (cyclic symmetry plus an orthogonal two-fold rotational axis) and the cubic point group symmetries including tetrahedral, octahedral, and icosahedral point group symmetry (multiple kinds of rotational axes). In one non-limiting embodiment, the oligomeric substructure comprises a dimer, trimer, tetramer, or pentamer of the protein. In a further non-limiting embodiment, the oligomeric substructure comprises a trimeric protein.

In the multimeric assemblies of the invention, there are at least two identical copies of the oligomeric substructure. In general, the number of copies of the oligomeric substructure is dictated by the number of symmetry axes in the designated mathematical symmetry group of the multimeric assembly that matches the symmetry axes in each oligomeric substructure. This relationship arises from the requirement that the symmetry axes of each copy of the oligomeric substructure must be aligned to symmetry axes of the same kind in the multimeric assembly. By way of non-limiting example, a multimeric assembly with tetrahedral point group symmetry can comprise exactly four copies of a trimeric substructure aligned along the exactly four three-fold symmetry axes passing through the center and vertices of a tetrahedron. In general, although every copy of the oligomeric substructure may have its symmetry axes aligned to symmetry axes of the same kind in the multimeric assembly, not all symmetry axes in the multimeric assembly must have an oligomeric building block aligned to them. By way of non-limiting example, we can consider a multimeric assembly with icosahedral point group symmetry comprising multiple copies of the oligomeric substructure. There are 30 two-fold, 20 three-fold, and 12 five-fold rotational symmetry axes in icosahedral point group symmetry. The multimeric assemblies of the invention may be those in which the oligomeric substructures are aligned along all instances of one type of symmetry axes in a designated mathematical symmetry group. Therefore, the multimeric assemblies in this non-limiting example could include icosahedral nanostructures comprising 30 dimeric substructures, or 12 pentameric substructures, or 20 trimeric substructures. In each case, two of the three types of symmetry axes are left unoccupied by oligomeric substructures.

The interaction between the oligomeric substructures is a non-natural (e.g., not an interaction seen in a naturally occurring protein multimer), non-covalent interaction at the O interface; this can comprise any suitable non-covalent interaction(s), including but not limited to one or more of electrostatic interactions, π-effects, van der Waals forces, hydrogen bonding, and hydrophobic effects. The interaction may occur at multiple identical (i.e., symmetrically related) O interfaces between the oligomeric substructures, wherein the O interfaces can be continuous or discontinuous. This symmetric repetition of the O interfaces between the oligomeric substructures results from the overall symmetry of the multimeric assemblies; because each protein is in a symmetrically equivalent position in the multimeric assembly, the interactions between them are also symmetrically equivalent.

Non-covalent interactions between the oligomeric substructures may orient the substructures such that their symmetry axes are aligned with symmetry axes of the same kind in a designated mathematical symmetry group as described above. This feature provides for the formation of regular, defined multimeric assemblies, as opposed to irregular or imprecisely defined structures or aggregates. Several structural features of the non-covalent interactions between the oligomeric substructures may help to provide a specific orientation between substructures. Generally, large interfaces that are complementary both chemically and geometrically and comprise many individually weak atomic interactions tend to provide highly specific orientations between protein molecules. In one embodiment of the subject invention, therefore, each symmetrically repeated instance of the O interface between the oligomeric substructures may bury between 1000-2000 Å$^2$ of solvent-accessible surface area (SASA) on the combined oligomeric substructures. SASA is a standard measurement of the surface area of molecules commonly used by those skilled in the art; many computer programs exist that can calculate both SASA and the change in SASA upon burial of a given interface for a given protein structure. A commonly used measure of the geometrical complementarity of protein-protein interfaces is the Shape Complementarity ($S_c$) value of Lawrence and Colman (*J. Mol. Biol.* 234:946-50 (1993)). In a further embodiment, each symmetrically repeated O interface between the oligomeric substructures may have an $S_c$ value between 0.5-0.8. Finally, in order to provide a specific orientation between the oligomeric substructures, in many embodiments the O interface between them may be formed by relatively rigid portions of each of the protein. This feature ensures that flexibility within each protein molecule does not lead to imprecisely defined orientations between the oligomeric substructures. Secondary structures in proteins, that is alpha helices and beta strands, generally make a large number of atomic interactions with the rest of the protein structure and therefore occupy relatively rigidly fixed positions. Therefore, in one embodiment, at least 50% of the atomic contacts comprising each symmetrically repeated, O interface between the oligomeric substructures are formed from amino acid residues residing in elements of alpha helix and/or beta strand secondary structure.

In a second aspect, the invention provides multimeric assemblies, comprising a plurality of subunit structures, wherein each subunit structure comprises a first protein that self-interacts to form a first oligomeric substructure comprising at least one axis of rotational symmetry, and a second protein that self-interacts to form a second oligomeric substructure comprising at least one axis of rotational symmetry, wherein each first protein and each second protein comprise one or more O interfaces that interact with each other, and wherein at least one of the first protein or the second protein comprises:

(a) one or more polypeptide domains that are capable of interacting with a lipid bilayer ("M domain"); and (c) one or more polypeptide domains that are capable of effecting membrane scission and release of an enveloped multimeric assembly from a cell by recruiting the ESCRT machinery to the site of budding by binding to one or more ESCRT proteins ("L domain");

wherein the M and L domains and O interfaces are not each present in a single naturally occurring protein, wherein the O interfaces in the first protein bind to the O interfaces present in the second protein to form a subunit structure, and wherein each subunit structure binds to other subunit structures through self-interactions within the first and second oligomeric substructures to form the multimeric assembly.

In this aspect, each of the first protein and the second protein comprise an O interface, while the M domain and the L domain may each independently be present only in the first protein, only in the second protein, or both. For example, the M domain may be part of the first protein and the L domain may be part of the second protein; in this embodiment, the first oligomeric substructure will include multiple copies of the M domain but no copies of the L domain, while the second oligomeric substructure will include multiple copies of the L domain but no copies of the M domain. A resulting subunit structure comprising both the first and second oligomeric domains will then include both the M domains and the L domains. In other embodiments, the first and second protein may both include one or more M domains and one or more L domains.

In this aspect, two different proteins (the first protein and the second protein) each self-interact to form a first oligomeric substructure and a second oligomeric substructure, respectively. The O interfaces present in the first and second oligomeric substructures non-covalently interact to form the subunit structures, which then bind to other subunit structures to form the multimeric assemblies of the invention. The first protein and the second protein are different.

In various embodiments, there are at least 2, 3, 4, 5, 6 or more subunit structures in the multimeric assembly. The first and second proteins of may be of any suitable length for a given purpose of forming oligomeric substructures. In one embodiment, the first and second proteins are typically between 30-250 amino acids in length. In various further embodiments, the first and second proteins are between 30-225, 30-200, 30-175, 50-250, 50-225, 50-200, 50-175, 75-250, 75-225, 75-200, 75-175, 100-250, 100-225, 100-200, 100-175, 125-250, 125-225, 125-200, 125-175, 150-250, 150-225, 150-200, and 150-175 amino acids in length.

The first protein self-interacts to form a first oligomeric substructure and the second protein self-interacts to form a second oligomeric substructure, where each oligomeric substructure may comprises at least one axis of rotational symmetry (as defined above). As will be understood by those of skill in the art, the self-interaction is a non-covalent protein-protein interaction and may comprise any suitable non-covalent interaction(s), as described above. The self-interaction in each of the two different oligomeric substructures may be natural or synthetic in origin; that is, the synthetic proteins making up the multimeric assemblies of the invention may be synthetic variations of natural proteins that self-interact to form multimeric substructures, or they may be fully synthetic proteins that have no amino acid sequence relationships to known natural proteins.

In one embodiment, one or both of the oligomeric substructures have cyclic symmetry, meaning rotation about a single axis (for example, a three-fold axis in the case of a trimeric protein; generally, oligomeric substructures with n subunits and cyclic symmetry will have n-fold rotational symmetry, sometimes denoted as Cn symmetry). In other embodiments, one or both oligomeric substructures possess symmetries comprising multiple rotational symmetry axes, including but not limited to dihedral symmetry (cyclic symmetry plus an orthogonal two-fold rotational axis) and the cubic point group symmetries including tetrahedral, octahedral, and icosahedral point group symmetry (multiple kinds of rotational axes). The first oligomeric substructure and the second oligomeric substructure may comprise the same or different rotational symmetry properties. In one non-limiting embodiment, the first oligomeric substructure comprises a dimer, trimer, tetramer, or pentamer of the first protein, and wherein the second oligomeric substructure comprises a dimer or trimer of the second protein. In a further non-limiting embodiment, the first oligomeric protein comprises a trimeric protein, and the second oligomeric protein comprises a dimeric protein. In another non-limiting embodiment, the first oligomeric protein comprises a trimeric protein, and the second oligomeric protein comprises a different trimeric protein.

In the multimeric assemblies of the invention, there are at least two identical copies of the first oligomeric substructure and at least two identical copies of the second oligomeric substructure in the assembly. In one embodiment, the number of copies of each of the first and second oligomeric substructures may be dictated by the number of symmetry axes in the designated mathematical symmetry group of the assembly that match the symmetry axes in each oligomeric substructure. This relationship arises from the preference that the symmetry axes of each copy of each oligomeric substructure are aligned to symmetry axes of the same kind in the assembly. By way of non-limiting example, an assembly with tetrahedral point group symmetry may comprise exactly four copies of a first trimeric substructure aligned along the exactly four three-fold symmetry axes passing through the center and vertices of a tetrahedron. Likewise, the same non-limiting example tetrahedral assembly can comprise six (but not five, seven, or any other number) copies of a dimeric substructure aligned along the six two-fold symmetry axes passing through the center and edges of the tetrahedron. In general, although every copy of each oligomeric substructure may have its symmetry axes aligned to symmetry axes of the same kind in the assembly, not all symmetry axes in the assembly must have a multimeric building block aligned to them. By way of non-limiting example, we can consider an assembly with icosahedral point group symmetry comprising multiple copies of each of a first oligomeric substructure and a second oligomeric substructure. There are 30 two-fold, 20 three-fold, and 12 five-fold rotational symmetry axes in icosahedral point group symmetry. The assemblies of this aspect of the invention are those in which two different oligomeric substructures are aligned along all instances of two types of symmetry axes in a designated mathematical symmetry group. Therefore, the assemblies in this non-limiting example could include icosahedral assemblies comprising 30 dimeric substructures and 20 trimeric substructures, or 30 dimeric substructures and 12 pentameric substructures, or 20 trimeric substructures and 12 pentameric substructures. In each case, one of the three types of symmetry axes is left unoccupied by oligomeric substructures.

The interaction between the first and second oligomeric substructures via the O interface is a non-natural (e.g., not an interaction seen in a naturally occurring protein multimer), non-covalent interaction; this can comprise any suitable non-covalent interaction(s), as discussed above. The interaction may occur at multiple identical O interfaces (symmetrical) between the first and second oligomeric substructures, wherein the O interfaces can be continuous or discontinuous. This symmetric repetition of the O interfaces between the first and second oligomeric substructures results from the overall symmetry of the subject assemblies; because each protein molecule of each of the first and second oligomeric substructures may be in a symmetrically equivalent position in the assembly, the interactions between them are also symmetrically equivalent.

Non-covalent interactions between the first oligomeric substructures and the second oligomeric substructures orient the substructures such that their symmetry axes are aligned with symmetry axes of the same kind in a designated mathematical symmetry group as described above. This feature provides for the formation of regular, defined assemblies, as opposed to irregular or imprecisely defined structures or aggregates. Several structural features of the non-covalent interactions between the first oligomeric substructures and the second oligomeric substructures help to provide a specific orientation between substructures. Generally, large interfaces that are complementary both chemically and geometrically and comprise many individually weak atomic interactions tend to provide highly specific orientations between protein molecules. In one embodiment of the subject invention, therefore, each symmetrically repeated instance of the O interface between the first oligomeric substructure and the second oligomeric substructure may bury between 1000-2000 $Å^2$ of solvent-accessible surface area (SASA) on the first oligomeric substructure and the second oligomeric substructure combined. In a further embodiment, each symmetrically repeated O interface between the first oligomeric substructure and the second oligomeric substructure has an $S_c$ value between 0.5-0.8. Finally, in order to provide a specific orientation between the first oligomeric substructures and the second oligomeric substructures, in many embodiments the O interface between them may be formed by relatively rigid portions of each of the oligomeric substructures. This feature ensures that flexibility within each protein molecule does not lead to imprecisely defined orientations between the first and second oligomeric substructures. In another embodiment, at least 50% of the atomic contacts comprising each symmetrically repeated, O interface between the first oligomeric substructure and the second oligomeric substructure are formed from amino acid residues residing in elements of alpha helix and/or beta strand secondary structure.

The multimeric assemblies of all aspects of the invention are capable of forming a variety of different structural classes based on the designated mathematical symmetry group of each assembly. As the teachings above indicate, the assemblies comprise multiple copies of substructures that interact at one or more O interfaces that orient the substructures such that their symmetry axes may align with symmetry axes of the same kind in a designated mathematical symmetry group. There are many symmetry groups that comprise multiple types of symmetry axes, including but not limited to dihedral symmetries, cubic point group symmetries, line or helical symmetries, plane or layer symmetries, and space group symmetries. Each individual assembly possesses a single, mathematically defined symmetry that results from the interface between the substructures orienting them such that their symmetry axes align to those in a designated mathematically symmetry group. Individual assemblies possessing different symmetries may find use in different applications; for instance, assemblies possessing cubic point group symmetries may form hollow shell- or cage-like structures that could be useful, for example, for packaging or encapsulating molecules of interest, while assemblies possessing plane group symmetries will tend to form regularly repeating two-dimensional protein layers that could be used, for example, to array molecules, nanostructures, or other functional elements of interest at regular intervals.

In one embodiment, the mathematical symmetry group is selected from the group consisting of tetrahedral point group symmetry, octahedral point group symmetry, and icosahedral point group symmetry.

As used herein, the O interface is any polypeptide region (contiguous or non-contiguous) that is capable of driving self-assembly of the proteins and/or oligomeric substructures of the assemblies of the present invention via non-covalent interactions. The O interfaces are non-natural protein interfaces, in that they are designed and are not naturally occurring. The O interfaces may utilize any suitable non-covalent interaction(s) to drive self-interaction of the proteins and/or oligomeric substructures, including but not limited to one or more of electrostatic interactions, π-effects, van der Waals forces, hydrogen bonding, and hydrophobic effects. In the first aspect, where the oligomeric substructures are formed from a single protein, the one or more O interfaces are identical. In the second aspect, where first and second proteins self-interact to form oligomeric assemblies, which interact via the O interfaces to form subunit structures, each O interface may be the same or different.

Based on the disclosure herein, it is well within the level of those of skill in the art to identify O interfaces suitable for use in producing the multimeric assemblies of the invention. In one embodiment, a suitable O interface can be identified as follows:

As described elsewhere in this application, an O interface for use in the present invention can be any polypeptide region (contiguous or non-contiguous) that is capable of driving self-assembly of the proteins and/or oligomeric substructures of the assemblies of the present invention via non-covalent interactions. The O interfaces are non-natural protein interfaces, in that they are designed and are not naturally occurring. As will be known to those of skill in the art, an O interface can be demonstrated to perform the function of driving self-assembly using a variety of standard biochemical and biophysical techniques for evaluating the apparent size of multi-subunit protein assemblies. Such assays include but are not limited to native (non-denaturing) polyacrylamide gel electrophoresis, size exclusion chromatography, multi-angle light scattering, dynamic light scattering, analytical ultracentrifugation, small-angle X-ray scattering, visualization by electron microscopy or cryo-electron microscopy, atomic force microscopy, and high-resolution structure determination by X-ray crystallography. In the case of multimeric assemblies that comprise a first oligomeric protein substructure and a second oligomeric protein substructure, techniques commonly used to identify interactions between two different proteins can additionally be used to demonstrate the ability of an O interface to drive self-assembly of the first and second proteins. Such techniques include but are not limited to co-precipitation or co-purification of the two proteins, isothermal titration calorimetry, fluorescence resonance energy transfer-based techniques, and fluorescence anisotropy. In all cases, disruption of the amino acid residues comprising the non-natural protein-protein interface within the O interface by mutation, or deletion of the O interface, can provide valuable controls for evaluating the function of the interface.

In various further embodiments, the O interface is present (contiguously or non-contiguously) in a polypeptide comprising or consisting of one of the following amino acid sequences, which are particularly useful in generating the assemblies of the first aspect of the invention:

| SEQ ID NO: 1 | | | |
|---|---|---|---|
| AA1 | M or absent | AA2 | ANY |
| AA3 | ANY | AA4 | A |
| AA5 | I | AA6 | G |
| AA7 | I | AA8 | L |
| AA9 | E | AA10 | L |
| AA11 | ANY | AA12 | S |
| AA13 | I | AA14 | A |
| AA15 | A | AA16 | G |
| AA17 | M | AA18 | E |

-continued

| SEQ ID NO: 1 | | | |
|---|---|---|---|
| AA19 | L | AA20 | G |
| AA21 | D | AA22 | A |
| AA23 | M | AA24 | L |
| AA25 | ANY | AA26 | S |
| AA27 | A | AA28 | ANY |
| AA29 | V | AA30 | ANY |
| AA31 | L | AA32 | L |
| AA33 | V | AA34 | S |
| AA35 | ANY | AA36 | T |
| AA37 | I | AA38 | ANY |
| AA39 | ANY | AA40 | G |
| AA41 | ANY | AA42 | F |
| AA43 | L | AA44 | L |
| AA45 | M | AA46 | L |
| AA47 | G | AA48 | G |
| AA49 | ANY | AA50 | ANY |
| AA51 | G | AA52 | A |
| AA53 | I | AA54 | Q |
| AA55 | ANY | AA56 | A |
| AA57 | I | AA58 | E |
| AA59 | T | AA60 | G |
| AA61 | T | AA62 | S |
| AA63 | Q | AA64 | A |
| AA65 | G | AA66 | E |
| AA67 | L | AA68 | ANY |
| AA69 | ANY | AA70 | ANY |
| AA71 | S | AA72 | ANY |
| AA73 | V | AA74 | L |
| AA75 | ANY | AA76 | ANY |
| AA77 | I | AA78 | ANY |
| AA79 | ANY | AA80 | S |
| AA81 | V | AA82 | L |
| AA83 | ANY | AA84 | A |
| AA85 | I | AA86 | ANY |
| AA87 | ANY | AA88 | ANY |
| AA89 | N | AA90 | ANY |
| AA91 | V | AA92 | ANY |
| AA93 | ANY | AA94 | ANY |
| AA95 | ANY | AA96 | A |
| AA97 | V | AA98 | G |
| AA99 | I | AA100 | V |
| AA101 | E | AA102 | T |
| AA103 | ANY | AA104 | S |
| AA105 | V | AA106 | A |
| AA107 | A | AA108 | C |
| AA109 | I | AA110 | S |
| AA111 | A | AA112 | A |
| AA113 | D | AA114 | ANY |
| AA115 | A | AA116 | V |
| AA117 | ANY | AA118 | G |
| AA119 | S | AA120 | ANY |
| AA121 | V | AA122 | T |
| AA123 | L | AA124 | V |
| AA125 | R | AA126 | V |
| AA127 | ANY | AA128 | M |
| AA129 | A | AA130 | ANY |
| AA131 | G | AA132 | I |
| AA133 | ANY | AA134 | G |
| AA135 | K | AA136 | C |
| AA137 | Y | AA138 | M |
| AA139 | V | AA140 | V |
| AA141 | A | AA142 | G |
| AA143 | ANY | AA144 | V |
| AA145 | S | AA146 | D |
| AA147 | V | AA148 | A |
| AA149 | L | AA150 | A |
| AA151 | V | AA152 | T |
| AA153 | V | AA154 | A |
| AA155 | S | AA156 | S |
| AA157 | S | AA158 | A |
| AA159 | G | AA160 | A |
| AA161 | Y | AA162 | ANY |
| AA163 | L | AA164 | L |
| AA165 | V | AA166 | Y |
| AA167 | A | AA168 | S |
| AA169 | L | AA170 | I |
| AA171 | ANY | AA172 | ANY |
| AA173 | P | AA174 | ANY |
| AA175 | ANY | AA176 | A |
| AA177 | M | AA178 | ANY |
| AA179 | ANY | AA180 | Q |
| AA181 | M | AA182 | V |
| AA183 | ANY | AA184 | ANY |

As used throughout this application, a "defined residue" means an amino acid position in the sequence listing that recites a specific amino acid residue. All undefined residues in SEQ ID NO:1 (i.e., residues that do not include a defined residue) are present on the polypeptide surface, and thus can be substituted with a different amino acid as desired for a given purpose without disruption of the polypeptide structure that permits polypeptide self-assembly. All defined residues are present in the polypeptide interior, and thus can be modified only by conservative substitutions to maintain overall polypeptide structure to permit polypeptide self-assembly. As used here, "conservative amino acid substitution" means that:

hydrophobic amino acids (Ala, Cys, Gly, Pro, Met, Sce, Sme, Val, Ile, Leu) can only be substituted with other hydrophobic amino acids;

hydrophobic amino acids with bulky side chains (Phe, Tyr, Trp) can only be substituted with other hydrophobic amino acids with bulky side chains;

amino acids with positively charged side chains (Arg, His, Lys) can only be substituted with other amino acids with positively charged side chains;

amino acids with negatively charged side chains (Asp, Glu) can only be substituted with other amino acids with negatively charged side chains; and amino acids with polar uncharged side chains (Ser, Thr, Asn, Gln) can only be substituted with other amino acids with polar uncharged side chains.

For ease of review, Table 1 provides a representation of SEQ ID NO:1, where the term "AA-" refers to the amino acid residue within SEQ ID NO:1, and the term "any" means an undefined residue. As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V). A residue in parentheses within the disclosed sequences means that the residue may be absent.

In one embodiment, an O interface polypeptide includes at least 2, 3, 4, 5, 6, 7, 8, 9, 10, or more amino acid substitutions relative to SEQ ID NO: 2 (3n79-wt).

```
                                              (SEQ ID NO: 2)
(M)SQAIGILELTSIAKGMELGDAMLKSANVDLLVSKTICPGKFLLMLGGD

IGAIQQAIETGTSQAGEMLVDSLVLANIHPSVLPAISGLNSVDKRQAVGIV

ETWSVAACISAADRAVKGSNVTLVRVHMAFGIGGKCYMVVAGDVSDVNNAV

TVASESAGEKGLLVYRSVIPRPHEAMWRQMVEG
```

In one such embodiment, at least two of the following amino acid positions are changed relative to SEQ ID NO:2: AA14, AA67, AA148, AA149, AA156, AA160, AA161, AA167, and AA 169. In various embodiments, 2, 3, 4, 5, 6, 7, 8, or all 9 residues (AA14, AA67, AA148, AA149, AA156, AA160, AA161, AA167, and AA 169) in the polypeptides of this aspect of the invention are changed relative to SEQ ID NO:2.

In a further embodiment, the O interface-containing polypeptide includes no more than 100 defined residues as per SEQ ID NO:1 are modified by a conservative amino acid substitution. In various further embodiments, no more than 90, 85, 80, 75, 70, 65, 60, 55, 50, 45, 40, 35, 30, 25, 30, 15, 10, 9, 8, 7, 6, 5, 4, 3, 2, or 1 defined residues as per SEQ ID NO:1 are modified by a conservative amino acid substitution. In a further embodiment, the 0 interface-containing polypeptide comprises or consists of SEQ ID NO:1 with no defined residues modified by a conservative amino acid substitution.

In a further embodiment, the O interface-containing polypeptide comprises or consists of an amino acid sequence with at least 75% identity to the amino acid sequence of SEQ ID NO:3 (also referred to herein as "03-33").

```
                                                  (SEQ ID NO: 3)
(M)SQAIGILELTSIAAGMELGDAMLKSANVDLLVSKTISPGKFLLMLGGD

IGAIQQAIETGTSQAGELLVDSLVLANIHPSVLPAISGLNSVDKRQAVGIV

ETWSVAACISAADRAVKGSNVTLVRVHMAFGIGGKCYMVVAGDVSDVALAV

TVASSSAGAYGLLVYASLIPRPHEAMWRQMVEG
```

In various embodiments, the 0 interface-containing polypeptide comprises or consists of an amino acid sequence with at least 80%, 85%, 90%, 95%, 96%, 97%, 98%, or 99% identity to the amino acid sequence of SEQ ID NO:3. In each of these embodiments, it is understood that residues in SEQ ID NO:3 corresponding to defined residues in SEQ ID NO:1 may only be substituted by conservative amino acid substitutions. In another embodiment, a polypeptide of the second aspect of the invention comprises or consists of the amino acid sequence of SEQ ID NO:3 (03-33), which is discussed by way of example herein.

In a further embodiment, the O interface-containing polypeptide comprises or consists of the amino acid sequence of SEQ ID NO:4, wherein any defined residue in SEQ ID NO:4 can be modified by a conservative amino acid substitution, and wherein the polypeptide does not comprise or consist of the amino acid sequence of SEQ ID NO: 5 (3 ftt-wt). For ease of review, Table 2 provides a representation of SEQ ID NO:4, where the term "AA-" refers to the amino acid residue within SEQ ID NO:4, and the term "any" means an undefined residue.

TABLE 2

| (SEQ ID NO: 4) | | | |
|---|---|---|---|
| AA1 | M or absent | AA2 | ANY |
| AA3 | ANY | AA4 | ANY |
| AA5 | ANY | AA6 | ANY |
| AA7 | ANY | AA8 | ANY |
| AA9 | ANY | AA10 | ANY |
| AA11 | K | AA12 | W |
| AA13 | ANY | AA14 | D |
| AA15 | A | AA16 | ANY |
| AA17 | F | AA18 | D |
| AA19 | ANY | AA20 | T |
| AA21 | ANY | AA22 | I |
| AA23 | N | AA24 | E |
| AA25 | R | AA26 | L |
| AA27 | R | AA28 | A |
| AA29 | K | AA30 | V |

TABLE 2-continued

| (SEQ ID NO: 4) | | | |
|---|---|---|---|
| AA31 | I | AA32 | C |
| AA33 | F | AA34 | A |
| AA35 | L | AA36 | N |
| AA37 | H | AA38 | T |
| AA39 | N | AA40 | P |
| AA41 | S, V | AA42 | ANY |
| AA43 | T | AA44 | L, M |
| AA45 | K, M | AA46 | ANY |
| AA47 | K | AA48 | V |
| AA49 | L | AA50 | I |
| AA51 | D | AA52 | A |
| AA53 | L | AA54 | F |
| AA55 | Q | AA56 | T |
| AA57 | T | AA58 | ANY |
| AA59 | ANY | AA60 | N |
| AA61 | ANY | AA62 | S |
| AA63 | I | AA64 | S |
| AA65 | I | AA66 | P |
| AA67 | F | AA68 | D |
| AA69 | T | AA70 | D |
| AA71 | Y | AA72 | G |
| AA73 | W | AA74 | N |
| AA75 | ANY | AA76 | K |
| AA77 | L | AA78 | ANY |
| AA79 | ANY | AA80 | N |
| AA81 | V | AA82 | Y |
| AA83 | V | AA84 | N |
| AA85 | T | AA86 | N |
| AA87 | C | AA88 | Y |
| AA89 | F | AA90 | M |
| AA91 | D | AA92 | ANY |
| AA93 | G | AA94 | ANY |
| AA95 | I | AA96 | T |
| AA97 | ANY | AA98 | G |
| AA99 | D | AA100 | N |
| AA101 | V | AA102 | F |
| AA103 | I | AA104 | G |
| AA105 | P | AA106 | N |
| AA107 | C | AA108 | G |
| AA109 | F | AA110 | Y |
| AA111 | ANY | AA112 | A |
| AA113 | T | AA114 | ANY |
| AA115 | P | AA116 | ANY |
| AA117 | ANY | AA118 | ANY |
| AA119 | H | AA120 | H |
| AA121 | ANY | AA122 | N |
| AA123 | ANY | AA124 | G |
| AA125 | ANY | AA126 | E |
| AA127 | K | AA128 | A |
| AA129 | G | AA130 | ANY |
| AA131 | I | AA132 | H |
| AA133 | I | AA134 | G |
| AA135 | S | AA136 | N |
| AA137 | T | AA138 | W |
| AA139 | F | AA140 | G |
| AA141 | G | AA142 | H |
| AA143 | V | AA144 | A |
| AA145 | V | AA146 | L |
| AA147 | P | AA148 | ANY |
| AA149 | V | AA150 | T |
| AA151 | ANY | AA152 | G |
| AA153 | E | AA154 | G |
| AA155 | S | AA156 | V |
| AA157 | I | AA158 | G |
| AA159 | A | AA160 | G |
| AA161 | S | AA162 | V |
| AA163 | ANY | AA164 | ANY |
| AA165 | K | AA166 | ANY |
| AA167 | ANY | AA168 | ANY |
| AA169 | P | AA170 | H |
| AA171 | S | AA172 | ANY |
| AA173 | A | AA174 | V |
| AA175 | ANY | AA176 | N |
| AA177 | ANY | AA178 | ANY |
| AA179 | ANY | AA180 | ANY |
| AA181 | ANY | AA182 | R |
| AA183 | ANY | AA184 | I |
| AA185 | ANY | AA186 | ANY |

TABLE 2-continued (SEQ ID NO: 4)

| | | | |
|---|---|---|---|
| AA187 | D | AA188 | L |
| AA189 | P | AA190 | S |
| AA191 | E | AA192 | T |
| AA193 | L | AA194 | N |
| AA195 | D | AA196 | E |
| AA197 | T | AA198 | I |
| AA199 | K | | |

In one embodiment, the O interface-containing polypeptide includes at least 2, 3, 4, 5, 6, 7, 8, 9, 10, or more amino acid substitutions relative to SEQ ID NO: 5 (3ftt-wt) or SEQ ID NO: 6 (3n79-wt).

(SEQ ID NO: 5)
(M)TEKEKMLAEKWYDANFDQYLINERARAKDICFELNHTRPSATNKRKEL

IDQLFQTTTDNVSISIPFDTDYGWNVKLGKNVYVNTNCYFMDGGQITIGDN

VFIGPNCGFYTATHPLNFHHRNEGFEKAGPIHIGSNTWFGGHVAVLPGVTI

GEGSVIGAGSVVTKDIPPHSLAVGNPCKVVRKIDNDLPSETLNDETIK

In one such embodiment, at least two of the following amino acid positions are changed relative to SEQ ID NO:5: AA20, AA26, AA30, AA34, AA39, AA41, AA44, AA48, and AA 52. In various embodiments, 2, 3, 4, 5, 6, 7, 8, or all 9 residues (AA20, AA26, AA30, AA34, AA39, AA41, AA44, AA48, and AA 52) in the polypeptides of the second aspect of the invention are changed relative to SEQ ID NO:5.

In a further embodiment, the O interface-containing polypeptide includes no more than 100 defined residues as per SEQ ID NO:4 are modified by a conservative amino acid substitution. In various further embodiments, no more than 90, 85, 80, 75, 70, 65, 60, 55, 50, 45, 40, 35, 30, 25, 30, 15, 10, 9, 8, 7, 6, 5, 4, 3, 2, or 1 defined residues as per SEQ ID NO:4 are modified by a conservative amino acid substitution. In a further embodiment, the O interface-containing polypeptide comprises or consists of SEQ ID NO:4 with no defined residues modified by a conservative amino acid substitution.

In a further embodiment, the O interface-containing polypeptide comprises or consists of an amino acid sequence with at least 75% identity to an amino acid sequence selected from the group consisting of SEQ ID NO:9, SEQ ID NO: 7 (also referred to herein as "T3-08"), and SEQ ID NO:8 (also referred to herein as "T3-10").

T3-08
(SEQ ID NO: 7)
(M)TEKEKMLAEKWYDANFDQTLINERLRAKVICFALNHTNPSATLKRKVL

IDALFQTTTDNVSISIPFDTDYGWNVKLGKNVYVNTNCYFMDGGQITIGDN

VFIGPNCGFYTATHPLNFHHRNEGFEKAGPIHIGSNTWFGGHVAVLPGVTI

GEGSVIGAGSVVTKDIPPHSLAVGNPCKVVRKIDNDLPSETLNDETIK

T3-10
(SEQ ID NO: 8) or SEQ ID NO: 9)
(M)TEKEKMLAEKWYDANFDQTLINERLRAKVICFALNHTNPVATMMRKVL

IDALFQTTTDNVSISIPFDTDYGWNVKLGKNVYVNTNCYFMDGGQITIGDN

VFIGPNCGFYTATHPLNFHHRNEGFEKAGPIHIGSNTWFGGHVAVLPGVTI

GEGSVIGAGSVVTKDIPPHSLAVGNPCKVVRKIDNDLPSETLNDETIK;.

In various embodiments, the O interface-containing polypeptide comprises or consists of an amino acid sequence with at least 80%, 85%, 90%, 95%, 96%, 97%, 98%, or 99% identity to an amino acid sequence selected from the group consisting of SEQ ID NO:7, SEQ ID NO: 8, and SEQ ID NO: 9. In each of these embodiments, it is understood that residues in SEQ ID NO:7, 8, or 9 corresponding to defined residues in SEQ ID NO:4 may only be substituted by conservative amino acid substitutions. In another embodiment, the O interface-containing polypeptide comprises or consists of an amino acid sequence selected from the group consisting of SEQ ID NO:7, SEQ ID NO:8, and SEQ ID NO:9, which are discussed by way of example herein.

In another embodiment, the O interface-containing polypeptide comprises or consists of a polypeptide selected from SEQ ID NOS: 10-19, which are particularly useful in generating the assemblies of the second aspect of the invention.

In another embodiment, the O interface-containing polypeptide comprises or consists of a polypeptide selected from SEQ ID NOS: 22-51.

In another embodiment, the O interface-containing polypeptide comprises or consists of a polypeptide with at least 75%, 80%, 85%, 90%, 95%, 96%, 97%, 98%, 99%, or 100% identity to the amino acid sequence of SEQ ID NO: 20 (I3-01) or 304 (I3-01(M3I); wherein the polypeptide includes at least 1, 2, 3, 4, 5, or more amino acid substitutions compared to SEQ NO: 21 (1wa3-wt).

SEQ ID: 20 (I3-01)
(M)KMEELFKKHKIVAVLRANSVEEAKKKALAVFLGGVHLIEITFTVPDAD

TVIKELSFLKEMGAIIGAGTVTSVEQCRKAVESGAEFIVSPHLDEEISQFC

KEKGVFYMPGVMTPTELVKAMKLGHTILKLFPGEVVGPQFVKAMKGPFPNV

KFVPTGGVNLDNVCEWFKAGVLAVGVGSALVKGTPVEVAEKAKAFVEKIRG

CTE;
or

SEQ ID 304: (I3-01(M3I)
(M)KIEELFKKHKIVAVLRANSVEEAKKKALAVFLGGVHLIEITFTVPDAD

TVIKELSFLKEMGAIIGAGTVTSVEQCRKAVESGAEFIVSPHLDEEISQFC

KEKGVFYMPGVMTPTELVKAMKLGHTILKLFPGEVVGPQFVKAMKGPFPNV

KFVPTGGVNLDNVCEWFKAGVLAVGVGSALVKGTPVEVAEKAKAFVEKIRG

CTE

SEQ ID: 21 (1wa3-wt)
MKMEELFKKHKIVAVLRANSVEEAKEKALAVFEGGVHLIEITFTVPDADTV

IKELSFLKEKGAIIGAGTVTSVEQCRKAVESGAEFIVSPHLDEEISQFCKE

KGVFYMPGVMTPTELVKAMKLGHTILKLFPGEVVGPQFVKAMKGPFPNVKF

VPTGGVNLDNVCEWFKAGVLAVGVGSALVKGTPDEVREKAKAFVEKIRGCT

E.

In another embodiment, the O-interface containing first protein and the second proteins comprise or consist of proteins selected from the following pairs of first and second proteins:

(a) T32-28A (SEQ ID NO: 22) and T32-28B (SEQ ID NO: 23);
(b) T33-09A (SEQ ID NO: 24) and T33-09B (SEQ ID NO: 25);
(c) T33-15A (SEQ ID NO: 26) and T33-15B (SEQ ID NO: 27);

(d) T33-21A (SEQ ID NO: 28) and T33-21B (SEQ ID NO: 29); and (e) T33-28A (SEQ ID NO: 30) and T33-28B (SEQ ID NO: 31).

In a further embodiment the O-interface containing first protein and the second proteins comprise or consist of proteins selected from the following pairs of first and second proteins:

(a) T32-28A (SEQ ID NO: 32) and T32-28B (SEQ ID NO: 33);

(b) T33-09A (SEQ ID NO: 34) and T33-09B (SEQ ID NO: 35);

(c) T33-15A (SEQ ID NO: 36) and T33-15B (SEQ ID NO: 37);

(d) T33-21A (SEQ ID NO: 38) and T33-21B (SEQ ID NO: 39); and (e) T33-28A (SEQ ID NO: 40) and T33-28B (SEQ ID NO: 41).

In another embodiment, the O-interface containing first protein and the second proteins comprise or consist of proteins selected from the following pairs of first and second proteins:

(a) T32-28A (SEQ ID NO: 42) and T32-28B (SEQ ID NO: 43);

(b) T33-09A (SEQ ID NO: 44) and T33-09B (SEQ ID NO: 45);

(c) T33-15A (SEQ ID NO: 46) and T33-15B (SEQ ID NO: 47);

(d) T33-21A (SEQ ID NO: 48) and T33-21B (SEQ ID NO: 49); and (e) T33-28A (SEQ ID NO: 50) and T33-28B (SEQ ID NO: 51).

In one embodiment, the O-interface containing first protein and the second proteins comprise or consist of proteins selected from the following pairs of first and second proteins:

(a) T32-28A (SEQ ID NO: 22, 32, or 42) and T32-28B SEQ ID NO: 23, 33, or 43), wherein the first protein is at least 70% identical to the amino acid sequence of SEQ ID NO: 1 and the second protein is at least 70% identical to the amino acid sequence of SEQ ID NO: 11;

(b) T33-09A SEQ ID NO: 24, 34, or 44) and T33-09B SEQ ID NO: 25, 35, or 45), wherein the first protein is at least 70% identical to the amino acid sequence of SEQ ID NO: 12 and the second protein is at least 70% identical to the amino acid sequence of SEQ ID NO: 13;

(c) T33-15A SEQ ID NO: 26, 36, or 46) and T33-15B SEQ ID NO: 27, 37, or 47), wherein the first protein is at least 70% identical to the amino acid sequence of SEQ ID NO: 14 and the second protein is at least 70% identical to the amino acid sequence of SEQ ID NO: 15;

(d) T33-21A SEQ ID NO: 28, 38 or 48) and T33-21B SEQ ID NO: 29, 39 or 49), wherein the first protein is at least 70% identical to the amino acid sequence of SEQ ID NO: 16 and the second protein is at least 70% identical to the amino acid sequence of SEQ ID NO: 17; and (e) T33-28A SEQ ID NO: 30, 40, or 50) and T33-28B SEQ ID NO: 31, 41, or 51), wherein the first protein is at least 70% identical to the amino acid sequence of SEQ ID NO: 18 and the second protein is at least 70% identical to the amino acid sequence of SEQ ID NO: 19.

In various further embodiments, the first and second proteins are at least 75%, 80%, 85%, 90%, 91%, 92%, 93%, 94%, 95%, 96%, 97%, or 98% identical to the amino acid sequence of the designed protein.

In various further embodiments, the O-interface containing first protein and the second proteins comprise or consist of proteins selected from the following pairs of first and second proteins (a) T32-28A (SEQ ID NO:10) and T32-28B (SEQ ID NO:11);

(b) T33-09A (SEQ ID NO:12) and T33-09B (SEQ ID NO:13);

(c) T33-15A (SEQ ID NO:14) and T33-15B (SEQ ID NO:15);

(d) T33-21A (SEQ ID NO:16) and T33-21B (SEQ ID NO:17); and (e) T33-28A (SEQ ID NO:18) and T33-28B (SEQ ID NO:19).

In various further embodiments, the O-interface containing first protein and the second proteins comprise or consist of proteins selected from the following pairs of first and second proteins:

(A) I53-34A (SEQ ID NO: 270) and I53-34B (SEQ ID NO: 271);

(B) I53-40A (SEQ ID NO: 272) and I53-40B (SEQ ID NO: 273);

(C) I53-47A (SEQ ID NO: 274) and I53-47B (SEQ ID NO: 275);

(D) I53-50A (SEQ ID NO: 276) and I53-50B (SEQ ID NO: 277); and (E) I53-51A (SEQ ID NO: 278) and I53-51B (SEQ ID NO: 279).

An "M domain" for use in the present invention can be any suitable polypeptide that is capable of binding to a lipid bilayer via any suitable mechanism, including but not limited to non-covalently interacting with the lipid bilayer membrane. In various embodiments, such interactions may include but are not limited to interacting via specific binding pockets with the polar head groups of lipid molecules in the lipid bilayer, interacting electrostatically with charged polar head groups, interacting non-covalently with the hydrophobic interior of the lipid bilayer, or by harboring a chemical modification (non-limiting examples may be fatty acid or acylation modifications such as myristoylation) that interacts non-covalently with the lipid bilayer. A given M domain may employ one or more mechanisms of interaction with a lipid bilayer. Each multimeric assembly comprises one or more M domains. In some embodiments, each oligomeric substructure in a multimeric assembly comprises one or more M domains. In other embodiments, some fraction (30%, 40%, 50%, 60%, 70%, 80%, 90%, or more) of the plurality of proteins comprise one or more M domains. In other embodiments, each protein in the plurality of proteins comprises one or more M domains. In all embodiments, one or more M domains is required per multimeric assembly in order to drive association of the multimeric assembly with the lipid bilayer via any suitable mechanism.

The M domains present in a resulting multimeric assembly may all be the same, all different, or some the same and some different.

In various embodiments, the one or more M domains may comprise or consist of a polypeptide having an acylation motif, including but not limited to N-terminal myristoylation motifs (including but not limited to MGXXXT/S (SEQ ID NO: 300) motif and non-limiting example sequences 1-92 below), palmitoylation motifs (including but not limited to non-limiting example sequences 93-99 below), farnesylation motifs, and geranylgeranylation motifs (Resh M (1999) Fatty acylation of proteins: new insights into membrane targeting of myristoylated and palmitoylated proteins. Biochim. Biophys. Acta 1451:1-16; Resh M (2013) Covalent lipid modifications of proteins. Curr. Biol. 23:R431-5); a polar headgroup-binding domain (including but not limited to non-limiting example sequences 100-106 in the attached appendices and the domains defined in: Stahelin R V (2009) Lipid binding domains: more than simple lipid effectors. J. Lipid Res. 50:S299-304); or transmembrane protein domains (the latter preferably when the multimeric assembly is enveloped by a lipid bilayer). In various further embodiments, the M domain may comprise envelope proteins of enveloped viruses, membrane protein transporters, membrane protein channels, B-cell receptors, T-cell receptors, transmembrane antigens of human pathogens, growth factors receptors, G-protein coupled receptors (GPCRs), complement regulatory proteins including but not limited to CD55 and CD59.

In further embodiments, the M domain may comprise or consist of one or more of the following peptides:

```
(Myr1; 6 N-terminal residues of HIV gag)
                                        (SEQ ID NO: 280)
(M)GARAS;

(Myr2; 6 N-terminal residues of MARCKS)
                                        (SEQ ID NO: 281)
(M)GAQFS;

(Myr3; 6 N-terminal residues of Src)
                                        (SEQ ID NO: 282)
(M)GSSKS;

(Myr4; 6 N-terminal residues of Neurocalcin)
                                        (SEQ ID NO: 283)
(M)GKQNS;

(Palm1; 13 N-terminal residues of Lyn kinase)
                                        (SEQ ID NO: 284)
(M)GCIKSKRKDNLN;

(Palm2; 13 N-terminal residues of Gαo)
                                        (SEQ ID NO: 285)
(M)GCTLSAEERAAL;

(Palm3; 13 N-terminal residues of GAP43)
                                        (SEQ ID NO: 286)
(M)LCCMRRTKQVEK;

(Palm4; 13 N-terminal residues of PSD-95)
                                        (SEQ ID NO: 287)
(M)DCLCIVTTKKYR;

(CaaX1; 13 C-terminal residues from K-Ras4B)
                                        (SEQ ID NO: 288)
KKKKKSKTKCVIM;

(CaaX2; 13 C-terminal residues from paralemmin)
                                        (SEQ ID NO: 289)
DMKKHRCKCCSIM;

(CaaX3; 13 C-terminal residues of RhoF)
                                        (SEQ ID NO: 290)
AQRQKKRRLCLLL;

(CaaX4; 13 C-terminal residues of type II inositol
1,4,5-trisphosphate 5-phosphatase isoform X7)
                                        (SEQ ID NO: 291)
AQEFIHQFLCNPL;

(PH; Residues 11-40 of rat PLCδ)
                                        (SEQ ID NO: 292)
HGLQDDPDLQALLKGSQLLKVKSSSWRRERFYKLQEDCKTIWQESRKVMRS

PESQLFSIEDIQEVRMGHRTEGLEKFARDIPEDRCFSIVFKDQRNTLDLIA

PSPADAQHWVQGLRKIIHHSGSMDQRQK;

(C1; residues 246-297 of human PCKδ isoform
X2)
                                        (SEQ ID NO: 293)
PHRFKVHNYMSPTFCDHCGSLLWGLVKQGLKCEDCGMNVHHKCREKVAN

LCG;

(C2; residues 1384-1509 of mouse PI3K)
                                        (SEQ ID NO: 294)
GAVKLSVSYRNGTLFIMVMHIKDLVTEDGADPNPYVKTYLLPDTHKTSKRK

TKISRKTRNPTFNEMLVYSGYSKETLRQRELQLSVLSAESLRENFFLGGIT

LPLKDFNLSKETVKWYQLTAATYL;
and/or (PX; residues 2-149 of human p40phox)
                                        (SEQ ID NO: 295)
AVAQQLRAESDFEQLPDDVAISANIADIEEKRGFTSHFVFVIEVKTKGGSK

YLIYRRYRQFHALQSKLEERFGPDSKSSALACTLPTLPAKVYVGVKQEIAE

MRIPALNAYMKSLLSLPVWVLMDEDVRIFFYQSPYDSEQVPQALRR
```

Further exemplary M domains may comprise or consist of one or more of the peptides that follow (Resh M (1999) Biochim. Biophys. Acta 1451:1-16; Resh M (2013) Curr. Biol. 23:R431-5; Stahelin R V (2009) J. Lipid Res. 50:S299-304).

A. The following peptides must be at the N terminus of the polypeptide in which they appear in order to function as an M domain.

1. Any amino acid sequence conforming to the consensus motif (M)GXXX(S/T) (SEQ ID NO: 300), where the M is in the initiator methionine at the N terminus of the polypeptide sequence.

```
2.
                                        (SEQ ID NO: 280)
    (M)GARAS 3.
                                        (SEQ ID NO: 296)
    (M)GCIKSKGKDSLS 4.
                                        (SEQ ID NO: 297)
    (M)GCINSKRKD 5.
                                        (SEQ ID NO: 298)
    (M)GSSKSKPKDPSQRRR 6.
                                        (SEQ ID NO: 299)
    (M)GCIKSKEDKGPAMKY 7.
                                        (SEQ ID NO: 52)
    (M)GCVQCKDKEATKLTE 8.
                                        (SEQ ID NO: 53)
    (M)GCIKSKRKDNLNDDE 9.
                                        (SEQ ID NO: 54)
    (M)GCVCSSNPEDDWMEN 10.
                                        (SEQ ID NO: 55)
    (M)GCMKSKFLQVGGNTG 11.
                                        (SEQ ID NO: 56)
    (M)GCVFCKKLEPVATAK
```

12.
(M)GCVHCKEKISGKGQG (SEQ ID NO: 57)

13.
(M)GLLSSKRQVSEKGKG (SEQ ID NO: 58)

14.
(M)GQQPGKVLGDQRRPS (SEQ ID NO: 59)

15.
(M)GQQVGRVGEAPGLQQ (SEQ ID NO: 60)

16.
(M)GNAAAAKKGSEQESV (SEQ ID NO: 61)

17.
(M)GNAATAKKGSEVESV (SEQ ID NO: 62)

18.
(M)GAQLSLVVQASPSIA (SEQ ID NO: 63)

19.
(M)GHALCVCSRGTVIID (SEQ ID NO: 64)

20.
(M)GQLCCFPFSRDEGKI (SEQ ID NO: 65)

21.
(M)GNEASYPLEMCSHFD (SEQ ID NO: 66)

22.
(M)GNSGSKQHTKHNSKK (SEQ ID NO: 67)

23.
(M)GCTLSAEDKAAVERS (SEQ ID NO: 68)

24.
(M)GCTLSAEERAALERS (SEQ ID NO: 69)

25.
(M)GAGASAEEKHSRELE (SEQ ID NO: 70)

26.
(M)GCRQSSEEKEAARRS (SEQ ID NO: 71)

27.
(M)GLSFTKLFSRLFAKK (SEQ ID NO: 72)

28.
(M)GNIFGNLLKSLIGKK (SEQ ID NO: 73)

29.
(M)GLTVSALFSRIFGKK (SEQ ID NO: 74)

30.
(M)GKVLSKIFGNKEMRI (SEQ ID NO: 75)

31.
(M)GNSKSGALSKEILEE (SEQ ID NO: 76)

32.
(M)GKQNSKLRPEVMQDL (SEQ ID NO: 77)

33.
(M)GKRASKLKPEEVEEL (SEQ ID NO: 78)

34.
(M)GKQNSKLRPEVLQDL (SEQ ID NO: 79)

35.
(M)GSRASTLLRDEELEE (SEQ ID NO: 80)

36.
(M)GSKLSKKKKGYNVND (SEQ ID NO: 81)

37.
(M)GKQNSKLRPEMLQDL (SEQ ID NO: 82)

38.
(M)GNVMEGKSVEELSST (SEQ ID NO: 83)

39.
(M)GQQFSWEEAEENGAV (SEQ ID NO: 84)

40.
(M)GNTKSGALSKEILEE (SEQ ID NO: 85)

41.
(M)GKQNSKLRPEVLQDL (SEQ ID NO: 86)

42.
(M)GAQFSKTAAKGEATA (SEQ ID NO: 87)

43.
(M)GSQSSKAPRGDVTAE (SEQ ID NO: 88)

44.
(M)GNRHAKASSPQGFDV (SEQ ID NO: 89)

45.
(M)GQDQTKQQIEKGLQL (SEQ ID NO: 90)

46.
(M)GQALSIKSCDFHAAE (SEQ ID NO: 91)

47.
(M)GNRAFKAHNGHYLSA (SEQ ID NO: 92)

48.
(M)GARASVLSGGELDRW (SEQ ID NO: 93)

49.
(M)GQTVTTPLSLTLDHW (SEQ ID NO: 94)

50.
(M)GQAVTTPLSLTLDHW (SEQ ID NO: 95)

51.
(M)GNSPSYNPPAGISPS (SEQ ID NO: 96)

-continued 52.
(SEQ ID NO: 97)
(M)GQTLTTPLSLTLTHF 53.
(SEQ ID NO: 98)
(M)GQTITTPLSLTLDHW 54.
(SEQ ID NO: 99)
(M)GQTVTTPLSLTLEHW 55.
(SEQ ID NO: 100)
(M)GQELSQHERYVEQLK 56.
(SEQ ID NO: 101)
(M)GVSGSKGQKLFVSVL 57.
(SEQ ID NO: 102)
(M)GGKWSKSSVVGWPTV 58.
(SEQ ID NO: 103)
(M)GQHPAKSMDVRRIEG 59.
(SEQ ID NO: 104)
(M)GAQVSRQNVGTHSTQ 60.
(SEQ ID NO: 105)
(M)GLAFSGARPCCCRHN 61.
(SEQ ID NO: 106)
(M)GNRGSSTSSRPPLSS 62.
(SEQ ID NO: 107)
(M)GSYFVPPANYFFKDI 63.
(SEQ ID NO: 108)
(M)GAQLSTLSRVVLSPV 64.
(SEQ ID NO: 109)
(M)GNLKSVGQEPGPPCG 65.
(SEQ ID NO: 110)
(M)GSKRSVPSRHRSLTT 66.
(SEQ ID NO: 111)
(M)GNGESQLSSVPAQKL 67.
(SEQ ID NO: 112)
(M)GAHLVRRYLGDASVE 68.
(SEQ ID NO: 113)
(M)GGKLSKKKKGYNVND 69.
(SEQ ID NO: 114)
(M)GSCCSCPDKDTVPDN 70.
(SEQ ID NO: 115)
(M)GSSEVSIIPGLQKEE 71.
(SEQ ID NO: 116)
(M)LCCMRRTKQVEKNDE 72.
(SEQ ID NO: 117)
(M)GCLGNSKTEDQRNE 73.
(SEQ ID NO: 118)
(M)TLESIMACCLSEEAKEA 74.
(SEQ ID NO: 119)
(M)SGVVRTLSRCLLPAEAG 75.
(SEQ ID NO: 120)
(M)ADFLPSRSVCFPGCVLTN 76.
(SEQ ID NO: 121)
(M)ARSLRWRCCPWCLTEDEKAA 77.
(SEQ ID NO: 122)
(M)LCCMRRTKQVEKNDDDQKIEQDGI 78.
(SEQ ID NO: 123)
(M)QCCGLVHRRRVRV 79.
(SEQ ID NO: 124)
(M)DCLCIVTTKKYRYQDEDTP 80.
(SEQ ID NO: 125)
(M)CKGLAGLPASCLRSAKDMK 81.
(SEQ ID NO: 126)
(M)GCIKSKEDKGPAMKY 82.
(SEQ ID NO: 127)
(M)GCVQCKDKEATKLTE 83.
(SEQ ID NO: 128)
(M)GCIKSKRKDNLNDDE 84.
(SEQ ID NO: 129)
(M)GCVCSSNPEDDWMEN 85.
(SEQ ID NO: 130)
(M)GCMKSKFLQVGGNTG 86.
(SEQ ID NO: 131)
(M)GCVFCKKLEPVATAK 87.
(SEQ ID NO: 132)
(M)GCVHCKEKISGKGQG 88.
(SEQ ID NO: 133)
(M)GCTLSAEDKAAVERS 89.
(SEQ ID NO: 134)
(M)GCTLSAEERAALERS 90.
(SEQ ID NO: 135)
(M)GCRQSSEEKEAARRS 91.
(SEQ ID NO: 136)
(M)GQLCCFPFSRDEGK 92.
(SEQ ID NO: 137)
(M)GNLKSVGQEPGPPCGLGLGLGLGLCGK B. The following peptides must be at the C terminus of the polypeptide in which they appear in order to function as an M domain.

93.
(SEQ ID NO: 138)
SGPGCMSCKCVLS 94.
(SEQ ID NO: 139)
GTQGCMGLPCVVM 95.
(SEQ ID NO: 140)
TPGCVKIKKCVIM 96.
(SEQ ID NO: 141)
DMKKHRCKCCSIM 97.
(SEQ ID NO: 142)
SKDGKKKKKSKTKCVIM 98.
(SEQ ID NO: 143)
KKKKKKSKTKCVIM 99.
(SEQ ID NO: 144)
SKTKCVIM

C. The following peptides are non-limiting examples of polar headgroup-binding domains that can function as M domains. These domains can appear anywhere in the polypeptides of the invention consistent with proper folding and multimerization of the multimeric assembly.

100.
(SEQ ID NO: 145)
HGLQDDPDLQALLKGSQLLKVKSSSWRRERFYKLQEDCKTIWQESRKVMRS

PESQLFSIEDIQEVRMGHRTEGLEKFARDIPEDRCFSIVFKDQRNTLDLIA

PSPADAQHWVQGLRKIIHHSGSMDQRQK 101.
(SEQ ID NO: 146)
(M)DSGRDFLTLHGLQDDPDLQALLKGSQLLKVKSSSWRRERFYKLQEDCK

TIWQESRKVMRSPESQLFSIEDIQEVRMGHRTEGLEKFARDIPEDRCFSIV

FKDQRNTLDLIAPSPADAQHWVQGLRKIIHHSGSMDQRQK 102.
(SEQ ID NO: 147)
(M)DSGRDFLTLHGLQDDPDLQALLKGSQLLKVKSSSWRRERFYKLQEDCK

TIWQESRKVMRSPESQLFSIEDIQEVRMGHRTEGLEKFARDIPEDRCFSIV

FKDQRNTLDLIAPSPADVQHWVQGLRKIIDRSGSMDQRQK 103.
(SEQ ID NO: 148)
(M)DSGRDFLTLHGLQDDEDLQALLKGSQLLKVKSSSWRRERFYKLQEDCK

TIWQESRKVMRTPESQLFSIEDIQEVRMGHRTEGLEKFARDVPEDRCFSIV

FKDQRNTLDLIAPSPADAQHWVLGLHKIIHHSGSMDQRQK 104.
(SEQ ID NO: 149)
HGLQDDEDLQALLKGSQLLKVKSSSWRRERFYKLQEDCKTIWQESRKVMRT

PESQLFSIEDIQEVRMGHRTEGLEKFARDVPEDRCFSIVFKDQRNTLDLIA

PSPADAQHWVLGLHKIIHHSGSMDQRQK 105.
(SEQ ID NO: 150)
(M)SGGKYVDSEGHLYTVPIREQGNIYKPNNKAMAEEMNEKQVYDAHTKEI

DLVNRDPKHLNDDVVKIDFEDVIAEPEGTHSFDGIWKASFTTFTVTKYWFY

RLLSALFGIPMALIWGIYFAILSFLHIWAVVPCIKSFLIEIQCISRVYSIY

VHTFCDPLFEAIGKIFSNIRINTQKEI 106.
(SEQ ID NO: 151)
(M)SGGKYVDSEGHLYTVPIREQGNIYKPNNKAMADELSEKQVYDAHTKEI

DLVNRDPKHLNDDVVKIDFEDVIAEPEGTHSFDGIWKASFTTFTVTKYWFY

RLLSALFGIPMALIWGIYFAILSFLHIWAVVPCIKSFLIEIQCISRVYSIY

VHTVCDPLFEAVGKIFSNVRINLQKEI

Based on the disclosure herein, it is well within the level of those of skill in the art to identify M domains suitable for use in producing the multimeric assemblies of the invention. In one embodiment, a suitable M domain can be identified as follows:

As described elsewhere in this application, an M domain for use in the present invention can be any suitable polypeptide domain that is capable of binding to a lipid bilayer via any suitable mechanism, including but not limited to non-covalently interacting with the lipid bilayer membrane. As will be known to those of skill in the art, an M domain can be demonstrated to perform the function of membrane binding using a variety of standard assays. Many in vitro assays exist for assaying whether or not a polypeptide interacts with lipid membranes and for evaluating the characteristics of the interaction, such as the nature of the interaction (e.g., electrostatic or hydrophobic), the strength of the interaction, and whether the interaction deforms or remodels the membrane. Such assays include but are not limited to vesicle sedimentation assays, vesicle co-flotation assays, isothermal titration calorimetry, measuring changes in intrinsic or extrinsic protein or lipid fluorescence, fluorescence anisotropy, and membrane morphology analysis by electron microscopy or fluorescence microscopy (Zhao H, Lappalainen P (2012) A simple guide to biochemical approaches for analyzing lipid-protein interactions. Mol. Biol. Cell 23:2823-30). In addition, M domain-dependent localization of proteins to membranes in cells can also be used as an assay for the interaction of an M domain with membranes, and can yield information about the specificity of a given M domain for particular membranes, membrane subdomains, or lipids (Zacharias D A, Violin J D, Newton A C, Tsien R Y (2002) Partitioning of lipid-modified GFPs into membrane microdomains in live cells. Science 296:913-916; Lemmon Mass. (2008) Membrane recognition by phospholipid-binding domains. Nat. Rev. Mol. Cell. Biol. 9:99-111). Whether in vitro or in cells, either an isolated M domain or an M domain linked via genetic fusion or another method to a carrier protein that facilitates observation (for example, green fluorescent protein) can be used to evaluate the ability of the M domain to interact with lipid membranes.

An L domain for use in the present invention can be any suitable polypeptide that is capable of effecting membrane scission by recruiting the ESCRT machinery to the site of budding by binding to one or more ESCRT or ESCRT-associated proteins directly or indirectly via any suitable mechanism, including but not limited to non-covalently or covalently. Preferably, the L domain interacts with proteins known to recruit the ESCRT machinery to sites of budding in vivo, such as Tsg101, ALIX, or the Nedd4 family of ubiquitin E3 ligases (McDonald B, Martin-Serrano J (2009) No strings attached: the ESCRT machinery in viral budding and cytokinesis. J. Cell Sci. 122:2167-77; Votteler J, Sundquist Wis. (2013) Virus budding and the ESCRT pathway. Cell Host & Microbe 14:232-41). Most preferably, the L domain interacts with the human, murine, or other mammalian forms of these proteins. Each protein subunit in a multimeric assembly contains one or more L domains. The L domains present in a resulting multimeric assembly may all be the same, all different, or some the same and some different.

In various embodiments, the one or more L domains may comprise or consist of a a linear amino acid sequence motif selected from the group consisting of P(T/S)AP (SEQ ID NO: 152), $\Theta YX_{0/2}(P/\Theta)X_{0/3}$ (L/I)(SEQ ID NO: 153), PPXY (SEQ ID NO: 154), and overlapping combinations thereof (Bieniasz P D (2006) Late budding domains and host proteins in enveloped virus release. Virology 344:55-63; Votteler J, Sundquist Wis. (2013) Virus budding and the ESCRT pathway. Cell Host & Microbe 14:232-41), where Θ denotes a hydrophobic residue, X can be any amino acid, and numbered subscripts indicate amino acid spacers of varying lengths. Such overlapping combinations include, but are not limited to

```
                                      (SEQ ID NO: 155)
P(T/S)APPXY, (SEQ ID NO: 156)
P(T/S)APYP(X)ₙL, (SEQ ID NO: 157)
PPXYP(T/S)AP, (SEQ ID NO: 158)
PPXYYP(X)ₙL, (SEQ ID NO: 159)
YP(X)ₙLPPXY,
and (SEQ ID NO: 160)
YP(X)ₙLPPXY.
```

Further exemplary L domains may comprise or consist of one or more of the peptides that follow:

```
                                      (SEQ ID NO: 161)
PTAPPEE;

(SEQ ID NO: 162)
YPLTSL;

(SEQ ID NO: 163)
PTAPPEY;

(SEQ ID NO: 164)
YPDL;

(SEQ ID NO: 165)
FPIV;

(SEQ ID NO: 166)
PTAPPEY;

(SEQ ID NO: 167)
PTAP;

(SEQ ID NO: 168)
PPEY;

(SEQ ID NO: 169)
YPLTSL;
and/or (SEO ID NO: 165)
FPIV.
```

As will be understood by those of skill in the art, the L domain may include additional sequences, beyond those directly responsible for recruiting the ESCRT machinery, as appropriate for an intended use, so long as the ESCRT-recruitment motifs are not buried in the peptide core in such a way as to render them inaccessible for binding their interaction partners. In various further embodiments, the L domain may comprise or consist of the following peptides that include one or more ESCRT-recruitment motifs plus additional residues (ESCRT-recruitment motifs noted by underlined text):

```
(HIV Gag p6 domain)
                                      (SEQ ID NO: 172)
LQSRPEPTAPPEESFRSGVETTTPPQKQEPIDKELYPLTSLRSLFGNDPSS
Q;

(residues 2-21 of Ebola VP40)
                                      (SEQ ID NO: 173)
RRVILPTAPPEYMEAIYPVR;

(EIAV Gag p9 domain)
                                      (SEQ ID NO: 174)
PIQQKSQHNKSVVQETPQTQNLYPDLSEIKKEYNVKEKDQVEDLNLDSLW
E;

(residues 12-31 of SV5 M)
                                      (SEQ ID NO: 175)
NPRQSIKAFPIVINSDGGEK;

(SEQ ID NO: 176)
PTAPPEYGGS;

(SEQ ID NO: 177)
PTAPGGS;

(SEQ ID NO: 178)
PPEYGGS;

(SEQ ID NO: 179)
YPLTSLGGS;

(SEQ ID NO: 180)
YPDLGGS;

(SEQ ID NO: 181)
FPIVGGS;

(HIV Gag p6 domain mutant (SEQ ID NO: 182),
p6(ΔPTAP))(SEQ ID NO: 183)
LQSRPEAAAAPEESFRSGVETTTPPQKQEPIDKELYPLTSLRSLFGNDPSS
Q;
and/or (HIV Gag p6 domain mutant (SEQ ID NO: 184),
p6(AYP))
LQSRPEPTAPPEESFRSGVETTTPPQKQEPIDKELAALTSLRSLFGNDPSS
Q
```

Further exemplary L domains comprise or consist of one or more of the following polypeptides:

1.
(SEQ ID NO: 186)
QSRPEPTAPPEESFRSGVETTTPPQKQEPIDKELYPLTSLRSLFGNDPSSQ 2.
(SEQ ID NO: 187)
DPQIPPPPYVEPTAPQV 3.
(SEQ ID NO: 188)
LLTEDPPPYRD 4.
(SEQ ID NO: 189)
TASAPPPPYVG 5.
(SEQ ID NO: 190)
TPQTQNLYPDLSEIK 6.
(SEQ ID NO: 191)
(M)RRVILPTAPPEYMEAI 7.
(SEQ ID NO: 192)
NTYMQYLNPPPYADHS 8.
(SEQ ID NO: 193)
LGIAPPPYEEDTSMEYAPSAP 9.
(SEQ ID NO: 194)
DDLWLPPPEYVPLKEL 10.
(SEQ ID NO: 195)
AAPTAPPTGAADSIPPPYSP 11.
(SEQ ID NO: 196)
TAPSSPPPYEE 12.
(SEQ ID NO: 197)
QSIKAFPIVINSDG 13.
(SEQ ID NO: 185)
SREKPYKEVTEDLLHLNSL 14.
(SEQ ID NO: 170)
AAGAYDPARKLLEQYAKK 15.
(SEQ ID NO: 171)
PNCFNSSINNIHEMEIQLKDALEKNQQWLVYDQQREVYVKGLLAKIFELEK

KTETAAHSLPQQTKKPESEGYLQEEKQKC 16.
(SEQ ID NO: 305)
RKSPTPSAPVPLTEPAAQ 17.
(SEQ ID NO: 306)
(M)SLYPSLEDLKVDKVIQAQTAFSANPANPAILSEASAPIPHDGNLYPRL

YPELSQYMGLSLN

Based on the disclosure herein, it is well within the level of those of skill in the art to identify L domains suitable for use in producing the multimeric assemblies of the invention. As described elsewhere in this application, an L domain for use in the present invention can be any suitable polypeptide domain that is capable of effecting membrane scission and release of an enveloped multimeric assembly from a cell by recruiting the ESCRT machinery to the site of budding by binding to one or more ESCRT proteins directly or indirectly via any suitable mechanism, including but not limited to non-covalently or covalently. As will be known to those with skill in the art, the ability of an L domain to recruit the ESCRT machinery and effect membrane scission and release of an enveloped multimeric assembly can be assessed using budding assays. In the budding assay, a candidate L domain is genetically fused to a viral structural protein that has been rendered defective in budding by mutation or deletion of its late domain, and the ability of the candidate L domain to restore budding of virus-like particles is evaluated by analyzing the culture supernatant for the presence of the viral structural protein using standard techniques such as SDS-PAGE and Western blotting (Parent L J, Bennett R P, Craven R C, Nelle T D, Krishna N K, Bowzard J B, Wilson C B, Puffer B A, Montelaro R C, Wills J W (1995) Positionally independent and exchangeable late budding functions of the Rous Sarcoma Virus and Human Immunodeficiency Virus Gag proteins. J. Virol. 69:5455-5460). Any viral structural protein that is known to be defective in budding can be used in the budding assay, including but not limited to budding-defective versions of HIV-1 Gag, RSV Gag, MuMoLV Gag, SV5 M, Ebola VP40 and other structural proteins from different families of enveloped viruses including retroviruses, filoviruses, rhabdoviruses, arenaviruses, and paramyxoviruses. In addition, as the inventors describe below, the multimeric assemblies of the invention can be used to test the ability of an L domain to effect membrane scission and release of an enveloped multimeric assembly in a similar manner. The L domain of an enveloped multimeric assembly can be replaced with a candidate L domain, and the ability of the resulting construct to be released from cells can be determined by analyzing the culture supernatant for the presence of the protein subunits of the multimeric assembly using standard techniques such as SDS-PAGE and Western blotting. Finally, as will be known to those with skill in the art, the ability of an L domain to bind to one or more ESCRT proteins directly or indirectly can be assessed using a variety of biochemical, biophysical, and cell biological techniques including but not limited to co-immunoprecipitation, pull-down assays, isothermal titration calorimetry, biosensor binding assays, NMR spectroscopy, and X-ray crystallography.

In a further embodiment, the multimeric assembly of any embodiment or combination of embodiments may further comprise a packaging moiety. As used herein, a "packaging moiety" may be any moiety capable of interacting with a desired "cargo", with the effect of recruiting the cargo to the multimeric assembly. The interaction between the packaging moiety and the cargo can be any type of interaction, covalent or non-covalent, that results in effective interaction with and recruitment to the multimeric assembly. As will be apparent to those of skill in the art, the ability to widely modify surface amino acid residues without disruption of the protein structure permits many types of modifications to endow the resulting self-assembled multimers with a variety of functions. In one non-limiting example, the protein, first protein, and/or second protein can be modified, such as by introduction of various cysteine residues or non-canonical amino acids at defined positions to facilitate linkage to one or more cargo of interest. In another non-limiting example, the protein may be modified to comprise as a genetic fusion a polypeptide domain or sequence known to interact with a desired cargo covalently or non-covalently. In one embodiment, a non-canonical amino acid can be incorporated recombinantly using amber codon suppression (see L. Wang, A. Brock, B. Herberich, P. G. Schultz, Science 292, 498 (2001)). In another embodiment, the packaging moiety comprises the polypeptide sequence: QSRPEPTAP-PEESFRSGVETTTPPQKQEPIDKELYPLTSLRSLFGND-PSSQ (SEQ ID NO: 186), wherein the packaging moiety polypeptide is expressed as a genetic fusion with the M domain, the L domain, or the O interface. This sequence is the p6 domain of HIV Gag, which is known to interact with the HIV protein Vpr (SEQ ID NO: 202) via a non-covalent protein-protein interaction (Cavrois M, et al. (2002) Nat. Biotech. 20:1151-4). By including SEQ ID NO: 186 in a multimeric assembly of the invention, any polypeptide sequence or other molecule that is fused, tethered, or otherwise connected to the Vpr sequence can be packaged into the multimeric assembly.

Additional packaging moieties may comprise or consist of one or more of the following peptides expressed as a genetic fusion with the M domain, the L domain, or the O interface, each of which binds to corresponding recognition sequences present in a nucleic acid cargo of interest, resulting in recruitment of the nucleic acid cargo of interest to the multimeric assembly.

```
(a)
                                     (SEQ ID NO: 198)
DRRRRGSRPSGAERRRRRAAAA (1g70), (b)
                                     (SEQ ID NO: 199)
AVPETRPNHTIYINNLNEKIKKDELKKSLHAIFSRFGQILDILVSRSLKMR

GQAFVIFKEVSSATNALRSMQGFPFYDKPMRIQYAKTDSDIIAKMK (u1a)

(c)
                                     (SEQ ID NO: 200)
(M)QKGNFRNQRKTVKCFNCGKEGHIAKNCRAPRKKGCWKCGKEGHQMKDC

TERQAN (HIV_NC),
and/or (d)
                                     (SEQ ID NO: 201)
RPRGTRGKGRRIRR (mnb)
```

In another embodiment, the multimeric assembly further comprises a cargo that interacts with the packaging moiety. Such a "cargo" may be anything of interest that can be linked to or interact with the packaging domain and thus recruited to the multimeric assembly, including but not limited to therapeutics, diagnostics, antigens, adjuvants, imaging agents, dyes, radioisotopes, etc. Alternatively, if the cargo is a protein or polypeptide, the cargo can be expressed as a genetic fusion with the M domain, the L domain, or the O interface in order to directly incorporate the cargo into the multimeric assembly without the use of a distinct packaging domain. In various embodiments, the cargo may be selected from the group consisting of proteins, nucleic acids, lipids, and small organic compounds. In various non-limiting embodiments, the cargo comprises a polypeptide with an amino acid sequence: EQAPEDQGPQREPHNEWTLEL-LEELKREAVRHFPRPWLHGLGQHIYETYGDTWAGV EAIIRILQQLLFIHFRIGCQHSRIGIIQQRRARRNGASRS (SEQ ID NO: 202), which is the Vpr protein from HIV, and known to interact with the p6 domain of HIV Gag as described above. An exemplary cargo comprising the Vpr protein comprises or consists of BlaM-Vpr, the packaging of which is described in the examples that follow:

```
                                     (SEQ ID NO: 203)
(M)SIQHFRVALIPFFAAFCLPVFAHPETLVKVKDAEDQLGARVGYIELDL

NSGKILESFRPEERFPMMSTFKVLLCGAVLSRIDAGQEQLGRRIHYSQNDL

VEYSPVTEKHLTDGMTVRELCSAAITMSDNTAANLLLTTIGGPKELTAFLH

NMGDHVTRLDRWEPELNEAIPNDERDTTMPVAMATTLRKLLTGELLTLASR

QQLIDWMEADKVAGPLLRSALPAGWFIADKSGAGERGSRGIIAALGPDGKP

SRIVVIYTTGSQATMDERNRQIAEIGASLIKHWGSEQAPEDQGPQREPHNE

WTLELLEELKREAVRHFPRPWLHGLGQHIYETYGDTWAGVEAIIRILQQLL

FIHFRIGCQHSRIGIIQQRRARRNGASRS.
```

In various further embodiments, the cargo comprises a polynucleotide with a nucleic acid sequence selected from the following sequences, which are recognition sequences known to bind to the corresponding polypeptide packaging domains described above, the packaging of which is described in the examples that follow.

```
(1g70 RNA sequence)
                                     (SEQ ID NO: 204)
GGUCUGGGCGCACUUCGGUGACGGUACAGGCC (u1a RNA sequence)
                                     (SEQ ID NO: 205)
AAUCCAUUGCACUCCGGAUUU (HIV_NC RNA sequence)
                                     (SEQ ID NO: 206)
GGCGACUGGUGAGUACGCCAAAAAUUUUGACUAGCGGAGGCUAG (1amb RNA sequence)
                                     (SEQ ID NO: 207)
GGCUCGUGUAGCUCAUUAGCUCCGAGCC
```

In various further embodiments, the cargo comprises a nucleic acid comprising one or more of these recognition sequences. Exemplary such mRNAs include the following nucleic acid sequences, each of which has been shown to interact with a multimeric assembly as disclosed in the examples that follow; the underlined portions of these sequence encode the (optional) N-terminal methionines and epitope tags (FLAG or myc, as denoted by construct name). The RNA recognition sequences for cargo packaging at the 5' and 3' end of each sequence are bolded.

```
FLAG-blaM-1g70:
                                     (SEQ ID NO: 208)
GGUCUGGGCGCACUUCGGUGACGGUACAGGCCUAGGAUUACUGCUCGGUGA

CUUAUAAUCAUCCUCCCCGCCACCAUGGACUACAAAGACGACGAUGACAAA

GGUUCUGACCCAGAAACGCUGGUGAAAGUAAAAGAUGCUGAAGAUCAGUUG

GGUGCACGAGUGGGUUACAUCGAACUGGAUCUCAACAGCGGUAAGAUCCUU

GAGAGUUUUCGCCCCGAAGAACGUUUUCCAAUGAUGAGCACUUUUAAAGUU

CUGCUAUGUGGCGCGGUAUUAUCCCGUAUUGACGCCGGGCAAGAGCAACUC

GGUCGCCGCAUACACUAUUCUCAGAAUGACUUGGUUGAGUACUCACCAGUC

ACAGAAAAGCAUCUUACGGAUGGCAUGACAGUAAGAGAAUUAUGCAGUGCU

GCCAUAACCAUGAGUGAUAACACUGCGGCCAACUUACUUCUGACAACGAUC
```

-continued

GGAGGACCGAAGGAGCUAACCGCUUUUUUGCACAACAUGGGGGAUCAUGUA

ACUCGCCUUGAUCGUUGGGAACCGGAGCUGAAUGAAGCCAUACCAAACGAC

GAGCGUGACACCACGAUGCCUGUAGCAAUGGCAACAACGUUGCGCAAACUA

UUAACUGGCGAACUACUUACUCUAGCUUCCCGGCAACAAUUAAUAGACUGG

AUGGAGGCGGAUAAAGUUGCAGGACCACUUCUGCGCUCGGCCCUUCCGGCU

GGCUGGUUUAUUGCUGAUAAAUCUGGAGCCGGUGAGCGUGGGUCUCGCGGU

AUCAUUGCAGCACUGGGGCCAGAUGGUAAGCCCUCCCGUAUCGUAGUUAUC

UACACGACGGGGAGUCAGGCAACUAUGGAUGAACGAAAUAGACAGAUCGCU

GAGAUAGGUGCCUCACUGAUUAAGCAUUGGUAACGAGCACACAUCCUAUUU

GGGCCUAGCAACCAACAGUAUGGGUCUGGGCGCACUUCGGUGACGGUACAG

GCC;

FLAG-blaM-u1a:

(SEQ ID NO: 209)

AAUCCAUUGCACUCCGGAUUUUAGGAUUACUGCUCGGUGACUUAUAAUCAU

CCUCCCCGCCACC<u>AUGGACUACAAAGACGACGAUGACAAAGGUUCU</u>GACCC

AGAAACGCUGGUGAAAGUAAAAGAUGCUGAAGAUCAGUUGGGUGCACGAGU

GGGUUACAUCGAACUGGAUCUCAACAGCGGUAAGAUCCUUGAGAGUUUUCG

CCCCGAAGAACGUUUUCCAAUGAUGAGCACUUUUAAAGUUCUGCUAUGUGG

CGCGGUAUUAUCCCGUAUUGACGCCGGGCAAGAGCAACUCGGUCGCCGCAU

ACACUAUUCUCAGAAUGACUUGGUUGAGUACUCACCAGUCACAGAAAAGCA

UCUUACGGAUGGCAUGACAGUAAGAGAAUUAUGCAGUGCUGCCAUAACCAU

GAGUGAUAACACUGCGGCCAACUUACUUCUGACAACGAUCGGAGGACCGAA

GGAGCUAACCGCUUUUUUGCACAACAUGGGGGAUCAUGUAACUCGCCUUGA

UCGUUGGGAACCGGAGCUGAAUGAAGCCAUACCAAACGACGAGCGUGACAC

CACGAUGCCUGUAGCAAUGGCAACAACGUUGCGCAAACUAUUAACUGGCGA

ACUACUUACUCUAGCUUCCCGGCAACAAUUAAUAGACUGGAUGGAGGCGGA

UAAAGUUGCAGGACCACUUCUGCGCUCGGCCCUUCCGGCUGGCUGGUUUAU

UGCUGAUAAAUCUGGAGCCGGUGAGCGUGGGUCUCGCGGUAUCAUUGCAGC

ACUGGGGCCAGAUGGUAAGCCCUCCCGUAUCGUAGUUAUCUACACGACGGG

GAGUCAGGCAACUAUGGAUGAACGAAAUAGACAGAUCGCUGAGAUAGGUGC

CUCACUGAUUAAGCAUUGGUAACGAGCACACAUCCUAUUUGGGCCUAGCAA

CCAACAGUAUGAAUCCAUUGCACUCCGGAUUU;

FLAG-blaM-HIV_NC:

(SEQ ID NO: 210)

GGCGACUGGUGAGUACGCCAAAAAUUUUGACUAGCGGAGGCUAGUAGGAUU

ACUGCUCGGUGACUUAUAAUCAUCCUCCCCGCCACC<u>AUGGACUACAAAGAC</u>

<u>GACGAUGACAAAGGUUCU</u>GACCCAGAAACGCUGGUGAAAGUAAAAGAUGCU

GAAGAUCAGUUGGGUGCACGAGUGGGUUACAUCGAACUGGAUCUCAACAGC

GGUAAGAUCCUUGAGAGUUUUCGCCCCGAAGAACGUUUUCCAAUGAUGAGC

ACUUUUAAAGUUCUGCUAUGUGGCGCGGUAUUAUCCCGUAUUGACGCCGGG

CAAGAGCAACUCGGUCGCCGCAUACACUAUUCUCAGAAUGACUUGGUUGAG

UACUCACCAGUCACAGAAAAGCAUCUUACGGAUGGCAUGACAGUAAGAGAA

UUAUGCAGUGCUGCCAUAACCAUGAGUGAUAACACUGCGGCCAACUUACUU

-continued

CUGACAACGAUCGGAGGACCGAAGGAGCUAACCGCUUUUUUGCACAACAUG

GGGGAUCAUGUAACUCGCCUUGAUCGUUGGGAACCGGAGCUGAAUGAAGCC

AUACCAAACGACGAGCGUGACACCACGAUGCCUGUAGCAAUGGCAACAACG

UUGCGCAAACUAUUAACUGGCGAACUACUUACUCUAGCUUCCCGGCAACAA

UUAAUAGACUGGAUGGAGGCGGAUAAAGUUGCAGGACCACUUCUGCGCUCG

GCCCUUCCGGCUGGCUGGUUUAUUGCUGAUAAAUCUGGAGCCGGUGAGCGU

GGGUCUCGCGGUAUCAUUGCAGCACUGGGGCCAGAUGGUAAGCCCUCCCGU

AUCGUAGUUAUCUACACGACGGGGAGUCAGGCAACUAUGGAUGAACGAAAU

AGACAGAUCGCUGAGAUAGGUGCCUCACUGAUUAAGCAUUGGUAACGAGCA

CACAUCCUAUUUGGGCCUAGCAACCAACAGUAUGGGCGACUGGUGAGUACG

CCAAAAAUUUUGACUAGCGGAGGCUAG;

FLAG-blaM-1mnb:

(SEQ ID NO: 211)

GGCUCGUGUAGCUCAUUAGCUCCGAGCCUAGGAUUACUGCUCGGUGACUUA

UAAUCAUCCUCCCCGCCACC<u>AUGGACUACAAAGACGACGAUGACAAAGGUU</u>

<u>CU</u>GACCCAGAAACGCUGGUGAAAGUAAAAGAUGCUGAAGAUCAGUUGGGUG

CACGAGUGGGUUACAUCGAACUGGAUCUCAACAGCGGUAAGAUCCUUGAGA

GUUUUCGCCCCGAAGAACGUUUUCCAAUGAUGAGCACUUUUAAAGUUCUGC

UAUGUGGCGCGGUAUUAUCCCGUAUUGACGCCGGGCAAGAGCAACUCGGUC

GCCGCAUACACUAUUCUCAGAAUGACUUGGUUGAGUACUCACCAGUCACAG

AAAAGCAUCUUACGGAUGGCAUGACAGUAAGAGAAUUAUGCAGUGCUGCCA

UAACCAUGAGUGAUAACACUGCGGCCAACUUACUUCUGACAACGAUCGGAG

GACCGAAGGAGCUAACCGCUUUUUUGCACAACAUGGGGGAUCAUGUAACUC

GCCUUGAUCGUUGGGAACCGGAGCUGAAUGAAGCCAUACCAAACGACGAGC

GUGACACCACGAUGCCUGUAGCAAUGGCAACAACGUUGCGCAAACUAUUAA

CUGGCGAACUACUUACUCUAGCUUCCCGGCAACAAUUAAUAGACUGGAUGG

AGGCGGAUAAAGUUGCAGGACCACUUCUGCGCUCGGCCCUUCCGGCUGGCU

GGUUUAUUGCUGAUAAAUCUGGAGCCGGUGAGCGUGGGUCUCGCGGUAUCA

UUGCAGCACUGGGGCCAGAUGGUAAGCCCUCCCGUAUCGUAGUUAUCUACA

CGACGGGGAGUCAGGCAACUAUGGAUGAACGAAAUAGACAGAUCGCUGAGA

UAGGUGCCUCACUGAUUAAGCAUUGGUAACGAGCACACAUCCUAUUUGGGC

CUAGCAACCAACAGUAUGGGCUCGUGUAGCUCAUUAGCUCCGAGCC;

Myc-blaM-1g70:

(SEQ ID NO: 212)

GGUCUGGGCGCACUUCGGUGACGGUACAGGCCUAGGAUUACUGCUCGGUGA

CUUAUAAUCAUCCUCCCCGCCACC<u>AUGGAACAGAAACUGAUUAGCGAAGAA</u>

<u>GAUCUGGGUUCU</u>GACCCAGAAACGCUGGUGAAAGUAAAAGAUGCUGAAGAU

CAGUUGGGUGCACGAGUGGGUUACAUCGAACUGGAUCUCAACAGCGGUAAG

AUCCUUGAGAGUUUUCGCCCCGAAGAACGUUUUCCAAUGAUGAGCACUUUU

AAAGUUCUGCUAUGUGGCGCGGUAUUAUCCCGUAUUGACGCCGGGCAAGAG

CAACUCGGUCGCCGCAUACACUAUUCUCAGAAUGACUUGGUUGAGUACUCA

CCAGUCACAGAAAAGCAUCUUACGGAUGGCAUGACAGUAAGAGAAUUAUGC

AGUGCUGCCAUAACCAUGAGUGAUAACACUGCGGCCAACUUACUUCUGACA
ACGAUCGGAGGACCGAAGGAGCUAACCGCUUUUUUGCACAACAUGGGGAU
CAUGUAACUCGCCUUGAUCGUUGGGAACCGGAGCUGAAUGAAGCCAUACCA
AACGACGAGCGUGACACCACGAUGCCUGUAGCAAUGGCAACAACGUUGCGC
AAACUAUUAACUGGCGAACUACUUACUCUAGCUUCCCGGCAACAAUUAAUA
GACUGGAUGGAGGCGGAUAAAGUUGCAGGACCACUUCUGCGCUCGGCCCUU
CCGGCUGGCUGGUUUAUUGCUGAUAAAUCUGGAGCCGGUGAGCGUGGGUCU
CGCGGUAUCAUUGCAGCACUGGGGCCAGAUGGUAAGCCCUCCCGUAUCGUA
GUUAUCUACACGACGGGGAGUCAGGCAACUAUGGAUGAACGAAAUAGACAG
AUCGCUGAGAUAGGUGCCUCACUGAUUAAGCAUUGGUAACGAGCACACAUC
CUAUUUGGGCCUAGCAACCAACAGUAUGGGUCUGGGCGCACUUCGGUGACG
GUACAGGCC;

Myc-blaM-u1a:
(SEQ ID NO: 213)
AAUCCAUUGCACUCCGGAUUUUAGGAUUACUGCUCGGUGACUUAUAAUCAU
CCUCCCCGCCACC<u>AUGGAACAGAAACUGAUUAGCGAAGAAGAUCUGGGUUC</u>
<u>UG</u>ACCCAGAAACGCUGGUGAAAGUAAAAGAUGCUGAAGAUCAGUUGGGUGC
ACGAGUGGGUUACAUCGAACUGGAUCUCAACAGCGGUAAGAUCCUUGAGAG
UUUUCGCCCCGAAGAACGUUUUCCAAUGAUGAGCACUUUUAAAGUUCUGCU
AUGUGGCGCGGUAUUAUCCCGUAUUGACGCCGGGCAAGAGCAACUCGGUCG
CCGCAUACACUAUUCUCAGAAUGACUUGGUUGAGUACUCACCAGUCACAGA
AAAGCAUCUUACGGAUGGCAUGACAGUAAGAGAAUUAUGCAGUGCUGCCAU
AACCAUGAGUGAUAACACUGCGGCCAACUUACUUCUGACAACGAUCGGAGG
ACCGAAGGAGCUAACCGCUUUUUUGCACAACAUGGGGGAUCAUGUAACUCG
CCUUGAUCGUUGGGAACCGGAGCUGAAUGAAGCCAUACCAAACGACGAGCG
UGACACCACGAUGCCUGUAGCAAUGGCAACAACGUUGCGCAAACUAUUAAC
UGGCGAACUACUUACUCUAGCUUCCCGGCAACAAUUAAUAGACUGGAUGGA
GGCGGAUAAAGUUGCAGGACCACUUCUGCGCUCGGCCCUUCCGGCUGGCUG
GUUUAUUGCUGAUAAAUCUGGAGCCGGUGAGCGUGGGUCUCGCGGUAUCAU
UGCAGCACUGGGGCCAGAUGGUAAGCCCUCCCGUAUCGUAGUUAUCUACAC
GACGGGGAGUCAGGCAACUAUGGAUGAACGAAAUAGACAGAUCGCUGAGAU
AGGUGCCUCACUGAUUAAGCAUUGGUAACGAGCACACAUCCUAUUUGGGCC
UAGCAACCAACAGUAUGAAUCCAUUGCACUCCGGAUUU;

Myc-blaM-HIV_NC:
(SEQ ID NO: 214)
GGCGACUGGUGAGUACGCCAAAAAUUUUGACUAGCGGAGGCUAGUAGGAUU
ACUGCUCGGUGACUUAUAAUCAUCCUCCCCGCCACC<u>AUGGAACAGAAACUG</u>
<u>AUUAGCGAAGAAGAUCUGGGUUCUG</u>ACCCAGAAACGCUGGUGAAAGUAAAA
GAUGCUGAAGAUCAGUUGGGUGCACGAGUGGGUUACAUCGAACUGGAUCUC
AACAGCGGUAAGAUCCUUGAGAGUUUUCGCCCCGAAGAACGUUUUCCAAUG
AUGAGCACUUUUAAAGUUCUGCUAUGUGGCGCGGUAUUAUCCCGUAUUGAC
GCCGGGCAAGAGCAACUCGGUCGCCGCAUACACUAUUCUCAGAAUGACUUG
GUUGAGUACUCACCAGUCACAGAAAAGCAUCUUACGGAUGGCAUGACAGUA AGAGAAUUAUGCAGUGCUGCCAUAACCAUGAGUGAUAACACUGCGGCCAAC
UUACUUCUGACAACGAUCGGAGGACCGAAGGAGCUAACCGCUUUUUUGCAC
AACAUGGGGGAUCAUGUAACUCGCCUUGAUCGUUGGGAACCGGAGCUGAAU
GAAGCCAUACCAAACGACGAGCGUGACACCACGAUGCCUGUAGCAAUGGCA
ACAACGUUGCGCAAACUAUUAACUGGCGAACUACUUACUCUAGCUUCCCGG
CAACAAUUAAUAGACUGGAUGGAGGCGGAUAAAGUUGCAGGACCACUUCUG
CGCUCGGCCCUUCCGGCUGGCUGGUUUAUUGCUGAUAAAUCUGGAGCCGGU
GAGCGUGGGUCUCGCGGUAUCAUUGCAGCACUGGGGCCAGAUGGUAAGCCC
UCCCGUAUCGUAGUUAUCUACACGACGGGGAGUCAGGCAACUAUGGAUGAA
CGAAAUAGACAGAUCGCUGAGAUAGGUGCCUCACUGAUUAAGCAUUGGUAA
CGAGCACACAUCCUAUUUGGGCCUAGCAACCAACAGUAUGGGCGACUGGUG
AGUACGCCAAAAAUUUUGACUAGCGGAGGCUAG;

Myc-blaM-1mnb:
(SEQ ID NO: 215)
GGCUCGUGUAGCUCAUUAGCUCCGAGCCUAGGAUUACUGCUCGGUGACUUA
UAAUCAUCCUCCCCGCCACC<u>AUGGAACAGAAACUGAUUAGCGAAGAAGAUC</u>
<u>UGGGUUCUG</u>ACCCAGAAACGCUGGUGAAAGUAAAAGAUGCUGAAGAUCAGU
UGGGUGCACGAGUGGGUUACAUCGAACUGGAUCUCAACAGCGGUAAGAUCC
UUGAGAGUUUUCGCCCCGAAGAACGUUUUCCAAUGAUGAGCACUUUUAAAG
UUCUGCUAUGUGGCGCGGUAUUAUCCCGUAUUGACGCCGGGCAAGAGCAAC
UCGGUCGCCGCAUACACUAUUCUCAGAAUGACUUGGUUGAGUACUCACCAG
UCACAGAAAAGCAUCUUACGGAUGGCAUGACAGUAAGAGAAUUAUGCAGUG
CUGCCAUAACCAUGAGUGAUAACACUGCGGCCAACUUACUUCUGACAACGA
UCGGAGGACCGAAGGAGCUAACCGCUUUUUUGCACAACAUGGGGGAUCAUG
UAACUCGCCUUGAUCGUUGGGAACCGGAGCUGAAUGAAGCCAUACCAAACG
ACGAGCGUGACACCACGAUGCCUGUAGCAAUGGCAACAACGUUGCGCAAAC
UAUUAACUGGCGAACUACUUACUCUAGCUUCCCGGCAACAAUUAAUAGACU
GGAUGGAGGCGGAUAAAGUUGCAGGACCACUUCUGCGCUCGGCCCUUCCGG
CUGGCUGGUUUAUUGCUGAUAAAUCUGGAGCCGGUGAGCGUGGGUCUCGCG
GUAUCAUUGCAGCACUGGGGCCAGAUGGUAAGCCCUCCCGUAUCGUAGUUA
UCUACACGACGGGGAGUCAGGCAACUAUGGAUGAACGAAAUAGACAGAUCG
CUGAGAUAGGUGCCUCACUGAUUAAGCAUUGGUAACGAGCACACAUCCUAU
UUGGGCCUAGCAACCAACAGUAUGGGCUCGUGUAGCUCAUUAGCUCCGAGC
C;

Myc-GFP-1g70:
(SEQ ID NO: 216)
GGUCUGGGCGCACUUCGGUGACGGUACAGGCCUAGGAUUACUGCUCGGUGA
CUUAUAAUCAUCCUCCCCGCCACC<u>AUGGAACAGAAACUGAUUAGCGAAGAA</u>
<u>GAUCUGGUGAGC</u>AAGGGCGAGGAGCUGUUCACCGGGGUGGUGCCCAUCCUG
GUCGAGCUGGACGGCGACGUAAACGGCCACAAGUUCAGCGUGUCCGGCGAG
GGCGAGGGCGAUGCCACCUACGGCAAGCUGACCCUGAAGUUCAUCUGCACC
ACCGGCAAGCUGCCCGUGCCCUGGCCCACCCUCGUGACCACCCUGACCUAC

```
GGCGUGCAGUGCUUCAGCCGCUACCCCGACCACAUGAAGCAGCACGACUUC
UUCAAGUCCGCCAUGCCCGAAGGCUACGUCCAGGAGCGCACCAUCUUCUUC
AAGGACGACGGCAACUACAAGACCCGCGCCGAGGUGAAGUUCGAGGGCGAC
ACCCUGGUGAACCGCAUCGAGCUGAAGGGCAUCGACUUCAAGGAGGACGGC
AACAUCCUGGGGCACAAGCUGGAGUACAACUACAACAGCCACAACGUCUAU
AUCAUGGCCGACAAGCAGAAGAACGGCAUCAAGGUGAACUUCAAGAUCCGC
CACAACAUCGAGGACGGCAGCGUGCAGCUCGCCGACCACUACCAGCAGAAC
ACCCCCAUCGGCGACGGCCCCGUGCUGCUGCCCGACAACCACUACCUGAGC
ACCCAGUCCGCCCUGAGCAAAGACCCCAACGAGAAGCGCGAUCACAUGGUC
CUGCUGGAGUUCGUGACCGCCGCCGGGAUCACUCUCGGCAUGGACGAGCUG
UACAAGUAACGAGCACACAUCCUAUUUGGCCUAGCAACCAACAGUAUGGG
UCUGGGCGCACUUCGGUGACGGUACAGGCC;

Myc-GFP-u1a
                              (SEQ ID NO: 217)
AAUCCAUUGCACUCCGGAUUUUAGGAUUACUGCUCGGUGACUUAUAAUCAU
CCUCCCCGCCACCAUGGAACAGAAACUGAUUAGCGAAGAAGAUCUGGUGAG
CAAGGGCGAGGAGCUGUUCACCGGGGUGGUGCCCAUCCUGGUCGAGCUGGA
CGGCGACGUAAACGGCCACAAGUUCAGCGUGUCCGGCGAGGGCGAGGGCGA
UGCCACCUACGGCAAGCUGACCCUGAAGUUCAUCUGCACCACCGGCAAGCU
GCCCGUGCCCUGGCCCACCCUCGUGACCACCCUGACCUACGGCGUGCAGUG
CUUCAGCCGCUACCCCGACCACAUGAAGCAGCACGACUUCUUCAAGUCCGC
CAUGCCCGAAGGCUACGUCCAGGAGCGCACCAUCUUCUUCAAGGACGACGG
CAACUACAAGACCCGCGCCGAGGUGAAGUUCGAGGGCGACACCCUGGUGAA
CCGCAUCGAGCUGAAGGGCAUCGACUUCAAGGAGGACGGCAACAUCCUGGG
GCACAAGCUGGAGUACAACUACAACAGCCACAACGUCUAUAUCAUGGCCGA
CAAGCAGAAGAACGGCAUCAAGGUGAACUUCAAGAUCCGCCACAACAUCGA
GGACGGCAGCGUGCAGCUCGCCGACCACUACCAGCAGAACACCCCCAUCGG
CGACGGCCCCGUGCUGCUGCCCGACAACCACUACCUGAGCACCCAGUCCGC
CCUGAGCAAAGACCCCAACGAGAAGCGCGAUCACAUGGUCCUGCUGGAGUU
CGUGACCGCCGCCGGGAUCACUCUCGGCAUGGACGAGCUGUACAAGUAAGC
UCCACACAUCCUAUUUGGGCCUAGCAACCAACAGUAUGAAUCCAUUGCACU
CCGGAUUU;

Myc-GFP-HIV_NC;
                              (SEQ ID NO: 218)
GGCGACUGGUGAGUACGCCAAAAAUUUUGACUAGCGGAGGCUAGUAGGAUU
ACUGCUCGGUGACUUAUAAUCAUCCUCCCCGCCACCAUGGAACAGAAACUG
AUUAGCGAAGAAGAUCUGGUGAGCAAGGGCGAGGAGCUGUUCACCGGGGUG
GUGCCCAUCCUGGUCGAGCUGGACGGCGACGUAAACGGCCACAAGUUCAGC
GUGUCCGGCGAGGGCGAGGGCGAUGCCACCUACGGCAAGCUGACCCUGAAG
UUCAUCUGCACCACCGGCAAGCUGCCCGUGCCCUGGCCCACCCUCGUGACC
ACCCUGACCUACGGCGUGCAGUGCUUCAGCCGCUACCCCGACCACAUGAAG
CAGCACGACUUCUUCAAGUCCGCCAUGCCCGAAGGCUACGUCCAGGAGCGC
ACCAUCUUCUUCAAGGACGACGGCAACUACAAGACCCGCGCCGAGGUGAAG
UUCGAGGGCGACACCCUGGUGAACCGCAUCGAGCUGAAGGGCAUCGACUUC
AAGGAGGACGGCAACAUCCUGGGGCACAAGCUGGAGUACAACUACAACAGC
CACAACGUCUAUAUCAUGGCCGACAAGCAGAAGAACGGCAUCAAGGUGAAC
UUCAAGAUCCGCCACAACAUCGAGGACGGCAGCGUGCAGCUCGCCGACCAC
UACCAGCAGAACACCCCCAUCGGCGACGGCCCCGUGCUGCUGCCCGACAAC
CACUACCUGAGCACCCAGUCCGCCCUGAGCAAAGACCCCAACGAGAAGCGC
GAUCACAUGGUCCUGCUGGAGUUCGUGACCGCCGCCGGGAUCACUCUCGGC
AUGGACGAGCUGUACAAGUAACAGCCACACAUCCUAUUUGGGCCUAGCAAC
CAACAGUAUGGGCGACUGGUGAGUACGCCAAAAAUUUUGACUAGCGGAGGC
UAG;
and Myc-GFP-1mnb:
                              (SEQ ID NO: 219)
GGCUCGUGUAGCUCAUUAGCUCCGAGCCUAGGAUUACUGCUCGGUGACUUA
UAAUCAUCCUCCCCGCCACCAUGGAACAGAAACUGAUUAGCGAAGAAGAUC
UGGUGAGCAAGGGCGAGGAGCUGUUCACCGGGGUGGUGCCCAUCCUGGUCG
AGCUGGACGGCGACGUAAACGGCCACAAGUUCAGCGUGUCCGGCGAGGGCG
AGGGCGAUGCCACCUACGGCAAGCUGACCCUGAAGUUCAUCUGCACCACCG
GCAAGCUGCCCGUGCCCUGGCCCACCCUCGUGACCACCCUGACCUACGGCG
UGCAGUGCUUCAGCCGCUACCCCGACCACAUGAAGCAGCACGACUUCUUCA
AGUCCGCCAUGCCCGAAGGCUACGUCCAGGAGCGCACCAUCUUCUUCAAGG
ACGACGGCAACUACAAGACCCGCGCCGAGGUGAAGUUCGAGGGCGACACCC
UGGUGAACCGCAUCGAGCUGAAGGGCAUCGACUUCAAGGAGGACGGCAACA
UCCUGGGGCACAAGCUGGAGUACAACUACAACAGCCACAACGUCUAUAUCA
UGGCCGACAAGCAGAAGAACGGCAUCAAGGUGAACUUCAAGAUCCGCCACA
ACAUCGAGGACGGCAGCGUGCAGCUCGCCGACCACUACCAGCAGAACACCC
CCAUCGGCGACGGCCCCGUGCUGCUGCCCGACAACCACUACCUGAGCACCC
AGUCCGCCCUGAGCAAAGACCCCAACGAGAAGCGCGAUCACAUGGUCCUGC
UGGAGUUCGUGACCGCCGCCGGGAUCACUCUCGGCAUGGACGAGCUGUACA
AGUAAGUCGCACACAUCCUAUUUGGGCCUAGCAACCAACAGUAUGGGCUCG
UGUAGCUCAUUAGCUCCGAGCC.
```

The following represent exemplary proteins that would result from translation of the exemplified packaged mRNAs disclosed above (which represent 3 proteins encoded by 4 distinct mRNAs, each incorporating a distinct recognition sequence):

FLAG-BlaM
                              (SEQ ID NO: 220)
(M)DYKDDDDK)GSDPETLVKVKDAEDQLGARVGYIELDLNSGKILESFRP
EERFPMMSTFKVLLCGAVLSRIDAGQEQLGRRIHYSQNDLVEYSPVTEKHL
TDGMTVRELCSAAITMSDNTAANLLLTTIGGPKELTAFLHNMGDHVTRLDR
WEPELNEAIPNDERDTTMPVAMATTLRKLLTGELLTLASRQQLIDWMEADK
VAGPLLRSALPAGWFIADKSGAGERGSRGIIAALGPDGKPSRIVVIYTTGS

```
QATMDERNRQIAEIGASLIKHW

Myc-BlaM
                                        (SEQ ID NO: 221)
(M)E(QKLISEEDL)GSDPETLVKVKDAEDQLGARVGYIELDLNSGKILES

FRPEERFPMMSTFKVLLCGAVLSRIDAGQEQLGRRIHYSQNDLVEYSPVTE

KHLTDGMTVRELCSAAITMSDNTAANLLLTTIGGPKELTAFLHNMGDHVTR

LDRWEPELNEAIPNDERDTTMPVAMATTLRKLLTGELLTLASRQQLIDWME

ADKVAGPLLRSALPAGWFIADKSGAGERGSRGIIAALGPDGKPSRIVVIYT

TGSQATMDERNRQIAEIGASLIKHW

Myc-GFP
                                        (SEQ ID NO: 222)
(M)E(QKLISEEDL)VSKGEELFTGVVPILVELDGDVNGHKFSVSGEGEGD

ATYGKLTLKFICTTGKLPVPWPTLVTTLTYGVQCFSRYPDHMKQHDFFKSA

MPEGYVQERTIFFKDDGNYKTRAEVKFEGDTLVNRIELKGIDFKEDGNILG

HKLEYNYNSHNVYIMADKQKNGIKVNFKIRHNIEDGSVQLADHYQQNTPIG

DGPVLLPDNHYLSTQSALSKDPNEKRDHMVLLEFVTAAGITLGMDELYK
```

As will be understood by those of skill in the art, the M and L domains, and O interfaces (and the packaging moiety in appropriate embodiments) may be contiguous in each protein, or may be separated by linker peptides as deemed appropriate. Any suitable linker may be used as deemed appropriate for an intended multimeric structure. In various non-limiting embodiments, the linkers may comprise or consist of one or more of the polypeptide sequences GSGS (SEQ ID NO: 223); GSDGSGRSGS(SEQ ID NO: 224); GSKSGSGSDSGS (SEQ ID NO: 225); and/or GSGSGDG-GRGSRGGDGSGGSSG (SEQ ID NO: 226).

As will further be understood by those of skill in the art, any suitable combination of M and L domains and O interfaces (and packaging moiety and linkers in appropriate embodiments) may be used to produce the protein that assembles to form an intended multimeric assembly of the invention. In various non-limiting embodiments the protein may comprise or consist of one of the following proteins, several of which are described in more detail in the examples that follow:

```
(Myr-I3-01-myc-p6)
                                        SEQ ID: 227
(M)GARASGSKSGSGSDSGSKMEELFKKHKIVAVLRANSVEEAKKKALAVFLGGVH

LIEITFTVPDADTVIKELSFLKEMGAIIGAGTVTSVEQCRKAVESGAEFIVSPHLDEEIS

QFCKEKGVFYMPGVMTPTELVKAMKLGHTILKLFPGEVVGPQFVKAMKGPFPNVKF

VPTGGVNLDNVCEWFKAGVLAVGVGSALVKGTPVEVAEKAKAFVEKIRGCTE(QKL

ISEEDL)QSRPEPTAPPEESFRSGVETTTPPQKQEPIDKELYPLTSLRSLFGNDPSSQ
Standard font: O domain
Bold and underlined M domain
Underlined only L domain
Bold font only linker (Late2-4GS-I3-01-10GS-PH-flag)
                                        SEQ ID: 228
(M)VRRVILPTAPPEYMEAIYPVRGSGSKMEELFKKHKIVAVLRANSVEEAKKKALA

VFLGGVHLIEITFTVPDADTVIKELSFLKEMGAIIGAGTVTSVEQCRKAVESGAEFIVS

PHLDEEISQFCKEKGVFYMPGVMTPTELVKAMKLGHTILKLFPGEVVGPQFVKAMK

GPFPNVKFVPTGGVNLDNVCEWFKAGVLAVGVGSALVKGTPVEVAEKAKAFVEKI

RGCTEGSDGSGRSGSHGLQDDPDLQALLKGSQLLKVKSSSWRRERFYKLQEDC

KTIWQESRKVMRSPESQLFSIEDIQEVRMGHRTEGLEKFARDIPEDRCFSIVFKD

QRNTLDLIAPSPADAQHWVQGLRKIIHHSGSMDCQRQK(DYKDDDDK)GS

Myr-I3-01-posT1-myc-p6
                                        (SEQ ID NO: 229)
(M)GARASGSKSGSGSDSGSKMEELFKKHKIVAVLRANSVEEAKKKALAVFLGGVHLIEITF

TVPDADTVIKELSFLKEMGAIIGAGTVTSVEQCRKAVESGAEFIVSPHLDEEISQFCKEKGVFY

MPGVMTPTELVKAMKLGHTILKLFPGEVVGPQFVKAMKGPFPNVKFVPTGGVNLKNVCKW

FKAGVLAVGVGKALVKGTPVEVAKKAKAFVKKIRGCTE(QKLISEEDL)QSRPEPTAPPEESF

RSGVETTTPPQKQEPIDKELYPLTSLRSLFGNDPSSQ

Myr1-12GS-I3-01(M3I)-myc-Late1 (EPN-01)
                                        (SEQ ID NO: 230)
(M)GARASGSKSGSGSDSGSKIEELFKKHKIVAVLRANSVEEAKKKALAVFLGGVHLIEITFT

VPDADTVIKELSFLKEMGAIIGAGTVTSVEQCRKAVESGAEFIVSPHLDEEISQFCKEKGVFY

MPGVMTPTELVKAMKLGHTILKLFPGEVVGPQFVKAMKGPFPNVKFVPTGGVNLDNVCEW
```

```
FKAGVLAVGVGSALVKGTPVEVAEKAKAFVEKIRGCTE(QKLISEEDL)QSRPEPTAPPEESFR

SGVETTTPPQKQEPIDKELYPLTSLRSLFGNDPSSQ

Myr2-12GS-I3-01(M3I)-myc-Late1 (EPN-03)
                                                   (SEQ ID NO: 231)
(M)GAQFSGSKSGSGSDSGSKIEELFKKHKIVAVLRANSVEEAKKKALAVFLGGVHLIEITFT

VPDADTVIKELSFLKEMGAIIGAGTVTSVEQCRKAVESGAEFIVSPHLDEEISQFCKEKGVFY

MPGVMTPTELVKAMKLGHTILKLFPGEVVGPQFVKAMKGPFPNVKFVPTGGVNLDNVCEW

FKAGVLAVGVGSALVKGTPVEVAEKAKAFVEKIRGCTE(QKLISEEDL)QSRPEPTAPPEESFR

SGVETTTPPQKQEPIDKELYPLTSLRSLFGNDPSSQ

Palm1-12GS-I3-01(M3I)-myc-Late1 (EPN-07)
                                                   (SEQ ID NO: 232)
(M)GCIKSKRKDNLNGSKSGSGSDSGSKIEELFKKHKIVAVLRANSVEEAKKKALAVFLGGV

HLIEITFTVPDADTVIKELSFLKEMGAIIGAGTVTSVEQCRKAVESGAEFIVSPHLDEEISQFCK

EKGVFYMPGVMTPTELVKAMKLGHTILKLFPGEVVGPQFVKAMKGPFPNVKFVPTGGVNLD

NVCEWFKAGVLAVGVGSALVKGTPVEVAEKAKAFVEKIRGCTE(QKLISEEDL)QSRPEPTAP

PEESFRSGVETTTPPQKQEPIDKELYPLTSLRSLFGNDPSSQ

Palm2-12GS-I3-01(M3I)-myc-Late1 (EPN-08)
                                                   (SEQ ID NO: 233)
(M)GCTLSAEERAALGSKSGSGSDSGSKIEELFKKHKIVAVLRANSVEEAKKKALAVFLGGV

HLIEITFTVPDADTVIKELSFLKEMGAIIGAGTVTSVEQCRKAVESGAEFIVSPHLDEEISQFCK

EKGVFYMPGVMTPTELVKAMKLGHTILKLFPGEVVGPQFVKAMKGPFPNVKFVPTGGVNLD

NVCEWFKAGVLAVGVGSALVKGTPVEVAEKAKAFVEKIRGCTE(QKLISEEDL)QSRPEPTAP

PEESFRSGVETTTPPQKQEPIDKELYPLTSLRSLFGNDPSSQ

Palm3-12GS-I3-01(M3I)-myc-Late1 (EPN-09)
                                                   (SEQ ID NO: 234)
(M)LCCMRRTKQVEKGSKSGSGSDSGSKIEELFKKHKIVAVLRANSVEEAKKKALAVFLGG

VHLIEITFTVPDADTVIKELSFLKEMGAIIGAGTVTSVEQCRKAVESGAEFIVSPHLDEEISQFC

KEKGVFYMPGVMTPTELVKAMKLGHTILKLFPGEVVGPQFVKAMKGPFPNVKFVPTGGVNL

DNVCEWFKAGVLAVGVGSALVKGTPVEVAEKAKAFVEKIRGCTE(QKLISEEDL)QSRPEPTA

PPEESFRSGVETTTPPQKQEPIDKELYPLTSLRSLFGNDPSSQ

Palm1-Late1-I3-01(M3I)-myc (EPN-11)
                                                   (SEQ ID NO: 235)
(M)GCIKSKRKDNLNLQSRPEPTAPPEESFRSGVETTTPPQKQEPIDKELYPLTSLRSLFGNDPS

SQKIEELFKKHKIVAVLRANSVEEAKKKALAVFLGGVHLIEITFTVPDADTVIKELSFLKEMG

AIIGAGTVTSVEQCRKAVESGAEFIVSPHLDEEISQFCKEKGVFYMPGVMTPTELVKAMKLG

HTILKLFPGEVVGPQFVKAMKGPFPNVKFVPTGGVNLDNVCEWFKAGVLAVGVGSALVKG

TPVEVAEKAKAFVEKIRGCTE(QKLISEEDL)

PH-4GS-I3-01(M3I)-myc-Late1 (EPN-18)
                                                   (SEQ ID NO: 236)
(M)HGLQDDPDLQALLKGSQLLKVKSSSWRRERFYKLQEDCKTIWQESRKVMRSPESQ

LFSIEDIQEVRMGHRTEGLEKFARDIPEDRCFSIVFKDQRNTLDLIAPSPADAQHWVQGL

RKIIHHSGSMDQRQKGSGSKIEELFKKHKIVAVLRANSVEEAKKKALAVFLGGVHLIEITFT

VPDADTVIKELSFLKEMGAIIGAGTVTSVEQCRKAVESGAEFIVSPHLDEEISQFCKEKGVFY

MPGVMTPTELVKAMKLGHTILKLFPGEVVGPQFVKAMKGPFPNVKFVPTGGVNLDNVCEW

FKAGVLAVGVGSALVKGTPVEVAEKAKAFVEKIRGCTE(QKLISEEDL)QSRPEPTAPPEESFR

SGVETTTPPQKQEPIDKELYPLTSLRSLFGNDPSSQ

Late2-4GS-I3-01(M3I)-myc-PH (EPN-20)
```

-continued (SEQ ID NO: 237)
(M)RRVILPTAPPEYMEAIYPVRGSGSKIEELFKKHKIVAVLRANSVEEAKKKALAVFLGGVH
LIEITFTVPDADTVIKELSFLKEMGAIIGAGTVTSVEQCRKAVESGAEFIVSPHLDEEISQFCKE
KGVFYMPGVMTPTELVKAMKLGHTILKLFPGEVVGPQFVKAMKGPFPNVKFVPTGGVNLD
NVCEWFKAGVLAVGVGSALVKGTPVEVAEKAKAFVEKIRGCTE(QKLISEEDL)HGLQDDPD
LQALLKGSQLLKVKSSSWRRERFYKLQEDCKTIWQESRKVMRSPESQLFSIEDIQEVRM
GHRTEGLEKFARDIPEDRCFSIVFKDQRNTLDLIAPSPADAQHWVQGLRKIIHHSGSMD
QRQK

Late1-PH-4GS-I3-01(M3I)-myc (EPN-23)
(SEQ ID NO: 238)
(M)LQSRPEPTAPPEESFRSGVETTTPPQKQEPIDKELYPLTSLRSLFGNDPSSQHGLQDDPDLQ
ALLKGSQLLKVKSSSWRRERFYKLQEDCKTIWQESRKVMRSPESQLFSIEDIQEVRMGH
RTEGLEKFARDIPEDRCFSIVFKDQRNTLDLIAPSPADAQHWVQGLRKIIHHSGSMDQR
QKGSGSKIEELFKKHKIVAVLRANSVEEAKKKALAVFLGGVHLIEITFTVPDADTVIKELSFL
KEMGAIIGAGTVTSVEQCRKAVESGAEFIVSPHLDEEISQFCKEKGVFYMPGVMTPTELVKA
MKLGHTILKLFPGEVVGPQFVKAMKGPFPNVKFVPTGGVNLDNVCEWFKAGVLAVGVGSA
LVKGTPVEVAEKAKAFVEKIRGCTE(QKLISEEDL)

PH-Late1-I3-01(M3I)-myc (EPN-24)
(SEQ ID NO: 239)
(M)HGLQDDPDLQALLKGSQLLKVKSSSWRRERFYKLQEDCKTIWQESRKVMRSPESQ
LFSIEDIQEVRMGHRTEGLEKFARDIPEDRCFSIVFKDQRNTLDLIAPSPADAQHWVQGL
RKIIHHSGSMDQRQKLQSRPEPTAPPEESFRSGVETTTPPQKQEPIDKELYPLTSLRSLFGNDP
SSQKIEELFKKHKIVAVLRANSVEEAKKKALAVFLGGVHLIEITFTVPDADTVIKELSFLKEMG
AIIGAGTVTSVEQCRKAVESGAEFIVSPHLDEEISQFCKEKGVFYMPGVMTPTELVKAMKLG
HTILKLFPGEVVGPQFVKAMKGPFPNVKFVPTGGVNLDNVCEWFKAGVLAVGVGSALVKG
TPVEVAEKAKAFVEKIRGCTE(QKLISEEDL)

I3-01(M3I)-myc-Late1-PH (EPN-25)
(SEQ ID NO: 240)
(M)KIEELFKKHKIVAVLRANSVEEAKKKALAVFLGGVHLIEITFTVPDADTVIKELSFLKEMG
AIIGAGTVTSVEQCRKAVESGAEFIVSPHLDEEISQFCKEKGVFYMPGVMTPTELVKAMKLG
HTILKLFPGEVVGPQFVKAMKGPFPNVKFVPTGGVNLDNVCEWFKAGVLAVGVGSALVKG
TPVEVAEKAKAFVEKIRGCTE(QKLISEEDL)QSRPEPTAPPEESFRSGVETTTPPQKQEPIDKEL
YPLTSLRSLFGNDPSSQHGLQDDPDLQALLKGSQLLKVKSSSWRRERFYKLQEDCKTIW
QESRKVMRSPESQLFSIEDIQEVRMGHRTEGLEKFARDIPEDRCFSIVFKDQRNTLDLIA
PSPADAQHWVQGLRKIIHHSGSMDQRQK

Myr1-12GS-I3-01(M3I)-myc-Late2 (EPN-36)
(SEQ ID NO: 241)
(M)GARASGSKSGSGSDSGSKIEELFKKHKIVAVLRANSVEEAKKKALAVFLGGVHLIEITFT
VPDADTVIKELSFLKEMGAIIGAGTVTSVEQCRKAVESGAEFIVSPHLDEEISQFCKEKGVFY
MPGVMTPTELVKAMKLGHTILKLFPGEVVGPQFVKAMKGPFPNVKFVPTGGVNLDNVCEW
FKAGVLAVGVGSALVKGTPVEVAEKAKAFVEKIRGCTE(QKLISEEDL)RRVILPTAPPEYME
AIYPVR Myr1-12GS-I3-01(M3I)-myc-Late3 (EPN-37)
(SEQ ID NO: 242)
(M)GARASGSKSGSGSDSGSKIEELFKKHKIVAVLRANSVEEAKKKALAVFLGGVHLIEITFT
VPDADTVIKELSFLKEMGAIIGAGTVTSVEQCRKAVESGAEFIVSPHLDEEISQFCKEKGVFY

```
MPGVMTPTELVKAMKLGHTILKLFPGEVVGPQFVKAMKGPFPNVKFVPTGGVNLDNVCEW

FKAGVLAVGVGSALVKGTPVEVAEKAKAFVEKIRGCTE(QKLISEEDL)PIQQKSQHNKSVVQ

ETPQTQNLYPDLSEIKKEYNVKEKDQVEDLNLDSLWE

Myr1-12GS-I3-01(M3I)-myc-Late4 (EPN-38)
                                                     (SEQ ID NO: 243)
 (M)GARASGSKSGSGSDSGSKIEELFKKHKIVAVLRANSVEEAKKKALAVFLGGVHLIEITFT

VPDADTVIKELSFLKEMGAIIGAGTVTSVEQCRKAVESGAEFIVSPHLDEEISQFCKEKGVFY

MPGVMTPTELVKAMKLGHTILKLFPGEVVGPQFVKAMKGPFPNVKFVPTGGVNLDNVCEW

FKAGVLAVGVGSALVKGTPVEVAEKAKAFVEKIRGCTE(QKLISEEDL)NPRQSIKAFPIVINS

DGGEK

Myr1-12GS-I3-01(M3I)-myc-22GS-Late1 (EPN-39)
                                                     (SEQ ID NO: 244)
 (M)GARASGSKSGSGSDSGSKIEELFKKHKIVAVLRANSVEEAKKKALAVFLGGVHLIEITFT

VPDADTVIKELSFLKEMGAIIGAGTVTSVEQCRKAVESGAEFIVSPHLDEEISQFCKEKGVFY

MPGVMTPTELVKAMKLGHTILKLFPGEVVGPQFVKAMKGPFPNVKFVPTGGVNLDNVCEW

FKAGVLAVGVGSALVKGTPVEVAEKAKAFVEKIRGCTE(QKLISEEDL)GSGSGDGGRGSRG

GDGSGGSSGLQSRPEPTAPPEESFRSGVETTTPPQKQEPIDKELYPLTSLRSLFGNDPSSQ

Myr1-12GS-I3-01(M3I)-myc-22GS-Late3 (EPN-41)
                                                     (SEQ ID NO: 245)
 (M)GARASGSKSGSGSDSGSKIEELFKKHKIVAVLRANSVEEAKKKALAVFLGGVHLIEITFT

VPDADTVIKELSFLKEMGAIIGAGTVTSVEQCRKAVESGAEFIVSPHLDEEISQFCKEKGVFY

MPGVMTPTELVKAMKLGHTILKLFPGEVVGPQFVKAMKGPFPNVKFVPTGGVNLDNVCEW

FKAGVLAVGVGSALVKGTPVEVAEKAKAFVEKIRGCTE(QKLISEEDL)GSGSGDGGRGSRG

GDGSGGSSGPIQQKSQHNKSVVQETPQTQNLYPDLSEIKKEYNVKEKDQVEDLNLDSLWE

Myr1-12GS-I3-01(M3I)-myc-22GS-Late4 (EPN-42)
                                                     (SEQ ID NO: 246)
 (M)GARASGSKSGSGSDSGSKIEELFKKHKIVAVLRANSVEEAKKKALAVFLGGVHLIEITFT

VPDADTVIKELSFLKEMGAIIGAGTVTSVEQCRKAVESGAEFIVSPHLDEEISQFCKEKGVFY

MPGVMTPTELVKAMKLGHTILKLFPGEVVGPQFVKAMKGPFPNVKFVPTGGVNLDNVCEW

FKAGVLAVGVGSALVKGTPVEVAEKAKAFVEKIRGCTE(QKLISEEDL)GSGSGDGGRGSRG

GDGSGGSSGNPRQSIKAFPIVINSDGGEK

Myr1-12GS-I3-01(M3I)-myc-22GS-Late5 (EPN-43)
                                                     (SEQ ID NO: 247)
 (M)GARASGSKSGSGSDSGSKIEELFKKHKIVAVLRANSVEEAKKKALAVFLGGVHLIEITFT

VPDADTVIKELSFLKEMGAIIGAGTVTSVEQCRKAVESGAEFIVSPHLDEEISQFCKEKGVFY

MPGVMTPTELVKAMKLGHTILKLFPGEVVGPQFVKAMKGPFPNVKFVPTGGVNLDNVCEW

FKAGVLAVGVGSALVKGTPVEVAEKAKAFVEKIRGCTE(QKLISEEDL)GSGSGDGGRGSRG

GDGSGGSSGPTAPPEYGGS

Myr1-12GS-I3-01(M3I)-myc-22GS-Late6 (EPN-44)
                                                     (SEQ ID NO: 248)
 (M)GARASGSKSGSGSDSGSKIEELFKKHKIVAVLRANSVEEAKKKALAVFLGGVHLIEITFT

VPDADTVIKELSFLKEMGAIIGAGTVTSVEQCRKAVESGAEFIVSPHLDEEISQFCKEKGVFY

MPGVMTPTELVKAMKLGHTILKLFPGEVVGPQFVKAMKGPFPNVKFVPTGGVNLDNVCEW

FKAGVLAVGVGSALVKGTPVEVAEKAKAFVEKIRGCTE(QKLISEEDL)GSGSGDGGRGSRG

GDGSGGSSGPTAPGGS

Myr1-12GS-I3-01(M3I)-myc-22GS-Late8 (EPN-46)
                                                     (SEQ ID NO: 249)
 (M)GARASGSKSGSGSDSGSKIEELFKKHKIVAVLRANSVEEAKKKALAVFLGGVHLIEITFT
```

```
VPDADTVIKELSFLKEMGAIIGAGTVTSVEQCRKAVESGAEFIVSPHLDEEISQFCKEKGVFY

MPGVMTPTELVKAMKLGHTILKLFPGEVVGPQFVKAMKGPFPNVKFVPTGGVNLDNVCEW

FKAGVLAVGVGSALVKGTPVEVAEKAKAFVEKIRGCTE(QKLISEEDL)GSGSGDGGRGSRG

GDGSGGSSGYPLTSLGGS

Myr1-12GS-I3-01(M3I)-myc-22GS-Late9 (EPN-47)
                                              (SEQ ID NO: 250)
(M)GARASGSKSGSGSDSGSKIEELFKKHKIVAVLRANSVEEAKKKALAVFLGGVHLIEITFT

VPDADTVIKELSFLKEMGAIIGAGTVTSVEQCRKAVESGAEFIVSPHLDEEISQFCKEKGVFY

MPGVMTPTELVKAMKLGHTILKLFPGEVVGPQFVKAMKGPFPNVKFVPTGGVNLDNVCEW

FKAGVLAVGVGSALVKGTPVEVAEKAKAFVEKIRGCTE(QKLISEEDL)GSGSGDGGRGSRG

GDGSGGSSGYPDLGGS

Myr1-12GS-I3-01(M3I)-myc-22GS-Late10 (EPN-48)
                                              (SEQ ID NO: 251)
(M)GARASGSKSGSGSDSGSKIEELFKKHKIVAVLRANSVEEAKKKALAVFLGGVHLIEITFT

VPDADTVIKELSFLKEMGAIIGAGTVTSVEQCRKAVESGAEFIVSPHLDEEISQFCKEKGVFY

MPGVMTPTELVKAMKLGHTILKLFPGEVVGPQFVKAMKGPFPNVKFVPTGGVNLDNVCEW

FKAGVLAVGVGSALVKGTPVEVAEKAKAFVEKIRGCTE(QKLISEEDL)GSGSGDGGRGSRG

GDGSGGSSGFPIVGGS

Late1-O3-33-myc-PH (EPN-51)
                                              (SEQ ID NO: 252)
(M)LQSRPEPTAPPEESFRSGVETTTPPQKQEPIDKELYPLTSLRSLFGNDPSSQSQAIGILELTSI

AAGMELGDAMLKSANVDLLVSKTISPGKFLLMLGGDIGAIQQAIETGTSQAGELLVDSLVLA

NIHPSVLPAISGLNSVDKRQAVGIVETWSVAACISAADRAVKGSNVTLVRVHMAFGIGGKCY

MVVAGDVSDVALAVTVASSSAGAYGLLVYASLIPRPHEAMWRQMVEG(QKLISEEDL)HGL

QDDPDLQALLKGSQLLKVKSSSWRRERFYKLQEDCKTIWQESRKVMRSPESQLFSIEDI

QEVRMGHRTEGLEKFARDIPEDRCFSIVFKDQRNTLDLIAPSPADAQHWVQGLRKIIHH

SGSMDQRQK

(truncated variant of Myr-I3-01-myc-p6 lacking N-terminal M domain
and linker)
                                              SEQ ID 317
MEELFKKHKIVAVLRANSVEEAKKKALAVFLGGVHLIEITFTVPDADTVIKELSFLKE

MGAIIGAGTVTSVEQCRKAVESGAEFIVSPHLDEEISQFCKEKGVFYMPGVMTPTELV

KAMKLGHTILKLFPGEVVGPQFVKAMKGPFPNVKFVPTGGVNLDNVCEWFKAGVL

AVGVGSALVKGTPVEVAEKAKAFVEKIRGCTE(QKLISEEDL)QRPEPTAPPEESFRS

GVETTTPPQKQEPIDKELYPLTSLRSLFGNDPSSQ
```

The following embodiments comprise proteins in which a protein cargo is genetically fused to the protein comprising the M, O, and L domains. As described above, no packaging moiety is required in such embodiments. In one embodiment, the cargo is a detectable protein, such as green fluorescent protein (GFP); this protein forms a fully functional multimeric assembly that is useful for visualizing the subcellular localization of the protein inside the cell in which it is produced and in recipient cells in which the assembly is used as a delivery vehicle. The underlined portion of the protein sequence is the protein cargo.

PH-GFP-4GS-I3-01(M3I)-myc-late1 ("EPN-18-GFP")
(SEQ ID NO: 253)

```
(M)HGLQDDPDLQALLKGSQLLKVKSSSWRRERFYKLQEDCKTIWQESRKV

MRSPESQLFSIEDIQEVRMGHRTEGLEKFARDIPEDRCFSIVFKDQRNTLD

LIAPSPADAQHWVQGLRKIIHHSGSMDQRQK__KGEELFTGVVPILVELDGDV__

__NGHKFSVRGEGEGDATNGKLTLKFICTTGKLPVPWPTLVTTLTYGVQCFAR__

__YPDHMKQHDFFKSAMPEGYVQERTISFKDDGTYKTRAEVKFEGDTLVNRIE__

__LKGIDFKEDGNILGHKLEYNFNSHNVYITADKQKNGIKANFKIRHNVEDGS__

__VQLADHYQQNTPIGDPVLLPDNHYLSTQSVLSKDPNEKRDHMVLLEFVTA__

__AGITHGMDELYGSGS__KIEELFKKHKIVAVLRANSVEEAKKKALAVFLGGVH
```

-continued

```
LIEITFTVPDADTVIKELSFLKEMGAIIGAGTVTSVEQCRKAVESGAEFIV

SPHLDEEISQFCKEKGVFYMPGVMTPTELVKAMKLGHTILKLFPGEVVGPQ

FVKAMKGPFPNVKFVPTGGVNLDNVCEWFKAGVLAVGVGSALVKGTPVEVA

EKAKAFVEKIRGCTE(QKLISEEDL)QSRPEPTAPPEESFRSGVETTTPPQ

KQEPIDKELYPLTSLRSLFGNDPSSQ
```

The following proteins are derived from EPN-01 (SEQ ID NO: 230) or a positively charged variant of Myr-I3-01-myc-p6 (Myr-I3-01-posT1-myc-p6; SEQ ID NO: 229) bearing a genetic fusion to a packaging domain intended to direct the packaging of nucleic acids of interest. For each packaging domain, two constructs were made—a direct genetic fusion and a "frameshift" variant in which the packaging domain should be included in only a fraction of the protein molecules produced due to the presence of a frameshift element in the gene encoding the protein. The frameshift variants are denoted by an "—FS" at the end of their names. A linker is underlined, and the packaging domain includes the residues C-terminal to the underlined linker sequence.

EPN-01-1g70
(SEQ ID NO: 254)
```
(M)GARASGSKSGSGSDSGSKIEELFKKHKIVAVLRANSVEEAKKKALAVFLGGVHLIEITFTV

PDADTVIKELSFLKEMGAIIGAGTVTSVEQCRKAVESGAEFIVSPHLDEEISQFCKEKGVFYMP

GVMTPTELVKAMKLGHTILKLFPGEVVGPQFVKAMKGPFPNVKFVPTGGVNLDNVCEWFK

AGVLAVGVGSALVKGTPVEVAEKAKAFVEKIRGCTE(QKLISEEDL)LQSRPEPTAPPEESFRS

GVETTTPPQKQEPIDKELYPLTSLRSLFGNDPSSQGGSKGSDRRRRGSRPSGAERRRRAAAA;
```

EPN-01-1g70-FS
(SEQ ID NO: 255)
```
(M)GARASGSKSGSGSDSGSKIEELFKKHKIVAVLRANSVEEAKKKALAVFLGGVHLIEITFTV

PDADTVIKELSFLKEMGAIIGAGTVTSVEQCRKAVESGAEFIVSPHLDEEISQFCKEKGVFYMP

GVMTPTELVKAMKLGHTILKLFPGEVVGPQFVKAMKGPFPNVKFVPTGGVNLDNVCEWFK

AGVLAVGVGSALVKGTPVEVAEKAKAFVEKIRGCTE(QKLISEEDL)LQSRPEPTAPPEESFRS

GVETTTPPQKQEPIDKELYPLTSLRSLFGNDPSSQGSFFREDLAFLQGKARELGGSKGSDRRRR

GSRPSGAERRRRAAAA;
```

EPN-01-posT1-1g70
(SEQ ID NO: 256)
```
(M)GARASGSKSGSGSDSGSKMEELFKKHKIVAVLRANSVEEAKKKALAVFLGGVHLIEITFT

VPDADTVIKELSFLKEMGAIIGAGTVTSVEQCRKAVESGAEFIVSPHLDEEISQFCKEKGVFY

MPGVMTPTELVKAMKLGHTILKLFPGEVVGPQFVKAMKGPFPNVKFVPTGGVNLKNVCKW

FKAGVLAVGVGKALVKGTPVEVAKKAKAFVKKIRGCTE(QKLISEEDL)QSRPEPTAPPEESF

RSGVETTTPPQKQEPIDKELYPLTSLRSLFGNDPSSQGGSKGSDRRRRGSRPSGAERRRRRAA

AA;
```

EPN-01-posT1-1g70-FS
(SEQ ID NO: 257)
```
(M)GARASGSKSGSGSDSGSKMEELFKKHKIVAVLRANSVEEAKKKALAVFLGGVHLIEITFT

VPDADTVIKELSFLKEMGAIIGAGTVTSVEQCRKAVESGAEFIVSPHLDEEISQFCKEKGVFY

MPGVMTPTELVKAMKLGHTILKLFPGEVVGPQFVKAMKGPFPNVKFVPTGGVNLKNVCKW

FKAGVLAVGVGKALVKGTPVEVAKKAKAFVKKIRGCTE(QKLISEEDL)QSRPEPTAPPEESF

RSGVETTTPPQKQEPIDKELYPLTSLRSLFGNDPSSQGSFFREDLAFLQGKARELGGSKGSDRR

RRGSRPSGAERRRRAAAA;
```

EPN-01-ula
(SEQ ID NO: 258)
```
(M)GARASGSKSGSGSDSGSKIEELFKKHKIVAVLRANSVEEAKKKALAVFLGGVHLIEITFTV

PDADTVIKELSFLKEMGAIIGAGTVTSVEQCRKAVESGAEFIVSPHLDEEISQFCKEKGVFYMP

GVMTPTELVKAMKLGHTILKLFPGEVVGPQFVKAMKGPFPNVKFVPTGGVNLDNVCEWFK

AGVLAVGVGSALVKGTPVEVAEKAKAFVEKIRGCTE(QKLISEEDL)LQSRPEPTAPPEESFRS

GVETTTPPQKQEPIDKELYPLTSLRSLFGNDPSSQGGSKGSAVPETRPNHTIYINNLNEKIKKD
```

-continued

ELKKSLHAIFSRFGQILDILVSRSLKMRGQAFVIFKEVSSATNALRSMQGFPFYDKPMRIQYAK
TDSDIIAKMK;

EPN-01-u1a-FS
(SEQ ID NO: 259)
(M)GARASGSKSGSGSDSGSKIEELFKKHKIVAVLRANSVEEAKKKALAVFLGGVHLIEITFTV
PDADTVIKELSFLKEMGAIIGAGTVTSVEQCRKAVESGAEFIVSPHLDEEISQFCKEKGVFYMP
GVMTPTELVKAMKLGHTILKLFPGEVVGPQFVKAMKGPFPNVKFVPTGGVNLDNVCEWFK
AGVLAVGVGSALVKGTPVEVAEKAKAFVEKIRGCTE(QKLISEEDL)LQSRPEPTAPPEESFRS
GVETTTPPQKQEPIDKELYPLTSLRSLFGNDPSSQGSFFREDLAFLQGKARELGGSKGSAVPET
RPNHTIYINNLNEKIKKDELKKSLHAIFSRFGQILDILVSRSLKMRGQAFVIFKEVSSATNALRS
MQGFPFYDKPMRIQYAKTDSDIIAKMK

>EPN-01-posT1-u1a
(SEQ ID NO: 260)
(M)GARASGSKSGSGSDSGSKMEELFKKHKIVAVLRANSVEEAKKKALAVFLGGVHLIEITFT
VPDADTVIKELSFLKEMGAIIGAGTVTSVEQCRKAVESGAEFIVSPHLDEEISQFCKEKGVFY
MPGVMTPTELVKAMKLGHTILKLFPGEVVGPQFVKAMKGPFPNVKFVPTGGVNLKNVCKW
FKAGVLAVGVGKALVKGTPVEVAKKAKAFVKKIRGCTE(QKLISEEDL)QSRPEPTAPPEESF
RSGVETTTPPQKQEPIDKELYPLTSLRSLFGNDPSSQGGSKGSAVPETRPNHTIYINNLNEKIKK
DELKKSLHAIFSRFGQILDILVSRSLKMRGQAFVIFKEVSSATNALRSMQGFPFYDKPMRIQYA
KTDSDIIAKMK EPN-01-posT1-u1a-FS
(SEQ ID NO: 261)
(M)GARASGSKSGSGSDSGSKMEELFKKHKIVAVLRANSVEEAKKKALAVFLGGVHLIEITFT
VPDADTVIKELSFLKEMGAIIGAGTVTSVEQCRKAVESGAEFIVSPHLDEEISQFCKEKGVFY
MPGVMTPTELVKAMKLGHTILKLFPGEVVGPQFVKAMKGPFPNVKFVPTGGVNLKNVCKW
FKAGVLAVGVGKALVKGTPVEVAKKAKAFVKKIRGCTE(QKLISEEDL)QSRPEPTAPPEESF
RSGVETTTPPQKQEPIDKELYPLTSLRSLFGNDPSSQGSFFREDLAFLQGKARELGGSKGSAVP
ETRPNHTIYINNLNEKIKKDELKKSLHAIFSRFGQILDILVSRSLKMRGQAPVIFKEVSSATNAL
RSMQGFPFYDKPMRIQYAKTDSDIIAKMK;

EPN-01-HIV_NC
(SEQ ID NO: 262)
(M)GARASGSKSGSGSDSGSKIEELFKKHKIVAVLRANSVEEAKKKALAVFLGGVHLIEITFTV
PDADTVIKELSFLKEMGAIIGAGTVTSVEQCRKAVESGAEFIVSPHLDEEISQFCKEKGVFYMP
GVMTPTELVKAMKLGHTILKLFPGEVVGPQFVKAMKGPFPNVKFVPTGGVNLDNVCEWFK
AGVLAVGVGSALVKGTPVEVAEKAKAFVEKIRGCTE(QKLISEEDL)LQSRPEPTAPPEESFRS
GVETTTPPQKQEPIDKELYPLTSLRSLFGNDPSSQGGSKGSMQKGNFRNQRKTVKCFNCGKE
GHIAKNCRAPRKKGCWKCGKEGHQMKDCTERQAN;

EPN-01-HIV_NC-FS
(SEQ ID NO: 263)
(M)GARASGSKSGSGSDSGSKIEELFKKHKIVAVLRANSVEEAKKKALAVFLGGVHLIEITFTV
PDADTVIKELSFLKEMGAIIGAGTVTSVEQCRKAVESGAEFIVSPHLDEEISQFCKEKGVFYMP
GVMTPTELVKAMKLGHTILKLFPGEVVGPQFVKAMKGPFPNVKFVPTGGVNLDNVCEWFK
AGVLAVGVGSALVKGTPVEVAEKAKAFVEKIRGCTE(QKLISEEDL)LQSRPEPTAPPEESFRS
GVETTTPPQKQEPIDKELYPLTSLRSLFGNDPSSQGSFFREDLAFLQGKARELGGSKGSMQKG
NFRNQRKTVKCFNCGKEGHIAKNCRAPRKKGCWKCGKEGHQMKDCTERQAN;

EPN-01-posT1-HIV_NC

-continued (SEQ ID NO: 264)
(M)GARASGSKSGSGSDSGSKMEELFKKHKIVAVLRANSVEEAKKKALAVFLGGVHLIEITFT
VPDADTVIKELSFLKEMGAIIGAGTVTSVEQCRKAVESGAEFIVSPHLDEEISQFCKEKGVFY
MPGVMTPTELVKAMKLGHTILKLFPGEVVGPQFVKAMKGPFPNVKFVPTGGVNLKNVCKW
FKAGVLAVGVGKALVKGTPVEVAKKAKAFVKKIRGCTE(QKLISEEDL)QSRPEPTAPPEESF
RSGVETTTPPQKQEPIDKELYPLTSLRSLFGNDPSSQGGSKGSMQKGNFRNQRKTVKCFNCG
KEGHIAKNCRAPRKKGCWKCGKEGHQMKDCTERQAN;

EPN-01-posT1-HIV_NC-FS
(SEQ ID NO: 265)
(M)GARASGSKSGSGSDSGSKMEELFKKHKIVAVLRANSVEEAKKKALAVFLGGVHLIEITFT
VPDADTVIKELSFLKEMGAIIGAGTVTSVEQCRKAVESGAEFIVSPHLDEEISQFCKEKGVFY
MPGVMTPTELVKAMKLGHTILKLFPGEVVGPQFVKAMKGPFPNVKFVPTGGVNLKNVCKW
FKAGVLAVGVGKALVKGTPVEVAKKAKAFVKKIRGCTE(QKLISEEDL)QSRPEPTAPPEESF
RS GVETTTPPQKQEPIDKELYPLTSLRSLFGNDPSSQGSFFREDLAFLQGKARELGGSKGSMQ
KGNFRNQRKTVKCFNCGKEGHIAKNCRAPRKKGCWKCGKEGHQMKDCTERQAN;

EPN-01-1mnb
(SEQ ID NO: 266)
(M)GARASGSKSGSGSDSGSKIEELFKKHKIVAVLRANSVEEAKKKALAVFLGGVHLIEITFTV
PDADTVIKELSFLKEMGAIIGAGTVTSVEQCRKAVESGAEFIVSPHLDEEISQFCKEKGVFYMP
GVMTPTELVKAMKLGHTILKLFPGEVVGPQFVKAMKGPFPNVKFVPTGGVNLDNVCEWFK
AGVLAVGVGSALVKGTPVEVAEKAKAFVEKIRGCTE(QKLISEEDL)LQSRPEPTAPPEESFRS
GVETTTPPQKQEPIDKELYPLTSLRSLFGNDPSSQGGSKGSRPRGTRGKGRRIRR;

EPN-01-1mnb-FS
(SEQ ID NO: 267)
(M)GARASGSKSGSGSDSGSKIEELFKKHKIVAVLRANSVEEAKKKALAVFLGGVHLIEITFTV
PDADTVIKELSFLKEMGAIIGAGTVTSVEQCRKAVESGAEFIVSPHLDEEISQFCKEKGVFYMP
GVMTPTELVKAMKLGHTILKLFPGEVVGPQFVKAMKGPFPNVKFVPTGGVNLDNVCEWFK
AGVLAVGVGSALVKGTPVEVAEKAKAFVEKIRGCTE(QKLISEEDL)LQSRPEPTAPPEESFRS
GVETTTPPQKQEPIDKELYPLTSLRSLFGNDPSSQGSFFREDLAFLQGKARELGGSKGSRPRGT
RGKGRRIRR;

EPN-01-posT1-1mnb
(SEQ ID NO: 268)
(M)GARASGSKSGSGSDSGSKMEELFKKHKIVAVLRANSVEEAKKKALAVFLGGVHLIEITFT
VPDADTVIKELSFLKEMGAIIGAGTVTSVEQCRKAVESGAEFIVSPHLDEEISQFCKEKGVFY
MPGVMTPTELVKAMKLGHTILKLFPGEVVGPQFVKAMKGPFPNVKFVPTGGVNLKNVCKW
FKAGVLAVGVGKALVKGTPVEVAKKAKAFVKKIRGCTE(QKLISEEDL)QSRPEPTAPPEESF
RSGVETTTPPQKQEPIDKELYPLTSLRSLFGNDPSSQGGSKGSRPRGTRGKGRRIRR;

and

EPN-01-posT1-1mnb-FS
(SEQ ID NO: 269)
(M)GARASGSKSGSGSDSGSKMEELFKKHKIVAVLRANSVEEAKKKALAVFLGGVHLIEITFT
VPDADTVIKELSFLKEMGAIIGAGTVTSVEQCRKAVESGAEFIVSPHLDEEISQFCKEKGVFY
MPGVMTPTELVKAMKLGHTILKLFPGEVVGPQFVKAMKGPFPNVKFVPTGGVNLKNVCKW
FKAGVLAVGVGKALVKGTPVEVAKKAKAFVKKIRGCTE(QKLISEEDL)QSRPEPTAPPEESF
RSGVETTTPPQKQEPIDKELYPLTSLRSLFGNDPSSQGSFFREDLAFLQGKARELGGSKGSRPR
GTRGKGRRIRR.

In another embodiment, the multimeric assembly of any embodiment or combination of embodiments further comprises a lipid bilayer enveloping the multimeric assembly, wherein one or more of the M domains of each multimeric assembly, oligomeric structure, and/or protein is bound to the lipid bilayer. As shown in the attached examples, the inventors have shown that such lipid bilayer membrane-enveloped multimeric assemblies can be readily produced by eukaryotic cells expressing the recombinant polypeptides and polypeptide compositions of the invention (see below). This embodiment of the multimeric assemblies of the invention is particularly useful for delivery of a desired cargo to a cell or tissue of interest. As described in the examples below, that inventors have shown that the preparation of enveloped multimeric assemblies requires the presence of M domains, O interfaces, and L domains in the multimeric assemblies. The M domains enable the multimeric assemblies to interact with the host cell membrane. As will be understood by those of skill in the art, it is not required that all M domains in a multimeric assembly actually interact with the lipid bilayer, so long as the plurality of M domains in the multimeric assembly are adequate to drive association with the membrane and/or result in deformation of the lipid bilayer upon multimerization. As such, and as the inventors have shown in the examples below, it is not required that all protein subunits in a multimeric assembly comprise an M domain, so long as the plurality of M domains in the multimeric assembly are adequate to drive association with the membrane and/or result in deformation of the lipid bilayer upon multimerization. Thus, in one embodiment, the multimeric assembly packages a cargo not by interacting directly with the cargo molecule, but rather by driving the packaging of a small volume of the eukaryotic host cell cytoplasm containing the cargo molecule inside a lipid bilayer envelope that contains one or more copies of the multimeric assembly. In this way, cargo molecules including but not limited to proteins, nucleic acids, lipids, small molecules, or any combination thereof can be packaged in combination with the multimeric assemblies. The cargo molecules packaged in this way may be endogenously produced molecules, or may be produced by overexpression of one or more recombinant genes in the host cell. Many enveloped viruses are known to package host cell molecules inside or within their membranes envelopes in this manner (e.g., Gentili M, et al. (2015) Transmission of innate immune signaling by packaging of cGAMP in viral particles. Science 349:1232-6; Bridgeman A, et al. (2015) Viruses transfer the antiviral second messenger cGAMP between cells. Science 349:1228-32; Apolonia L et al. (2015), PLoS Pathogens 11:e1004609; Rosa A et al. (2015), 526:212-7; Usami Y, et al. (2015), Nature 526:218-23). In one non-limiting embodiment, the small molecule immune activator 2',3'-cyclic GMP-AMP (cGAMP) (Wu et al, Science 15 Feb. 2013: 826-830) may be packaged as a cargo molecule, as described in the examples that follow. In a further non-limiting embodiment, the cGAMP may be produced by expression of recombinant cyclic GMP-AMP synthase (cGAS) (Sun et al, Science 15 Feb. 2013: 786-791) in the host cell using an expression plasmid.

The O interfaces are required to drive self-assembly or multimerization of the multimeric assemblies. This process both defines the structure of the multimeric assemblies as described above and enhances membrane binding and/or drives deformation of the lipid bilayer membrane to form bud-like structures that remain tethered to the host cell by a membrane neck. The L domains are required to recruit the host cell ESCRT machinery to the site of budding in order to effect release of the budding enveloped multimeric assembly from the host cell by scission of the membrane neck. The L domains may recruit the ESCRT machinery by interacting directly or indirectly with protein subunits of the ESCRT complex. In certain embodiments, it is preferred that the L domains of the multimeric assemblies interact with host proteins known to recruit the ESCRT machinery to sites of virus budding in cells. Such proteins include but are not limited to Tsg101, ALIX, and members of the Nedd4 family of ubiquitin ligases (McDonald B, Martin-Serrano J (2009) No strings attached: the ESCRT machinery in viral budding and cytokinesis. J. Cell Sci. 122:2167-77).

In another embodiment, the enveloped multimeric assembly further comprises one or more transmembrane protein or membrane-anchored protein embedded in the lipid bilayer. This embodiment may be used to add additional functionality of any desired type to the multimeric assemblies. In this embodiment, the transmembrane protein or membrane-anchored protein may be one not present as part of the oligomeric substructure or protein subunit, in that they are added to the assembly during or after envelopment of the multimeric assembly by the lipid bilayer and do not necessarily interact with the protein subunits of the multimeric assembly either covalently or non-covalently. Any suitable transmembrane protein or membrane-anchored protein can be added that provides any desired additional functionality to the assembly, in terms of cell targeting, the display of transmembrane or membrane-anchored antigen for vaccines, or other desired use. In one non-limiting example, the transmembrane protein or membrane-anchored protein embedded in the lipid bilayer comprises a viral envelope protein that enables the enveloped multimeric assembly to enter cells via receptor-mediated endocytosis and/or mediates fusion of the lipid bilayer of the enveloped multimeric assembly with cellular membranes. In the study of enveloped viruses, the practice of incorporating a foreign viral envelope protein in the membrane of an enveloped virus is referred to as "pseudotyping." By co-expressing the foreign viral envelope protein with the viral or virus-like particle proteins, the foreign viral envelope protein becomes embedded in the membrane bilayer of the cells, and is therefore incorporated into the membrane envelope of the budding virions or virus-like particles. As the inventors have shown below, viral envelope proteins (in one embodiment, the G protein of Vesicular Stomatitis Virus) can be incorporated in the membrane envelopes of the enveloped multimeric assemblies of the invention in a similar manner. In various non-limiting embodiments, additional classes of membrane proteins can be incorporated into the membrane envelopes of the multimeric assemblies of the invention. In various non-limiting embodiments, the transmembrane or membrane-anchored protein is selected from the group consisting of the envelope proteins of enveloped viruses, membrane protein transporters, membrane protein channels, B cell receptors, T cell receptors, transmembrane antigens of human pathogens, growth factors receptors, G-protein coupled receptors (GPCRs), complement regulatory proteins including but not limited to CD55 and CD59, or processed versions thereof.

In specific embodiments, the one or more transmembrane protein or membrane-anchored protein embedded in the lipid bilayer comprise one or more of the following polypeptides, or a processed version thereof. As will be understood by those of skill in the art, the polypeptide sequences provided are full-length protein precursors, which are cleaved or otherwise processed (i.e., "processed") to generate the final envelope protein embedded in the lipid bilayer.

VSV-G
(SEQ ID NO: 307)
MKCLLYLAFLFIGVNCKFTIVFPHNQKGNWKNVPSNYHYCPSSSDLNWHNDLIGTALQVKM

PKSHKAIQADGWMCHASKWVTTCDFRWYGPKYITHSIRSFTPSVEQCKESIEQTKQGTWLNP

GFPPQSCGYATVTDAEAVIVQVTPHHVLVDEYTGEWVDSQFINGKCSNYICPTVHNSTTWHS

DYKVKGLCDSNLISMDITFFSEDGELSSLGKEGTGFRSNYFAYETGGKACKMQYCKHWGVR

LPSGVWFEMADKDLFAAARFPECPEGSSISAPSQTSVDVSLIQDVERILDYSLCQETWSKIRAG

LPISPVDLSYLAPKNPGTGPAFTIINGTLKYFETRYIRVDIAAPILSRMVGMISGTTTERELWDD

WAPYEDVEIGPNGVLRTSSGYKFPLYMIGHGMLDSDLHLSSKAQVFEHPHIQDAASQLPDDE

SLFFGDTGLSKNPIELVEGWFSSWKSSIASFFFIIGLIIGLFLVLRVGIHL-
CIKLKHTKKRQIYTDI

EMNRLGK;

Ecotropic envelope protein from Moloney Murine Leukemia Virus or
"Eco"
(SEQ ID NO: 308)
MARSTLSKPLKNKVNPRGPLIPLILLMLRGVSTASPGSSPHQVYNITWEVTNGDRETVWATS

GNHPLWTWWPDLTPDLCMLAHHGPSYWGLEYQSPFSSPPGPPCCSGGSSPGCSRDCEEPLTS

LTPRCNTAWNRLKLDQTTHKSNEGFYVCPGPHRPRESKSCGGPDSFYCAYWGCETTGRAYW

KPSSSWDFITVNNNLTSDQAVQVCKDNKWCNPLVIRFTDAGRRVTSWTTGHYWGLRLYVS

GQDPGLTFGIRLRYQNLGPRVPIGPNPVLADQQPLSKPKPVKSPSVTKPPSGTPLSPTQLPPAG

TENRLLNLVDGAYQALNLTSPDKTQECWLCLVAGPPYYEGVAVLGTYSNHTSAPANCSVAS

QHKLTLSEVTGQGLCIGAVPKTHQALCNTTQTSSRGSYYLVAPTGTMWACSTGLTPCISTTIL

NLTTDYCLVELWPRVTYHSPSYVYGLFERSNRHKREPVSLTLALLLGGLTMGGIAAGIGTG

TTALMATQQFQQLQAAVQDDLREVEKSISNLEKSLTSLSEVVQNRRGLDLLFLKEGGLCAA

LKEECCFYADHTGLVRDSMAKLRERLNQRQKLFESTQGWFEGLFNRSPWFTTLISTIMGPLIV

LLMILLFGPCILNRLVQFVKDRISVVQALVLTQQYHQLKPIEYEP;

Amphotropic Murine Leukemia Virus Envelope 4070A
(SEQ ID NO: 309)
MARSTLSKPPQDKINPWKPLIVMGVLLGVGMAESPHQVFNVTWRVTNLMTGRTANATSLL

GTVQDAFPKLYFDLCDLVGEEWDPSDQEPYVGYGCKYPAGRQRTRTFDFYVCPGHTVKSG

CGGPGEGYCGKWGCETTGQAYWKPTSSWDLISLKRGNTPWDTGCSKVACGPCYDLSKVSN

SFQGATRGGRCNPLVLEFTDAGKKANWDGPKSWGLRLYRTGTDPITMFSLTRQVLNVGPRV

PIGPNPVLPDQRLPSSPIEIVPAPQPPSPLNTSYPPSTTSTPSTSPSVPQPPPGTG

DRLLALVKGAYQALNLTNPDKTQECWLCLVSGPPYYEGVAVVGTYTNHSTAPANCTATSQ

HKLTLSEVTGQGLCMGAVPKTHQALCNTTQSAGSGSYYLAAPAGTMWACSTGLTPCLSTT

VLNLTTDYCVLVELWPRVIYHSPDYMYGQLEQRTKYKREPVSLTLALLLGGLTMGGIAAG

IGTGTTALIKTQQFEQLHAAIQTDLNEVEKSITNLEKSLTSLSEVVLQNRRGLDLLFLKE

GGLCAALKEECCFYADHTGLVRDSMAKLRERLNQRQKLFETGQGWFEGLFNRSPWFTTLI

STIMGPLIVLLLILLFGPCILNRLVQFVKDRISVVQALVLTQQYHQLKPIEYEP;

Sindbis virus E3-E2-6K-E1 envelope polyprotein
(SEQ ID NO: 310)
SAAPLVTAMCLLGNVSFPCDRPPTCYTREPSRALDILEENVNHEAYDTLLNAILRCGSSG

RSKRSVIDDFTLTSPYLGTCSYCHHTVPCFSPVKIEQVWDEADDNTIRIQTSAQFGYDQSGAA

SANKYRYMSLKQDHTVKEGTMDDIKISTSGPCRRLSYKGYFLLAKCPPGDSVTVSIVSSNSAT

SCTLARKIKPKFVGREKYDLPPVHGKKIPCTVYDRLKETTAGYITMHRPRPHAYTSYL

EESSGKVYAKPPSGKNITYECKCGDYKTGTVSTRTEITGCTAIKQCVAYKSDQTKWVFNS

-continued

```
PDLIRHDDHTAQGKLHLPFKLIPSTCMVPVAHAPNVIHGFKHISLQLDTDHLTLLTTRRL

GANPEPTTEWIVGKTVRNFTVDRDGLEYIWGNHEPVRVYAQESAPGDPHGWPHEIVQHYY

HRHPVYTILAVASATVAMMIGVTVAVLCACKARRECLTPYALAPNAVIPTSLALLCCVRS

ANAETFTETMSYLWSNSQPFFWVQLCIPLAAFIVLMRCCSCCLPFLVVAGAYLAKVDAYEHA

TTVPNVPQIPYKALVERAGYAPLNLEITVMSSEVLPSTNQEYITCKFTTVVPSPKIKCCGSLEC

QPAAHADYTCKVFGGVYPFMWGGAQCFCDSENSQMSEAYVELSADCASDHAQAIKVHTAA

MKVGLRIVYGNTTSFLDVYVNGVTPGTSKDLKVIAGPISASFTPFDHKVVIH

RGLVYNYDFPEYGAMKPGAFGDIQATSLTSKDLIASTDIRLLKPSAKNVHVPYTQASSGF

EMWKNNSGRPLQETAPFGCKIAVNPLRAVDCSYGNIPISIDIPNAAFIRTSDAPLVSTVK

CEVSECTYSADFGGMATLQYVSDREGQCPVHSHSSTATLQESTVHVLEKGAVTVHFSTAS

PQANFIVSLCGKKTTCNAECKPPADHIVSTPHKNDQEFQAAISKTSWSWLFALFGGASSL

LIIGLMIFACSMMLTSTRR;

Ebola GP (Zaire Mayinga strain)
                                                    (SEQ ID NO: 311)
MGVTGILQLPRDRFKRTSFFLWVIILFQRTFSIPLGVIHNSTLQVSDVDKLVCRDKLSST

NQLRSVGLNLEGNGVATDVPSATKRWGFRSGVPPKVVNYEAGEWAENCYNLEIKKPDGSE

CLPAAPDGIRGFPRCRYVHKVSGTGPCAGDFAFHKEGAFFLYDRLASTVIYRGTTFAEGV

VAFLILPQAKKDFFSSHPLREPVNATEDPSSGYYSTTIRYQATGFGTNETEYLFEVDNLT

YVQLESRFTPQFLLQLNETIYTSGKRSNTTGKLIWKVNPEIDTTIGEWAFWETKKNLTRK

IRSEELSFTVVSNGAKNISGQSPARTSSDPGTNTTTEDHKIMASENSSAMVQVHSQGREA

AVSHLTTLATISTSPQSLTTKPGPDNSTHNTPVYKLDISEATQVEQHHRRTDNDSTASDT

PSATTAAGPPKAENTNTSKSTDFLDPATTTSPQNHSETAGNNNTHHQDTGEESASSGKLG

LITNTIAGVAGLITGGRRTRREAIVNAQPKCNPNLHYWTTQDEGAAIGLAWIPYFGPAAE

GIYIEGLMHNQDGLICGLRQLANETTQALQLFLRATTELRTFSILNRKAIDFLLQRWGGT

CHILGPDCCIEPHDWTKNITDKIDQIIHDFVDKTLPDQGDNDNWWTGWRQWIPAGIGVTG

VIIAVIALFCICKFVF;

Human Immunodeficiency Virus envelope glycoprotein precursor
gp160
                                                    (SEQ ID NO: 312)
MRVKEKYQHLWRWGWKWGIMLLGILMICSATENLWVTVYYGVPVWKEATTTLFCASDAK

AYDTEVHNVCATHACVPTDPNPQEVILVNVTENFDMWKNDMVEQMHEDIISLWDQSLKPC

VKLTPLCVNLKCTDLKNDTNTNSSNGRMIMEKGEIKNCSFNISTSIRNKVQKEYAFFYKLD

IRPIDNTTYRLISCNTSVITQACPKVSFEPIPIHYCAPAGFAILKCNDKTFNGTGPCTNV

STVQCTHGIRPVVSTQLLLNGSLAEEEGVIRSANFTDNAKTIIVQLNTSVEINCTRPNNN

TRKSIRIQRGPGRAFVTIGKIGNMRQAHCNISRAKWMSTLKQIASKLREQFGNNKTVIFK

QSSGGDPEIVTHSFNCGGEFFYCNSTQLFNSTWFNSTWSTEGSNNTEGSDTITLPCRIKQ

FINMWQEVGKAMYAPPISGQIRCSSNITGLLLTRDGGKNTNESEVFRPGGGDMRDNWRSE

LYKYKVVKIETLGVAPTKAKRRVVQREKRAVGIGALFLGFLGAAGSTMGAASMTLTVQAR

QLLSGIVQQQNNLLRAIEAQQHLLQLTVWGIKQLQARILAVERYLKDQQLLGIWGCSGKL

ICTTAVPWNASWSNKSLEQFWNNMTWMEWDREINNYTSLIHSLIDESQNQQEKNEQELLE

LDKWASLWNWFNITNWLWYIKIFIMIVGGLVGLRIVFAVLSIVNRVRQGYSPLSFQTHLP

NRGGPDRPEGIEEEGGERDRDRSVRLVNGSLALIWDDLRSLCLFSYHRLRDLLLIVTRIV

ELLGRRGWEALKYWWNLLQYWSQELKNSAVSLLNATAIAVAEGTDRVIEVVQGAYRAIRH
```

IPRRIRQGLERIL;

Respiratory Syncytial Virus F protein precursor
(SEQ ID NO: 313)
MELLILKANAITTILTAVTFCFASGQNITEEFYQSTCSAVSKGYLSALRTGWYTSVITIE
LSNIKENKCNGTDAKVKLIKQELDKYKNAVTELQLLMQSTPPTNNRARRELPRFMNYTLN
NAKKTNVTLSKKRKRRFLGFLLGVGSAIASGVAVSKVLHLEGEVNKIKSALLSTNKAVVS
LSNGVSVLTSKVLDLKNYIDKQLLPIVNKQSCSISNIETVIEFQQKNNRLLEITREFSVN
AGVTTPVSTYMLTNSELLSLINDMPITNDQKKLMSNNVQIVRQQSYSIMSIIKEEVLAYV
VQLPLYGVIDTPCWKLHTSPLCTTNTKEGSNICLTRTDRGWYCDNAGSVSFFPQAETCKV
QSNRVFCDTMNSLTLPSEINLCNVDIFNPKYDCKIMTSKTDVSSSVITSLGAIVSCYGKT
KCTASNKNRGIIKTFSNGCDYVSNKGMDTVSVGNTLYYVNKQEGKSLYVKGEPIINFYDP
LVFPSDEFDASISQVNEKINQSLAFIRKSDELLHNVAGKSTTNIMITTIIIVIIVILLS
LIAVGLLLYCKARSTPVTLSKDQLSGINNIAFSN;

SARS Coronavirus spike protein
(SEQ ID NO: 314)
MFIFLLFLTLTSGSDLDRCTTFDDVQAPNYTQHTSSMRGVYYPDEIFRSDTLYLTQDLFL
PFYSNVTGFHTINHTFGNPVIPFKDGIYFAATEKSNVVRGWVFGSTMNNKSQSVIIINNS
TNVVIRACNFELCDNPFFAVSKPMGTQTHTMIFDNAFNCTFEYISDAFSLDVSEKSGNFK
HLREFVFKNKDGFLYVYKGYQPIDVVRDLPSGFNTLKPIFKLPLGINITNFRAILTAFSP
AQDIWGTSAAAYFVGYLKPTTFMLKYDENGTITDAVDCSQNPLAELKCSVKSFEIDKGIY
QTSNFRVVPSGDVVRFPNITNLCPFGEVFNATKFPSVYAWERKKISNCVADYSVLYNSTF
FSTFKCYGVSATKLNDLCFSNVYADSFVVKGDDVRQIAPGQTGVIADYNYKLPDDFMGCV
LAWNTRNIDATSTGNYNYKYRYLRHGKLRPFERDISNVPFSPDGKPCTPPALNCYWPLND
YGFYTTTGIGYQPYRVVVLSFELLNAPATVCGPKLSTDLIKNQCVNFNFNGLTGTGVLTP
SSKRFQPFQQFGRDVSDFTDSVRDPKTSEILDISPCSFGGVSVITPGTNASSEVAVLYQD
VNCTDVSTAIHADQLTPAWRIYSTGNNVFQTQAGCLIGAEHVDTSYECDIPIGAGICASY
HTVSLLRSTSQKSIVAYTMSLGADSSIAYSNNTIAIPTNFSISITTEVMPVSMAKTSVDC
NMYICGDSTECANLLLQYGSFCTQLNRALSGIAAEQDRNTREVFAQVKQMYKTPTLKYFG
GFNFSQILPDPLKPTKRSFIEDLLFNKVTLADAGFMKQYGECLGDINARDLICAQKFNGL
TVLPPLLTDDMIAAYTAALVSGTATAGWTFGAGAALQIPFAMQMAYRFNGIGVTQNVLYE
NQKQIANQFNKAISQIQESLTTTSTALGKLQDVVNQNAQALNTLVKQLSSNFGAISSVLN
DILSRLDKVEAEVQIDRLITGRLQSLQTYVTQQLIRAAEIRASANLAATKMSECVLGQSK
RVDFCGKGYHLMSFPQAAPHGVVFLHVTYVPSQERNFTTAPAICHEGKAYFPREGVFVFN
GTSWFITQRNFFSPQIITTDNTFVSGNCDVVIGIINNTVYDPLQPELDSFKEELDKYFKN
HTSPDVDLGDISGINASVVNIQKEIDRLNEVAKNLNESLIDLQELGKYEQYIKWPWYVWL
GFIAGLIAIVMVTILLCCMTSCCSCLKGACSCGSCCKFDEDDSEPVLKGVKLHYT;

Influenza hemagglutinin
(SEQ ID NO: 315)
MKTIIALSYIFCLALGQDLPGNDNSTATLCLGHHAVPNGTLVKTITDDQIEVTNATELVQ
SSSTGKICNNPHRILDGIDCTLIDALLGDPHCDVFQNETWDLFVERSKAFSNCYPYDVPD
YASLRSLVASSGTLEFITEGFTWTGVTQNGGSNACKRGPGSGFFSRLNWLTKSGSTYPVL
NVTMPNNDNFDKLYIWGIHHPSTNQEQTSLYVQASGRVTVSTRRSQQTIIPNIGSRPWVR
GLSSRISIYWTIVKPGDVLVINSNGNLIAPRGYFKMRTGKSSIMRSDAPIDTCISECITP -continued

```
NGSIPNDKPFQNVNKITYGACPKYVKQNTLKLATGMRNVPEKQTRGLFGAIAGFIENGWE

GMIDGWYGFRHQNSEGTGQAADLKSTQAAIDQINGKLNRVIEKTNEKFHQIEKEFSEVEG

RIQDLEKYVEDTKIDLWSYNAELLVALENQHTIDLTDSEMNKLFEKTRRQLRENAEEMGN

GCFKIYHKCDNACIESIRNGTYDHDVYRDEALNNRFQIKGVELKSGYKDWILWISFAISC

FLLCVVLLGFIMWACQRGNIRCNICI.
```

In another aspect, the invention provides recombinant polypeptides comprising
- (a) a polypeptide-polypeptide interface ("O interface"); and
- (b) a polypeptide domain that is capable of interacting with one or more proteins in the eukaryotic ESCRT complex ("L domain");

wherein the L domain, and the O interface are not each present in a single naturally occurring protein.

In another embodiment, the recombinant polypeptides comprising
- (a) a polypeptide domain that is capable of interacting with a lipid bilayer ("M domain");
- (b) a polypeptide-polypeptide interface ("O interface"); and
- (c) a polypeptide domain that is capable of interacting with one or more proteins in the eukaryotic ESCRT complex ("L domain");

wherein the M domain, the L domain, and the O interface are not each present in a single naturally occurring protein.

In a further aspect, the invention provides recombinant polypeptide compositions, comprising a first polypeptide and a second polypeptide, wherein the first polypeptide and the second polypeptide each comprise an O interface, wherein the O interface on the first polypeptide is capable of interacting with the O interface on the second polypeptide, and wherein at least one of the first polypeptide or the second polypeptide comprises:
- (a) an optional domain capable of interacting with a lipid bilayer ("M domain"); and
- (b) a domain capable of interacting with one or more proteins in the eukaryotic ESCRT complex ("L domain");

wherein the M domain (if present), the L domain, and the O interface are not each present in a single naturally occurring protein.

The recombinant polypeptides and polypeptide compositions of the invention can be used, for example, to generate the multimeric assemblies of the invention. All definitions and examples described herein for the multimeric assemblies of the invention are applicable to the polypeptides of the invention. Thus, any embodiment of the M domain, L domain, O interface, and combinations thereof that are described herein can be used in the recombinant polypeptides and polypeptide complexes of the invention. Thus, in various embodiments, the M domain is capable of non-covalently interacting with a lipid bilayer; the L domain is capable of non-covalently interacting with one or more proteins in the ESCRT complex; the M domain comprises a polypeptide having an acylation motif (including but not limited to N-terminal myristoylation motifs, palmitoylation motifs, farnesylation motifs, and geranylgeranylation motifs), a polar headgroup-binding domains (including but not limited to those disclosed herein, and in: Stahelin R V (2009) Lipid binding domains: more than simple lipid effectors. J. Lipid Res. 50:5299-304), or transmembrane protein domains; the M domain is selected from the group consisting of the M domains disclosed herein; the O interface comprises a non-natural polypeptide; the O interface-containing polypeptide comprises or consists of a polypeptide selected from the group consisting of the O interface-containing polypeptides disclosed herein and in the attached appendices; the L domain comprises a linear amino acid sequence motif selected from the group consisting of P(T/S)AP (SEQ ID NO: 152), YP(X)$_n$L (SEQ ID NO: 301), PPxY (SEQ ID NO: 154), and overlapping combinations thereof (including but not limited to P(T/S)APPxY (SEQ ID NO: 155), P(T/S)AP YP(X)$_n$L (SEQ ID NO: 156), PPxYP(T/S)AP (SEQ ID NO: 157), PPxYYP(X)$_n$L (SEQ ID NO: 158), YP(X)$_n$LPPxY (SEQ ID NO: 159), and YP(X)$_n$LPPxY) (SEQ ID NO: 160); the L domain is selected from the group consisting of the late domains disclosed herein.

In further embodiments, the recombinant polypeptide or polypeptide composition further comprises a packaging moiety, as described herein. In various embodiments, the packaging moiety comprises a cysteine residue, a non-canonical amino acid residue, any polypeptide that interacts with a cargo covalently or non-covalently to recruit the cargo to the multimeric assembly, or a polypeptide sequence selected from the group consisting of the packaging moieties disclosed herein.

In another aspect, the invention provides polypeptides comprising an amino acid sequence at least 75% identical over its full length to SEQ ID: 20 (I3-01)

```
(SEQ ID NO: 20)
(M)KMEELFKKHKIVAVLRANSVEEAKKKALAVFLGGVHLIEITFTVPDAD

TVIKELSFLKEMGAIIGAGTVTSVEQCRKAVESGAEFIVSPHLDEEISQFC

KEKGVFYMPGVMTPTELVKAMKLGHTILKLFPGEVVGPQFVKAMKGPFPNV

KFVPTGGVNLDNVCEWFKAGVLAVGVGSALVKGTPVEVAEKAKAFVEKIRG

CTE,
or

SEQ ID 304: (I3-01(M3I)
(M)KIEELFKKHKIVAVLRANSVEEAKKKALAVFLGGVHLIEITFTVPDAD

TVIKELSFLKEMGAIIGAGTVTSVEQCRKAVESGAEFIVSPHLDEEISQFC

KEKGVFYMPGVMTPTELVKAMKLGHTILKLFPGEVVGPQFVKAMKGPFPNV

KFVPTGGVNLDNVCEWFKAGVLAVGVGSALVKGTPVEVAEKAKAFVEKIRG

CTE;
``` wherein the polypeptide includes at least 1, 2, 3, 4, 5, or more amino acid substitutions compared to SEQ NO: 21 (1wa3-wt)

```
(1wa3-wt)
                                              SEQ ID: 21
MKMEELFKKHKIVAVLRANSVEEAKEKALAVFEGGVHLIEITFTVPDADTV

IKELSFLKEKGAIIGAGTVTSVEQCRKAVESGAEFIVSPHLDEEISQFCKE
```

```
KGVFYMPGVMTPTELVKAMKLGHTILKLFPGEVVGPQFVKAMKGPFPNVKF

VPTGGVNLDNVCEWFKAGVLAVGVGSALVKGTPDEVREKAKAFVEKIRGCT

E
```

In various further embodiments, the polypeptide is at least 80%, 85%, 90%, 95%, 96%, 97%, 98%, 99%, or 100% identity to the amino acid sequence of SEQ ID NO: 20 or 304.

As used throughout the present application, the term "protein" or "polypeptide" are used in their broadest sense to refer to a sequence of subunit amino acids. The proteins or polypeptides of the invention may comprise L-amino acids, D-amino acids (which are resistant to L-amino acid-specific proteases in vivo), or a combination of D- and L-amino acids. The proteins or polypeptides described herein may be chemically synthesized or recombinantly expressed.

In another aspect, the present invention provides recombinant nucleic acids encoding the recombinant polypeptides or polypeptide compositions of the present invention. The isolated nucleic acid sequence may comprise RNA or DNA. Such recombinant nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the recombinant polypeptides or polypeptide compositions of the invention.

In a further aspect, the present invention provides recombinant expression vectors comprising the recombinant nucleic acid of any embodiment or combination of embodiments of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited to plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In non-limiting embodiments, the expression vector may comprise a plasmid or a viral vector.

In another aspect, the present invention provides recombinant host cells that comprise the recombinant expression vectors disclosed herein, wherein the host cells can be either prokaryotic or eukaryotic, such as mammalian cells. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection or transduction. (See, for example, *Molecular Cloning: A Laboratory Manual* (Sambrook, et al., 1989, Cold Spring Harbor Laboratory Press; *Culture of Animal Cells: A Manual of Basic Technique*, $2^{nd}$ Ed. (R. I. Freshney. 1987. Liss, Inc. New York, N.Y.).

As will be understood by those of skill in the art, some components of the lipid-enveloped multimeric assemblies may be encoded on different recombinant expression vectors that are present in the recombinant host cells. In one embodiment, the one or more transmembrane proteins or membrane-anchored proteins may be encoded on a second recombinant expression vector in the recombinant host cell, operatively linked to a suitable control sequence. In various embodiments, the second recombinant expression vector encodes a protein selected from the group consisting of SEQ ID NOS: 307-315.

In another embodiment, a the recombinant host cell may comprise a third recombinant expression vector comprising a recombinant nucleic acid encoding cyclic GMP-AMP synthase (cGAS) protein (SEQ ID NO:328) operatively linked to a promoter. This embodiment is useful when the desired cargo is 2',3'-cyclic GMP-AMP (cGAMP), as described in detail in the examples that follow. In another embodiment, the third recombinant expression vector comprises a recombinant nucleic acid encoding a cargo operatively linked to a promoter. Such cargo can be any suitable cargo as disclosed herein, including but not limited to a polypeptide or polynucleotide selected from the group consisting of SEQ ID NOS:202-219.

A method of producing a polypeptide according to the invention is an additional part of the invention. The method comprises the steps of (a) culturing a recombinant host according to this aspect of the invention under conditions conducive to the expression of the polypeptide, and (b) optionally, recovering the expressed polypeptide.

In a further aspect, the invention provides methods for producing a multimeric assembly comprising a lipid bilayer enveloping the multimeric assembly, comprising culturing eukaryotic recombinant host cells of the invention (such as mammalian cells) under conditions suitable to promote expression of the encoded recombinant polypeptide or polypeptide composition, wherein expression of the encoded recombinant polypeptide or polypeptide composition in the eukaryotic host cell results in (a) production of the multimeric assembly, and (b) interaction of one or more of the M domains of the multimeric assembly with the lipid bilayer membrane of the eukaryotic host cell, and wherein attachment of the one or more M domains of the multimeric assembly to the lipid bilayer membrane of the eukaryotic host cell results in the multimeric assembly being enveloped by eukaryotic host-derived lipid bilayer membrane, followed by recruitment of the ESCRT machinery to the site of budding by the L domains of the multimeric assembly, which releases the enveloped multimeric assembly from the eukaryotic host cell by catalyzing membrane scission.

Any suitable eukaryotic host cell can be used, including but not limited to mammalian cells. Exemplary such host cells include Chinese hamster ovary (CHO) cells and human primary cells or established human cell lines such as HEK293 cells.

In this embodiment, the M domain chosen for use may be one that binds to the membrane of the eukaryotic host cell to be used for expression, and the L domain chosen for use may be one that binds to interacts directly or indirectly with protein subunits of the host cell ESCRT complex, or interacts with proteins of the host cell known to recruit the ESCRT complex of the host cell to sites of budding.

EXAMPLES

Computational Design of I3-01, a Self-Assembling Protein Icosahedron

The I3-01 polypeptide sequence (SEQ ID 20) was designed using the method of King et al. (Neil P King, William Sheffler, Michael R Sawaya, Breanna S Vollmar, John P Sumida, Ingemar André, Tamir Gonen, Todd O Yeates, David Baker (2012) Computational design of self-assembling protein nanomaterials with atomic level accuracy. Science 336:1171-1174; Neil P King, Jacob B Bale, William Sheffler, Dan E McNamara, Shane Gonen, Tamir Gonen, Todd O Yeates, David Baker (2014) Accurate design of co-assembling multi-component protein nanomaterials. Nature 510:103-108; U.S. Pat. No. 8,969,521; WO2014/124301). The structure of the trimeric 2-keto-3-deoxy-6-phosphogluconate (KDPG) aldolase from *Thermotoga maritima* (SEQ ID 21; PDB entry 1wa3) was used as the starting point for design in combination with a symmetry definition file suitable for modeling a 60-subunit icosahedral assembly constructed from trimeric building blocks. The designed polypeptide sequence was predicted to spontaneously assemble to a 60-subunit multimeric assembly with icosahedral symmetry when expressed recombinantly. The assembly process was predicted to be driven by the low-energy, inter-trimer protein-protein interface designed computationally (O interface), which comprises five mutations from the natural sequence (1wa3-wt; SEQ ID 21) in addition to several amino acids that remained unchanged from the natural sequence.

Recombinant Expression and Purification of I3-01

A synthetic gene encoding the designed protein I3-01 was constructed and cloned into a bacterial expression vector. *E. coli* cells expressing I3-01 were lysed, and the protein was purified by ammonium sulfate precipitation, heating, and size exclusion chromatography. The *E. coli* cells were resuspended in 25 mM Tris, 150 mM NaCl, pH 8.0 supplemented with 1 mM PMSF, 1 mg/mL DNase, and 1 mg/mL lysozyme and lysed by sonication. The lysates were clarified by centrifugation (20,000×g for 25 minutes at 4° C.) and protein was precipitated by the addition of ammonium sulfate to 60% saturation. The pellet was collected by centrifugation (20,000×g for 15 minutes at 25° C.) and resuspended in 25 mM Tris, 150 mM NaCl, pH 8.0. The solution was heated at 80° C. for 10 minutes, and insoluble material was pelleted by centrifugation (20,000×g for 15 minutes at 4° C.). The supernatant was concentrated using a centrifugal filtration device prior to size exclusion chromatography on an AKTA Pure system equipped with a Superose 6 10/300 column (GE Healthcare). Fractions containing pure protein in the assembled (icosahedral) state were collected and concentrated using a centrifugal filtration device.

Characterization of the Oligomerization State of I3-01

Figure 2:
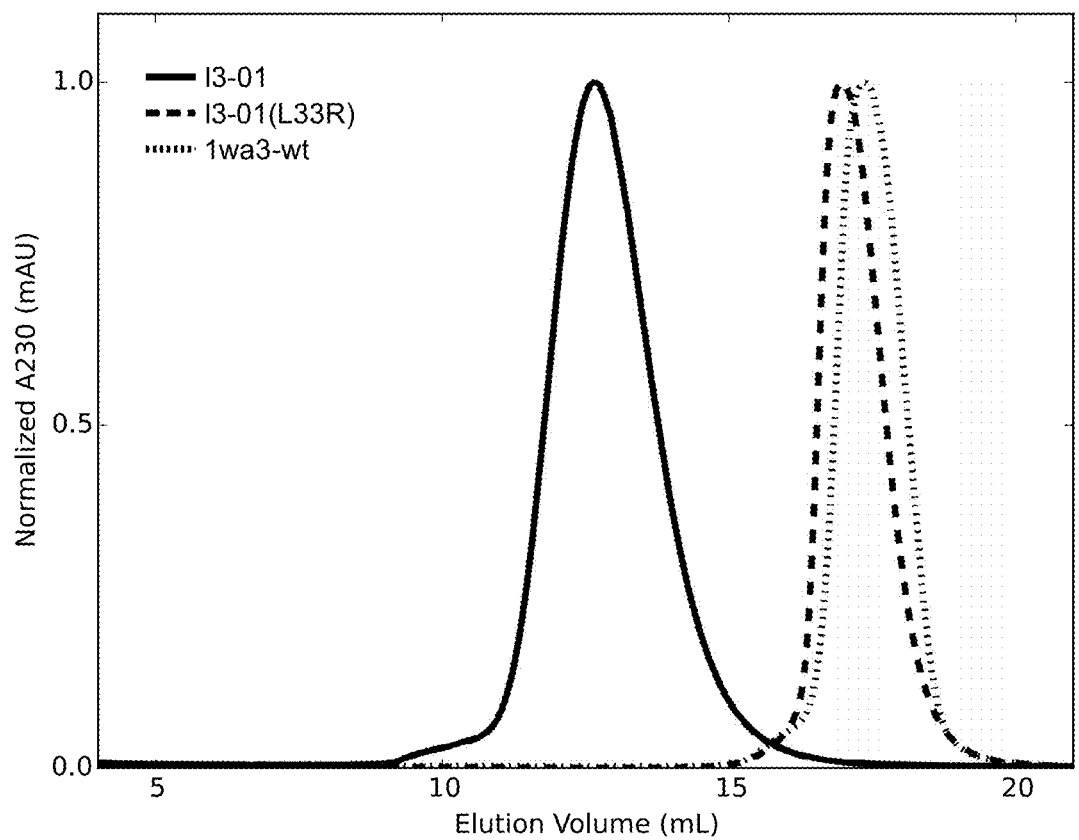
Figure 3:
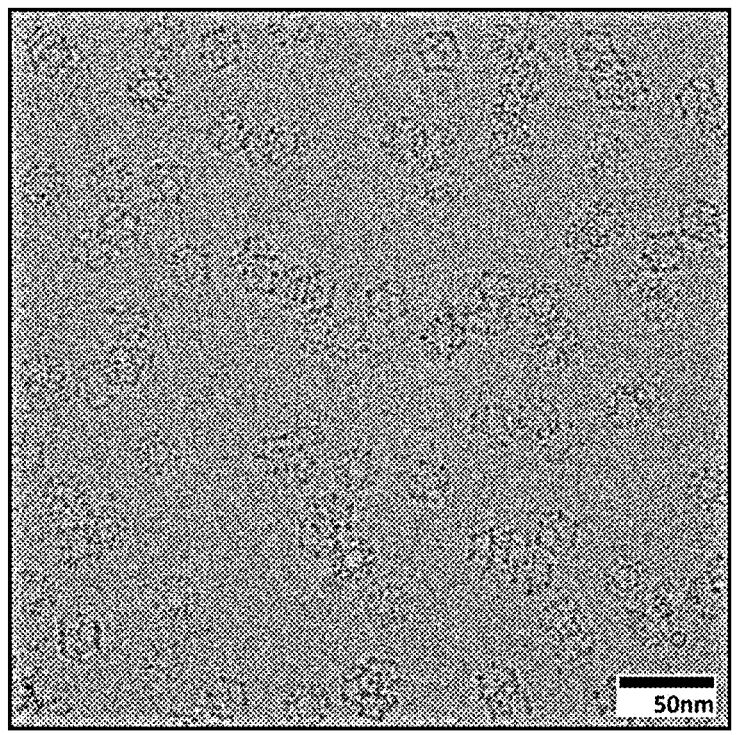
Figure 4:
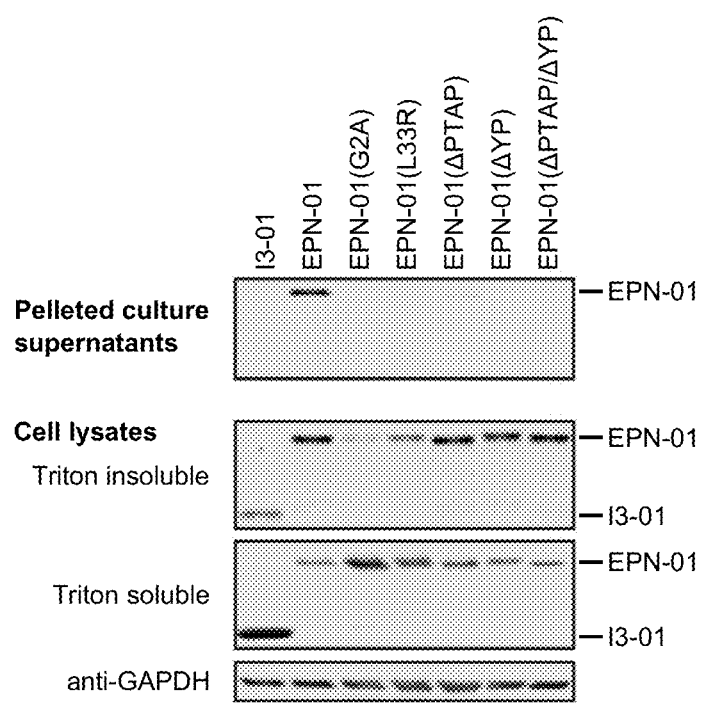

Purified I3-01 eluted from the Superose 6 column as a single peak with an apparent size of about 60 subunits. In contrast, 1wa3-wt as well as a variant of I3-01 in which the leucine at position 33 was mutated to arginine [I3-01 (L33R)] both eluted in the expected trimeric state (FIG. 2). The L33R mutation was predicted to disrupt the designed O interface in I3-01 by introducing steric bulk that could not be accommodated. The observation that this mutation indeed disrupted assembly of I3-01 indicated that the designed O interface drives assembly of the protein to the designed icosahedral oligomeric assembly. We also observed that I3-01 migrates more slowly than 1wa3-wt and I3-01(L33R) during non-denaturing (native) polyacrylamide gel electrophoresis (PAGE) of the three proteins, which provided additional support that I3-01 self-assembles to a higher-order oligomerization state. Finally, visualization of I3-01 by cryo-electron microscopy revealed monodisperse particles of the expected size and shape (FIG. 3), and class averages derived from the cryo-electron micrographs closely resembled projections calculated from the I3-01 computational design model, demonstrating that I3-01 assembles to the designed icosahedral multimeric assembly in solution.

Design of Enveloped Multimeric Assemblies

We hypothesized that the minimal requirements for efficient release from cells of multimeric protein assemblies enveloped in a lipid bilayer membrane were threefold. First, the multimeric protein assembly must interact with a cellular membrane bilayer. Second, the multimeric protein assembly must deform the membrane to form a bud structure by virtue of its interaction with the membrane and its multimerization through the interactions of its O interfaces. Third, the multimeric protein assembly must recruit cellular factors such as the ESCRT complexes to catalyze the fission of the membrane neck between the bud and the cell, thereby effecting release of the multimeric protein assembly from the cell in the form of an enveloped protein nanoparticle. Protein constructs for providing multimeric protein assemblies comprising functional elements that meet all three criteria will hereafter be referred to as enveloped multimeric assemblies (FIG. 1). As described below, the constructs comprise proteins comprising M domains that interact with a cellular membrane, O interfaces that drive assembly of the multimeric protein assemblies and therefore membrane deformation, and L domains that recruit cellular factors for catalyzing membrane fission. As the examples below demonstrate, a variety of M domains, O interfaces, and L domains can be used, as long as each domain or interface demonstrably performs its required function and protein subunit of each multimeric protein assembly comprises at least one O interface and one L domain, and each multimeric protein assembly comprises at least one M domain.

A first series of constructs for providing enveloped multimeric assemblies was designed using the I3-01 polypeptide to provide the O interface. In this series of constructs, a variety of M domains and L domains were genetically fused to the I3-01 sequence.

In one embodiment (SEQ ID 227; Myr-I3-01-myc-p6), the N-terminal six amino acids of the HIV Gag protein were fused to the N terminus of I3-01 via a flexible linker to provide an M domain and the p6 domain of the HIV Gag protein was fused to the C terminus of I3-01 to provide an L domain; the construct also includes a myc tag to facilitate specific detection of the protein using anti-myc antibodies.

In another embodiment (SEQ ID 228; Late2-4GS-I3-01-10GS-PH-flag), 22 residues of the Ebola VP40 protein encompassing the polypeptide motif PTAPPEY, which is known to recruit the ESCRT pathway to facilitate the budding and release of Ebola from host cells, were fused to the N terminus of I3-01 to provide an L domain and the pleckstrin homology (PH) domain of the rat phospholipase C-δ1 protein was fused to the C terminus of I3-01 to provide an M domain; the construct also includes a FLAG tag to facilitate specific detection of the protein using anti-FLAG antibodies.

Initial Identification of Enveloped Multimeric Assemblies Using the Budding Assay To quantify release of I3-01-derived enveloped multimeric assemblies from cells, HEK293T cells ($8\times10^5$/well) were seeded in 6 well plates 24 h prior to transfection. Cells were transfected with 2.5 μg of plasmid DNA expressing I3-01-based constructs using LIPOFECTAMINE® 2000 (Invitrogen) following the manufacturer's instructions. Cells and culture supernatants were harvested 24 h post transfection. Enveloped multimeric assemblies were collected from the culture supernatants by centrifugation through a 20% sucrose cushion for 90 min at 21,000×g at 4° C. Cells were lysed in cold lysis buffer (50 mM Tris pH 7.4, 150 mM NaCl, 1% Triton X-100, protease inhibitors) and lysates were cleared by centrifugation for 5 min, 16,000×g, 4° C. Triton-insoluble material was solubilized in 2× Laemmli sample buffer by boiling for 10 min. The Triton-soluble and insoluble cellular fractions as well as the pelleted enveloped multimeric assemblies boiled in 1× Laemmli sample buffer were separated by 12% SDS-PAGE gels, transferred onto PVDF membranes, and probed with antibodies against the myc and/or FLAG tags. The presence of I3-01-based proteins in the culture supernatants pelleted through a 20% sucrose cushion suggests release of the proteins in the form of enveloped multimeric assemblies. Quantities of myc-tagged I3-01-based proteins in each fraction were measured using a standard curve generated with known amounts of recombinant, non-enveloped Myr-I3-01-myc-p6 protein produced in *E. coli*. Bacteria have neither ESCRT nor N-myristoyltransferase, both necessary for the budding and release of Myr-I3-01-myc-p6 as an enveloped multimeric assembly, and therefore Myr-I3-01-myc-p6 produced in *E. coli* forms a non-enveloped icosahedral multimeric assembly that resembles I3-01 by size exclusion chromatography and negative stain electron microscopy.

Whereas Myr-I3-01-myc-p6 and Late2-4GS-I3-01-10GS-PH-flag were found in the pelleted culture supernatants, unmodified I3-01 was not detectable in the pelleted culture supernatant. This result indicated that Myr-I3-01-myc-p6 and Late2-4GS-I3-01-10GS-PH-flag were released from cells as enveloped multimeric assemblies due to the additional functional domains they comprise relative to unmodified I3-01. Typical release levels for Myr-I3-01-p6 were roughly 100 $\mu g/10^6$ cells.

Although Myr-I3-01-myc-p6 was designed to comprise a myristoylation motif (the 6 N-terminal amino acids of HIV Gag) to function as the M domain on each protein subunit in the multimeric assembly, during the course of our characterization of the protein we discovered that the M domain was only present on about half of the protein subunits in each multimeric assembly. Myr-I3-01-myc-p6 migrates as two distinct but closely spaced bands (a "doublet") of equal intensity on SDS-PAGE or Western blots. Upon mutation of a methionine residue at the N terminal end of the I3-010 interface to isoleucine, the new protein (EPN-01) migrated as a single band. This result demonstrates that the two bands observed in the Myr-I3-01-myc-p6 doublet were in fact two different molecules, one the full-length protein and one a truncated version of the same protein that lacked the N-terminal M domain and linker (SEQ ID NO: 317) due to the initiation of translation by the ribosome at the internal start codon. EPN-01—which bears the N-terminal M domain and linker on each subunit of the multimeric assembly—and Myr-I3-01-myc-p6 behave identically in terms of the ability to bud and be released from cells, package cargoes, be pseudotyped with viral envelope proteins, deliver cargoes to the cytoplasm of recipient cells, and appear to be indistinguishable structurally. This result demonstrates that not every subunit in a multimeric assembly needs to comprise an M domain, so long as the plurality of M domains in the multimeric assembly are adequate to drive association with the membrane and/or result in deformation of the lipid bilayer upon multimerization.

The budding and release of several mutants of EPN-01 were also evaluated using the budding assay described above in order to test the hypothesis that all three functions—membrane binding, multimerization, and recruitment of host factors for membrane scission—are necessary to effect efficient budding and release of enveloped multimeric assemblies. A G2A mutant of EPN-01 [Myr-I3-01-myc-p6 (G2A)] that eliminates the ability of the M domain to be myristoylated (Freed E O, Orenstein J M, Buckler-White A J, Martin M A (1994) Single amino acid changes in the human immunodeficiency virus type 1 matrix protein block virus particle production. *J. Virol.* 68:5311-20) was used to test the requirement for membrane interaction. A variant containing the L33R mutation described above [EPN-01 (L33R)] was used to test the requirement for higher-order multimerization to enhance membrane binding and/or induce membrane deformation. Three variants were made to test the requirement for recruitment of ESCRT to catalyze membrane fission. The p6 domain of the HIV Gag protein is known to contain at least two linear polypeptide motifs, PTAP (SEQ ID NO: 167) and YPLTSL (SEQ ID NO: 169), that respectively interact with Tsg101 and ALIX, proteins involved in the recruitment of proteins in the ESCRT pathway to the site of budding (McCullough J, Colf La., Sundquist Wis. (2013) Membrane Fission Reactions of the Mammalian ESCRT Pathway. Annu. Rev. Biochem. 82:663-92; Bieniasz P D (2006) Late budding domains and host proteins involved in enveloped virus release. Virology 344:55-63). Therefore, variants in which the polypeptide motif PTAP (SEQ ID NO:167) was mutated to AAAA (SEQ ID NO: 316) [EPN-01(ΔPTAP)], the YP dipeptide of the polypeptide motif YPLTSL (SEQ ID NO: 169) was mutated to AA [EPN-01(ΔYP)], or both motifs were simultaneously mutated [EPN-01(ΔPTAP/ΔYP)] were used to test the requirement for the recruitment of ESCRT to catalyze membrane fission. Mutation of these motifs in various retroviruses has been previously shown to disrupt ESCRT-dependent virus budding and release (Bieniasz P D (2006) Late budding domains and host proteins involved in enveloped virus release. Virology 344:55-63, and references cited therein). Results of the budding assay with these variants of EPN-01 confirmed that the presence of all three functional elements is required for efficient budding and release of enveloped multimeric assemblies (FIG. 4). EPN-01(G2A) and EPN-01(L33R) were both undetectable in the pelleted culture supernatants, indicating that the functions of membrane binding and multimerization provided by the M domain and O interface are necessary for efficient budding and release. The release of EPN-1(ΔPTAP) from cells was significantly reduced, the release of EPN-01(ΔYP) was more significantly reduced, and the release of EPN-01(ΔPTAP/ΔYP) was undetectable, demonstrating that recruitment of ESCRT by an L domain comprising one or more polypeptide motifs known to interact directly or indirectly with proteins of the ESCRT pathway is also necessary for budding and release. Together, these results confirm the requirement for all three functional elements—membrane binding, multimerization, and recruitment of host factors for membrane scission—for efficient budding and release of enveloped multimeric assemblies.

(truncated variant of Myr-I3-01-myc-p6 lacking N-terminal M domain and linker)
SEQ ID 317
MEELFKKHKIVAVLRANSVEEAKKKALAVFLGGVHLIEITFTVPDADTVI

KELSFLKEMGAIIGAGTVTSVEQCRKAVESGAEFIVSPHLDEEISQFCKE

KGVFYMPGVMTPTELVKAMKLGHTILKLFPGEVVGPQFVKAMKGPFPNVK

FVPTGGVNLDNVCEWFKAGVLAVGVGSALVKGTPVEVAEKAKAFVEKIRG

CTE(QKLISEEDL)QSRPEPTAPPEESFRSGVETTTPPQKQEPIDKELYP

LTSLRSLFGNDPSSQ.

Visualization of Myr-I3-01-Myc-p6 and EPN-01 by Electron Cryo-Tomography (ECT)

Extracellular vesicles were purified from culture supernatants of HEK293T cells ($2 \times 10^6$ per 10 cm dish, up to 36 dishes seeded 24 h prior to transfection) that were transiently transfected with a plasmid encoding Myr-I3-01-myc-p6 or EPN-01 using $CaPO_4$. Transfected cells were incubated overnight before media was replaced with exosome production media (D-MEM supplemented with 10% FBS, depleted from contaminating extracellular particles by centrifugation overnight at 100,000×g at 4° C. and subsequently filtered through a 0.22 μm filter) and cells were grown for another 24 h. Extracellular vesicles released from cells were purified by a series of filtering and centrifugation steps (adapted from (Théry C, Clayton A, Amigorena S, Raposo G (2006) Isolation and Characterization of Exosomes from Cell and Culture Supernatants and Biological Fluids. Current Protocols in Cell Biology 3.22.1-3.22.19)). Cell debris was removed by centrifugation of the supernatant at 1,000×g for 5 min followed by filtering through a 0.22 μm filter. Extracellular vesicles were collected by centrifugation at 100,000×g in a SW32Ti (BeckmanCoulter) at 4° C. for at least 1 h. Pellets were resuspended in PBS and pooled in one tube (SW41 rotor, BeckmanCoulter). PBS was added to fill the tube completely and vesicles were collected by centrifugation at 100,000×g at 4° C. for at least 1 h. Pellets were resuspended in 1 ml of PBS and finally concentrated by centrifugation 100,000×g at 4° C. for at least 1 h in a tabletop ultracentrifuge using a TLS-55 rotor.

To prepare samples for ECT, 3 μl of purified vesicles in PBS were mixed with 3 μl of BSA coated gold fiducials (10 nm size, Electron Microscopy Sciences). 3.5 μl of the suspension was applied to a glow discharged 2/2 holey carbon coated EM grid (Quantifoil), which was previously placed in the environmental chamber of a Mark Vitrobot (FEI) maintained at 4° C., 80% relative humidity. Excess liquid was blotted for 7.5 s (0 mm offset) from the grids before plunge freezing in liquid ethane. Cryo-grids were then imaged in a 200 kV Tecnai TF20 microscope equipped with a K2 summit direct electron detector (Gatan). Tilt series were recorded bidirectionally starting from 0° to ±60° using a 1° step size at a magnification of 22,500× and a defocus of ~8 μm (total dose per specimen was ~150e$^-$/Å). Image alignment and tomogram reconstructions were done using the IMOD software package (Kremer J. R., D. N. Mastronarde and J. R. McIntosh (1996) Computer visualization of three-dimensional image data using IMOD. J. Struct. Biol. 116:71-76).

Multiple icosahedral structures 25 nm in diameter incorporated within larger membrane envelopes were observed in the pelleted culture supernatant from cells transfected with either Myr-I3-01-myc-p6 or EPN-01 (FIG. 5). The assemblies appear to be located primarily at the membrane of the vesicles, suggesting that they interact directly with the membrane via the M domain. Together with the results from the budding assay, these observations indicate that multimeric assemblies of Myr-I3-01-myc-p6 and EPN-01 are incorporated within large membrane-bounded vesicles that contain multiple multimeric assemblies.

Enveloped Multimeric Assemblies are Highly Modular

After our initial success in designing enveloped multimeric assemblies, we screened a large set of candidate enveloped multimeric assemblies (51 different constructs) to explore the modularity and generality of the platform. The first 48 EPN constructs all use I3-01 as the self-assembly or oligomerization (O) domain, but both the identities and locations of the membrane interaction (M) domain and the ESCRT recruitment (L) domain vary among the constructs. Various classes of membrane interaction domains were included in the set: myristoylation motifs, N-terminal palmitoylation motifs, C-terminal palmitoylation motifs, and four different types of globular protein domains that bind to various lipid polar head groups (PH, PX, C1, and C2 domains). ESCRT recruitment domains used in the set vary from intact viral late domains (e.g., the p6 domain of HIV Gag) to peptide motifs as small as four amino acids known to play a key role in the protein-protein interactions that recruit ESCRT to sites of virus budding in vivo (e.g., PTAP). We also included in the set several constructs in which the L domain was omitted or mutations were made to inhibit membrane interactions in the M domain; these negative control constructs were not expected to bud and be released from cells as enveloped multimeric assemblies.

To facilitate the screening of the 51 constructs, we developed two biochemical assays that provide rapid assessments of both the yield of a given enveloped multimeric assembly as well as the integrity of the enveloped multimeric assembly membrane envelope. Both are based on the principle that an intact membrane envelope will prevent access of an added molecule to the protein subunits of the enveloped multimeric assembly, while the addition of detergent will enable access by disrupting the integrity of the membrane. In the first assay, trypsin was incubated with enveloped multimeric assemblies in the presence or absence of detergent and proteolysis of the protein subunits of the enveloped multimeric assembly was evaluated by Western blot. Lack of proteolysis in the sample without detergent indicated that the protein subunits of the enveloped multimeric assembly were not accessible to trypsin. Proteolysis in the presence of trypsin and detergent indicated that the protein subunits of the enveloped multimeric assembly are accessible to trypsin. Therefore, detergent-dependent proteolysis demonstrated that the membrane envelope was intact in the absence of detergent and responsible for preventing trypsin access. The second assay made use of a previously described spectrophotometric enzyme assay (Griffiths J S, Wymer N J, Njolito E, Niranjanakumari S, Fierke Calif., Toone E J (2002), Bioorganic & Medicinal Chemistry 10:545-50). The assay was specific for enveloped multimeric assemblies comprising I3-01 as the oligomerization (O) domain because it takes advantage of the fact that I3-01 was designed using a trimeric KDPG aldolase as the scaffold protein and the enzymatic activity is retained in the icosahedral multimeric assembly. Because the substrate KDPG is unable to cross lipid membranes, detergent-dependent enzymatic activity provided another readout for membrane integrity.

The day of transfection, 1 mL of HEK293F (Invitrogen) cells were plated at $2.5 \times 10^6$ cells/mL in 12-well plates. Cells were transfected with 1 μg of plasmid DNA encoding enveloped multimeric assembly constructs using EXPI-FECTAMINE® 293 Reagent (Invitrogen) following the manufacturer's instructions. Cells and culture supernatants were harvested 40-48 h post transfection by centrifugation at 1000×g for 5 min at 4° C. to pellet the cells. Culture supernatants were then filtered through 0.45 μm filters (Millipore) and enveloped multimeric assemblies were collected by centrifugation through a 20% sucrose cushion for 2 h at 21,000×g at 4° C. Pelleted enveloped multimeric assemblies were resuspended in phosphate buffered saline (PBS). For the protease assay, aliquots of the resuspended enveloped multimeric assemblies were incubated for 30 min at room temperature with Trypsin-EDTA (Gibco) with the trypsin at a final concentration of 50 μg/mL in the presence or absence of 1% Triton X-100 (Sigma). After 30 min, freshly prepared phenylmethanesulfonyl fluoride (PMSF) trypsin inhibitor was added to trypsin-containing samples to a final concentration of 1 mM. Samples of the cell pellets, resuspended enveloped multimeric assemblies, enveloped multimeric assemblies+trypsin, and enveloped multimeric assemblies+trypsin+triton were mixed with Laemmli Sample Buffer, boiled for 10 minutes at 95° C., and analyzed by Western blot using an anti-myc primary antibody (9B11, Cell Signaling Technology). The enzyme assay was performed in 25 mM HEPES pH 7.0, 20 mM NaCl in the presence of NADH (0.1 mM), L-lactate dehydrogenase (0.11 U/μL), and 2-keto-3-deoxy-6-phosphogluconate (KDPG, 1 mM) at 25° C. Aliquots of the resuspended enveloped multimeric assemblies were added to reaction mixtures in the presence or absence of 1% Triton X-100 and enzyme activity was measured by monitoring the loss of absorbance at 339 nm due to oxidation of the NADH cofactor.

Screening of the first 48 enveloped multimeric assemblies that use I3-01 as the oligomerization (0) domain using the protease and enzyme activity assays described above demonstrated that 22 of the enveloped multimeric assemblies were released from cells in enveloped form with intact membrane envelopes (Table 3). Another 9 enveloped multimeric assemblies were released into the cell supernatant but did not appear to have fully intact membrane envelopes (that is, access of trypsin and/or KDPG to the subunits of the multimeric assemblies was detergent-independent); the reason for this is currently unclear. 17 out of the first 48 enveloped multimeric assembly constructs failed to be released into the cell supernatant; of these, 5 were designed as negative controls and were intended to not be released. The three constructs that use 03-33 as the oligomerization (0) domain were also evaluated using the protease assay described above. One (EPN-49) was a negative control not intended to bud and be released from cells; one (EPN-50) was not released from cells; and one (EPN-51) was released from cells, pelleted through a 20% sucrose cushion, and underwent detergent-dependent proteolysis by trypsin, demonstrating that it formed an enveloped multimeric assembly of the invention (FIG. 6). The 23 successful enveloped multimeric assemblies we have identified clearly demonstrate that the enveloped multimeric assemblies of the invention are general and highly modular in the sense that a wide variety of functional groups (M domains, O interfaces, and L domains) can be used to readily design new enveloped multimeric assemblies. Additionally, as described above, the inventors have provided assaysthatcanbeusedtoidentifytheenvelopedmultimericassembliesofthe invention.

TABLE 3

Summary of results from enzyme assay analyzing Myr-I3-01-myc-p6, I3-01, and EPNs 01-48.

| Construct | Enzyme activity | Conclusion |
| --- | --- | --- |
| Myr-I3-01-myc-p6 | Detergent-dependent | Released from cells as an enveloped multimeric assembly of the invention |
| I3-01 (negative control) | None | Not released from cells |
| EPN-01 | Detergent-dependent | Released from cells as an enveloped multimeric assembly of the invention |
| EPN-02 (negative control) | None | Not released from cells |
| EPN-03 | Detergent-dependent | Released from cells as an enveloped multimeric assembly of the invention |
| EPN-04 | None | Not released from cells |
| EPN-05 | None | Not released from cells |
| EPN-06 | None | Not released from cells |
| EPN-07 | Detergent-dependent | Released from cells as an enveloped multimeric assembly of the invention |
| EPN-08 | Detergent-dependent | Released from cells as an enveloped multimeric assembly of the invention |
| EPN-09 | Detergent-dependent | Released from cells as an enveloped multimeric assembly of the invention |
| EPN-10 | Detergent-independent | Released from cells without an intact membrane |
| EPN-11 | Detergent-dependent | Released from cells as an enveloped multimeric assembly of the invention |
| EPN-12 | None | Not released from cells |
| EPN-13 | Detergent-independent | Released from cells without an intact membrane |
| EPN-14 | Detergent-independent | Released from cells without an intact membrane |
| EPN-15 | None | Not released from cells |
| EPN-16 | None | Not released from cells |
| EPN-17 (negative control) | None | Not released from cells |
| EPN-18 | Detergent-dependent | Released from cells as an enveloped multimeric assembly of the invention |
| EPN-19 | Detergent-independent | Released from cells without an intact membrane |
| EPN-20 | Detergent-dependent | Released from cells as an enveloped multimeric assembly of the invention |
| EPN-21 | Detergent-independent | Released from cells without an intact membrane |
| EPN-22 | Detergent-independent | Released from cells without an intact membrane |
| EPN-23 | Detergent-dependent | Released from cells as an enveloped multimeric assembly of the invention |
| EPN-24 | Detergent-dependent | Released from cells as an enveloped multimeric assembly of the invention |
| EPN-25 | Detergent-dependent | Released from cells as an enveloped multimeric assembly of the invention |
| EPN-26 | Detergent-independent | Released from cells without an intact membrane |
| EPN-27 (negative control) | None | Not released from cells |

TABLE 3-continued

Summary of results from enzyme assay analyzing Myr-I3-01-myc-p6, I3-01, and EPNs 01-48.

| Construct | Enzyme activity | Conclusion |
| --- | --- | --- |
| EPN-28 | None | Not released from cells |
| EPN-29 | Detergent-independent | Released from cells without an intact membrane |
| EPN-30 (negative control) | None | Not released from cells |
| EPN-31 | None | Not released from cells |
| EPN-32 | None | Not released from cells |
| EPN-33 (negative control) | None | Not released from cells |
| EPN-34 | None | Not released from cells |
| EPN-35 | Detergent-independent | Released from cells without an intact membrane |
| EPN-36 | Detergent-dependent | Released from cells as an enveloped multimeric assembly of the invention |
| EPN-37 | Detergent-dependent | Released from cells as an enveloped multimeric assembly of the invention |
| EPN-38 | Detergent-dependent | Released from cells as an enveloped multimeric assembly of the invention |
| EPN-39 | Detergent-dependent | Released from cells as an enveloped multimeric assembly of the invention |
| EPN-40 | None | Not released from cells |
| EPN-41 | Detergent-dependent | Released from cells as an enveloped multimeric assembly of the invention |
| EPN-42 | Detergent-dependent | Released from cells as an enveloped multimeric assembly of the invention |
| EPN-43 | Detergent-dependent | Released from cells as an enveloped multimeric assembly of the invention |
| EPN-44 | Detergent-dependent | Released from cells as an enveloped multimeric assembly of the invention |
| EPN-45 | None | Not released from cells |
| EPN-46 | Detergent-dependent | Released from cells as an enveloped multimeric assembly of the invention |
| EPN-47 | Detergent-dependent | Released from cells as an enveloped multimeric assembly of the invention |
| EPN-48 | Detergent-dependent | Released from cells as an enveloped multimeric assembly of the invention |

BlaM Protein Delivery Assay

The ability of the enveloped multimeric assemblies to package and deliver a protein cargo to the cytoplasm of recipient cells was evaluated using a modified version of the beta-lactamase (BlaM) delivery assay originally developed by Cavrois et al. to measure the membrane fusion event effected by the HIV envelope protein (Cavrois M, de Naronha C, Greene W C (2002), Nat. Biotech. 20:1151-4). In the original version of the assay, a chimeric protein in which BlaM is fused to the HIV Vpr protein (SEQ ID 203; BlaM-Vpr) is co-expressed with DNA encoding HIV virions or virus-like particles in mammalian cells. A non-covalent, protein-protein interaction between Vpr and the p6 domain of the HIV Gag protein results in incorporation of the BlaM-Vpr fusion protein in enveloped virions or virus-like particles that bud and are released from the cell surface. The BlaM-Vpr-containing enveloped virions or virus-like particles can then be added to recipient cells, upon which the envelope protein binds to its target receptor, facilitating cellular uptake and fusion of the viral or VLP membrane with cellular membranes, thereby releasing the virion with its BlaM-Vpr cargo into the cytosol. The recipient cells are treated with the fluorescent dye CCF2-AM, which contains two fluorophores that make an efficient FRET pair connected by a beta-lactam ring. If BlaM (or, in this case, BlaM-Vpr) is present in the cytosol of the cells, it will cleave the CCF2-AM substrate, resulting in a change of the fluorescence emission maximum from 520 nm to 447 nm. This change in the fluorescence signal can be detected using a variety of instruments capable of detecting fluorescent signals, including but not limited to spectrophotometers, fluorimeters, plate readers, and flow cytometers.

In our modified version of the BlaM delivery assay, enveloped Myr-I3-01-myc-p6 or EPN-01 multimeric assemblies replaced the HIV virions or virus-like particles in packaging and facilitating the entry of BlaM-Vpr into the recipient cells. Although a wide variety of potential packaging moieties could be used to package BlaM into enveloped multimeric assemblies, the p6 domain of Myr-I3-01-myc-p6 (SEQ ID 186) in combination with the Vpr domain of the BlaM-Vpr fusion protein (SEQ ID 203) served as a convenient and effective packaging moiety. In other embodiments, other polypeptide sequences known to interact with a cargo of interest could be used to package the cargo. In other embodiments, packaging moieties selected from the set disclosed herein and in the attached appendices could be used to package a cargo of interest. In addition, because the Myr-I3-01-myc-p6 polypeptide does not comprise a polypeptide domain capable of facilitating cell entry and membrane fusion, we pseudotyped the enveloped multimeric assemblies with a viral fusion protein by co-expression in the producer cells. A wide variety of viral fusion proteins could be used to facilitate cell entry and membrane fusion. In one embodiment, the glycoprotein from vesicular stomatitis virus (VSV-G) was incorporated into the membrane envelope of Myr-I3-01-myc-p6 enveloped multimeric assemblies. In other embodiments, a protein selected from the set of known viral envelope proteins and sequences disclosed herein and in the attached appendices could be used to facilitate cell entry and membrane fusion.

Myr-I3-01-myc-p6 enveloped multimeric assemblies packaging the BlaM-Vpr fusion protein and pseudotyped with VSV-G were produced by co-transfecting HEK293T cells ($5 \times 10^6$ cells in a 10 cm dish seeded 24 h prior to transfection) with 9 μg of pCMV-Myr-I3-01-myc-p6 DNA, 5 μg of myc-BlaM-Vpr expression construct (derived from pMM310) (Cavrois M, de Naronha C, Greene W C (2002), Nat. Biotech. 20:1151-4; Tobiume, M., et al., J Virol, 2003. 77(19): p. 10645-50), and 1 μg VSV-G-myc expression construct (derived from pCMV-VSV-G) (Yee, J. K., T. Friedmann, and J. C. Burns, Methods in cell biology, 1994. 43 Pt A: p. 99-112; Olsen, J. C., Gene transfer vectors derived from equine infectious anemia virus. Gene Ther, 1998. 5(11): p. 1481-7) using LIPOFECTAMINE® 2000 (Invitrogen). Enveloped multimeric assemblies were harvested by centrifugation though a 20% sucrose cushion (24,000 rpm in a SW41Ti rotor [BeckmanCoulter], 2 h, 4° C.) 24-36 h post transfection. The amounts of the Myr-I3-01-myc-p6, BlaM-Vpr, and VSV-G proteins incorporated into the enveloped multimeric assemblies were quantified by Western blotting.

For the BlaM delivery assay, either $2 \times 10^4$ cells/well were seeded in a 96 well plate or $1 \times 10^5$ cells were seeded in a 24 well plate. 24 h later, a serial dilution of standardized quantities of enveloped nanoparticles were added to the cells and incubated for 2 h at 37° C. and 5% $CO_2$. After two hours, enveloped multimeric assembly-containing supernatants were replaced by CCF2-AM-labelling media prepared according to the manufacturer's instructions (Invitrogen).

Cells were labeled for 16 h at 13° C. and assayed for a change in fluorescence emission spectrum from green (520 nm) to blue (447 nm) by flow cytometry (FACSCanto, BD Biosciences).

The BlaM delivery assay was performed using Myr-I3-01-myc-p6 enveloped multimeric assemblies packaging BlaM-Vpr and pseudotyped with VSV-G (FIG. 7). The incorporation of Myr-I3-01-myc-p6, BlaM-Vpr, and VSV-G in the enveloped multimeric assemblies was confirmed by Western blotting (FIG. 8). Replacing Myr-I3-01-myc-p6 with I3-01, which lacks the membrane interaction and ESCRT recruitment domains required for budding and release as an enveloped multimeric assembly, resulted in no VSV-G or BlaM-Vpr in the pelleted culture supernatants. Recipient cells treated with increasing amounts of Myr-I3-01-myc-p6 enveloped multimeric assemblies packaging BlaM-Vpr and pseudotyped with VSV-G showed a dose-dependent increase in the number of BlaM-positive cells (FIG. 9). In contrast, significant numbers of BlaM-positive cells were not observed for enveloped multimeric assemblies that were either: 1) pseudotyped with a mutant VSV-G incapable of membrane fusion [VSV-G(P127D) (SEQ ID NO: 307)] or lacked significant levels of packaged BlaM-Vpr owing to the use of a Myr-I3-01-myc-p6 mutant that disrupted the non-covalent interface between p6 and Vpr [Myr-I3-01-myc-p6(LF$_{45}$AA) (SEQ ID NO: 318)]. Together, these results demonstrate that Myr-I3-01-myc-p6 enveloped multimeric assemblies that packaged BlaM-Vpr and were pseudotyped with VSV-G delivered the BlaM-Vpr protein to the cytoplasm of the recipient cells via VSV-G-mediated membrane fusion.

```
(Myr-I3-01-myc-p6(LF45AA))
                                                    SEQ ID 318
(M)GARASGSKSGSGSDSGSKMEELFKKHKIVAVLRANSVEEAKKKALAVF

LGGVHLIEITFTVPDADTVIKELSFLKEMGAIIGAGTVTSVEQCRKAVESG

AEFIVSPHLDEEISQFCKEKGVFYMPGVMTPTELVKAMKLGHTILKLFPGE

VVGPQFVKAMKGPFPNVKFVPTGGVNLDNVCEWFKAGVLAVGVGSALVKGT

PVEVAEKAKAFVEKIRGCTE(QKLISEEDL)QSRPEPTAPPEESFRSGVET

TTPPQKQEPIDKELYPLTSLRSAAGNDPSSQ
```

Packaging mRNA Cargoes into Enveloped Multimeric Assemblies

We designed and evaluated a series of constructs intended to package messenger RNA (mRNA) cargoes within the membrane envelope of the enveloped multimeric assemblies of the invention. For each of the four mRNA packaging moieties disclosed herein (SEQ IDs 198, 199, 200, 201), four constructs were made—direct genetic fusions to either EPN-01-posT1 (SEQ ID 229) or EPN-01 (SEQ ID 230), and a "frameshift" variant of each fusion in which the packaging domain is expected to be included in only a fraction of the protein molecules produced owing to the presence of a frameshift element in the gene (SEQ IDs 254, 255, 256, 257, 258, 259, 260, 261, 262, 263, 264, 265, 266, 267, 268, 269). The frameshift element, located in the linker between EPN-01 and the packaging domain, was derived from HIV Gag-Pol and causes the ribosome to undergo a −1 frameshift during roughly 5-10% of its encounters with the frameshift element during mRNA translation (Biswas P, Jiang X, Pacchia A L, Dougherty J P, Peltz S W (2004), *J. Virol.* 78:2082-7). The frameshift sequences were designed such that a successful frameshift would result in translation of the RNA packaging moiety, so that 5-10% of the protein subunits would be expected to comprise the packaging moiety as a genetic fusion. The four packaging moieties tested were all polypeptide motifs or domains that have been shown to bind preferentially to a specific RNA recognition sequence (SEQ IDs 204, 205, 206, 207; Gosser Y, Hermann T, Majumdar A, Hu W, Frederick R, Jiang F, Xu W, Patel D J (2001), Nat. Struct. Biol. 8:146-50; Oubridge C, Ito N, Evans P R, Teo C H, Nagai K (1994), Nature 372:432-8; De Guzman R N, Wu Z R, Stalling C C, Pappalardo L, Borer P N, Summers M F (1998), Science 279:384-8; Puglisi J D, Chen L, Blanchard S, Frankel A D (1995), Science 270: 1200-3). We also designed expression plasmids encoding mRNA cargo molecules (SEQ IDs 208, 209, 210, 211, 212, 213, 214, 215, 216, 217, 218, 219) that contained the corresponding recognition sequences both upstream (5') and downstream (3') of a reporter construct [either beta lactamase (BlaM) or GFP]. Upon co-expression of a multimeric assembly bearing a packaging moiety and the mRNA cargo bearing the cognate recognition sequence, the interaction between the packaging moiety and the recognition sequence should recruit the mRNA cargo to the multimeric assembly, resulting in its packaging within the membrane envelope of the enveloped multimeric assembly. We used reverse transcription quantitative polymerase chain reaction (RT-qPCR) to detect and determine relative concentrations of packaged mRNA cargoes.

Plasmids encoding the packaging moiety-bearing proteins and the mRNA cargoes were co-transfected into $1.25 \times 10^8$ HEK293F cells using EXPIFECTAMINE® (Invitrogen) according to the manufacturer's instructions. 40 hours after transfection, cells were pelleted by centrifugation at 1500×g for 5 min, and enveloped multimeric assemblies were purified from the supernatant by filtration through a 0.45 μm filter and pelleting through a 20% sucrose cushion as described above. The enveloped multimeric assemblies were resuspended in phosphate buffered saline (PBS). In some experiments, the enveloped multimeric assemblies were treated with RNase A, Triton X-100, or both prior to detection of packaged mRNA by RT-qPCR. Relative RNA levels were analyzed by RT-qPCR as follows. RNA was extracted from enveloped multimeric assemblies by mixing 100 μL of enveloped multimeric assemblies with 500 μL Trizol and freezing overnight. The next day, 100 μL of chloroform was added to the thawed sample and the tube was shaken vigorously before centrifugation at 20,000×g for 10 minutes at 4° C. Next, 200 μL of aqueous phase was mixed with 200 μL of 100% ethanol and purified using a Qiagen RNEASY® kit according to the manufacturer's protocols. The purified RNA was eluted in 45 μL distilled water (dH$_2$O) and treated with 5 μL of 10× Turbo DNase buffer and 1 μL of Turbo DNase at 37° C. for 20 minutes. DNase was then removed by purifying the RNA with Ampure RNAclean XP beads according to the manufacturer's protocols and eluting in 30 μL dH$_2$O. A reverse transcription primer compatible with all mRNA cargoes tested (CATACTGTTGGTTGCTAGGC (SEQ ID NO: 319)) was annealed to the purified RNA by incubation of the following reaction at 65° C. for 5 minutes: 2 μL RNA, 1 μL reverse transcription primer (unless otherwise noted, all primer stock concentrations were 10 μM), 6 μL dH$_2$O, 0.5 μL 0.1 M DTT, and 0.5 μL SUPERase-In RNase Inhibitor. For the detection of mitochondrial RNA, the reverse transcription primer was substituted with primers specific to cytochrome c oxidase subunit I (GCTGTGACGATAACGTTGTAGATG (SEQ ID NO: 320)) or cytochrome c oxidase subunit II (GGACGATGGGCATGAAACTG (SEQ ID NO: 321)). Reverse transcription was performed with the following reaction using a THERMOSCRIPT® Reverse Transcriptase kit (ThermoFisher Scientific): 5 µL of hybridization reaction, 2 µL cDNA synthesis buffer, 0.5 µL 0.1 M DTT, 0.5 µL SUPERASE®-In RNase Inhibitor, 1 µL 10 mM dNTPs, and 1 µL THERMOSCRIPT® Reverse Transcriptase. Negative controls were also performed in which the reverse transcriptase was replaced with dH$_2$O. The reverse transcription reaction was performed at 52° C. for 1 hour followed by heat inactivation at 80° C. for 5 minutes. The crude cDNA was then used as template in a qPCR reaction: 5 µL 2× Kapa HIFI HOTSTART® READY MIX®, 0.5 µL SYBR green, 0.5 µL forward primer TAGGATTACTGCTCGGTGAC (SEQ ID NO: 322), 0.5 µL reverse primer CCAAATAGGATGTGTGCGAC (SEQ ID NO: 323), 2.5 µL dH2O, and 1 µL cDNA. For amplification of mitochondrial cDNAs, the primers were substituted with primers specific to cytochrome c oxidase subunit I (forward: CCACAAAGACATTGGAACACTATACC (SEQ ID NO: 324); reverse: GCTGTGACGATAACGTTGTAGATG (SEQ ID NO: 325)) or cytochrome c oxidase subunit II (forward: CCTTATCTGCTTCCTAGTCCTGTATG (SEQ ID NO: 326); reverse: GGACGATGGGCATGAAACTG (SEQ ID NO: 327)). The thermocycler program was 3 minutes at 95° C. followed by 29 cycles of 20 seconds at 98° C., 15 seconds at 64° C., 90 seconds at 72° C., and the SYBR® green signal was then read.

Analysis of enveloped multimeric assemblies bearing the nucleic acid packaging domains described herein by RT-qPCR revealed the presence of packaged mRNA cargoes within the membrane envelopes of the enveloped multimeric assemblies. The enveloped multimeric assemblies based on EPN-01 in which the packaging moieties were included in 5-10% of the protein subunits due to the frameshift element yielded lower levels of mRNA cargo incorporation than those in which the packaging moiety was fused directly to EPN-01, suggesting that higher numbers of packaging moieties assist in the packaging of more mRNA cargoes. In contrast, the direct fusion and the frameshift constructs based on EPN-01-posT1 yielded similarly high levels of mRNA cargo incorporation, suggesting that the high number of positively charged residues on the interiors of the multimeric assemblies was able to drive packaging of the mRNA cargoes irrespective of the number of copies of the packaging moiety.

Experiments in which the enveloped multimeric assemblies were challenged with detergent, RNase A, or both prior to analysis by RT-qPCR demonstrated that the packaged mRNA is contained within the membrane envelope of the enveloped multimeric assemblies. These experiments were similar to the protease and enzyme activity assays described above in that they evaluated the accessibility of the mRNA cargoes to RNase A in the presence and absence of detergent. A mixture of four pooled mRNA-packaging enveloped multimeric assemblies [produced from four different co-transfections with plasmids encoding the four EPN-01-posT1 constructs (SEQ IDs 256, 260, 264, and 268) and corresponding mRNA cargoes (SEQ IDs 208, 209, 210, and 211)] yielded similar levels of mRNA cargoes after incubation in PBS for 10 minutes (no treatment), incubation with 20 µg/mL RNase A for 10 minutes, or incubation with 1% Triton X-100 for 10 minutes prior to RT-qPCR (FIG. 10). In contrast, the level of packaged mRNA cargo was depleted by more than three orders of magnitude when the same mixture of mRNA-packaging enveloped multimeric assemblies was incubated with 20 µg/mL RNase A and 1% Triton X-100 for 10 minutes prior to RT-qPCR. This detergent-dependent degradation of the mRNA cargoes by RNase demonstrated that the membrane envelope of the enveloped multimeric nanoparticles provides an effective barrier that protects the packaged mRNA cargoes from degradation. In other experiments, we have observed no degradation of packaged mRNA cargoes when the RNase incubation is extended to 16 hours (in the absence of detergent).

Control experiments in which we analyzed enveloped multimeric assemblies for the presence of mitochondrial RNAs demonstrated that they are free of cellular (or mitochondrial) contamination. Mitochondrial mRNAs encoding cytochrome c oxidase subunits I and II were readily detected by RT-qPCR of the cell pellets of cells expressing the enveloped multimeric particles. In contrast, the same mRNAs were not detectable in the purified enveloped multimeric assemblies. This result demonstrates that the packaged and protected mRNA cargoes we observed in the experiments described above were not present inside cells contaminating the enveloped multimeric assemblies, but were in fact packaged within the membrane envelopes of the enveloped multimeric assemblies.

We further analyzed the interactions between the packaging moieties and their cognate recognition sequences by performing an all-against-all comparison. Each of the four constructs in which the packaging domains disclosed herein were fused to EPN-01-posT1 (SEQ IDs 256, 260, 264, and 268) was co-transfected with plasmids encoding the four different versions of an mRNA cargo comprising the four recognition sequences disclosed herein (SEQ IDs 208, 209, 210, and 211) for a total of 16 co-transfections. The yield of packaged mRNA cargo from each resulting enveloped multimeric assembly was assessed by RT-qPCR as described above. While all four RNA binding domains showed the highest packaging yield for the mRNA cargoes bearing their cognate recognition sequences, the 1g70 and 1mnb RNA packaging moieties exhibited the highest specificity (FIG. 11).

Packaging Cytoplasmic Cargoes in Enveloped Multimeric Assemblies

Recently, it was shown that enveloped viruses such as HIV and influenza can package small organic molecules—specifically, 2',3'-cyclic GMP-AMP (cGAMP)—from the host cell cytoplasm, and that the packaged cGAMP is capable of inducing the type I interferon response in the cells they go on to infect (Gentili M, et al. (2015), Science 349:1232-6; Bridgeman A, et al. (2015), Science 349:1228-32). cGAMP is a second messenger synthesized by the cytosolic DNA-sensing protein cyclic GMP-AMP synthase (cGAS) as part of the recently discovered cGAS-STING innate immune pathway that activates the type I interferon response (Sun L, Wu J, Du F, Chen X, Chen Z J (2013), Science 339:786-91; Wu J, Sun L, Chen X, Du F, Shi H, Chen C, Chen Z J (2013), Science 339:826-30). In the non-limiting embodiments described below, the inventors have shown that cGAMP can be packaged within the lumen of the membrane envelope of the enveloped multimeric assemblies of the invention and, if the enveloped multimeric assemblies also comprise a protein capable of mediating membrane fusion, the packaged cGAMP can be delivered to the cytoplasm of recipient cells, where it induces a functional interferon response by binding to and activating STING. From these data, those of skill in the art will recognize the ability of the enveloped multimeric assemblies of the invention to package other types of molecules, such as proteins, nucleic acids, lipids, or other small organic molecules, from the cytoplasm of the cell in which they are produced.

cGAMP-loaded enveloped multimeric assemblies were prepared by transfecting ~2.5×10⁶ HEK293T cells in a 10-cm tissue culture dish with 6 μg of plasmid encoding either EPN-01-posT1 or Myr-I3-01-myc-p6, 10 μg plasmid encoding human cGAS, and 1.5 μg plasmid encoding either VSV-G or the ecotropic envelope protein of Murine Moloney Leukemia Virus (Eco). Control transfections were also performed in which one or more of the plasmids was omitted. HEK293T cells are known to not express cGAS; therefore, cGAMP production requires expression of recombinant cGAS. HEK293T cell culture supernatants were harvested 36-48 hours after transfection and filtered through a 0.45 μm filter. In some experiments, enveloped multimeric assemblies were pelleted by centrifugation through a 20% sucrose cushion at 70,000×g, resuspended in 100 μl PBS, and diluted in complete media (DMEM supplemented with 10% fetal bovine serum). In the experiments described below, the filtered supernatants were used directly to administer the enveloped multimeric assemblies to macrophages. The ability of the enveloped multimeric assemblies to package and deliver cGAMP was evaluated using a macrophage stimulation assay as follows. Primary murine bone marrow-derived macrophages were cultured from the following mice: C57BL6/J (wild-type). cGAS$^{-/-}$ (Mb21d1$^{-/-}$; Gray E E, Trueting P M, Woodward J J, Stetson D B (2015), J. Immunol. 195.1939-43), or Tmem173$^{-/-}$. (STING-deficient: Ishikawa H, Barber G N (2008). Nature 455:674-8). Macrophages were incubated with cGAMP-loaded or control enveloped multimeric assemblies for 6-8 hours. Type I interferons in culture supernatants from stimulated macrophages were quantified using an interferon bioassay in which L929 cells expressing an interferon-stimulated response element (ISRE)-luciferase reporter were incubated with macrophage culture supernatants for 6 hours. L929-ISRE reporter cells were lysed and luciferase activity was quantified using a Luciferase Assay System (Promega) and Centro LB 960 Microplate Luminometer (Berthold Technologies). In this assay, luciferase activity is correlated with the concentration of interferons in the macrophage supernatants, which is in turn proportional to the amount of bioactive cGAMP delivered to the macrophage cytoplasm by the enveloped multimeric assemblies.

In a first set of experiments, we used VSV-G as the envelope protein that mediates fusion of the enveloped multimeric assembly membrane with recipient cell membranes (FIG. 12). Enveloped multimeric assemblies prepared from HEK293T cells expressing EPN-01-posT1, cGAS, and VSV-G induced interferon production in wild-type macrophages roughly equivalent to that of transfected calf thymus DNA, a commonly used positive control for measuring cGAS- and STING-dependent innate immune responses. The same enveloped multimeric assemblies also induced a strong interferon response in cGAS-deficient macrophages, suggesting that the stimulus associated with the enveloped multimeric assemblies responsible for inducing interferon production was not DNA. In contrast, interferon production was reduced to background levels in STING-deficient macrophages. The cGAS-independent, STING-dependent nature of the response strongly suggests that the enveloped multimeric assembly-associated stimulus was cGAMP, the known activating ligand of STING. Additional controls confirmed this suggestion: enveloped multimeric assemblies produced in cells that did not express cGAS, VSV-G. or both failed to induce interferon production in any macrophages. Together, these data show that the stimulus for interferon production was dependent on expression of cGAS and dependent on the presence of a protein capable of mediating membrane fusion. Interestingly, filtered supernatants from cells expressing cGAS and VSV-G, but not EPN-01-posT1, induced interferon production in wild-type and cGAS-deficient cells but not STING-deficient cells in a manner closely resembling the behavior of enveloped multimeric assemblies produced in cells expressing all three proteins. Given the known ability of VSV-G to induce the formation of extracellular vesicles on its own (Mangeot P, Dollet S, Girard M, Ciancia C, Joly S, Peschanski M, Lotteau V (2011) Protein transfer into human cells by VSV-G-induced nanovesicles. Mol. Therapy 19:1656-66), we hypothesized that VSV-G-induced extracellular vesicles were packaging and delivering cGAMP in a manner similar to the enveloped multimeric assemblies. We therefore evaluated the ability of an alternative envelope protein, that of the Moloney Murine Leukemia Virus (Eco), which is not known to induce extracellular vesicle formation upon expression in human cells, to mediate cytoplasmic delivery of packaged cGAMP. Enveloped multimeric assemblies prepared from HEK293T cells expressing Myr-I3-01-myc-p6, cGAS, and Eco induced an interferon response in wild-type macrophages, while those prepared from HEK293T cells expressing cGAS and Eco with I3-01, which we have shown does not produce enveloped multimeric assemblies (see above), did not induce interferon production (FIG. 13). This experiment demonstrated that in the absence of background vesicles derived from VSV-G-induced vesicle formation, a functional enveloped multimeric assembly protein was required in order to mediate the packaging and delivery of cGAMP to recipient cells via the enveloped multimeric assemblies of the invention. Taken together, the results of the macrophage stimulation assays described here demonstrate that the enveloped multimeric assemblies of the invention package cGAMP and deliver it to the cytoplasm of the recipient cells, where it stimulates a functional interferon response. The lack of any known interactions between cGAMP and the protein subunits of the enveloped multimeric assembly, in combination with similar packaging and delivery of cGAMP by both enveloped viruses and VSV-G-derived extracellular vesicles (described above), establishes that packaging of cGAMP inside the membrane envelope of the enveloped multimeric assemblies is the result of the packaging of a volume of host cell cytoplasm which contains cGAMP rather than specific recruitment of cGAMP to the enveloped multimeric assemblies by a packaging moiety. As will be known to those of skill in the art, this property of the enveloped multimeric assemblies enables the packaging of a variety of molecules present in the host cell cytoplasm, including but not limited to proteins, nucleic acids, lipids, and other small organic molecules.

(human cGAS)

SEQ ID 328

ME(QKLISEEDL)QPWHGKAMQRASEAGATAPKASARNARGAPMDPTESPA

APEAALPKAGKFGPARKSGSRQKKSAPDTQERPPVRATGARAKKAPQRAQD

TQPSDATSAPGAEGLEPPAAREPALSRAGSCRQRGARCSTKPRPPPGPWDV

PSPGLPVSAPILVRRDAAPGASKLRAVLEKLKLSRDDISTAAGMVKGVVDH

LLLRLKCDSAFRGVGLLNIGSYYEHVKISAPNEFDVMFKLEVPRIQLEEYS

NTRAYYPVKFKRNPKENPLSQFLEGEILSASIKMLSKFRKIIKEEINDIKD

TDVIMKRKRGGSPAVTLLISEKISVDITLALESKSSWPASTQEGLRIQNWL

SAKVRKQLRLKPFYLVPKHAKEGNGFQEETWRLSFSHIEKEILNNHGKSKT

-continued

CCENKEEKCCRKDCLKLMKYLLEQLKERFKDKKHLDKFSSYHVKTAFFHVC

TQNPQDSQWDRKDLGLCFDNCVTYFLQCLRTEKLENYFIPEFNLFSSNLID

KRSKEFLTKQIEYERNNEFPVFDEF (Ecotropic envelope protein from Moloney Murine Leukemia Virus or "Eco")

SEQ ID 308

MARSTLSKPLKNKVNPRGPLIPLILLMLIRGVSTASPGSSPHQVYNITWEV

TNGDRETVWATSGNHPLWTWWPDLTPDLCMLAHHGPSYWGLEYQSPFSSPP

GPPCCSGGSSPGCSRDCEEPLTSLTPRCNTAWNRLKLDQITHKSNEGFYVC

PGPHRPRESKSCGGPDSFYCAYWGCETTGRAYWKPSSSWDFITVNNNLTSD

QAVQVCKDNKWCNPLVIRFTDAGRRVTSWTTGHYWGLRLYVSGQDPGLTFG

-continued

IRLRYQNLGPRVPIGPNPVLADQQPLSKPKPVKSPSVTKPPSGTPLSPTQL

PPAGTENRLLNLVDGAYQALNLTSPDKTQECWLCLVAGPPYYEGVAVLGTY

SNHTSAPANCSVASQHKLTLSEVTGQGLCIGAVPKTHQALCNTTQTSSRGS

YYLVAPTGTMWACSTGLTPCISTTILNLTTDYCVLVELWPRVTYHSPSYVY

GLFERSNRIIKREPVSLTLALLLGGLTMGGIAAGIGTGTTALMATQQFQQL

QAAVQDDLREVEKSISNLEKSLTSLSEVVLQNRRGLDLLFLKEGGLCAALK

EECCFYADHTGLVRDSMAKLRERLNQRQKLFESTQGWFEGLFNRSPWFTTL

ISTIMGPLIVLLMILLFGPCILNRILVQFVKDRISVVQALVLTQQYHQLKP

IEYEP

---

We claim:

1. A multimeric assembly, comprising a plurality of oligomeric substructures, wherein each oligomeric substructure comprises a plurality of proteins that self-interact around at least one axis of rotational symmetry, wherein each protein comprises:
  (a) one or more polypeptide-polypeptide interface ("O interface"); and
  (b) one or more polypeptide domain that is capable of effecting membrane scission and release of an enveloped multimeric assembly from a cell by recruiting the ESCRT machinery to the site of budding by binding directly or indirectly to one or more ESCRT or ESCRT-associated proteins ("L domain");
  wherein one or more protein in the multimeric assembly comprises one or more polypeptide domain that is capable of interacting with a lipid bilayer ("M domain"), wherein the one or more M domains are selected from the group consisting of SEQ ID NOs: 52-151, 283-297, and 299-300 and wherein (i) at least one protein in each oligomeric substructure comprises one or more M domain, or (ii) wherein each protein comprises one or more M domain;
  wherein the M domain, L domain, and O interface are not each present in a single naturally occurring protein, wherein the plurality of oligomeric substructures interact with each other at the one or more O interfaces.

2. The multimeric assembly of claim 1, wherein the one or more O interfaces of different proteins in the oligomeric substructure orient the plurality of oligomeric substructures such that their symmetry axes are aligned with symmetry axes of the same kind in a designated mathematical symmetry group.

3. The multimeric assembly of claim 1, wherein the one or more O interfaces in each protein of each oligomeric substructure are identical.

4. The multimeric assembly of claim 1, wherein the one or more M domains are capable of non-covalently interacting with a lipid bilayer.

5. The multimeric assembly of claim 1, wherein the one or more L domains are capable of non-covalently interacting with one or more proteins in the ESCRT pathway.

6. The multimeric assembly of claim 1, wherein the one or more L domains comprise a linear amino acid sequence motif selected from the group consisting of SEQ ID NOs: 152-197 or 305-306, or overlapping combinations thereof.

7. The multimeric assembly of claim 1, further comprising a packaging moiety present in one or more of the proteins.

8. The multimeric assembly of claim 7, further comprising a cargo interacting with the packaging moiety.

9. The multimeric assembly of claim 1, further comprising a lipid bilayer enveloping the multimeric assembly, wherein one or more of the M domains is bound to the lipid bilayer.

10. The multimeric assembly of claim 9, further comprising one or more transmembrane protein or membrane-anchored protein embedded in the lipid bilayer.

11. The multimeric assembly of claim 10, wherein the transmembrane or membrane-anchored protein is selected from the group consisting of the envelope proteins of enveloped viruses, membrane protein transporters, membrane protein channels, B-cell receptors, T-cell receptors, transmembrane antigens of human pathogens, growth factors receptors, G-protein coupled receptors (GPCRs), and complement regulatory proteins.

12. The multimeric assembly of claim 10 wherein the one or more transmembrane protein or membrane-anchored protein embedded in the lipid bilayer comprises one or more polypeptide selected from the group consisting of SEQ ID NOs: 307-315.

13. A recombinant polypeptide comprising
  (a) a polypeptide domain that is capable of interacting with a lipid bilayer ("M domain"), wherein the one or more M domains are selected from the group consisting of SEQ ID NOs: 52-151, 283-297, and 299-300;
  (b) a polypeptide-polypeptide interface ("O interface");
  (c) a polypeptide domain that is capable of effecting membrane scission and release of an enveloped multimeric assembly from a cell by recruiting the ESCRT machinery to the site of budding by binding to one or more proteins in the eukaryotic ESCRT complex ("L domain"); and (d) a packaging moiety;
   wherein the M domain, the L domain, and the O interface are not each present in a single naturally occurring protein.

14. The recombinant polypeptide of claim 13, wherein the M domain is capable of non-covalently interacting with a lipid bilayer.

15. The recombinant polypeptide of claim 13, wherein the L domain is capable of non-covalently interacting with one or more proteins in the ESCRT machinery or proteins known to recruit the ESCRT machinery to the site of budding by binding to one or more ESCRT proteins directly or indirectly.

16. The recombinant polypeptide of claim 13, wherein the L domains comprise a linear amino acid sequence motif selected from the group consisting of SEQ ID NOs: 152-197 or 305-306, or overlapping combinations thereof.

17. A recombinant polypeptide comprising an amino acid sequence having at least 97% sequence identity to the amino acid sequence of SEQ ID NO: 20 or SEQ ID NO: 304, wherein the polypeptide includes at least 1, 2, 3, 4, 5, or more amino acid substitutions compared to SEQ NO: 21.

18. A recombinant nucleic acid encoding the recombinant polypeptide of claim 13.

19. A recombinant expression vector comprising the recombinant nucleic acid of claim 18 operatively linked to a promoter.

20. A recombinant host cell comprising the recombinant expression vector of claim 19.

* * * * *